US008314251B2

(12) United States Patent
Ling et al.

(10) Patent No.: US 8,314,251 B2
(45) Date of Patent: Nov. 20, 2012

(54) TOTAL SYNTHESIS OF SALINOSPORAMIDE A AND ANALOGS THEREOF

(75) Inventors: Taotao Ling, Germantown, TN (US); Samuel Danishefsky, Englewood, NJ (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/184,356

(22) Filed: Jul. 15, 2011

(65) Prior Publication Data

US 2011/0269969 A1 Nov. 3, 2011

Related U.S. Application Data

(62) Division of application No. 12/399,382, filed on Mar. 6, 2009, now Pat. No. 8,003,802.

(60) Provisional application No. 61/034,900, filed on Mar. 7, 2008, provisional application No. 61/073,545, filed on Jun. 18, 2008.

(51) Int. Cl.
*C07D 263/00* (2006.01)
*C07D 498/04* (2006.01)

(52) U.S. Cl. ..................................... 548/217

(58) Field of Classification Search .................... None
See application file for complete search history.

(56) References Cited

U.S. PATENT DOCUMENTS

| 7,144,723 B2 | 12/2006 | Fenical et al. |
| 7,176,232 B2 | 2/2007 | Fenical et al. |
| 7,176,233 B2 | 2/2007 | Fenical et al. |
| 7,179,834 B2 | 2/2007 | Fenical et al. |
| 7,183,417 B2 | 2/2007 | Corey |
| 7,276,530 B2 | 10/2007 | Potts et al. |
| 7,371,875 B2 | 5/2008 | Xiao et al. |
| 7,465,720 B2 | 12/2008 | Corey et al. |
| 7,511,156 B2 | 3/2009 | Corey |
| 7,544,814 B2 | 6/2009 | Potts et al. |
| 7,579,371 B2 | 8/2009 | Palladino et al. |
| 7,635,712 B2 | 12/2009 | Fenical et al. |
| 7,691,896 B2 | 4/2010 | Myers et al. |
| 7,842,814 B2 | 11/2010 | Ling et al. |
| 7,879,576 B2 | 2/2011 | Fenical et al. |
| 7,910,616 B2 | 3/2011 | Macherla et al. |
| 7,928,138 B2 | 4/2011 | Fenical et al. |
| 8,003,802 B2 | 8/2011 | Ling et al. |
| 8,067,616 B2 | 11/2011 | Ling et al. |
| 2005/0049294 A1 | 3/2005 | Palladino et al. |
| 2006/0008852 A1 | 1/2006 | Fenical et al. |
| 2006/0264495 A1 | 11/2006 | Palladino et al. |
| 2006/0287520 A1 | 12/2006 | Danishefsky et al. |
| 2007/0004676 A1 | 1/2007 | Palladino et al. |
| 2007/0225350 A1 | 9/2007 | Anderson et al. |
| 2008/0070273 A1 | 3/2008 | Fenical et al. |
| 2008/0280968 A1 | 11/2008 | Palladino |
| 2009/0035390 A1 | 2/2009 | Anderson et al. |
| 2009/0069401 A1 | 3/2009 | Fenical et al. |
| 2009/0148445 A1 | 6/2009 | Bonavida et al. |
| 2009/0156469 A1 | 6/2009 | Ghobrial et al. |
| 2009/0182027 A1 | 7/2009 | Palladino et al. |
| 2009/0197937 A1 | 8/2009 | Fenical et al. |
| 2009/0234137 A1 | 9/2009 | Ling et al. |
| 2009/0298906 A1 | 12/2009 | Macherla et al. |
| 2009/0318529 A1 | 12/2009 | Fenical et al. |
| 2010/0144826 A1 | 6/2010 | Fenical et al. |
| 2010/0168046 A1 | 7/2010 | Palladino |

FOREIGN PATENT DOCUMENTS

| WO | WO 96/32105 | 10/1996 |
| WO | WO 99/09006 | 2/1999 |
| WO | WO 99/15183 | 4/1999 |
| WO | WO 2004/071382 | 8/2004 |
| WO | WO 2005/002572 | 1/2005 |
| WO | WO 2005/099687 | 10/2005 |
| WO | WO 2005/113558 | 12/2005 |
| WO | WO 2006/005551 | 1/2006 |
| WO | WO 2006/028525 | 3/2006 |
| WO | WO 2006/060676 | 6/2006 |
| WO | WO 2006/060809 | 6/2006 |
| WO | WO 2006/118973 | 11/2006 |
| WO | WO 2007/021897 | 2/2007 |
| WO | WO 2007/033039 | 3/2007 |
| WO | WO 2007/117591 | 10/2007 |
| WO | WO 2009/140287 | 11/2009 |

OTHER PUBLICATIONS

Andrews, et al., "Highly Functionalised Pyroglutamates by Intramolecular Aldol Reactions: Towards the Pyroglutamate Skeleton of Oxazolomycin", Synlett: Letters (1996) 612-614.

Andrews, et al., "Regioselective dieckmann cyclisations leading to enantiopure highly functionalized tetramic acid derivatives", J. Chem. Soc., Perkin Trans. (1998) 1:223-235.

Caubert et al., "Stereoselective formal synthesis of the potent proteasome inhibitor: salinosporamide A" Tetrahedron Lett. (2007) 48 : 381-4.

Caubert et al., "Studies toward the synthesis of salinosporamide A, a potent proteasome inhibitor" Tetrahedron Lett (2006) 47:4473-5.

Corey, et al., "An efficient tool synthesis of a new and highly active analog of lactacystin", Tetrahedron Letters (1998) 39:7475-7478.

Definition of "aminals" from IUPAC Compendium of Chemical Terminology, ($2^{nd}$ Ed., 1997).

Endo, et al., "Total synthesis of salinosporamide A", J. Am. Chem. Soc. (2005) 127:8298-8299 and S1-S23.

Fukuda et al. "Total Synthesis of Salinosporamide A" (2008) 10(19):4239-42.

Hogan, et al., "Proteasome inhibition by a totally synthetic β-lactam related to salinosporamide A and omuralide", J. Am. Chem. Soc. (2005) 127:15386-15387.

(Continued)

Primary Examiner — Joseph K. McKane
Assistant Examiner — Alicia L Otton
(74) Attorney, Agent, or Firm — Knobbe Martens Olson & Bear, LLP

(57) ABSTRACT

The present application relates to certain compounds and to methods for the preparation of certain compounds that can be used in the fields of chemistry and medicine. Specifically, described herein are methods for the preparation of various compounds and intermediates, and the compounds and intermediates themselves. More specifically, described herein are methods for synthesizing Salinosporamide A and its analogs that includes forming a compound of formula (VIII).

5 Claims, 61 Drawing Sheets

OTHER PUBLICATIONS

Kramer et al., "Organoboranes : XIX *. The Preparation and Some Unusual Chemistry of B-allyl Derivatives of 9-Borabicyclo[3.3.1]nonane" J. Organomet. Chem (1977) 132 :9-27.

Ling et al., "Enantioselective Total Synthesis of (−)-Salinosporamide A (NPI-0052)" Org. Lett (2007) 9:2289-92 and Supporting Information S1-S34.

Ling et al., "Concise Formal Synthesis of (−)-Salinosporamide A (Marizomib) Using a Regio- and Stereoselective Epoxidation and Reductive Oxirane Ring-Opening Strategy" J. Org. Chem. (2010) 75(11):3882-5.

Ma, et al., Concise total synthesis of (±)-salinosporamide A, (±)-cinnabaramide A, and derivatives via a bis-cyclization process: implications for a biosynthetic pathway?, Org. Lett., (2007) 9(11):2143-2146.

Manam et al. "Stereoselective enzymatic reduction of keto-salinosporamide to (−)-salinosporamide A (NPI-0052)" Tetrahedron Lett (2007) 48 :2537-40.

Margalef, et al, "Formal Synthesis of Salinosporamide A Using a Nickel-catalyzed Reductive Aldol Cyclization-Iactonization as a Key Step,", Tetrahedron, (2008) 64(34):7896-7901.

Momose et al. "Formal Synthesis of Salinosporamide A Starting from D-Glucose"(2009) Synthesis, 17:2983-2991.

Mosey et al, "New Synthetic Route to Access (±) Salinosporamide A via an Oxazolone-Mediated Ene-Type Reaction" Tetrahedron Letters (2009) 50:295-7.

Mulholland, et al., "A concise total synthesis of salinosporamide A", Org. Biomol. Chem. (2006) 4:2845-2846.

Potts et al. "Generating a Generation of Proteasome Inhibitors: From Microbial Fermentation to Total Synthesis of Salinosporamide A (Marizomib) and Other Salinosporamides" Marine Drugs (2010) 8(4):835-80.

Reddy, et al., "A simple sterecontrolled synthesis of salinosporamide A", J. Am. Chem. Soc. (2004) 126:6230-6231.

Reddy, et al., "An efficient, stereocontrolled synthesis of a potent omuralide-salinosporin hybrid for selective proteasome inhibition", J. Am. Chem. Soc. (2005) 127:8974-8976.

Reddy, et al., "New synthetic route for the enantioselective total synthesis of salinosporamide A and biologically active analogues", Org. Lett. (2005) 7(13): 2699-2701.

Seebach et al., "73. Structure and Reactivity of Five- and Siz-Ring N,N-, N,O-, and O,O-Acetals: A Lesson in Allylic 1,3-Strain (A1,3 Strain)" Helv Chim Acta (1992) 75:913-34.

Seebach et al., "Self-Regeneration of Stereocenters (SRS)—Applications, Limitations, and Abandonment of a Synthetic Principle" Angew Chem Int. Ed (1996) 35:2708-48.

Seebach, et al., "α-Alkylation of serine with self-reproduction of the center of chirality", Tetrahedron Letters (1984) 25(24):2545-2548.

Struble et al., "Formal Synthesis of Salinosporamide Aj via NHC-Catalyzed Intramolecular Lactonization" Tetrahedron (2009) 65:4957-67.

Takahashi, et al., "Entry of Heterocycles Based on Indium Catalyzed Conia-Ene Reactions: Asymmetric Synthesis of (−)-Salinosporamide A" Angew. Chemie. Int. Ed., (2008) 47:1-4.

International Preliminary Report on Patenability dated Oct. 16, 2008 for PCT Application No. PCT/US2009/008562, Filed Apr. 6, 2007.

International Search Report and Written Opinion dated Mar. 26, 2008, for PCT/US2007/008562, filed Apr. 6, 2007.

International Search Report and Written Opinion dated Sep. 28, 2010 for PCT Application No. PCT/US2009/036376, Filed Mar. 6, 2009.

International Preliminary Report on Patenability dated Oct. 5, 2010 for PCT Application No. PCT/US2009/036376, Filed Mar. 6, 2009.

EFS of U.S. Appl. No. 11/697,689, filed Apr. 6, 2007.

EFS of U.S. Appl. No. 12/913,624, filed Oct. 27, 2010 as of Jul. 6, 2011.

EFS of U.S. Appl. No. 10/821,621, filed Apr. 9, 2004.

EFS of U.S. Appl. No. 11/539,648, filed Oct. 9, 2006.

EFS of U.S. Appl. No. 12/028,024, filed Feb. 8, 2008.

EFS of U.S. Appl. No. 11/224,589, filed Sep. 12, 2005.

EFS of U.S. Appl. No. 12/399,382, filed Mar. 6, 2009 as of Apr. 18, 2011.

Hayes et al., "Enantioselective Total Synthesis of Omuralide , 7-epi-Omuralide, and (+)-Lactacystin" J. Org. Chem. (2008) 73(6):2041-2051.

Jao et al., "Preparation of (2,2-Dimehtylhexahydro[2,3-c]pyrrole-6-yl)methanol: A Conformationally Restricted Congener of Nonproteinogenic 3-Hydroxy-4-methylproline" Synthesis (2003) 17:2643-2646.

EFS of U.S. Appl. No. 12/399,382, filed Mar. 6, 2009.

EFS of U.S. Appl. No. 12/913,624, filed Oct. 27, 2010.

For Schemes 1-4d:
$R^1$ = hydrogen, unsubstituted or substituted $C_{1-6}$ alkyl or unsubstituted or substituted aryl; $R^2$ = hydrogen, an unsubstituted or substituted $C_{1-6}$ alkyl, an unsubstituted or substituted aryl, or an unsubstituted or substituted arylalkyl.

Figure 4d
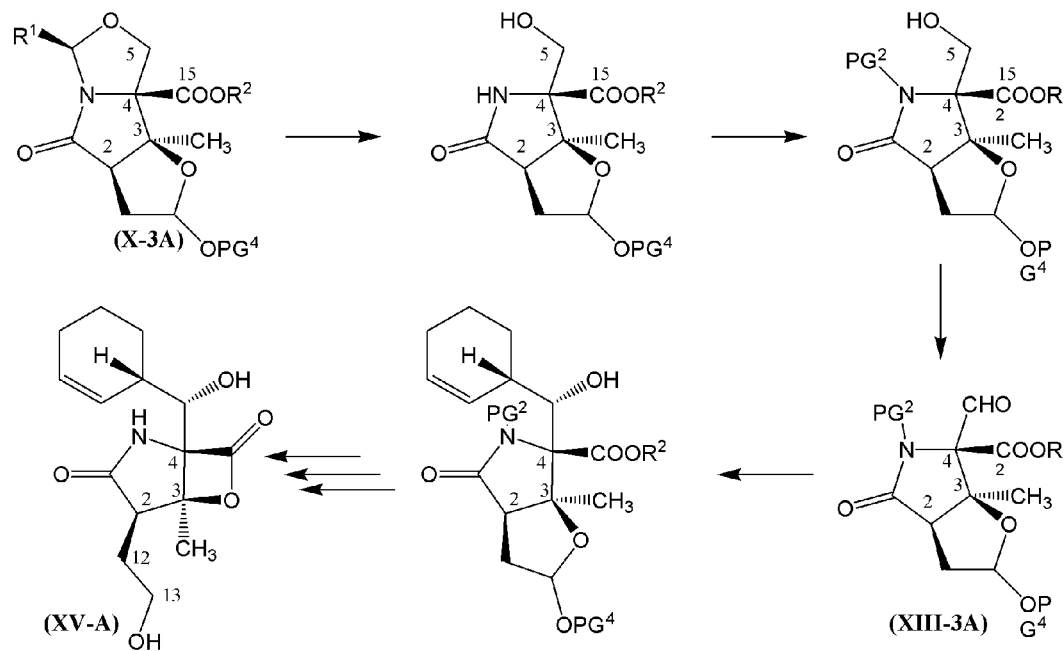
Figure 4e
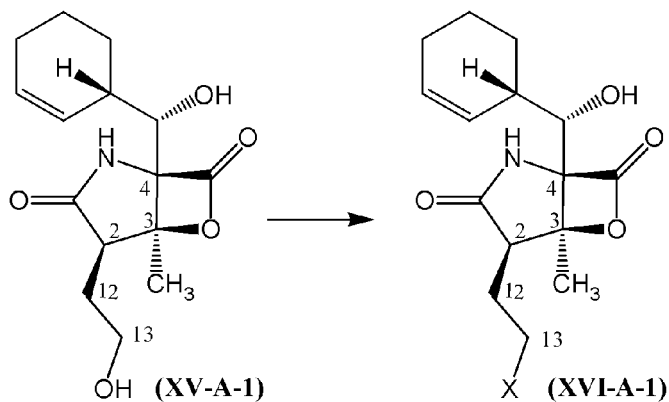
For Scheme 4e:
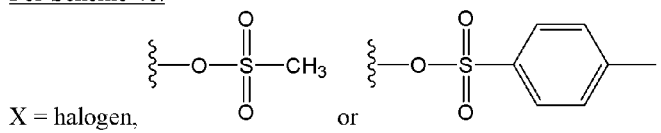
X = halogen,

Figure 5
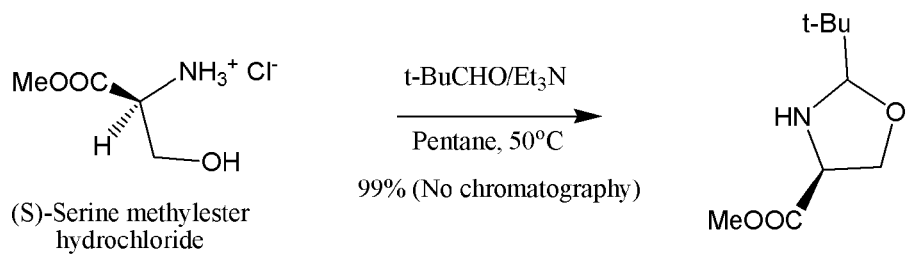
Figure 6. Structure of Salinosporamide A (NPI-0052)
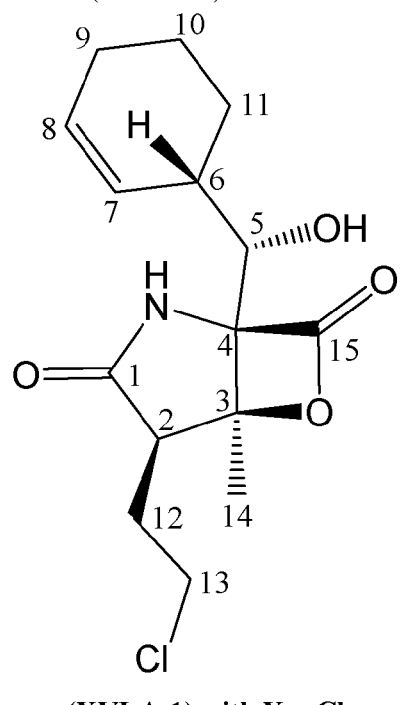
(XVI-A-1) with X = Cl

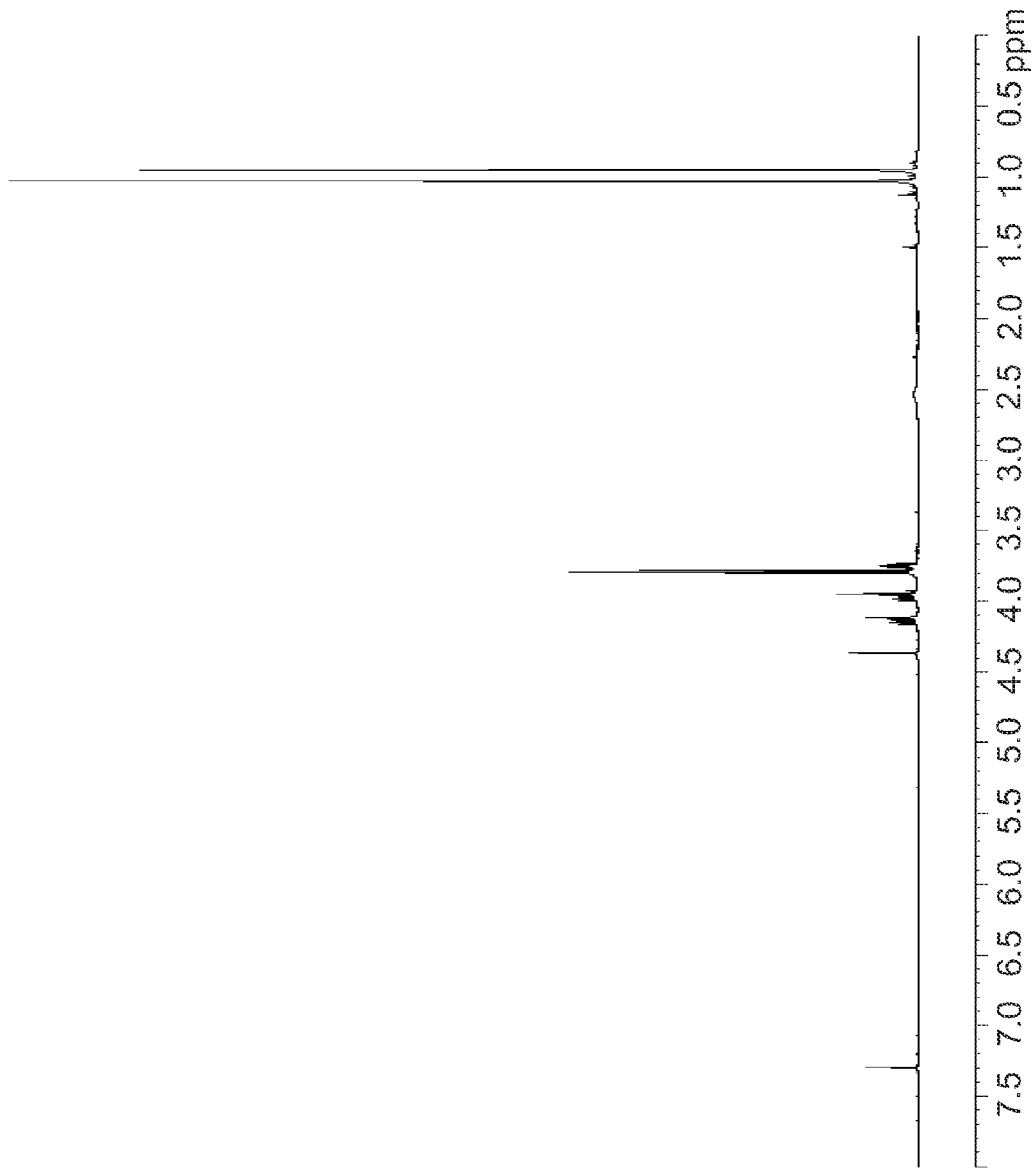
FIG. 7: $^1$H-NMR of Compound (I-B) ($R^1$ = t-butyl and $R^2$ = methyl) in $CDCl_3$

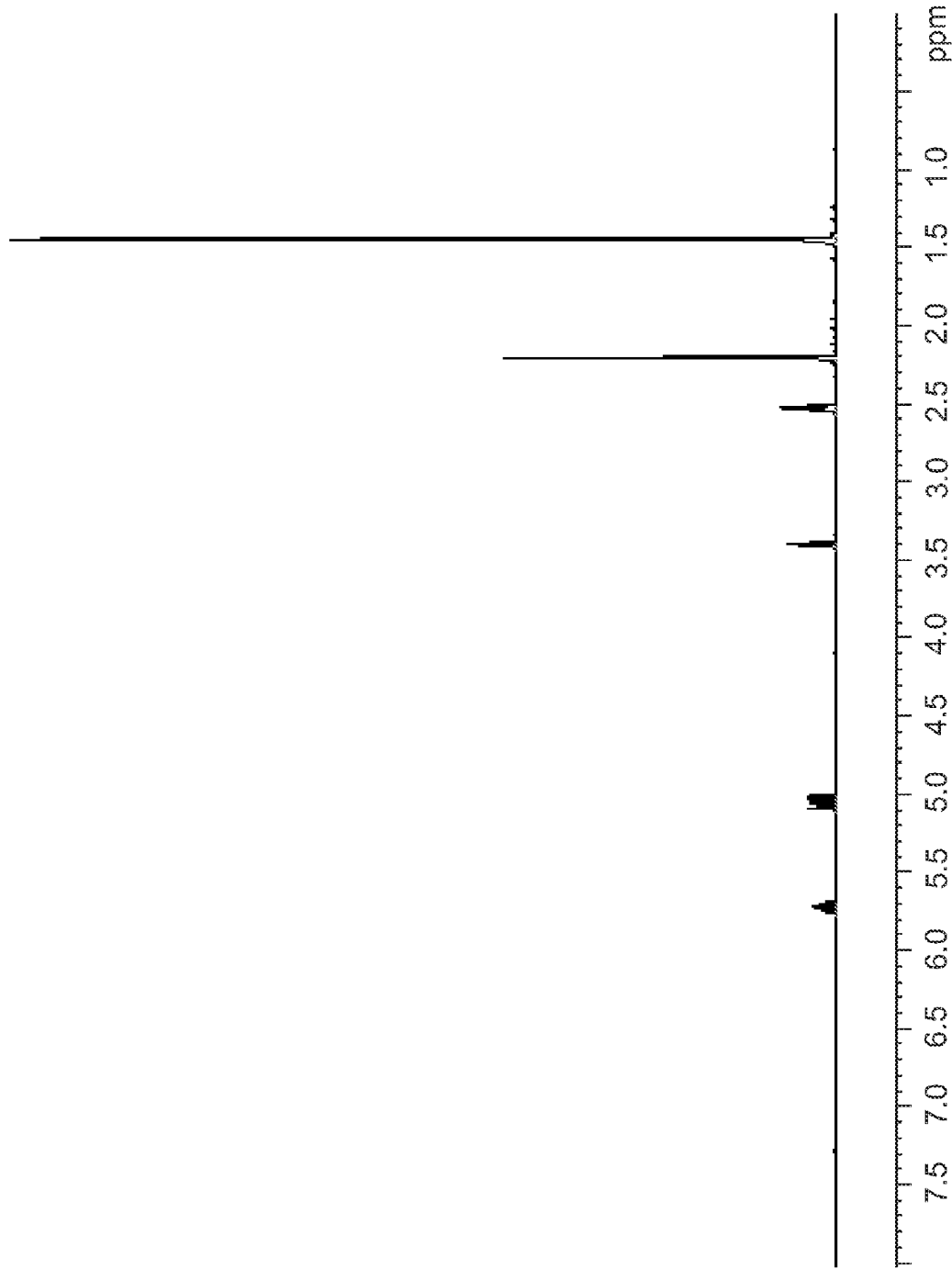
FIG. 8: ¹H-NMR of the ester precursor to the Compound (II) in CDCl₃

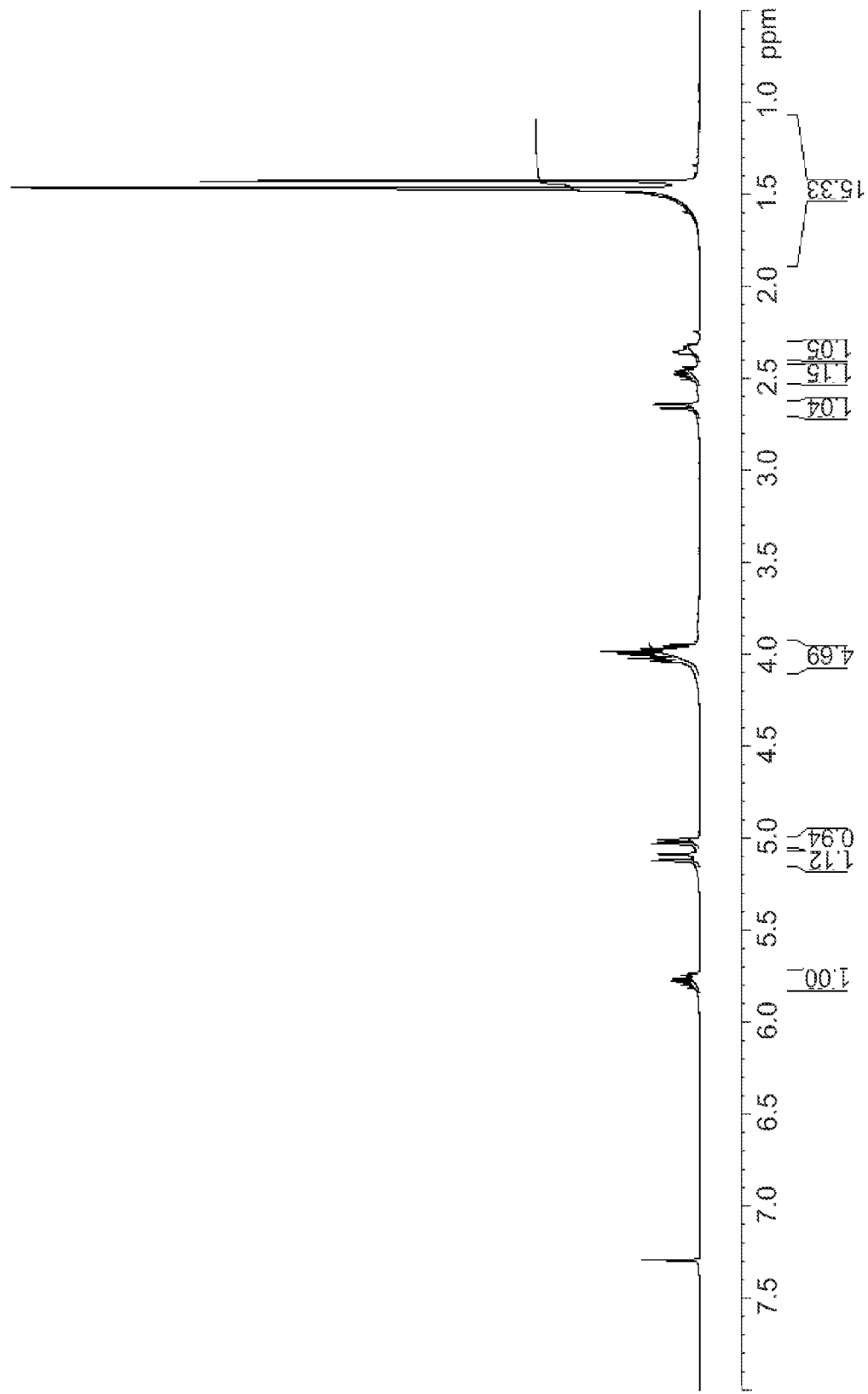
FIG. 9: ¹H-NMR of Compound the protected ester precursor of the Compound (II) in CDCl₃

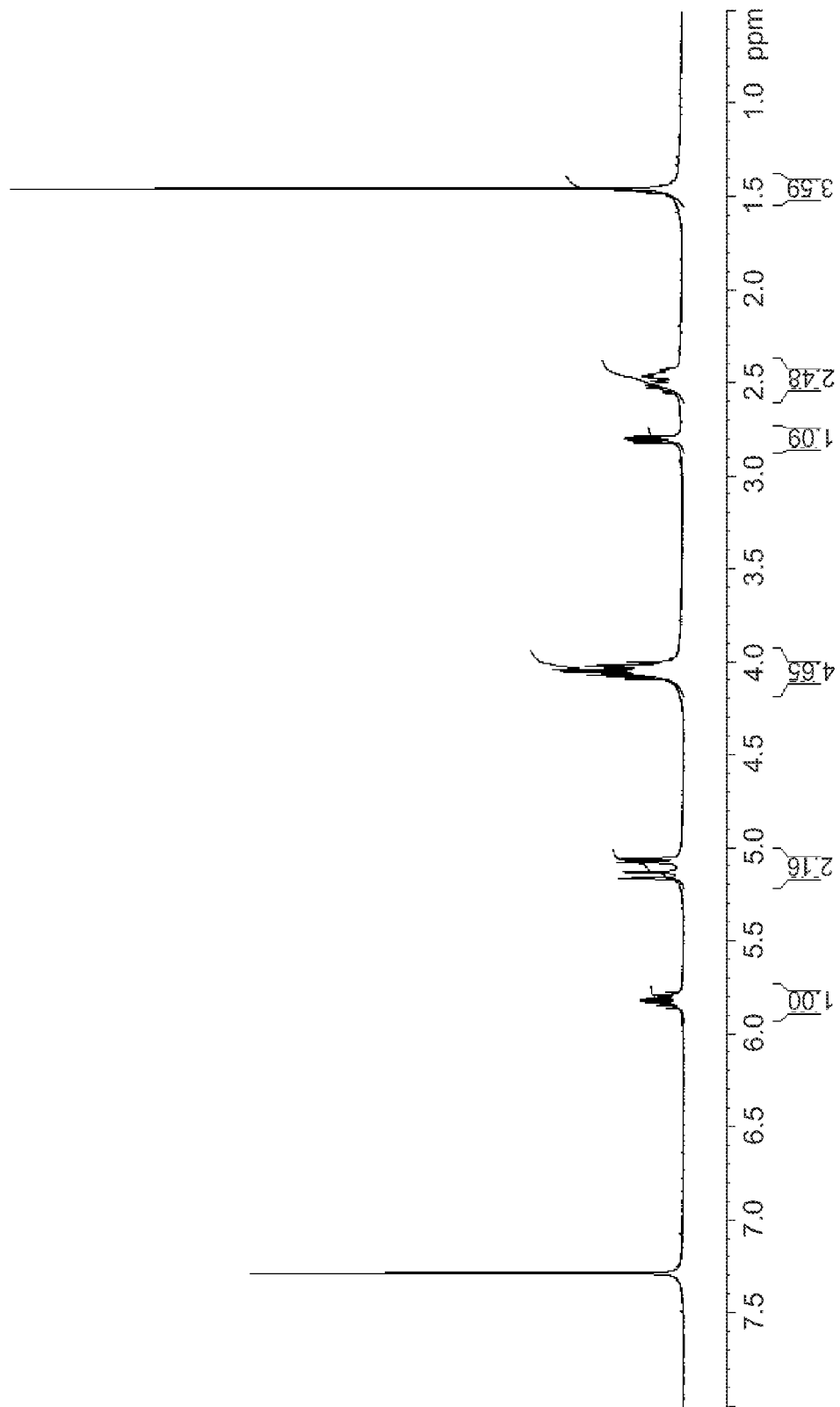
FIG. 10: 1H-NMR of the Compound (II) in CDCl3

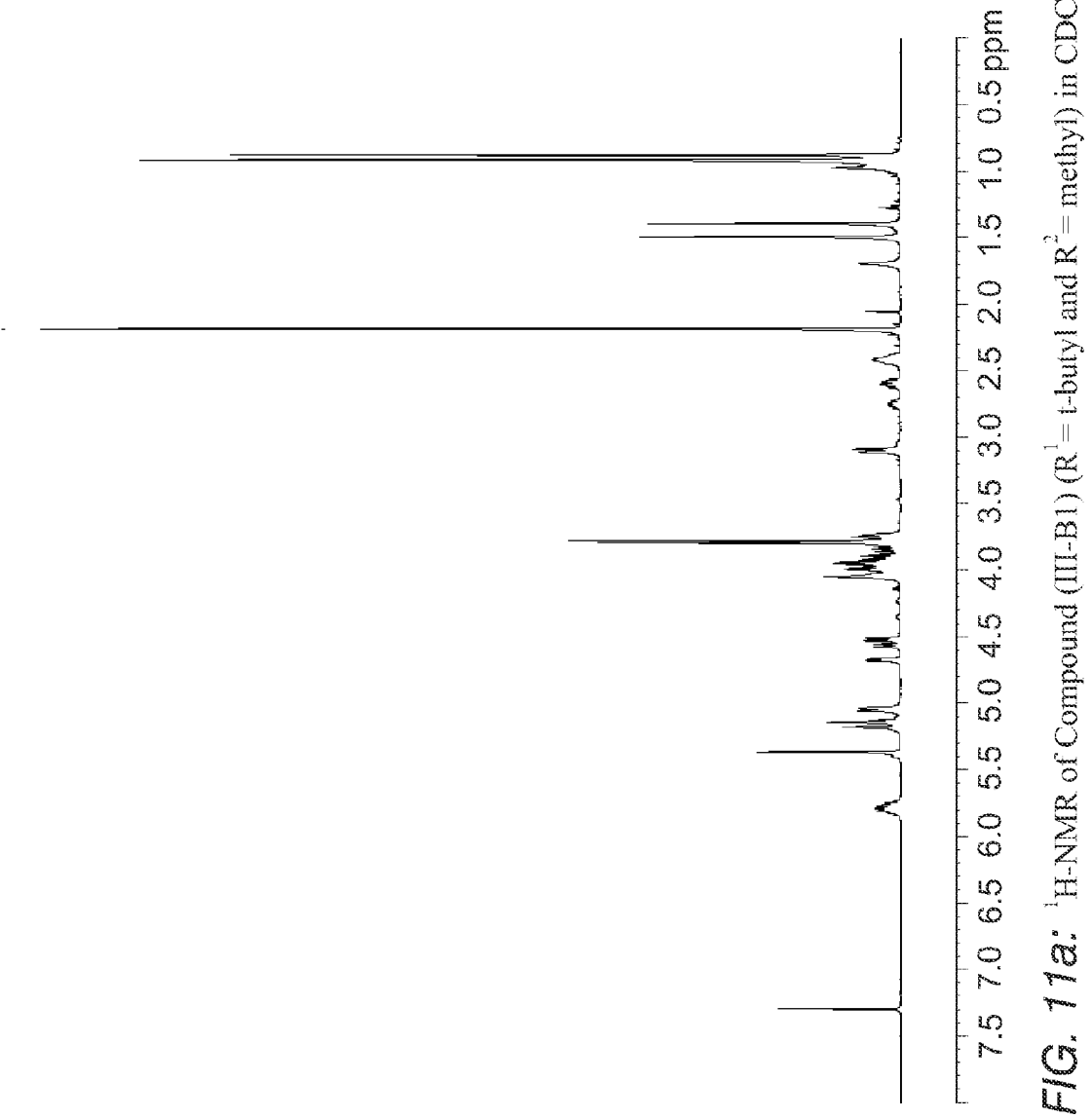
FIG. 11a: $^1$H-NMR of Compound (III-B1) ($R^1$ = t-butyl and $R^2$ = methyl) in $CDCl_3$

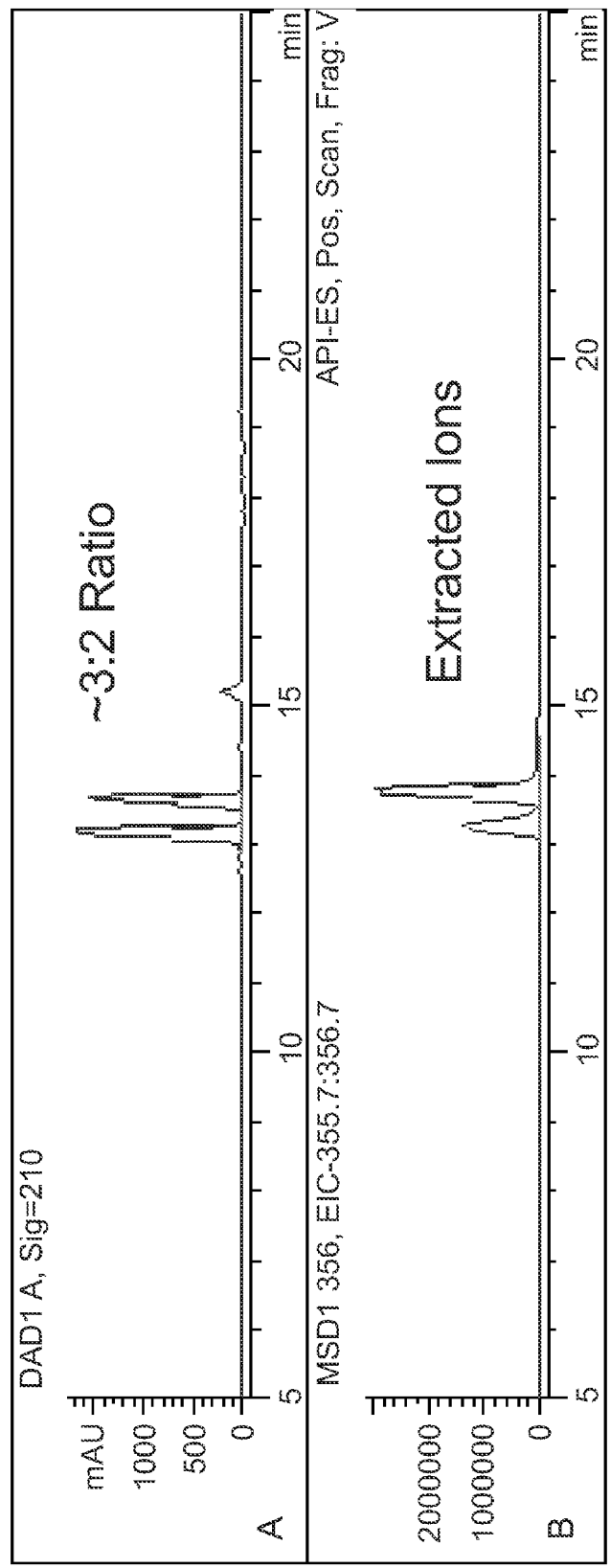
FIG. 11b: LC-MS of Compound (III-1B) ($R^1$ = t-butyl and $R^2$ = methyl)

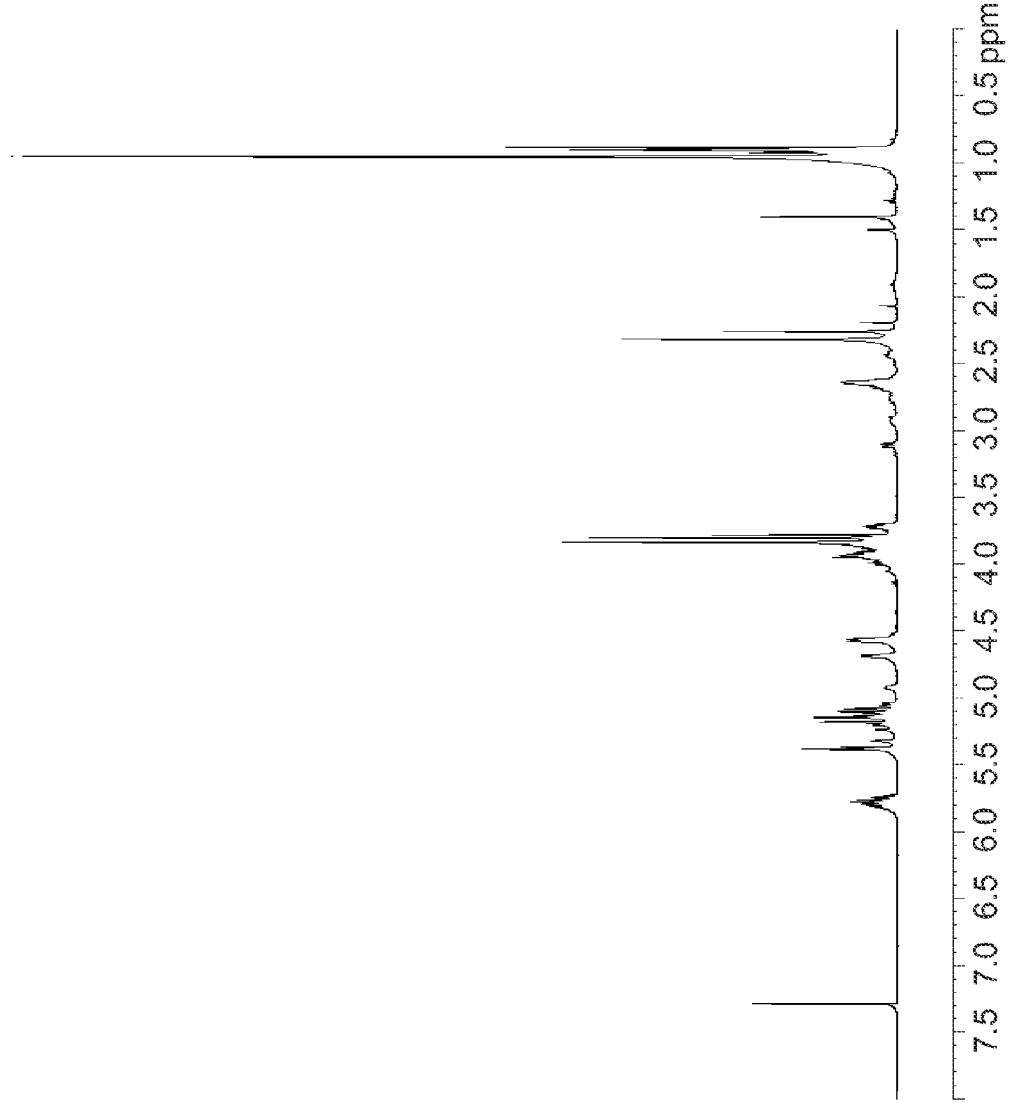
FIG. 12a: $^1$H-NMR of Compound (IV-B) ($R^1$ = t-butyl and $R^2$ = methyl) in CDCl$_3$ NOESY of Compound (IV-B) ($R^1$ = t-butyl and $R^2$ = methyl)

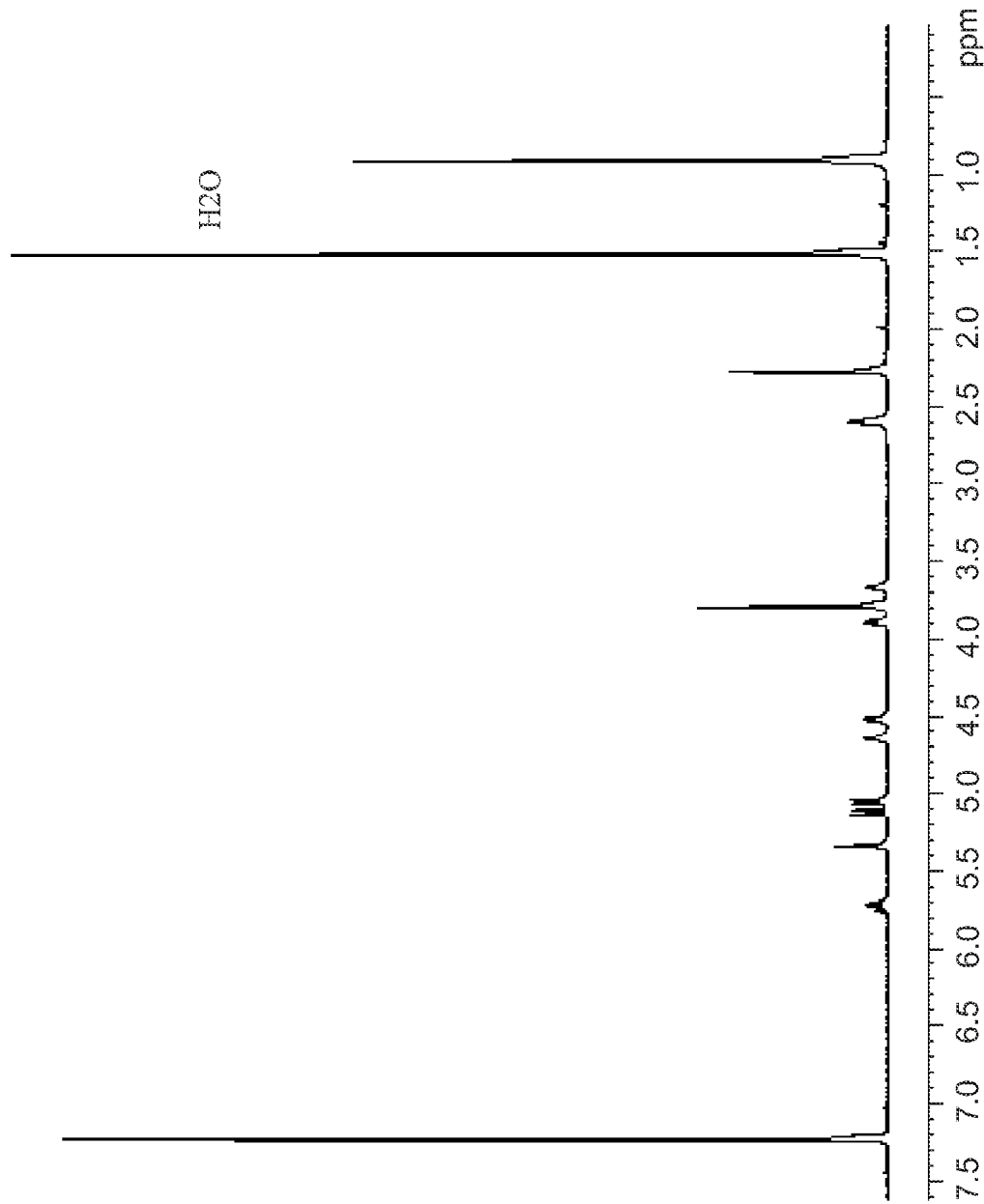
FIG. 12C: $^1$H-NMR of Compound (IV-B1) ($R^1$ = t-butyl and $R^2$ = methyl) in CDCl$_3$

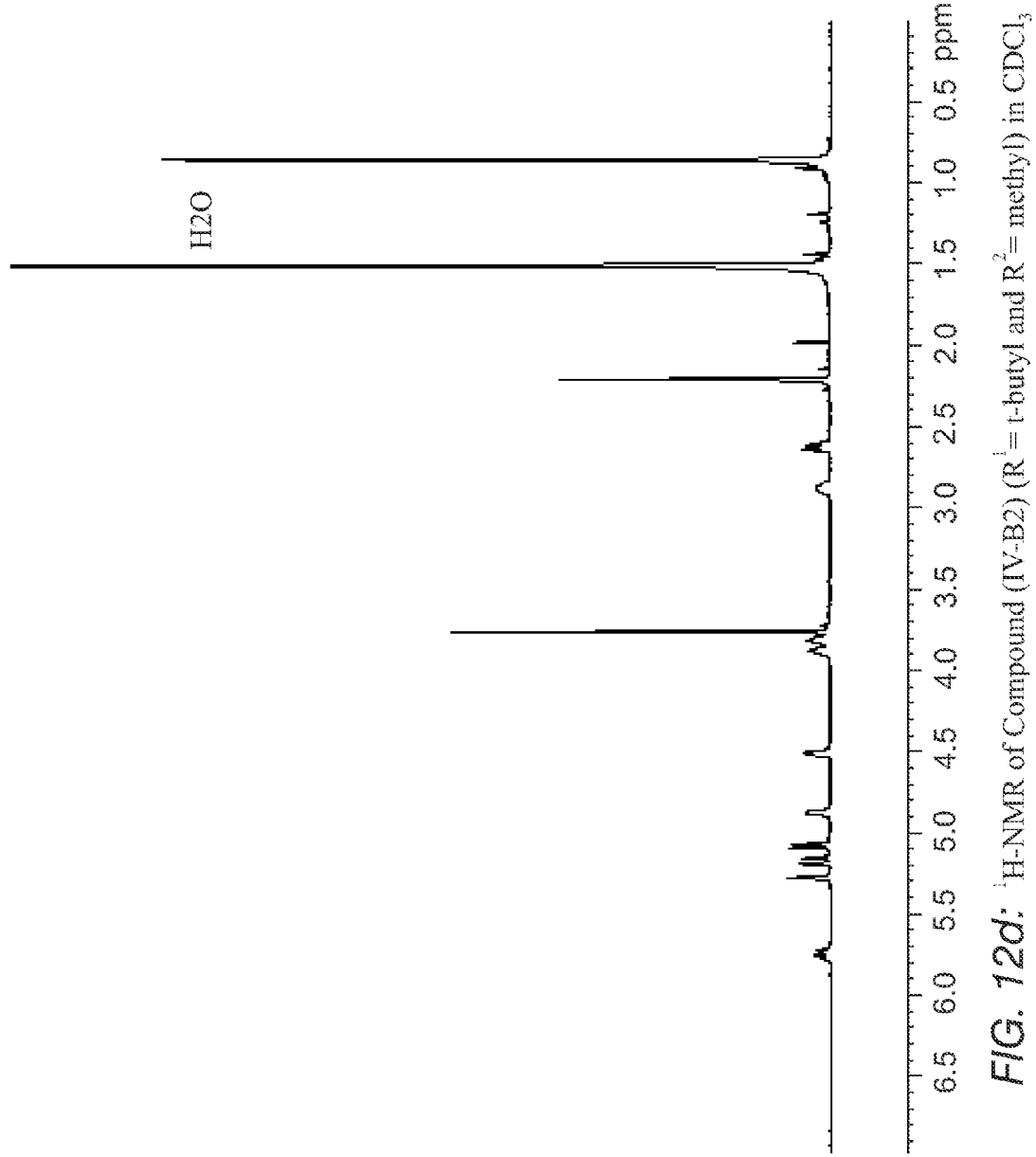
FIG. 12d: $^1$H-NMR of Compound (IV-B2) ($R^1$ = t-butyl and $R^2$ = methyl) in CDCl$_3$

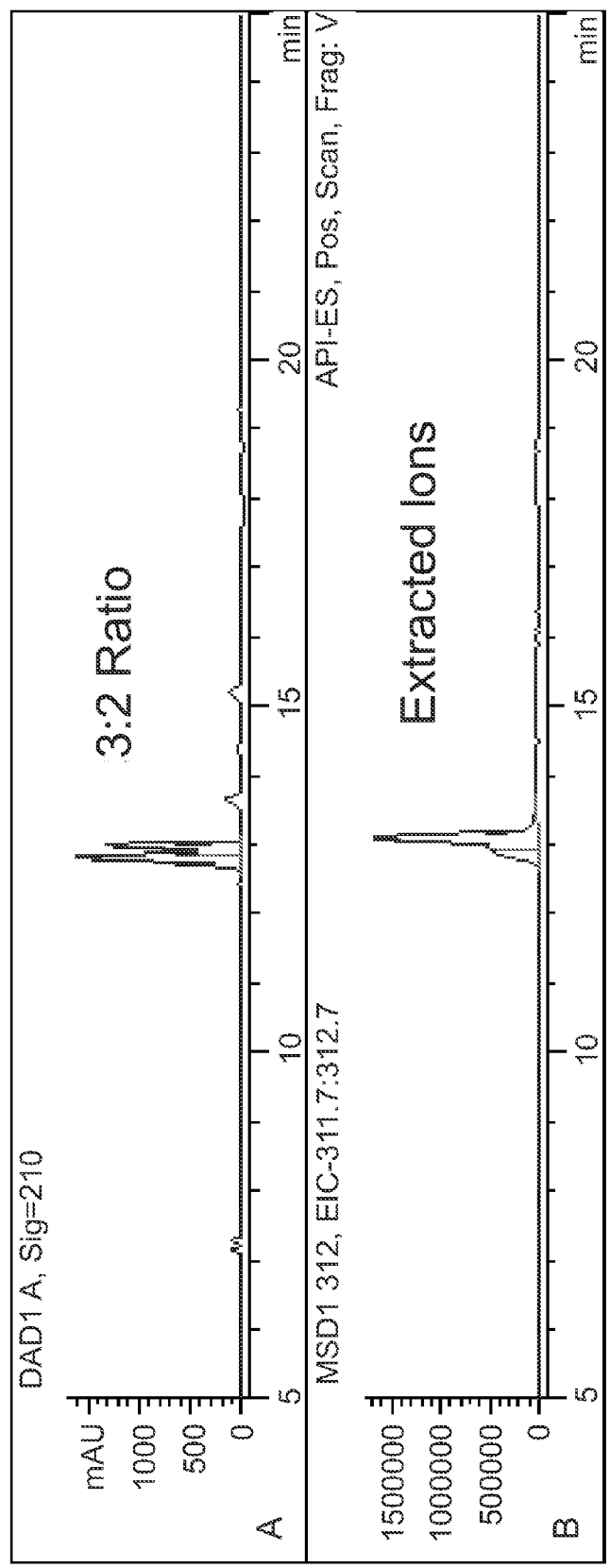
FIG. 12e: LC-MS of Compound (IV-B) ($R^1$ = t-butyl and $R^2$ = methyl)

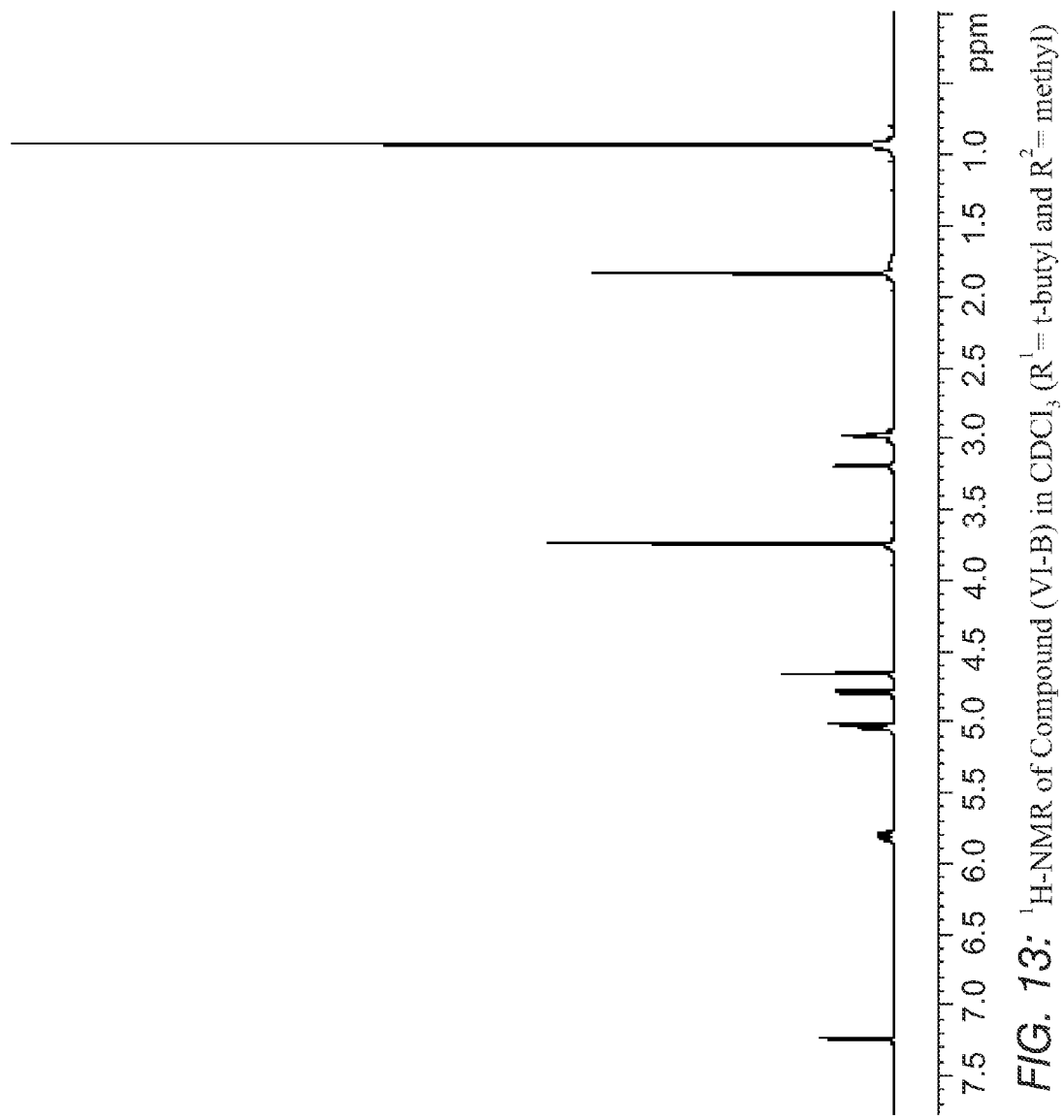

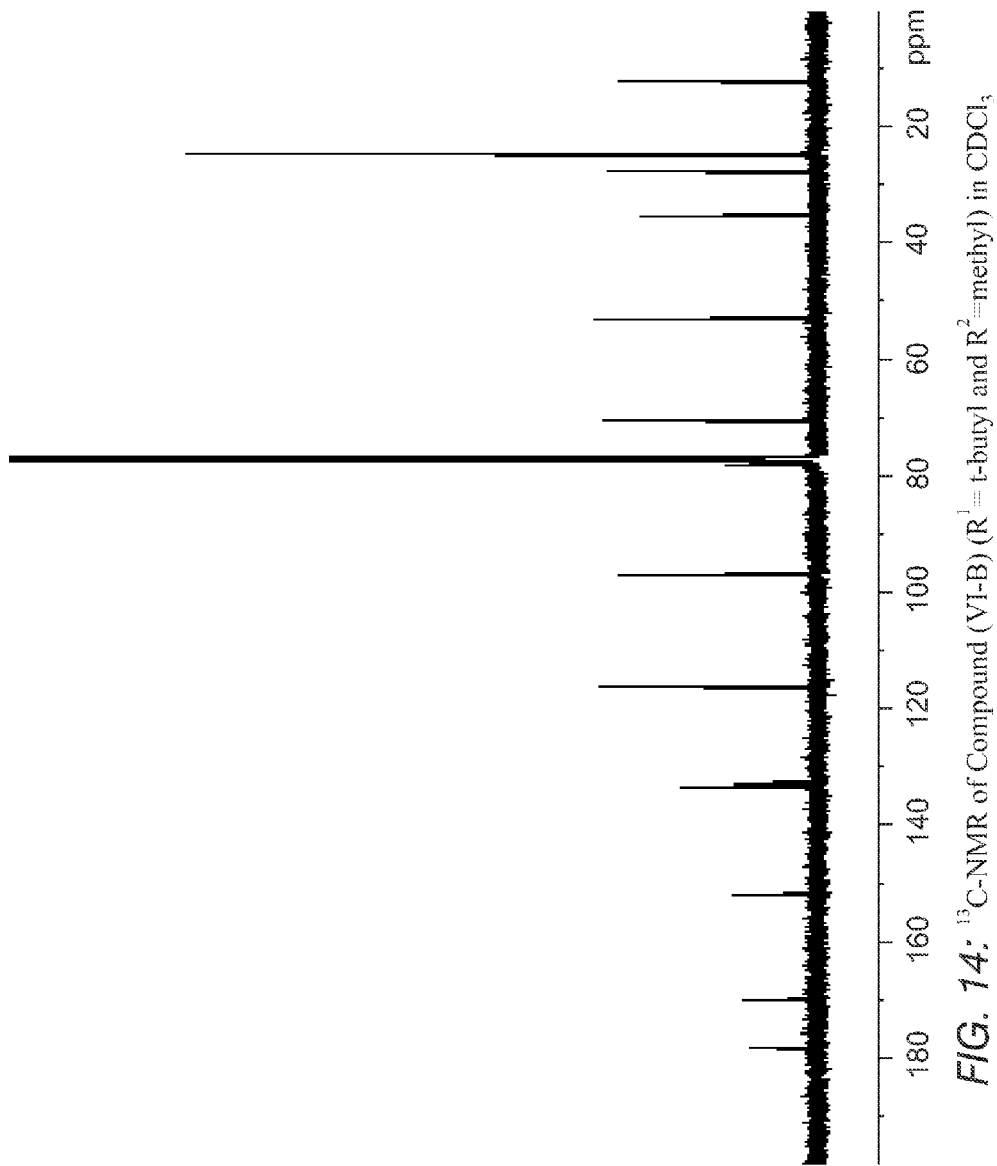

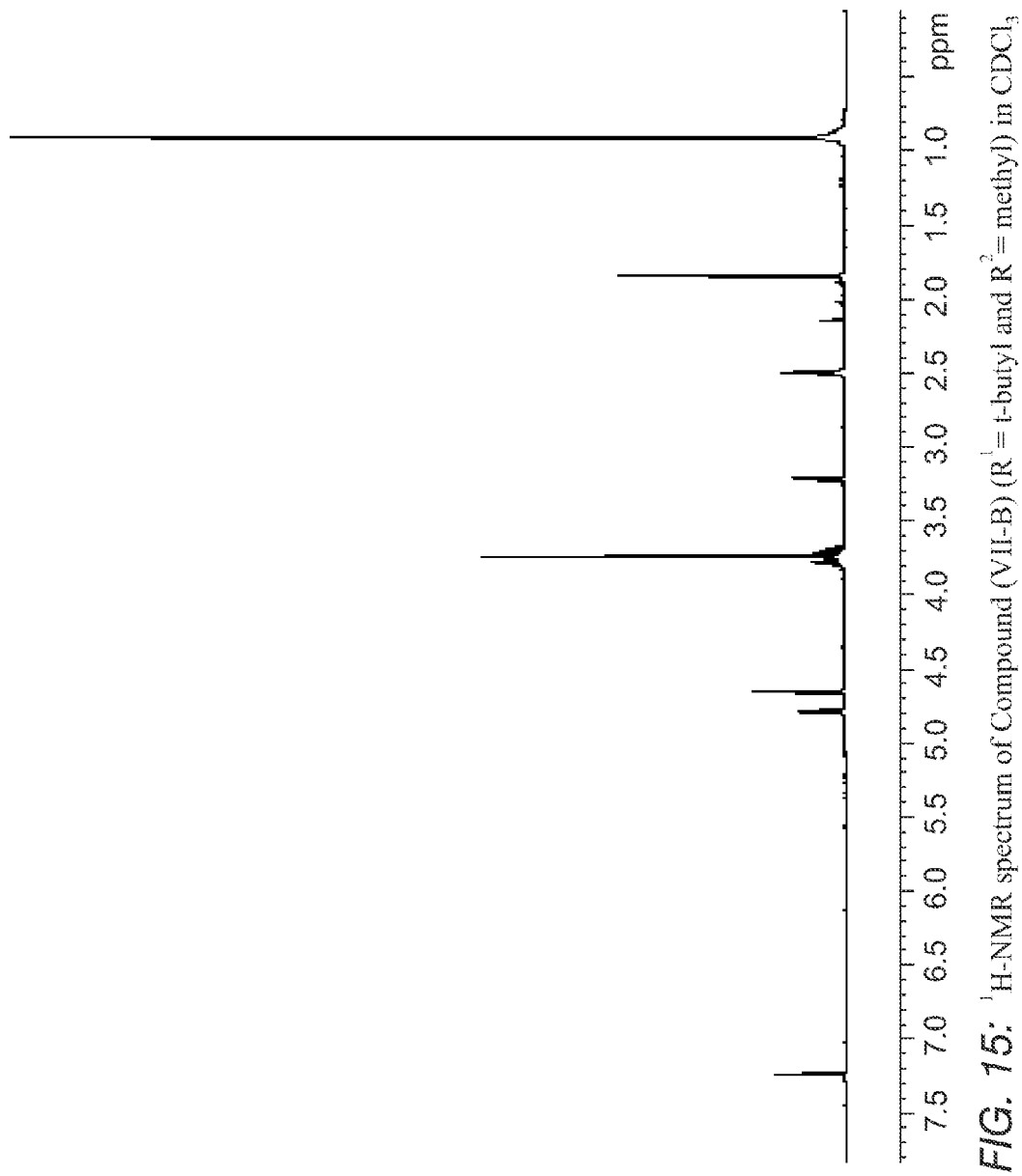
FIG. 15: $^1$H-NMR spectrum of Compound (VII-B) ($R^1$ = t-butyl and $R^2$ = methyl) in CDCl$_3$

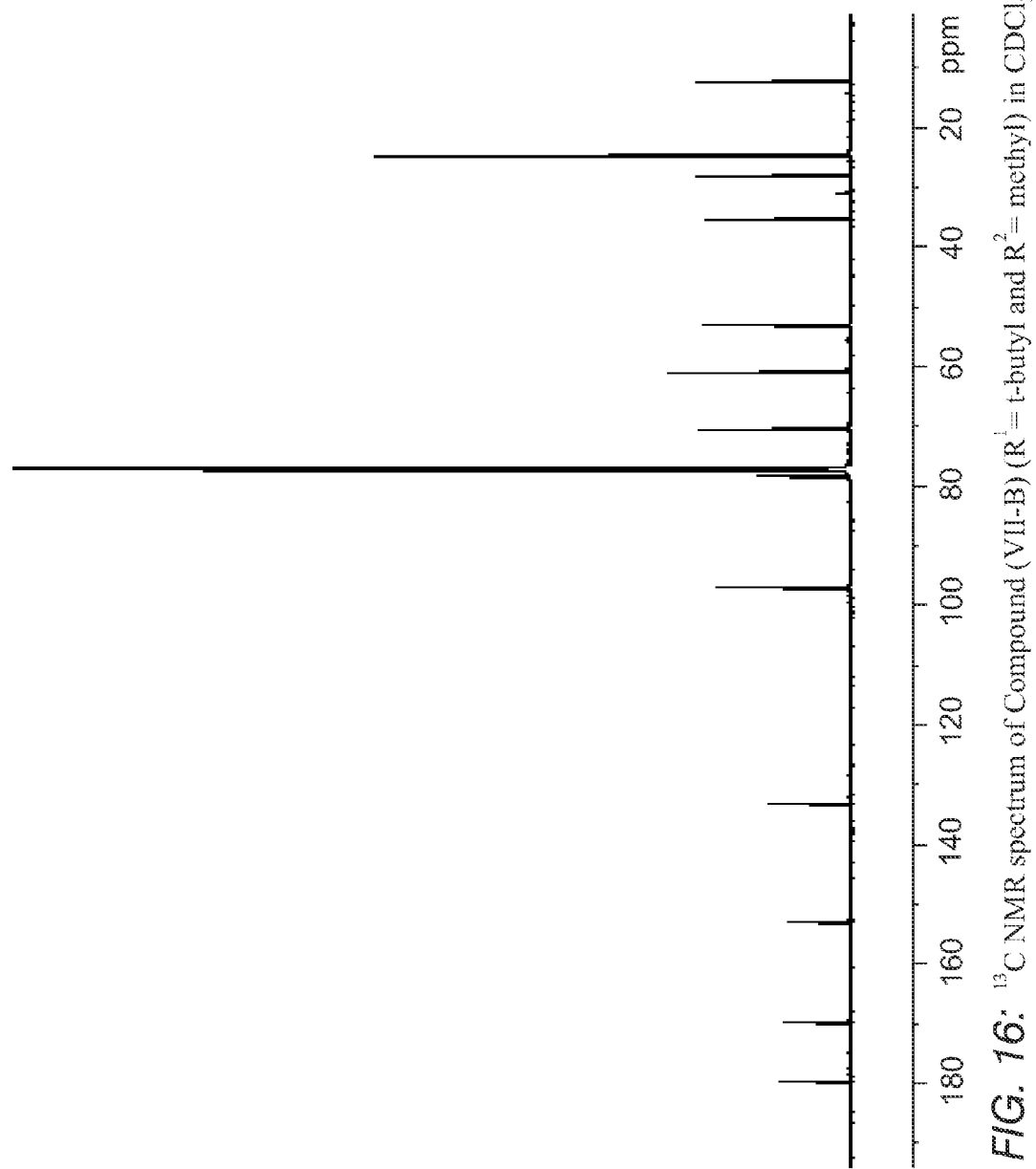
FIG. 16: $^{13}$C NMR spectrum of Compound (VII-B) ($R^1$ = t-butyl and $R^2$ = methyl) in $CDCl_3$

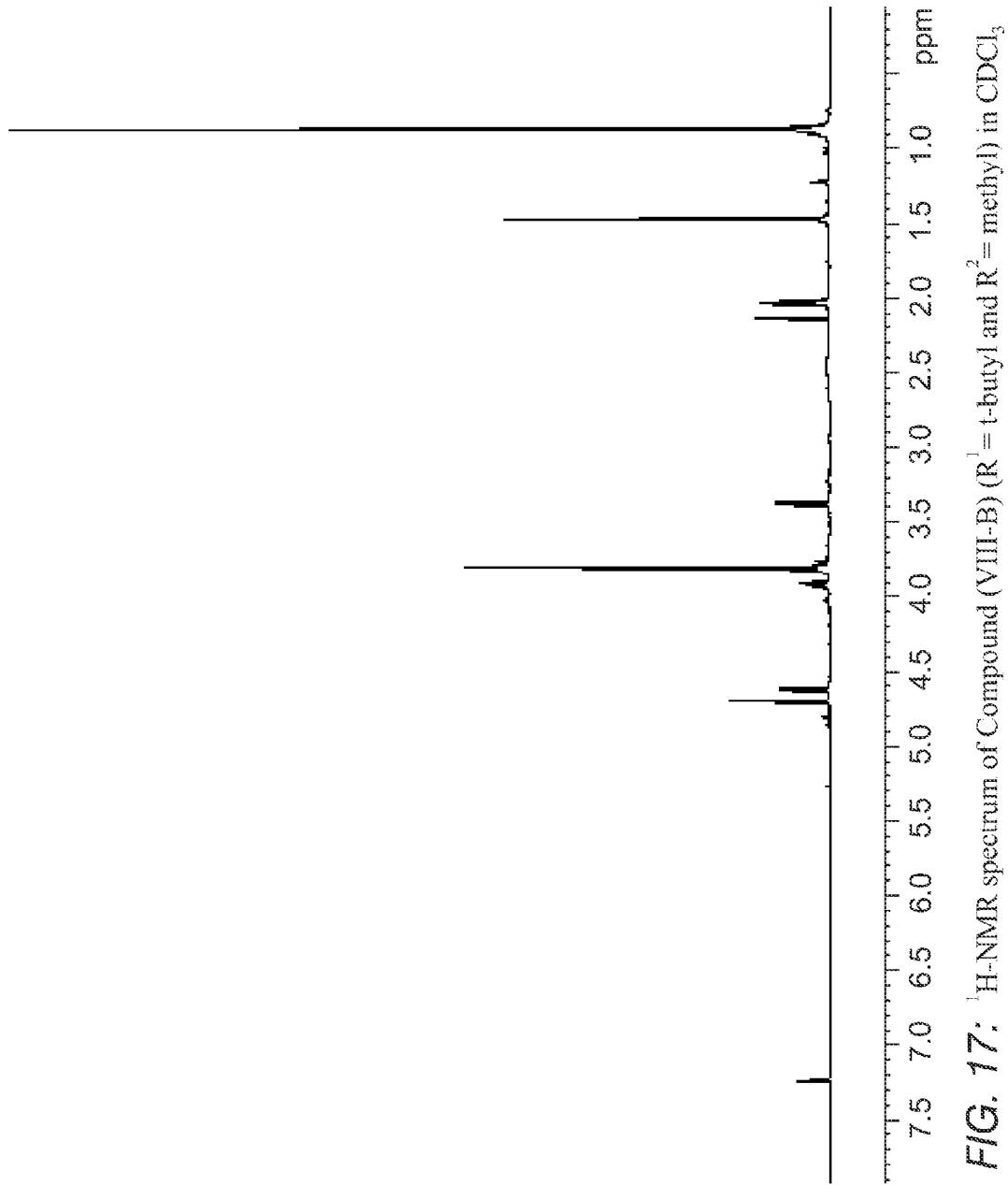
FIG. 17: $^1$H-NMR spectrum of Compound (VIII-B) ($R^1$ = t-butyl and $R^2$ = methyl) in $CDCl_3$

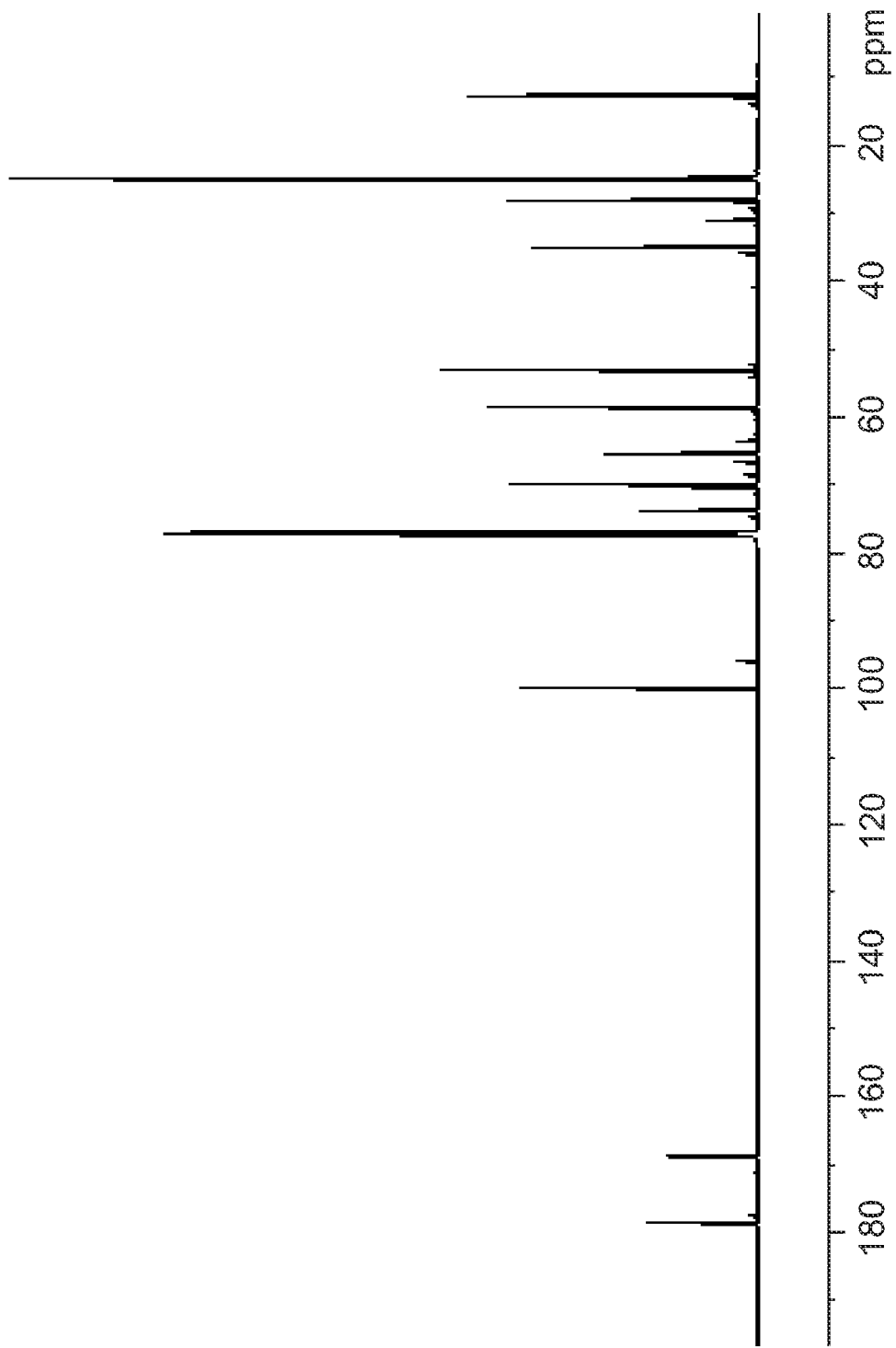
FIG. 18: $^{13}C$ NMR spectrum of Compound (VIII-B) ($R^1$ = t-butyl and $R^2$ = methyl) in $CDCl_3$ NOESY spectrum of Compound (VIII-B) ($R^1$ = t-butyl and $R^2$ = methyl) in $CDCl_3$ FIG. 20. $^1$H-NMR spectrum of Compound (X-1B) (PG$^1$ = Bz, R$^1$ = t-butyl and R$^2$ = methyl) in CDCl$_3$ FIG. 21: ¹³C NMR spectrum of Compound (X-1B) (PG¹ = Bz, R¹ = t-butyl and R² = methyl) in CDCl₃

NOESY spectrum of Compound (X-1B) (PG$^1$ = Bz, R$^1$ = t-butyl and R$^2$ = methyl) in CDCl$_3$ FIG. 23: $^1$H-NMR spectrum of Compound (XI-1B) (PG$^1$ = Bz, R$^2$ = methyl) in CDCl$_3$ FIG. 24: $^{13}$C NMR spectrum of Compound (XI-1B) (PG$^1$ = Bz, and R$^2$ = methyl) in CDCl$_3$ FIG. 26: $^{13}$C NMR spectrum of Compound (X-2B) ($R^2$ = methyl) in CDCl$_3$ X-ray crystal structure of Compound (X-2B) ( $R^2$ = methyl)

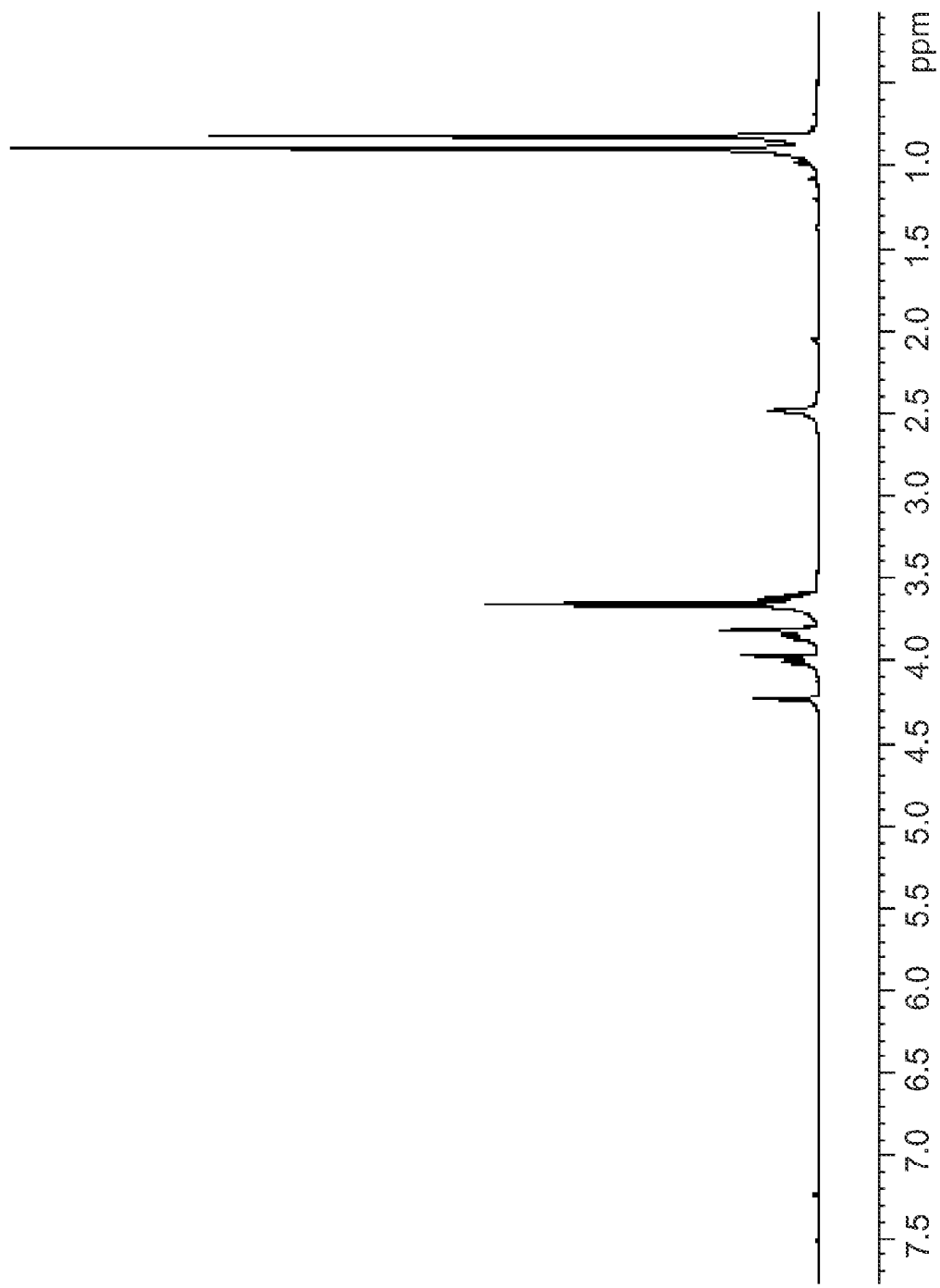
FIG. 28: ¹H-NMR spectrum of Compound (I-A) ($R^1$ = t-butyl and $R^2$ = methyl) in $CDCl_3$

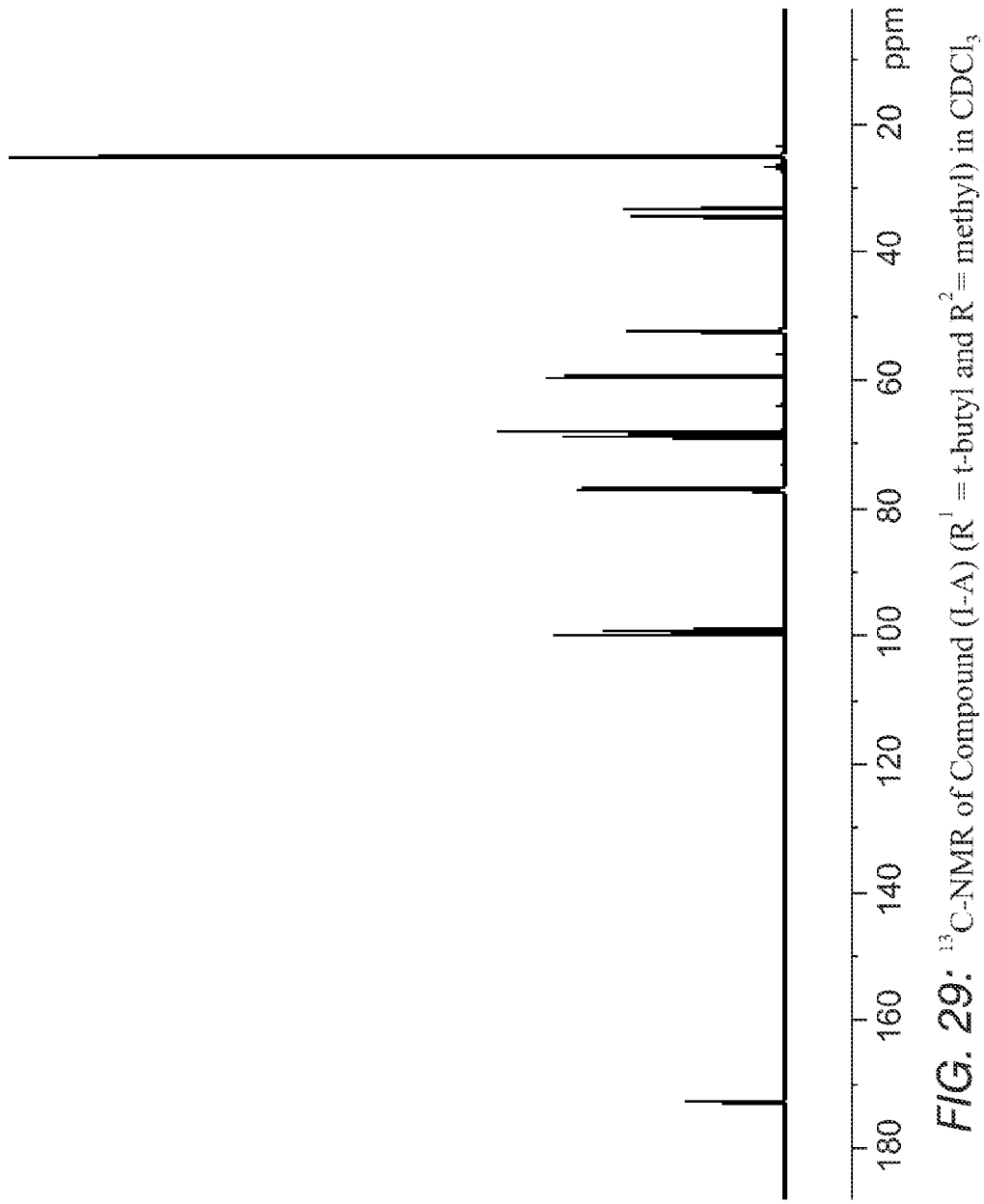

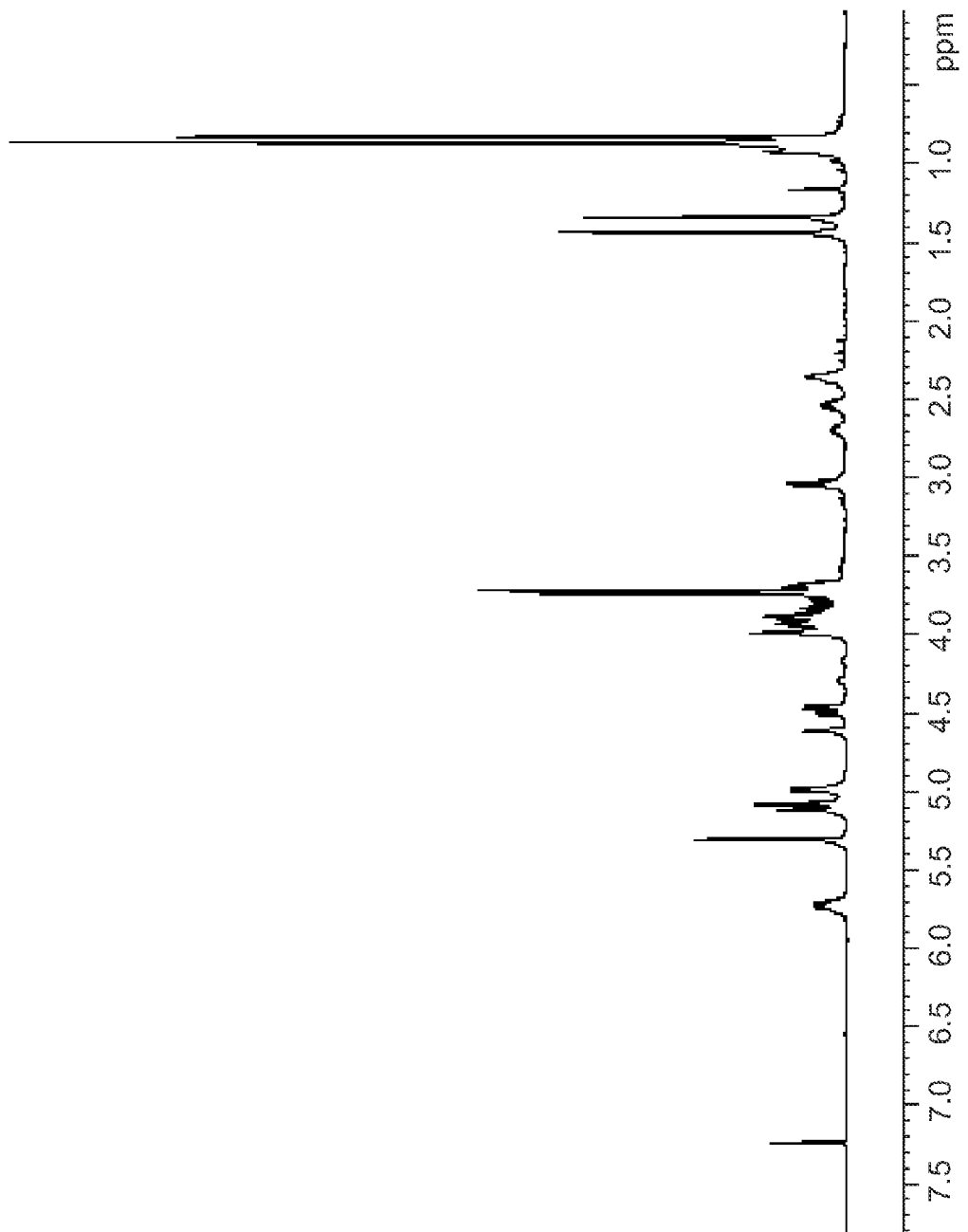
FIG. 30. $^1$H NMR spectrum of Compound (III-A) ($R^1$ = t-butyl and $R^2$ = methyl) in $CDCl_3$

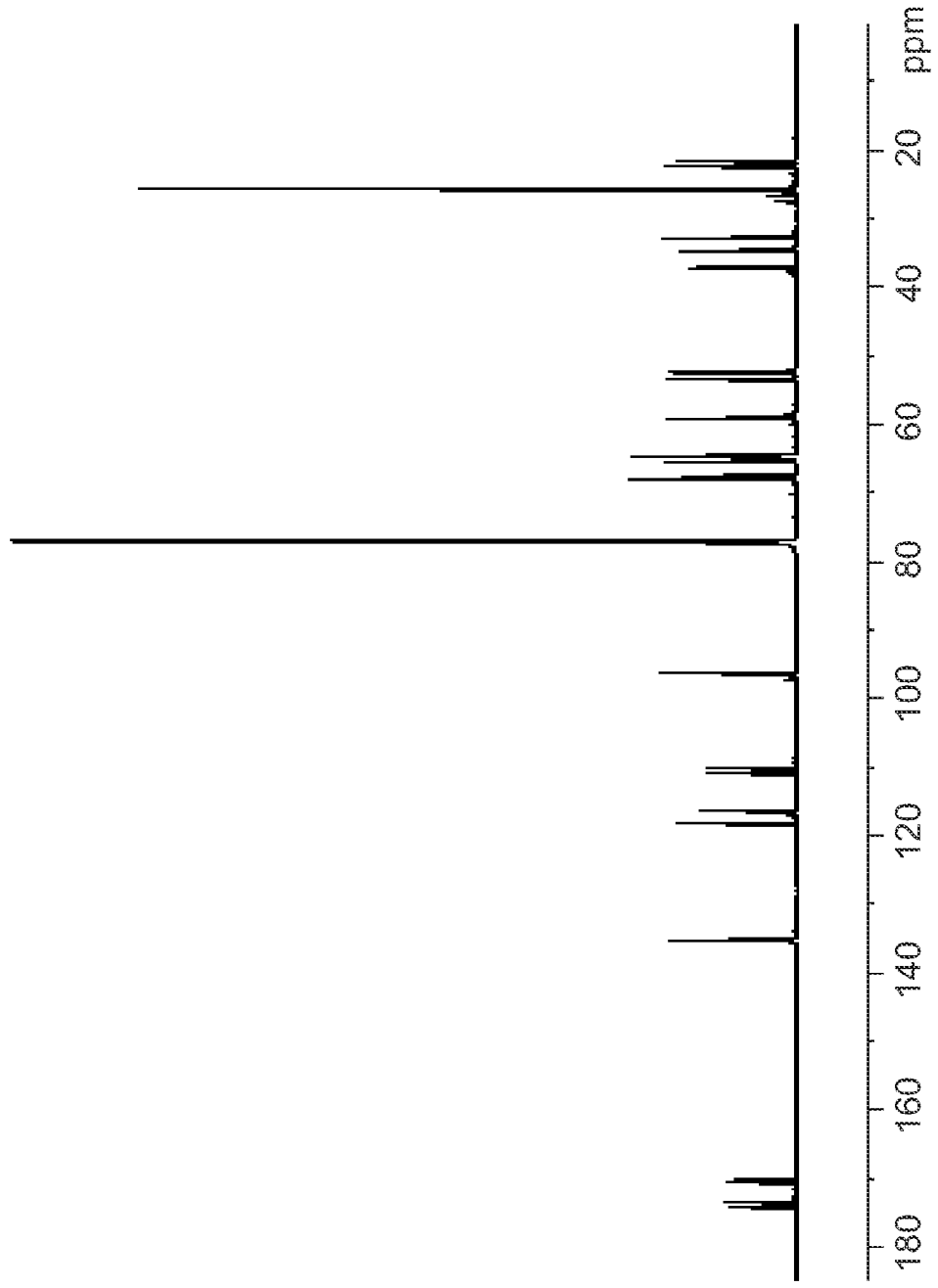
FIG. 31: $^{13}$C NMR spectrum of Compound (III-A) ($R^1$ = t-butyl and $R^2$ = methyl) in CDCl$_3$

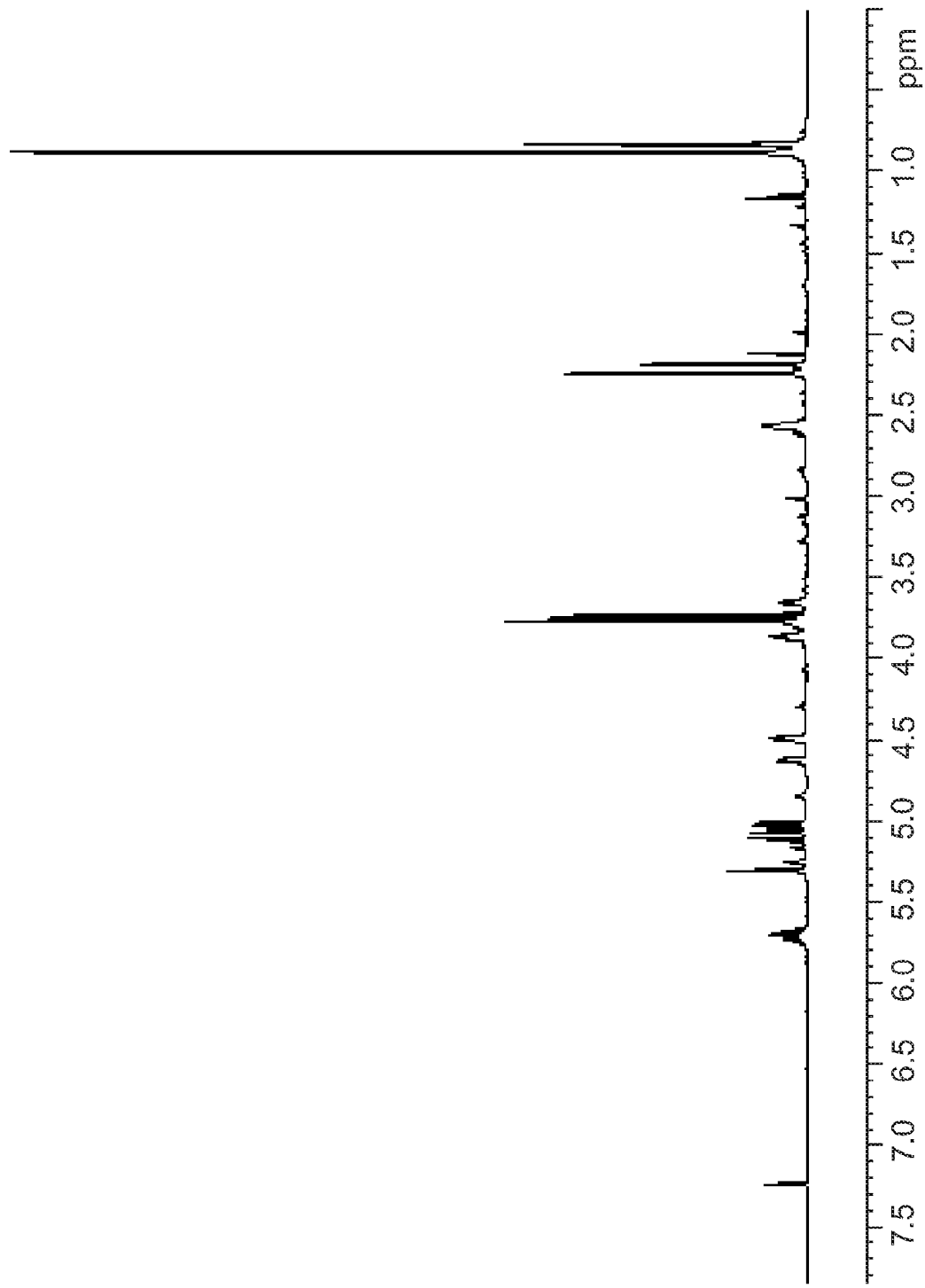
FIG. 32: $^1$H NMR spectrum of Compound (IV-A) ($R^1$ = t-butyl and $R^2$ = methyl) in $CDCl_3$

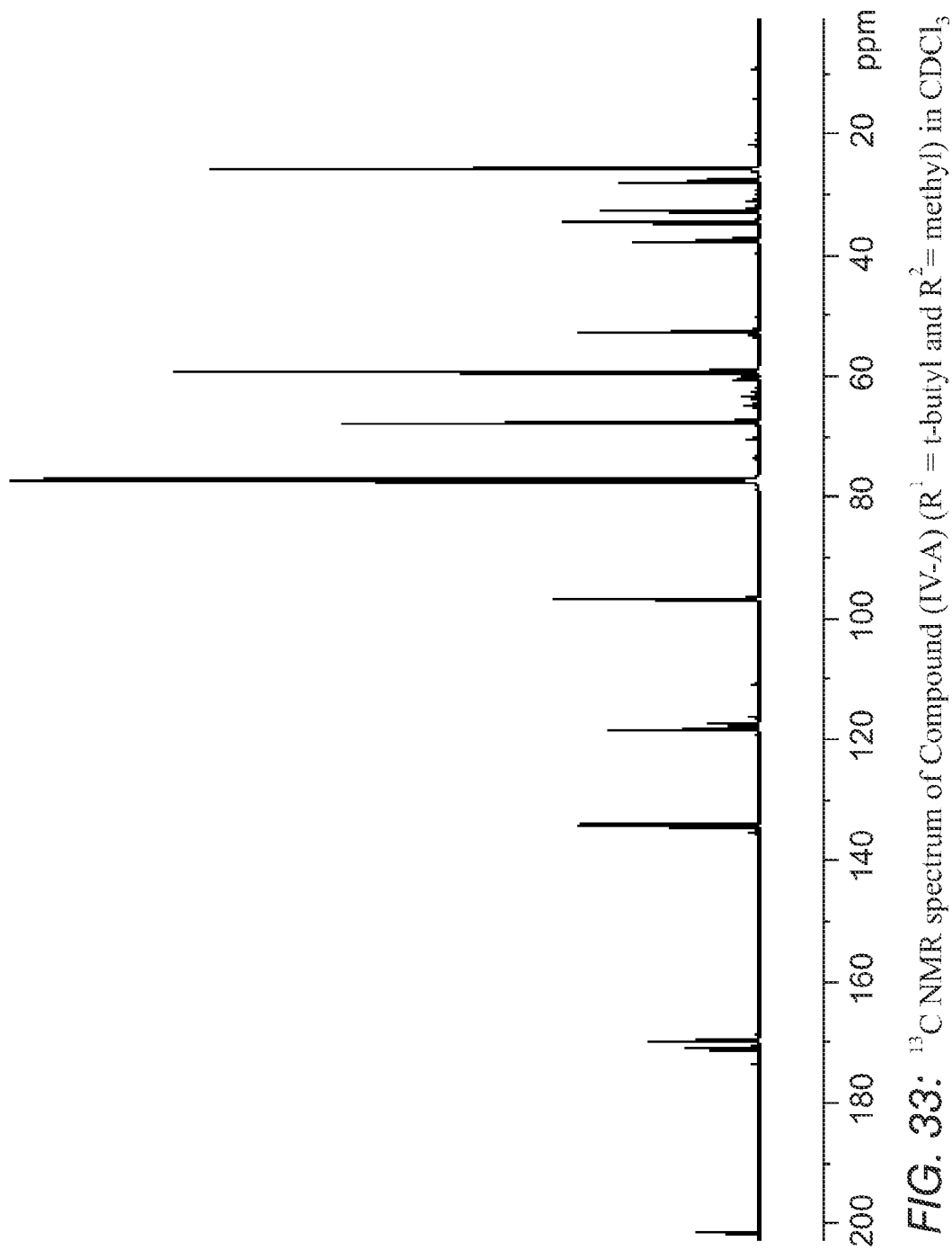
FIG. 33: $^{13}$C NMR spectrum of Compound (IV-A) ($R^1$ = t-butyl and $R^2$ = methyl) in CDCl$_3$

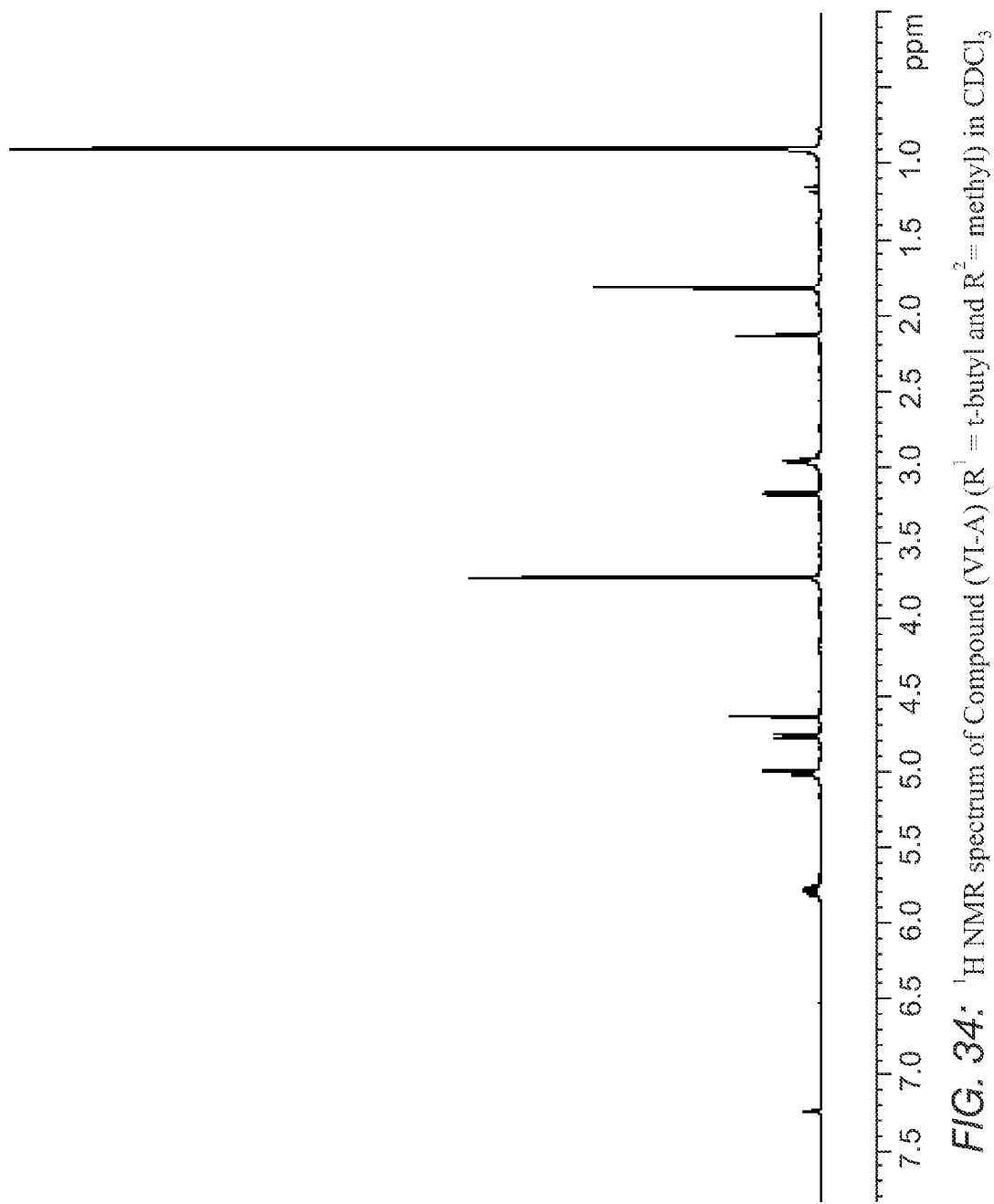
FIG. 34: ¹H NMR spectrum of Compound (VI-A) (R¹ = t-butyl and R² = methyl) in CDCl₃

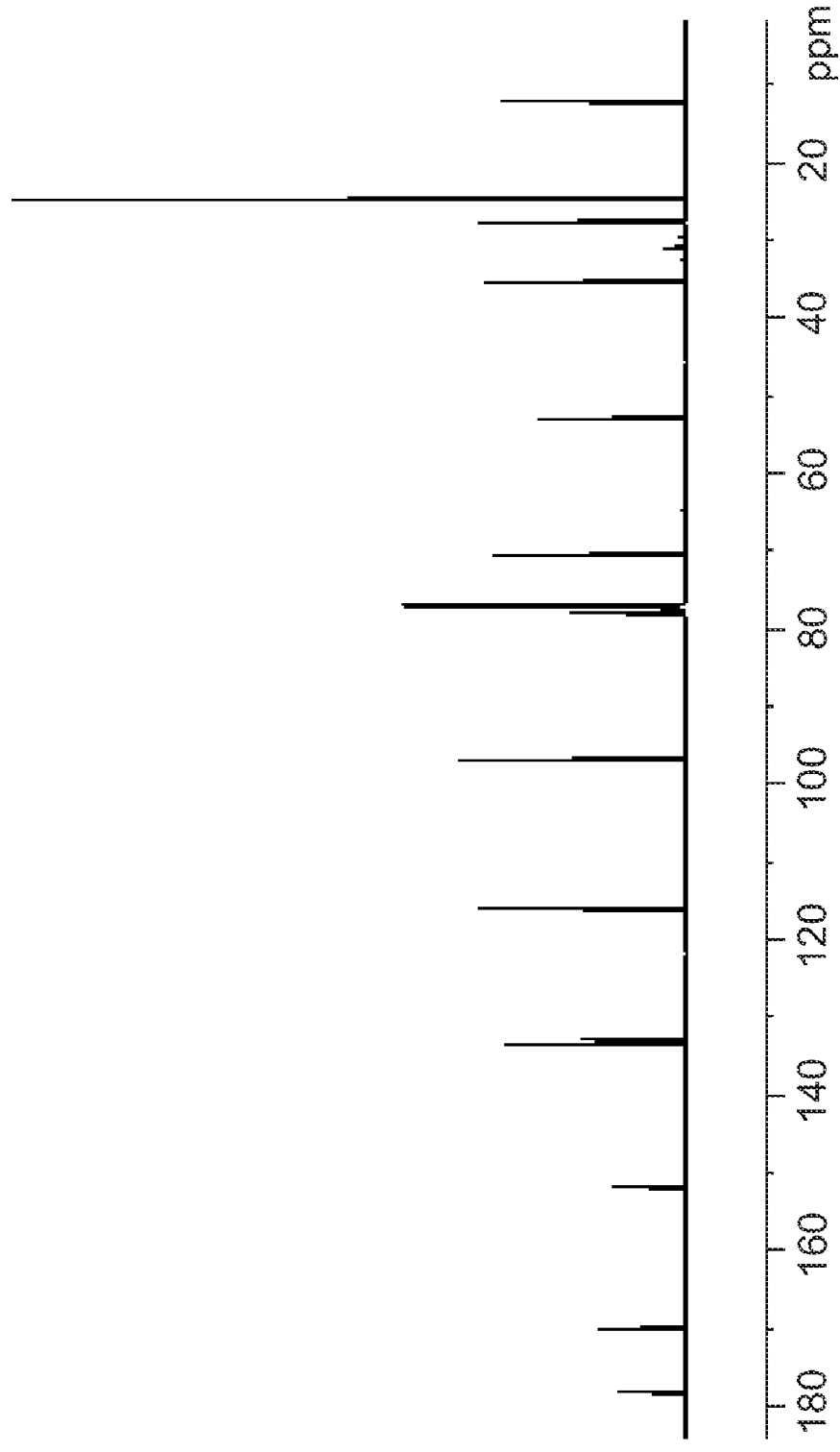
FIG. 35: $^{13}$C NMR spectrum of Compound (VI-A) ($R^1$ = t-butyl and $R^2$ = methyl) in $CDCl_3$

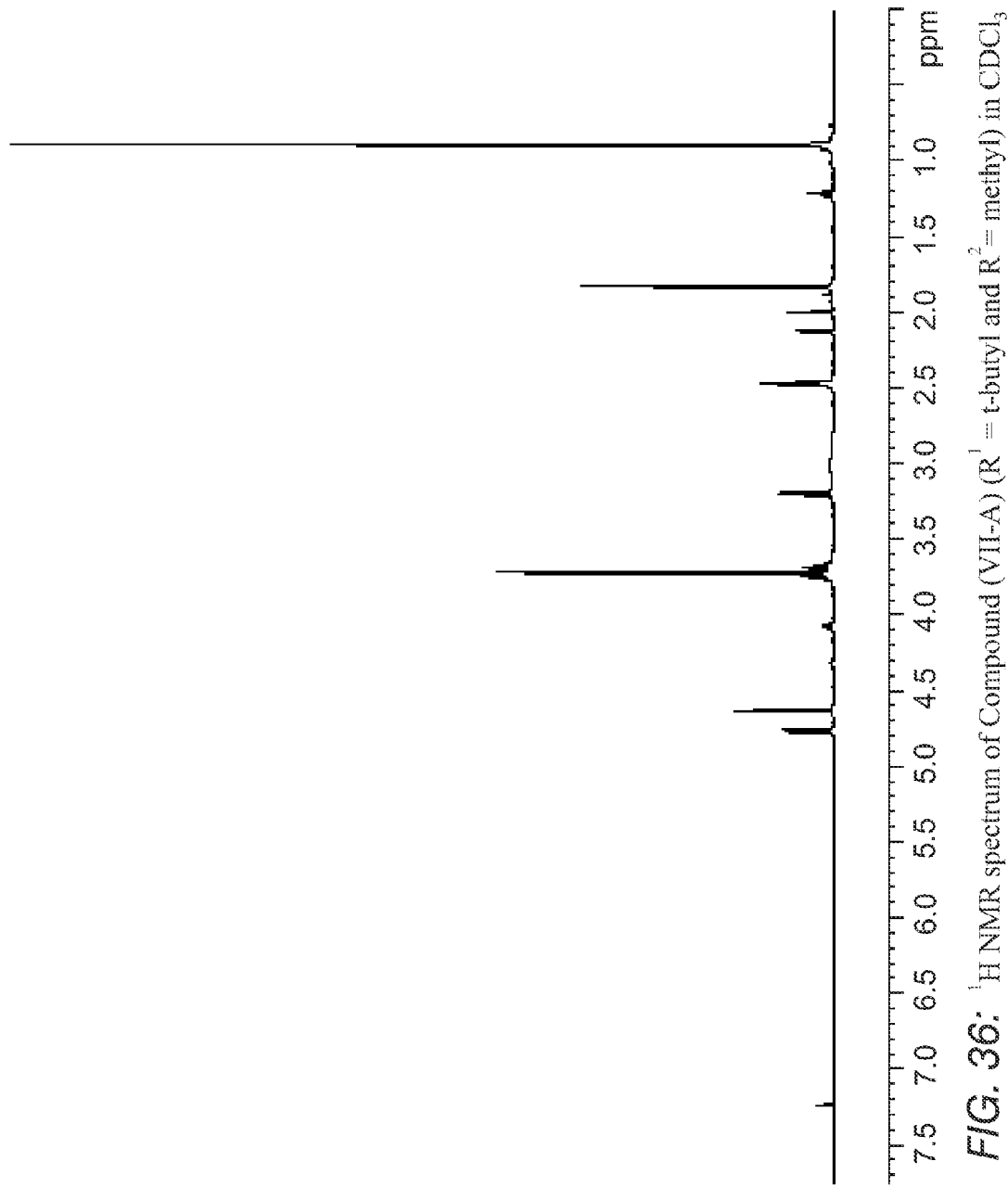
FIG. 36: $^1$H NMR spectrum of Compound (VII-A) ($R^1$ = t-butyl and $R^2$ = methyl) in $CDCl_3$

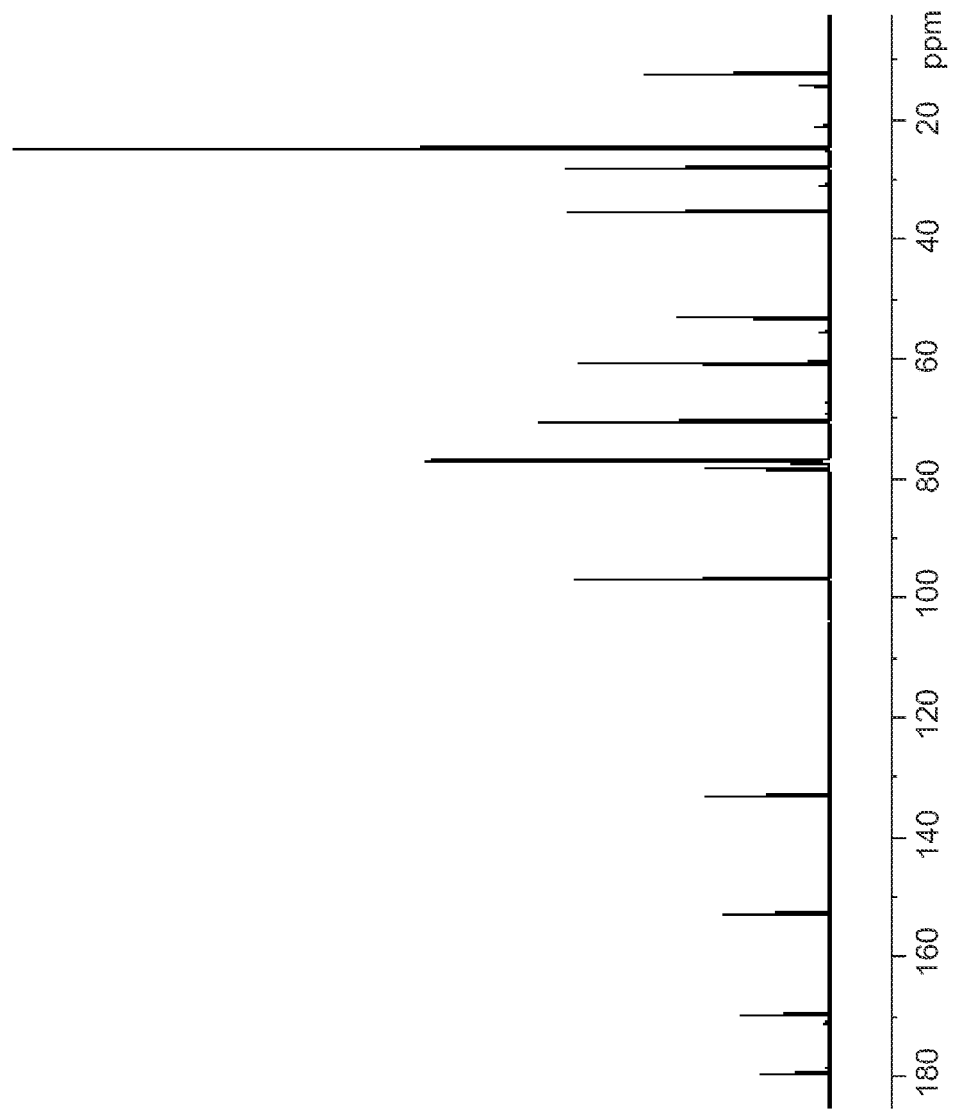
FIG. 37: $^{13}$C NMR spectrum of Compound (VII-A) ($R^1$ = t-butyl and $R^2$ = methyl) in $CDCl_3$

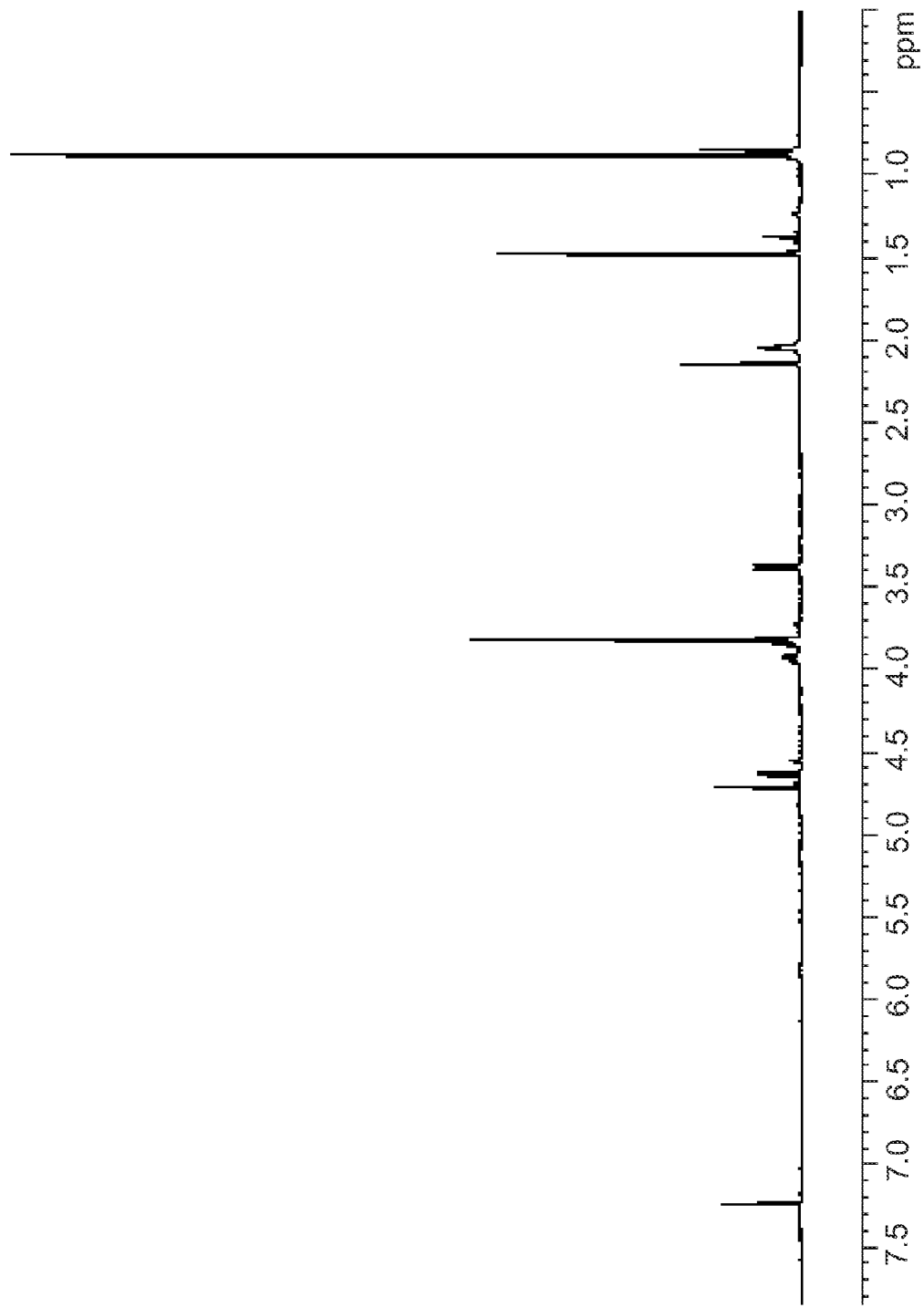
FIG. 38: $^1$H NMR spectrum of Compound (VIII-A) ($R^1$ = t-butyl and $R^2$ = methyl) in CDCl$_3$

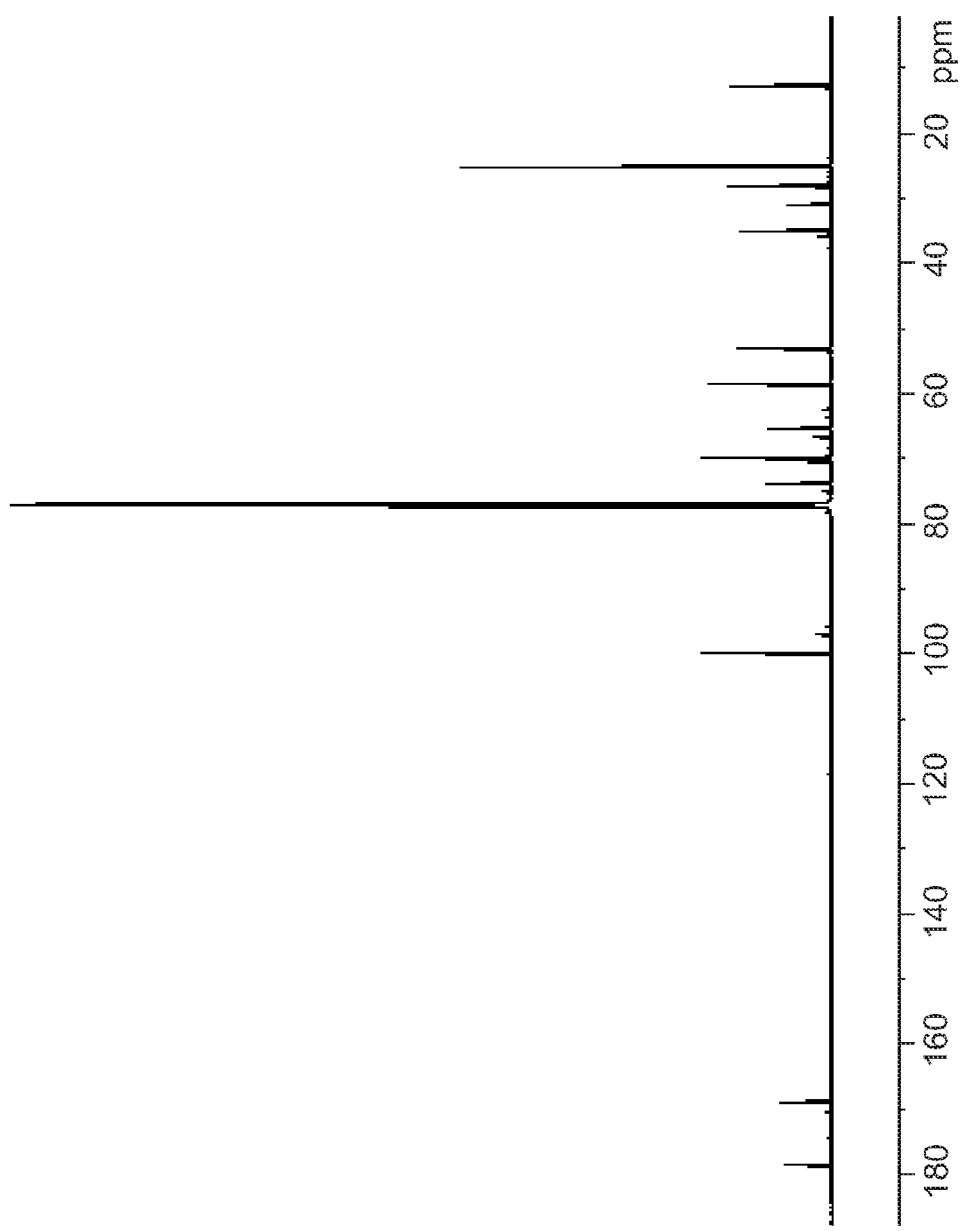
FIG. 39: ¹³C NMR spectrum of Compound (VIII-A) ($R^1$ = t-butyl and $R^2$ = methyl) in $CDCl_3$

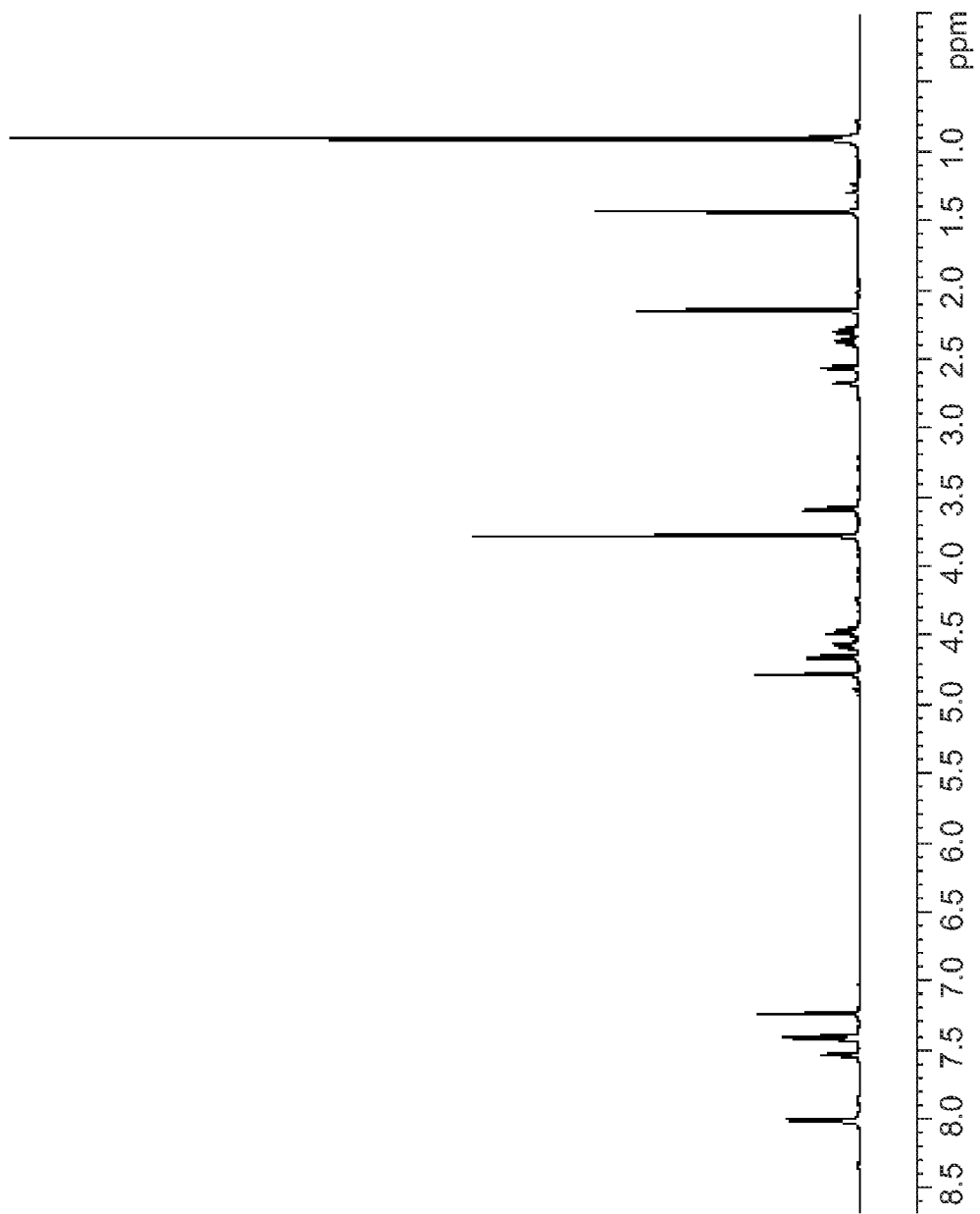
FIG. 40: $^1$H NMR spectrum of Compound (X-1A) (PG$^1$ = Bz, R$^1$ = t-butyl and R$^2$ = methyl) in CDCl$_3$

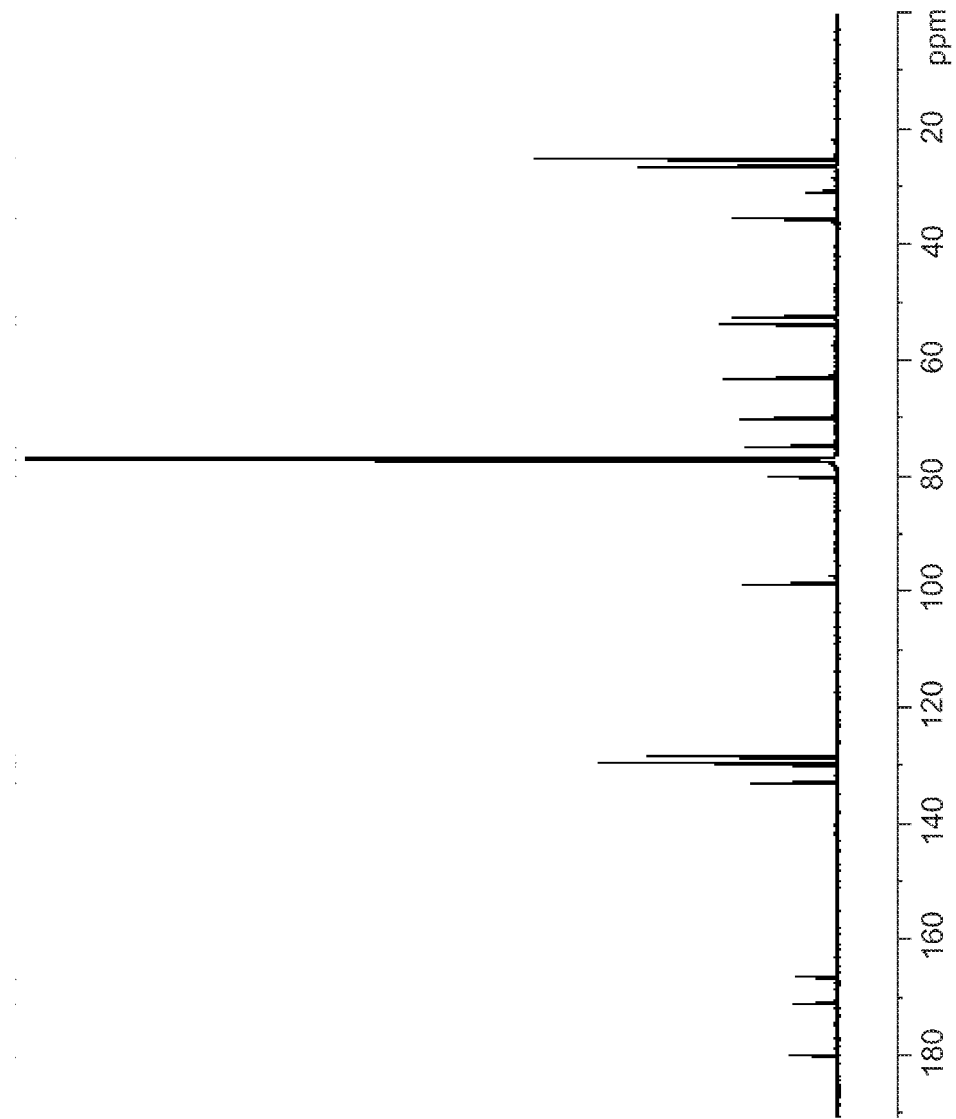
FIG. 41: $^{13}C$ NMR spectrum of Compound (X-1A) (PG$^1$ = Bz, R$^1$ = t-butyl and R$^2$ = methyl) in CDCl$_3$

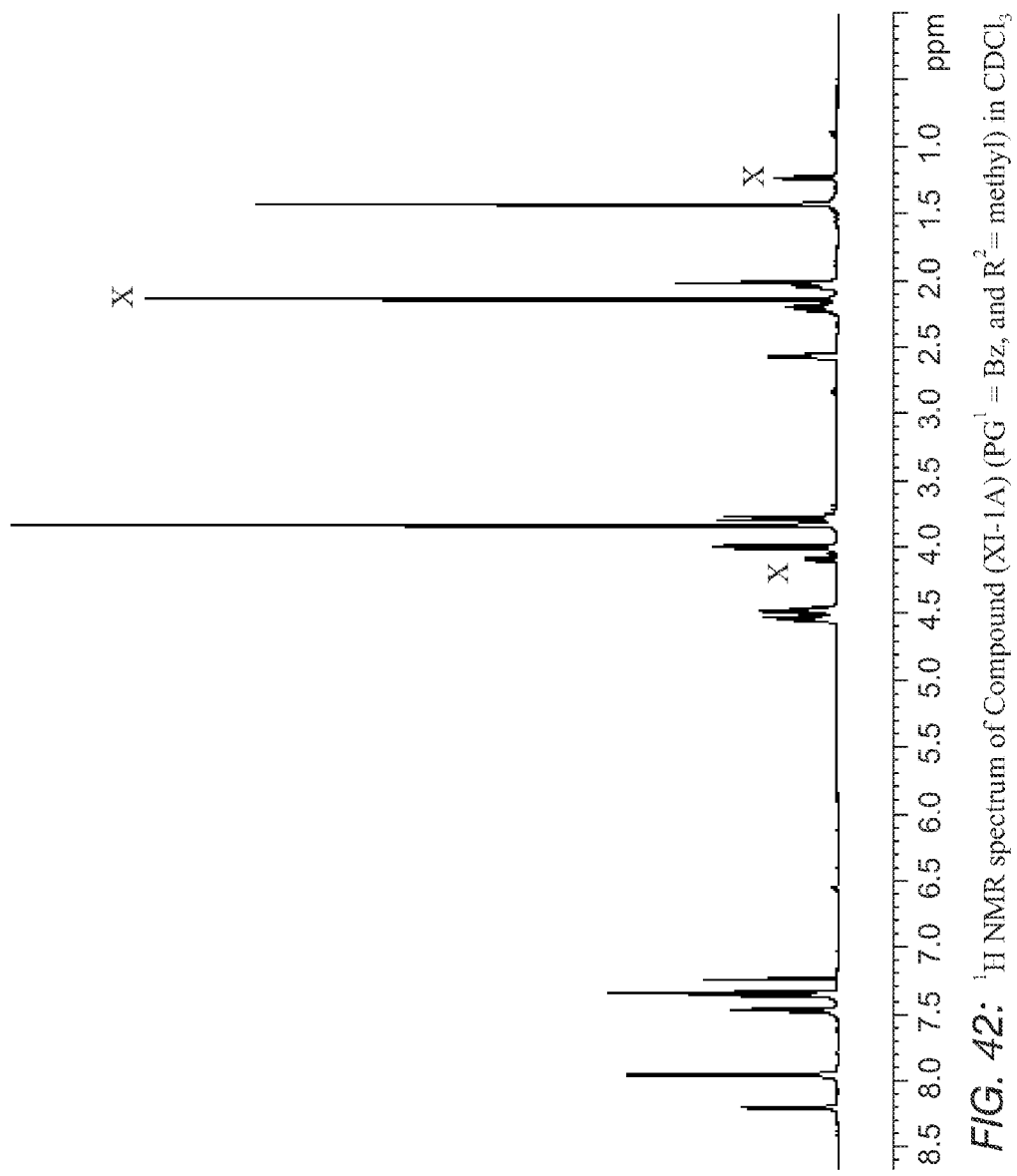

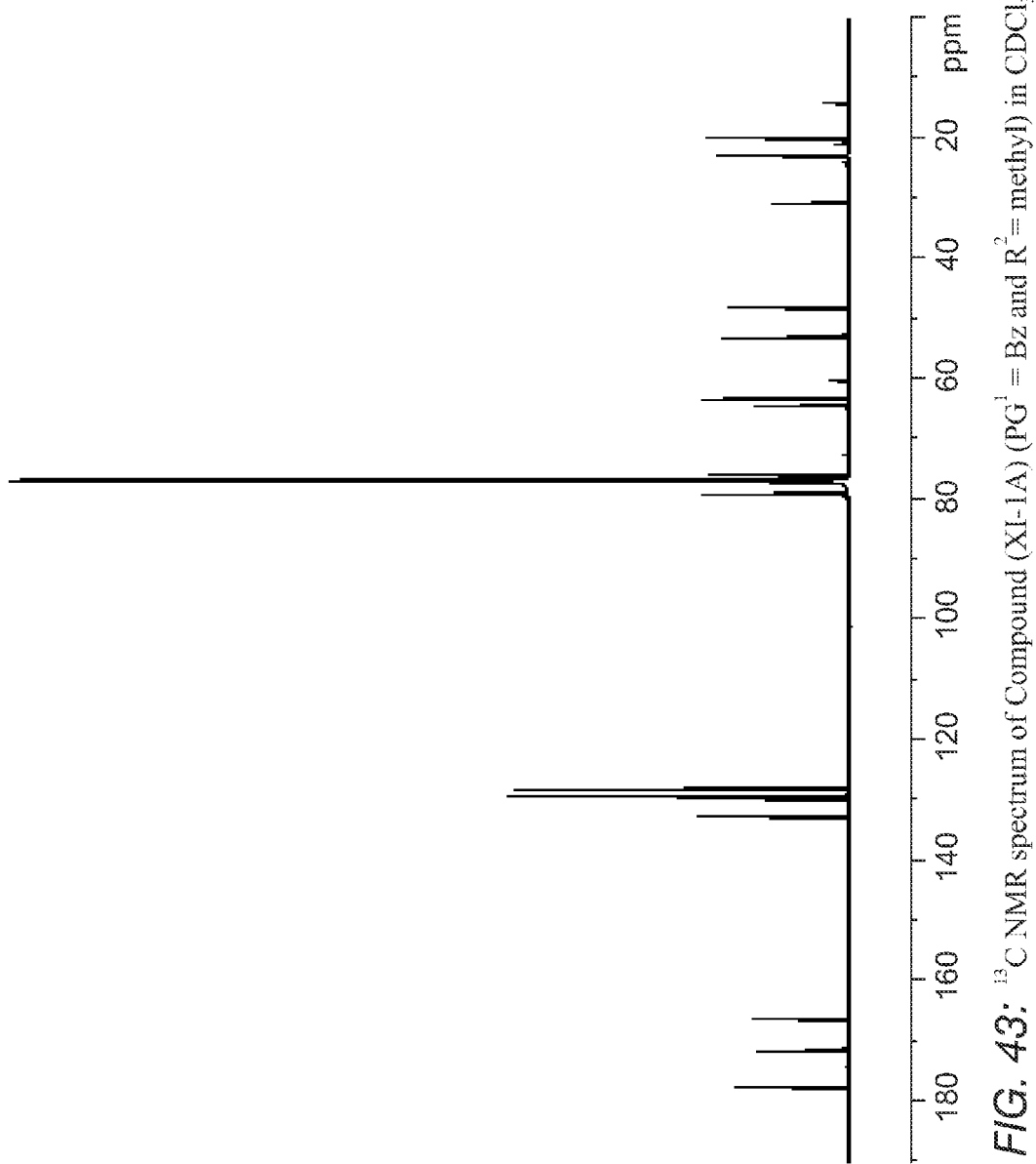
FIG. 43: $^{13}$C NMR spectrum of Compound (XI-1A) (PG$^1$ = Bz and R$^2$ = methyl) in CDCl$_3$

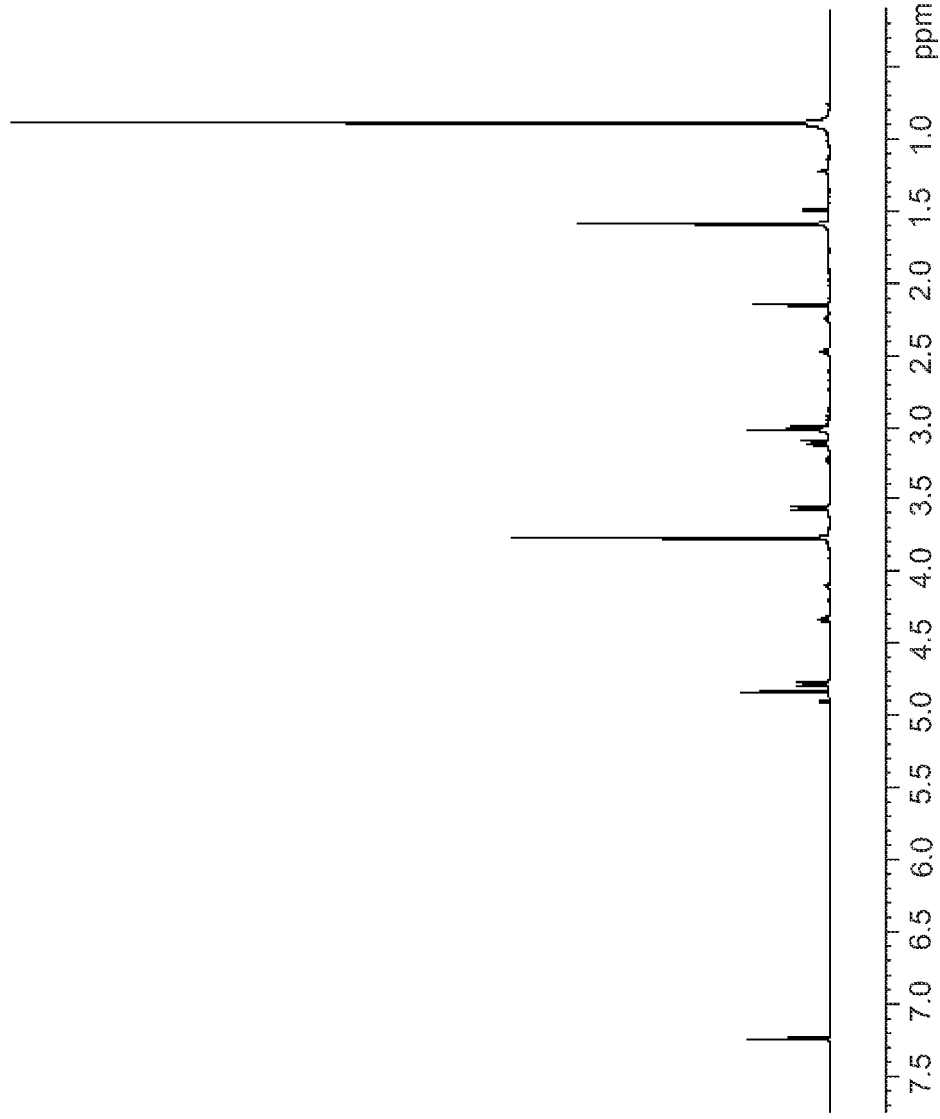
FIG. 44: $^1$H NMR spectrum of Compound (X-2A) ($R^1$ = t-butyl and $R^2$ = methyl) in CDCl$_3$

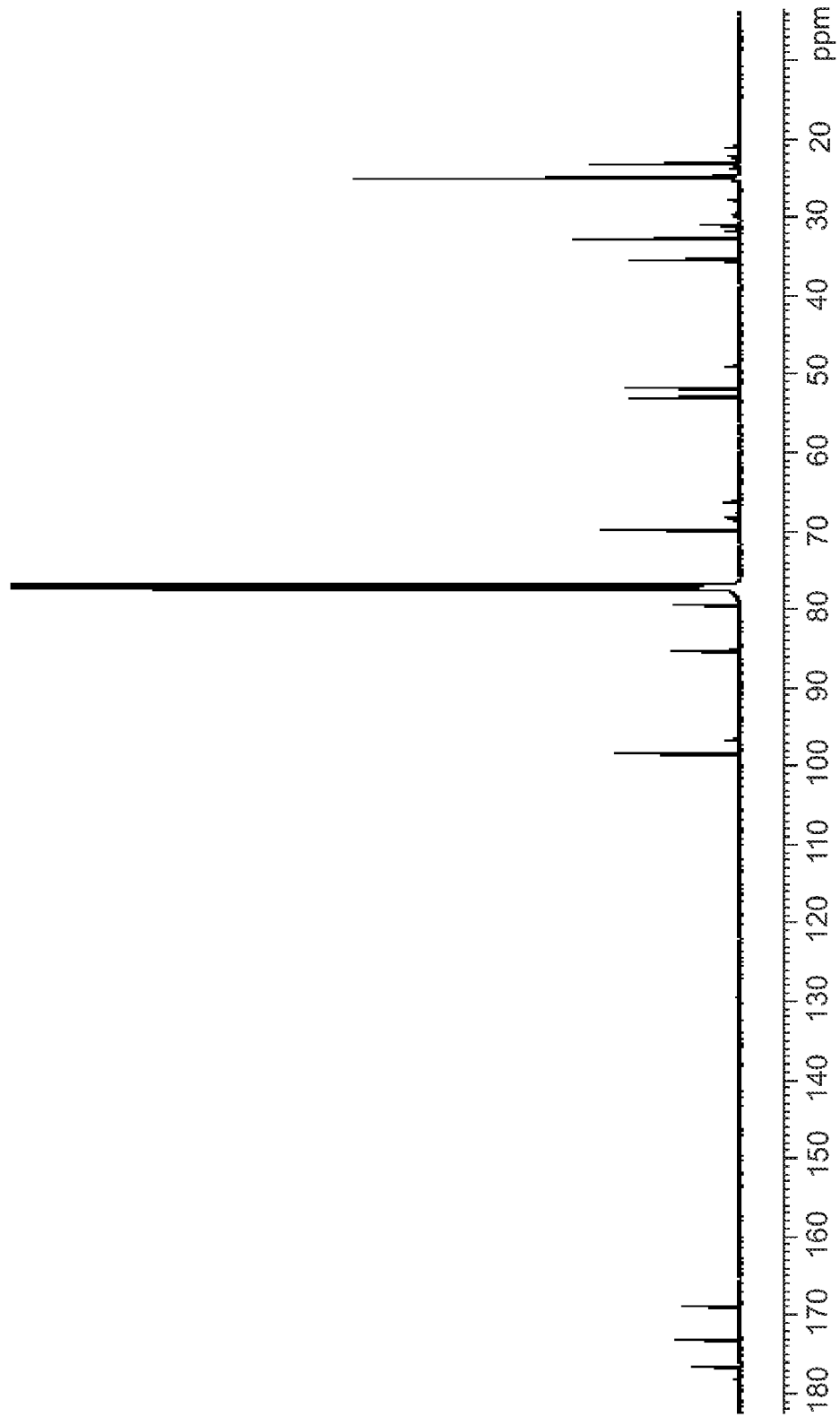
FIG. 45: $^{13}C$ NMR spectrum of Compound (X-2A) ($R^1$ = t-butyl and $R^2$ = methyl) in $CDCl_3$

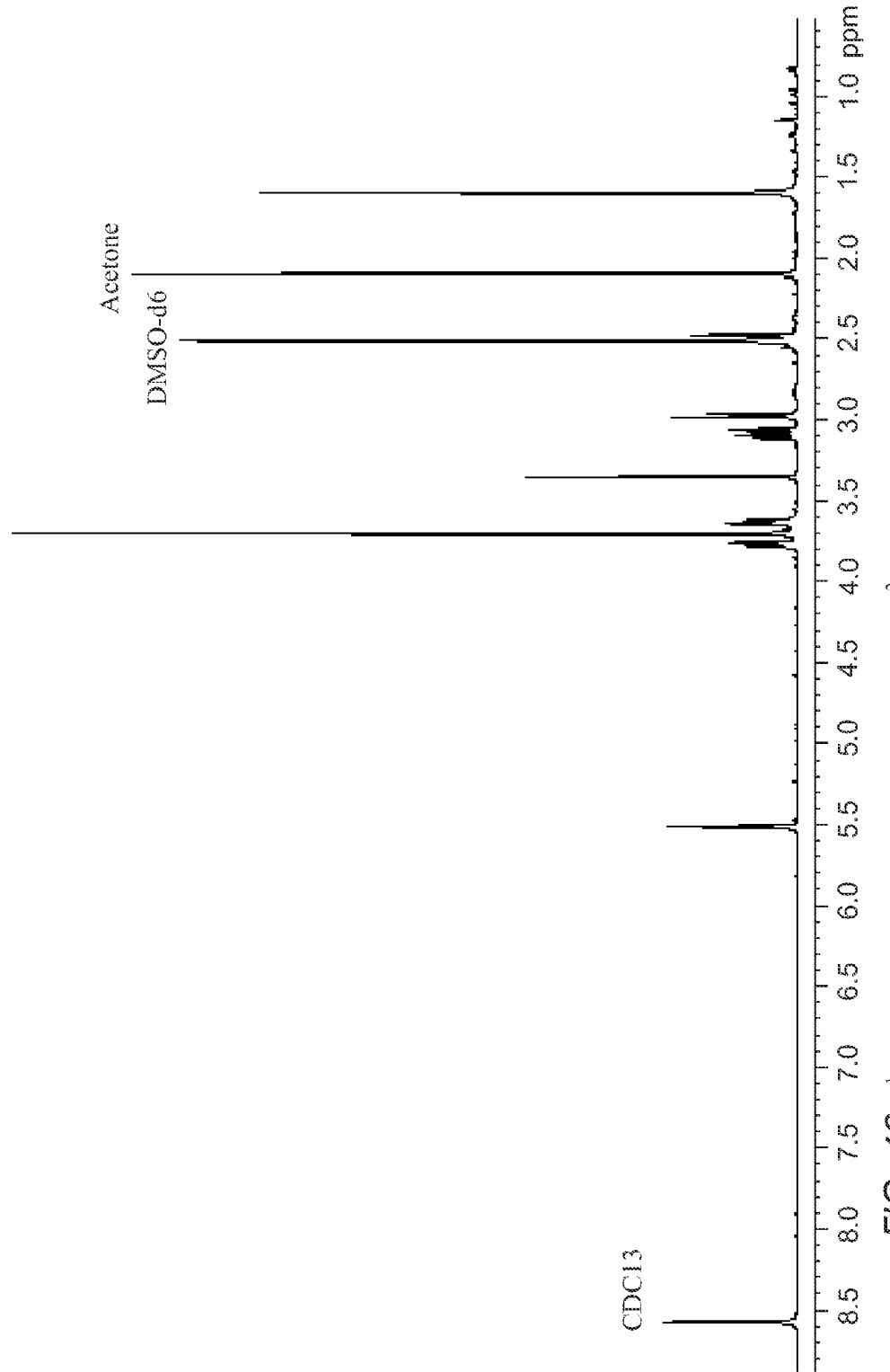
FIG. 46: $^1$H NMR spectrum of Compound (XI-2A) ($R^2$ = methyl) in DMSO-$d_6$ and CDCl$_3$ mixture

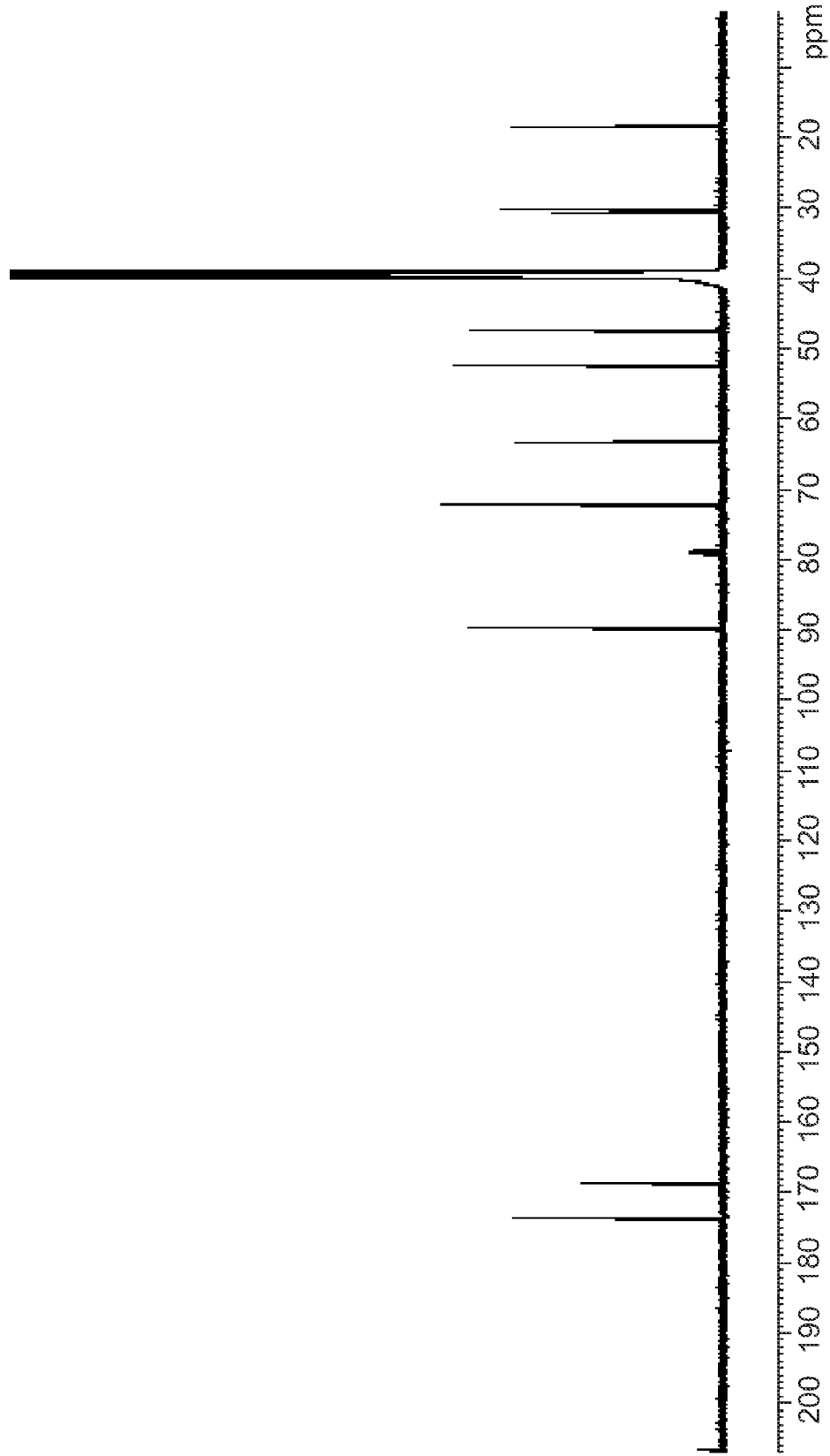
FIG. 47: $^{13}C$ NMR spectrum of Compound (XI-2A) ($R^2$ = methyl) in DMSO-$d_6$ and CDCl$_3$ mixture

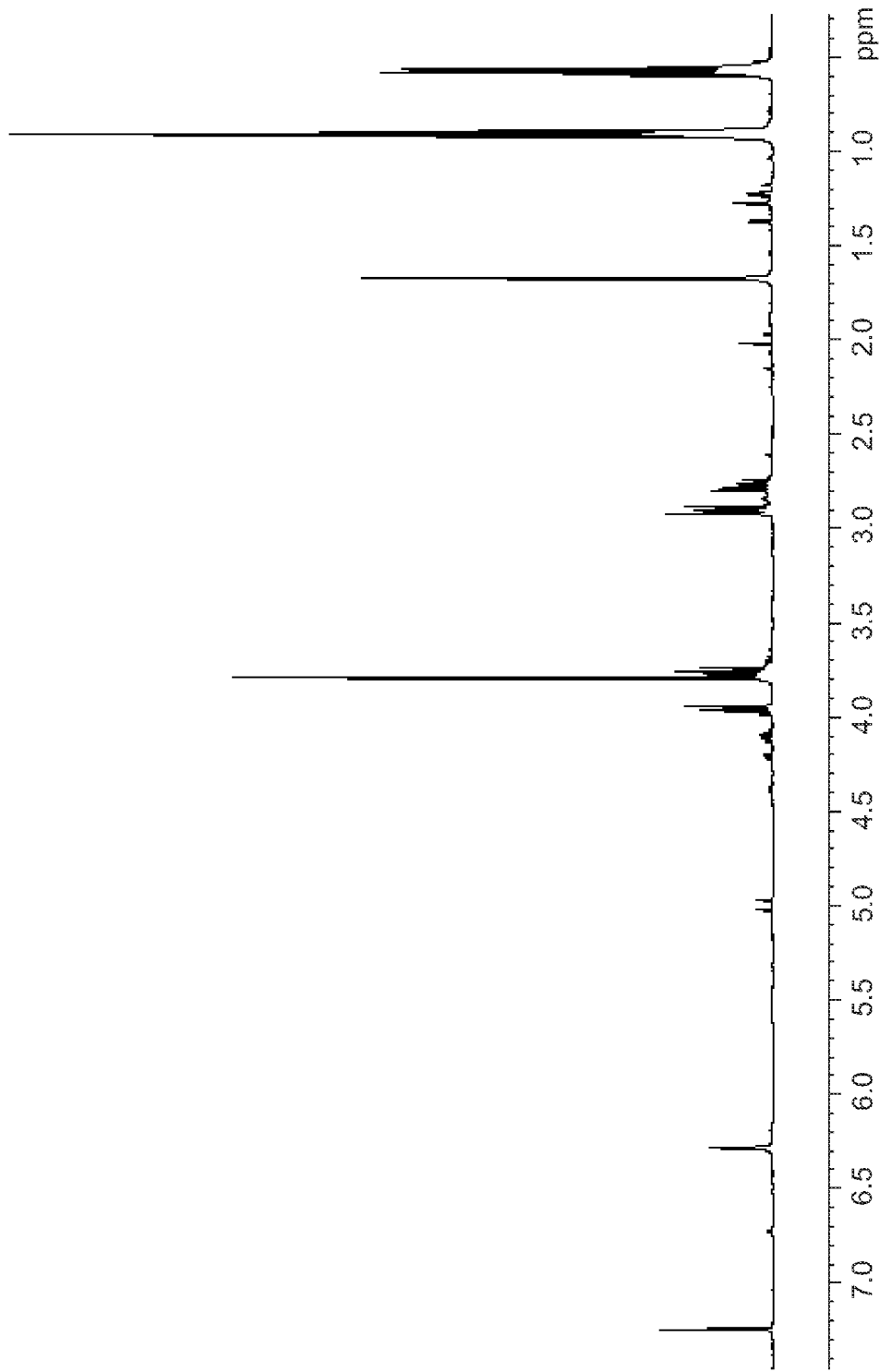
FIG. 48: $^1$H NMR spectrum of Compound (XI-2A) ($R^2$ = methyl and C-5-O-TES) in $CDCl_3$

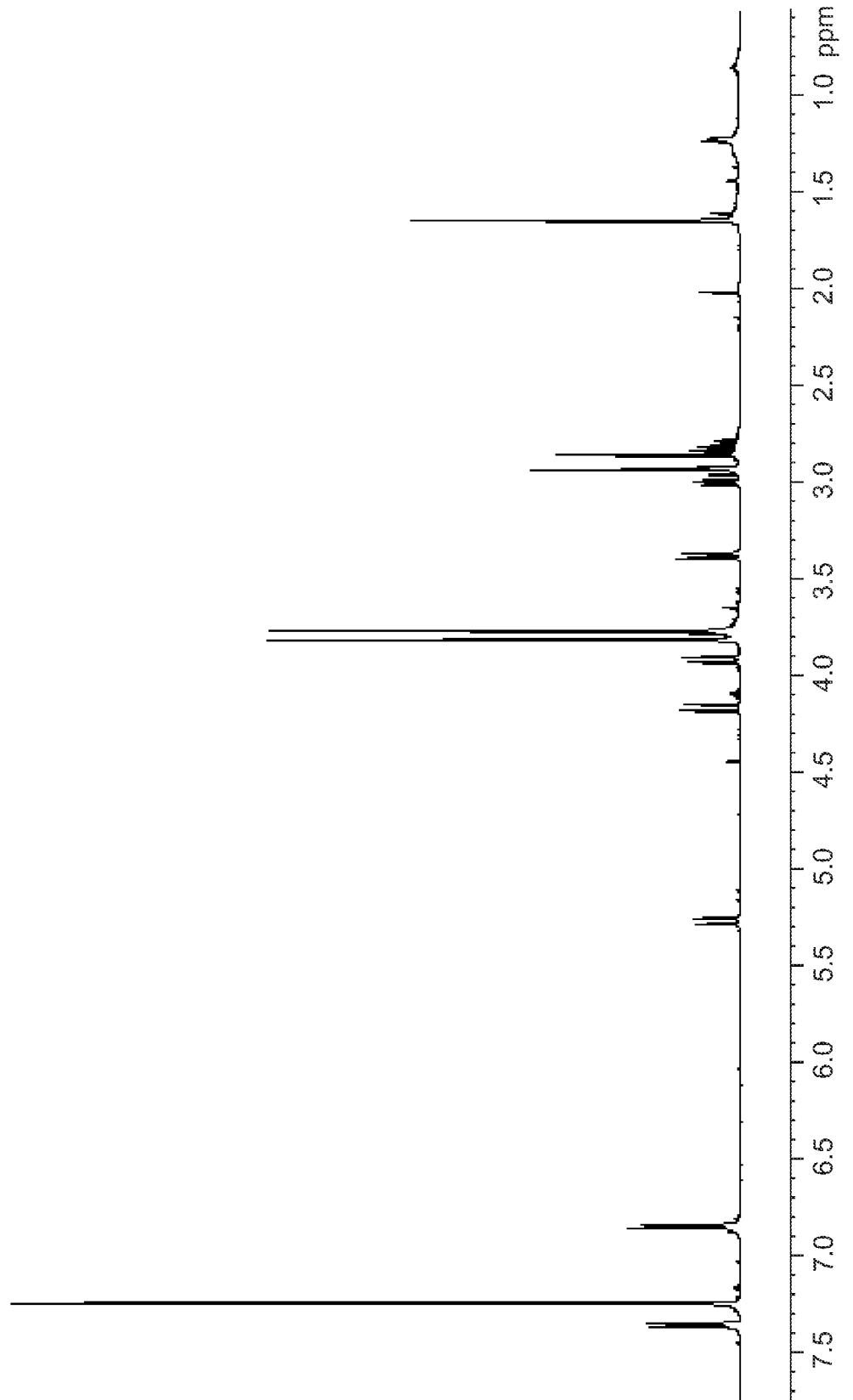
FIG. 49. $^1$H NMR spectrum of Compound (XII-2A) ($R^2$ = methyl) in $CDCl_3$

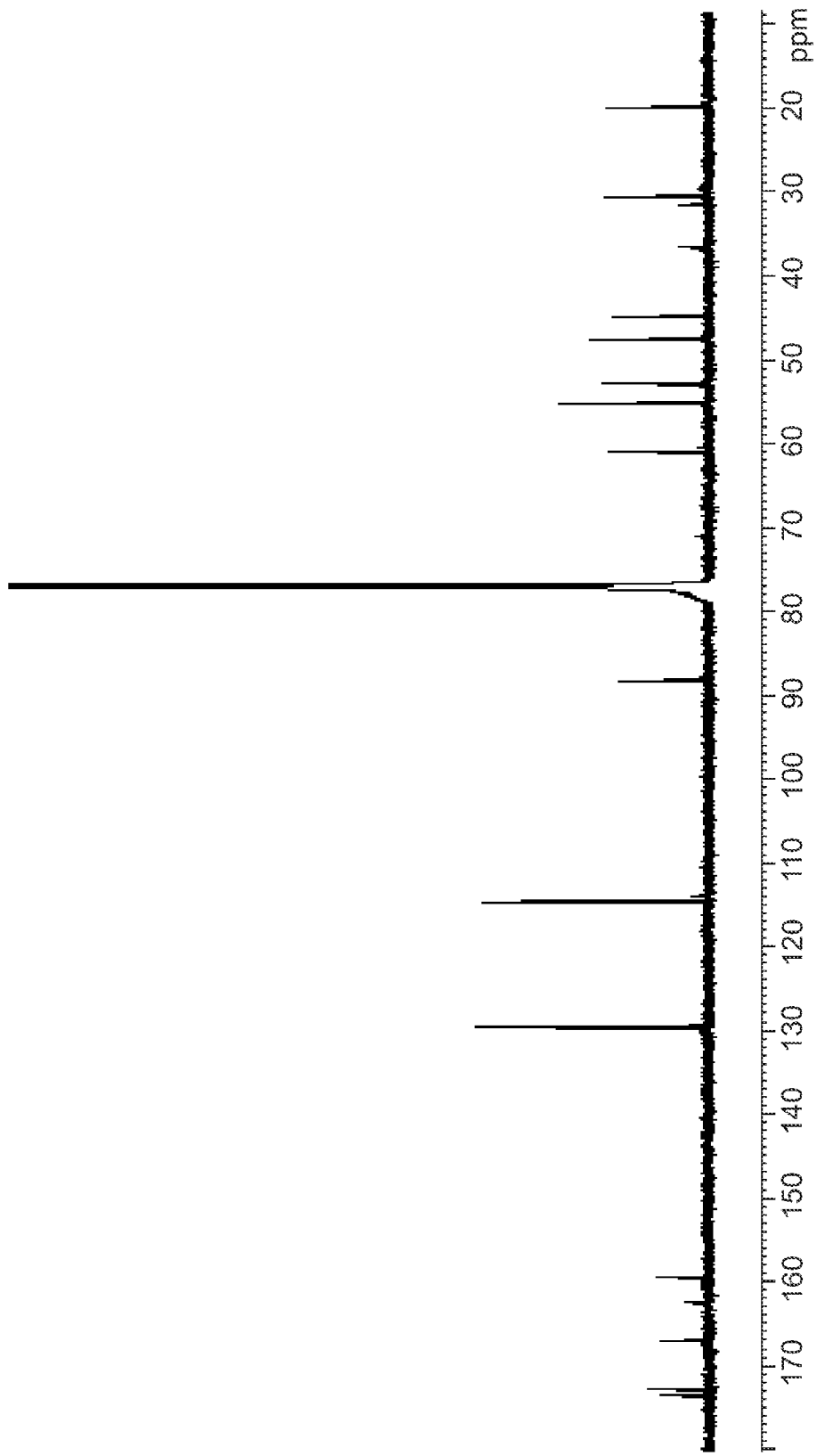
FIG. 50: $^{13}C$ NMR spectrum of Compound (XII-2A) ($R^2$ = methyl) in $CDCl_3$

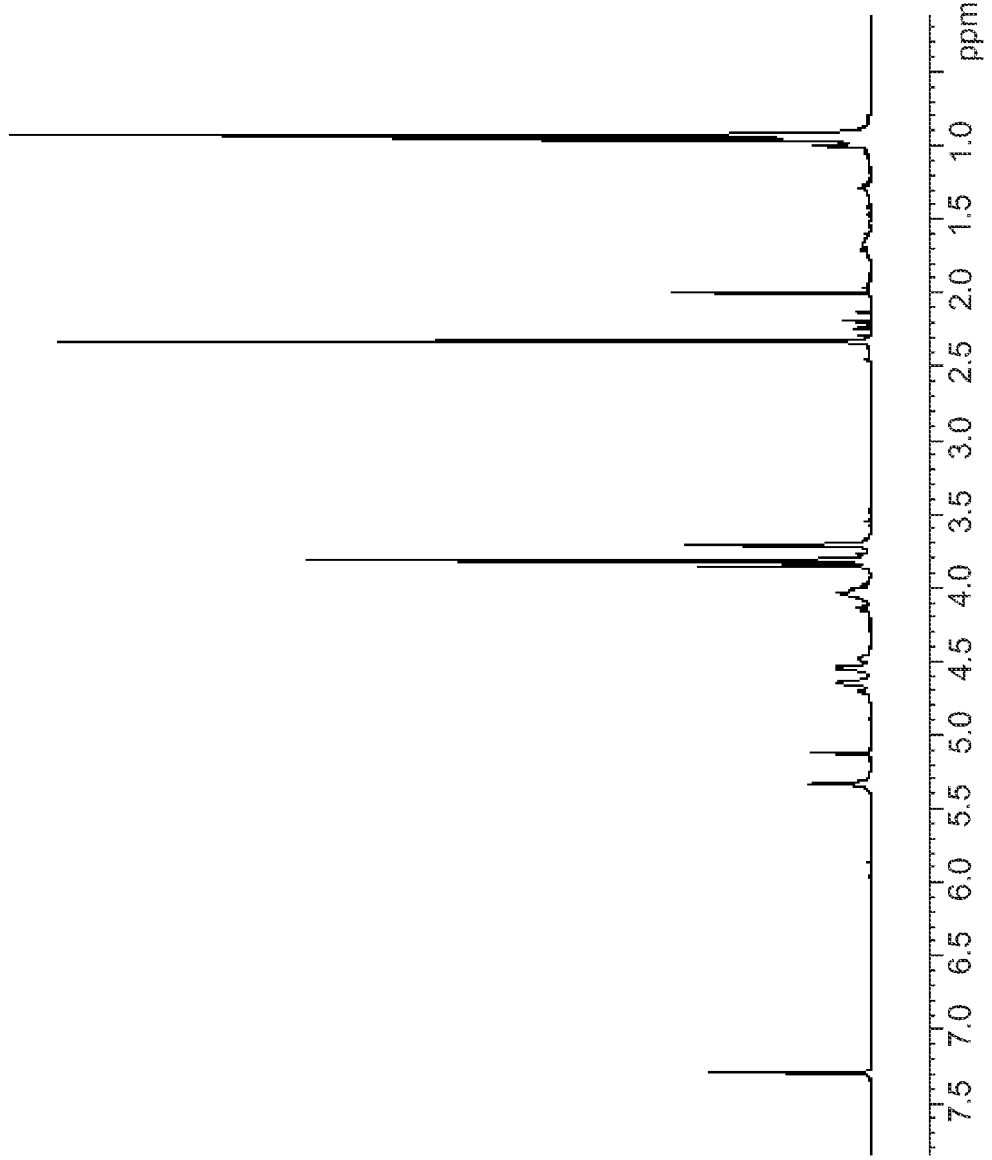
FIG. 51: $^1$H NMR spectrum of the compound of formula (III-2A) ($R^1$ = t-butyl and $R^2$ = methyl) in CDCl$_3$

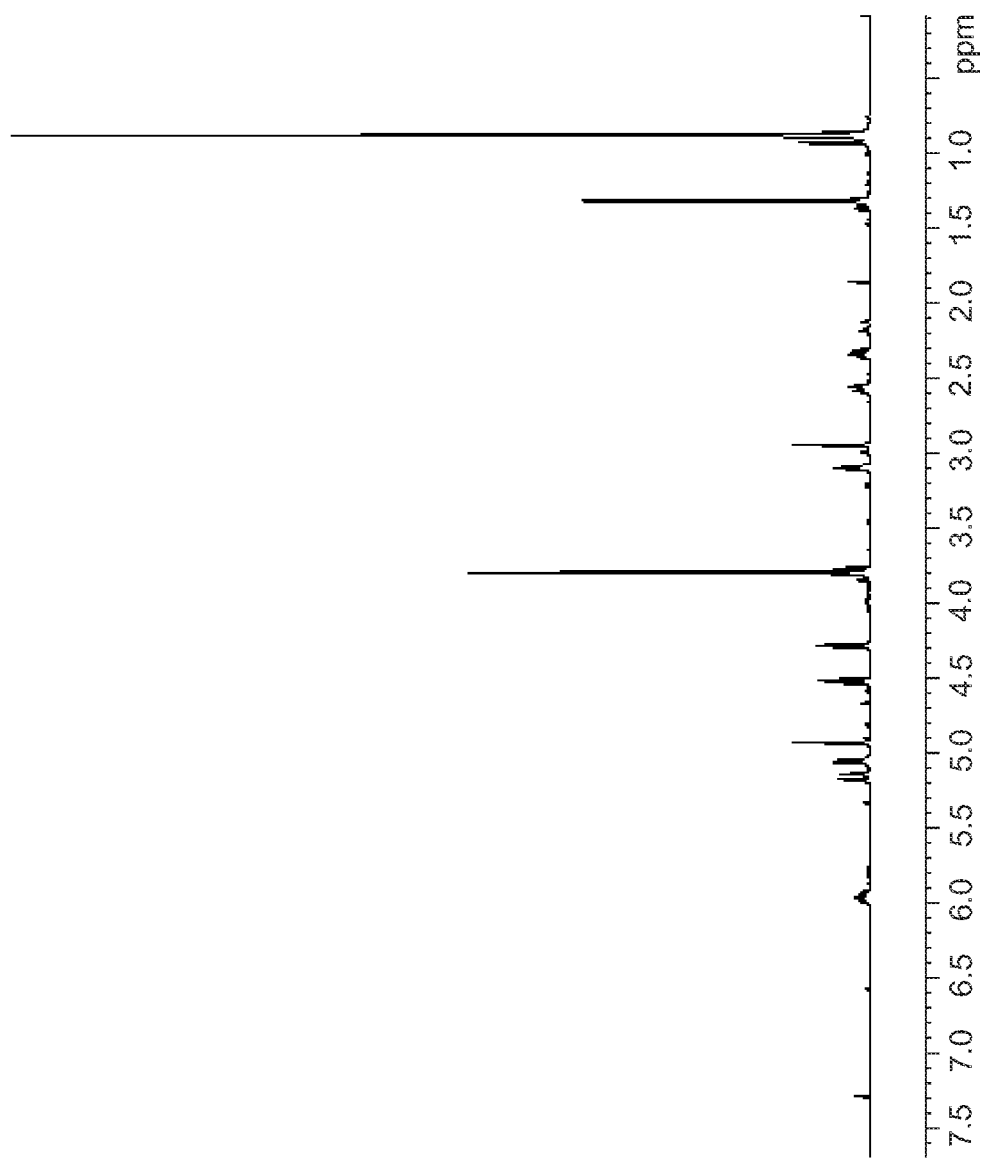
FIG. 52: $^1$H NMR spectrum of the compound of formula (Va-A) ($R^1$ = t-butyl and $R^2$ = methyl) in $CDCl_3$

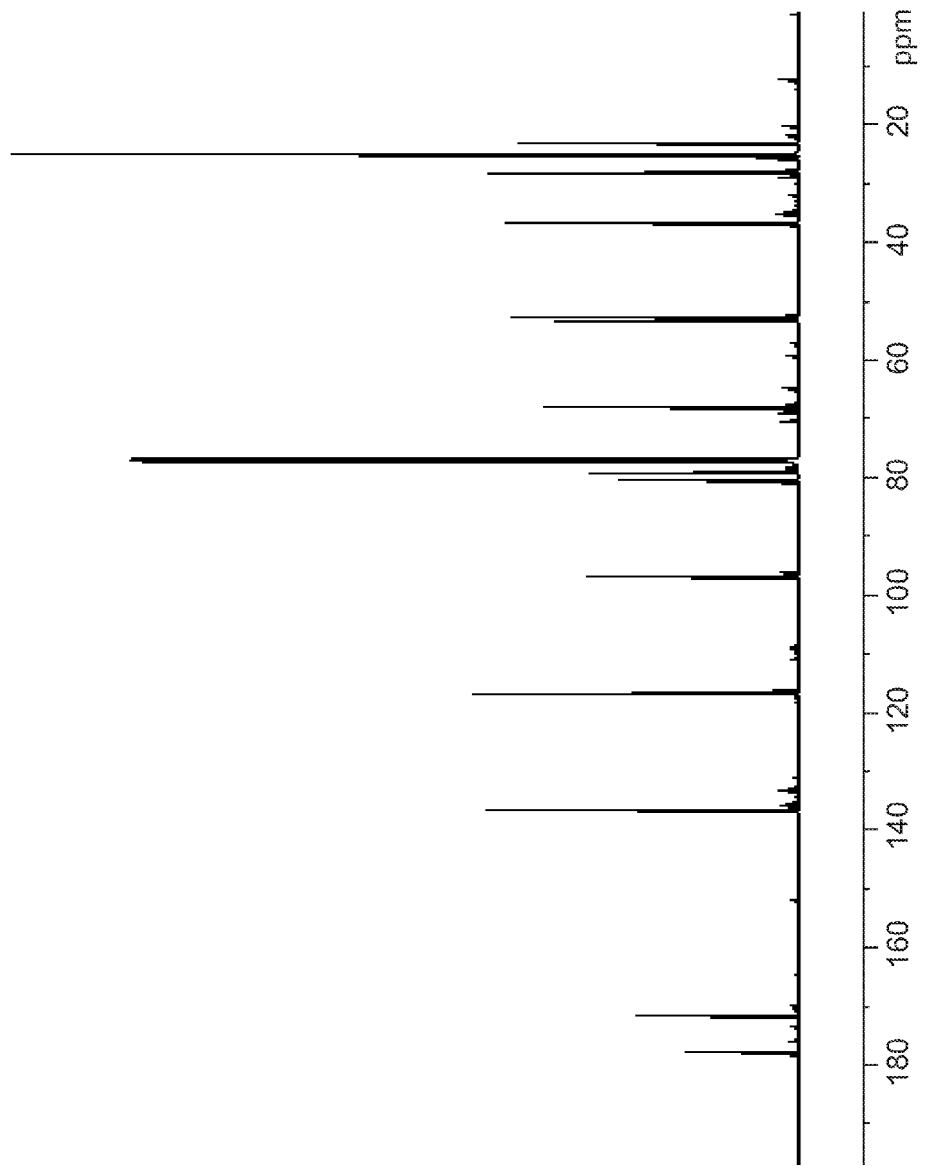
FIG. 53: $^{13}$C NMR spectrum of the compound of formula (Va-A) ($R^1$ = t-butyl and $R^2$ = methyl) in CDCl$_3$

TOTAL SYNTHESIS OF SALINOSPORAMIDE A AND ANALOGS THEREOF

CROSS-REFERENCE TO RELATED APPLICATIONS

This application is a divisional of U.S. patent application Ser. No. 12/399,382, entitled "Total Synthesis of Salinosporamide A and Analogs Thereof," filed Mar. 6, 2009, which claims priority to U.S. Provisional Patent Application Nos. 61/034,900, entitled "Total Synthesis of Salinosporamide A and Analogs Thereof," filed Mar. 7, 2008; and 61/073,545, entitled "Total Synthesis of Salinosporamide A and Analogs Thereof," filed Jun. 18, 2008, all of which are incorporated herein by reference in their entirety, including any drawings.

BACKGROUND

1. Field

The present application discloses certain compounds and methods for the preparation of certain compounds that can be used in the fields of chemistry and medicine.

2. Description

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria, fungi and protozoa are becoming increasingly difficult to treat and cure. For example, more and more bacteria, fungi and protozoa are developing resistance to current antibiotics and chemotherapeutic agents. Examples of such microbes include *Bacillus, Leishmania, Plasmodium* and *Trypanosoma*.

Furthermore, a growing number of diseases and medical conditions are classified as inflammatory diseases. Such diseases include conditions such as asthma to cardiovascular diseases. These diseases continue to affect larger and larger numbers of people worldwide despite new therapies and medical advances.

Therefore, a need exists for additional chemotherapeutics, anti-microbial agents, and anti-inflammatory agents to treat cancer, inflammatory diseases and infectious disease. A continuing effort is being made by individual investigators, academia and companies to identify new, potentially useful chemotherapeutic and anti-microbial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY

The embodiments disclosed herein generally relate to the total synthesis of chemical compounds, including heterocyclic compounds and analogs thereof. Some embodiments are directed to the desired chemical compound and intermediate compounds. Other embodiments are directed to the individual methods of synthesizing the chemical compound and intermediate compounds.

An embodiment disclosed herein relates to a method for synthesizing Salinosporamide A and analogs thereof, wherein Salinosporamide A has the following structure:

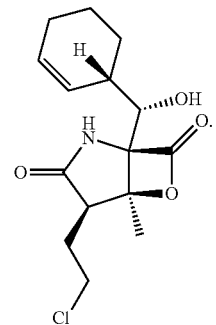

One embodiment described herein relates to a method of synthesizing a compound of formula (IX) from compounds of formulae (VII) and (VIII), in which the compound of formula (IX) can be used to synthesize Salinosporamide A and its analogs.

Another embodiment described herein relates to a method of synthesizing a compound of formula (XV) from compounds of formulae (IX), (X-1), (XI-1), (XII-1), (XIII-1) and (XIV-1), in which the compound of formula (XV) can be used to synthesize Salinosporamide A and its analogs.

Still another embodiment described herein relates to a method of synthesizing a compound of formula (XV) from compounds of formulae (IX), (X-2), (XI-2), (XII-2), (XIII-2), (XIV-2) and (XVII), in which the compound of formula (XV) can be used to synthesize Salinosporamide A and its analogs.

Yet still another embodiment described herein relates to a method of synthesizing a compound of formula (XV) from compounds of formulae (IX), (X-3), (XI-3), (XII-3), (XIII-3), (XIV-3) and (XVII), in which the compound of formula (XV) can be used to synthesize Salinosporamide A and its analogs.

One embodiment described herein relates to a method of synthesizing a compound of formula (VII) from compounds of formulae (I), (II), (III-1), (IV), (V) and (VI), in which the compound of formula (VII) can be used to synthesize Salinosporamide A and its analogs.

Another embodiment described herein relates to a method of synthesizing a compound of formula (VI) from diketene and compounds of formulae (I), (III-2) and (V), in which the compound of formula (VI) can be used to synthesize a compound of formula (VII) along with Salinosporamide A and its analogs. In some embodiments, a compound of formula (VI) can be synthesized from diketene and compounds of formulae (I) and (III-2). In an embodiment, a compound of formula (VI) can be obtained from diketene and compounds of formulae (I) and (III-2) without isolation of any intermediate compounds that are formed during the reaction.

Still another embodiment described herein relates to a method of synthesizing a compound of formula (VI) from acetoacetic acid and compounds of formulae (I), (III-2) and (V), in which the compound of formula (VI) can be used to synthesize a compound of formula (VII), Salinosporamide A and analogs of Salinosporamide A. In other embodiments, a compound of formula (VI) can be synthesized from acetoacetic acid and compounds formulae (I) and (III-2). In an embodiment, a compound of formula (VI) can be obtained from acetoacetic acid and compounds of formulae (I) and (III-2) without isolation of any intermediate compounds that are formed during the reaction.

Yet still another embodiment described herein relates to a method for synthesizing Salinosporamide A and its analogs through an intermediate compound of formula (III-2). Still another embodiment described herein relates to a method for synthesizing Salinosporamide A and its analogs through an intermediate compound of formula (VII). Yet still another embodiment described herein relates to a method for synthesizing Salinosporamide A and its analogs through an intermediate compound of formula (VIII). One embodiment described herein relates to a method for synthesizing Salinosporamide A and its analogs through an intermediate compound of formula (IX).

Some embodiments described herein relates to a method for synthesizing Salinosporamide A and its analogs through an intermediate compound of formula (XXII). In some embodiments, a compound of formula (XXII) can be used to obtain a compound of formula (VII), in which the compound of formula (VII) can be used to synthesize Salinosporamide A and its analogs.

Other embodiments described herein relates to a method for synthesizing analogs for Salinosporamide A through one or more of the following compounds of formulae (XXII), (XXIV), (XXV), (XXVI), (XXVII), (XXVIII), (XXIX), (XXX) and (XXXI). In some embodiments, analogs of Salinosporamide A can be obtained through a compound of formula (XXII). In an embodiment, analogs of Salinosporamide A can have the structure of a compound of formula (XXXI-A-1). In another embodiment, analogs of Salinosporamide A can have the structure of a compound of formula (XXXV).

Still other embodiments described herein relates to a method of synthesizing a compound of formula (XXV) from compounds of formulae (XXII) and (XXIV), in which the compound of formula (XXIV) can be used to synthesize Salinosporamide A and its analogs.

An embodiment described herein relates to a method of synthesizing a compound of formula (VIII) from a compound of formula (VII). Other embodiments described herein relate to a method synthesizing a compound of formula (IX) from a compound of formula (VIII). Some embodiments described herein relate to a method of synthesizing a compound of formula (VI), for example a compound of formula (VI-A), from a compound of formula (V) such as a compound of formula (Va-A). Other embodiments described herein relate to a method of obtaining a compound of formula (VII) from a compound of formula (VI). Still other embodiments described herein relate to a method of synthesizing a compound of formula (X-2) from a compound of formula (IX). An embodiment described herein relates to a method of synthesizing a compound of formula (XXIV) from a compound of formula (XXII). Other embodiments described herein relate to a method synthesizing a compound of formula (XXV) from a compound of formula (XXIV).

One embodiment described herein relates to a compound of formula (Va-A). Another embodiment described herein relates to a compound of formula (VI-A). Still another embodiment described herein relates to a compound of formula (VII). Yet still another embodiment described herein relates to a compound of formula (VIII). Still another embodiment described herein relates to a compound of formula (IX). An embodiment described herein relates to a compound of formula (XXII). Another embodiment described herein relates to a compound of formula (XXIV). Still another embodiment described herein relates to a compound of formula (XXV).

BRIEF DESCRIPTION OF THE DRAWINGS

FIGS. 4 and 4a-e illustrates methods of synthesizing Salinosporamide A and analogs thereof starting with a compound of formula (I) and a compound of formula (II), a compound of formula (I) and acetoacetic acid or a compound of formula (I) and diketene.

FIG. 5 illustrates a method of synthesizing a compound of formula (I) from (S)-serine.

FIG. 6 shows the chemical structure of Salinosporamide A.

FIG. 7 shows a $^1$H NMR spectrum of a compound of formula (I-B) ($R^1$=t-butyl and $R^2$=methyl) in $CDCl_3$.

FIG. 8 shows a $^1$H NMR spectrum of the ester precursor to a compound of formula (II) in $CDCl_3$.

FIG. 9 shows a $^1$H NMR spectrum of the protected ester precursor of a compound of formula (II) in $CDCl_3$.

FIG. 10 shows a $^1$H NMR spectrum of a compound of formula (II) in $CDCl_3$.

FIG. 11a shows a $^1$H NMR spectrum of a compound of formula (III-1B) ($R^1$=t-butyl and $R^2$=methyl) in $CDCl_3$.

FIG. 11b shows a LC-MS of a compound of formula (III-1B) ($R^1$=t-butyl and $R^2$=methyl).

FIG. 12a shows a $^1$H NMR spectrum of a compound of formula (IV-B) ($R^1$=t-butyl and $R^2$=methyl) in $CDCl_3$.

FIG. 12c shows a $^1$H NMR spectrum of a compound of formula (IV-B1) ($R^1$=t-butyl and $R^2$=methyl) in $CDCl_3$.

FIG. 12d shows a $^1$H NMR spectrum of a compound of formula (IV-B2) ($R^1$=t-butyl and $R^2$=methyl) in $CDCl_3$.

FIG. 12e shows a LC-MS of a compound of formula (IV-B) ($R^1$=t-butyl and $R^2$=methyl).

FIG. 13 shows a $^1$H NMR of a compound (VI-B) ($R^1$=t-butyl and $R^2$=methyl) in $CDCl_3$.

FIG. 14 shows a $^{13}$C NMR spectrum of a compound (VI-B) (R$^1$=t-butyl and R$^2$=methyl) in CDCl$_3$.

FIG. 15 shows a $^1$H NMR spectrum of a compound (VII-B) (R$^1$=t-butyl and R$^2$=methyl) in CDCl$_3$.

FIG. 16 shows a $^{13}$C NMR spectrum of a compound (VII-B) (R$^1$=t-butyl and R$^2$=methyl) in CDCl$_3$.

FIG. 17 shows a $^1$H NMR spectrum of a compound (VIII-B) (R$^1$=t-butyl and R$^2$=methyl) in CDCl$_3$.

FIG. 18 shows a $^{13}$C NMR spectrum of a compound (VIII-B) (R$^1$=t-butyl and R$^2$=methyl) in CDCl$_3$.

FIG. 28 shows a $^1$H NMR spectrum of a compound of formula (I-A) (R$^1$=t-butyl and R$^2$=methyl) in CDCl$_3$.

FIG. 29 shows a $^{13}$C NMR spectrum of a compound of formula (I-A) (R$^1$=t-butyl and R$^2$=methyl) in CDCl$_3$.

FIG. 30 shows a $^1$H NMR spectrum of a compound (III-1A) (R$^1$=t-butyl and R$^2$=methyl) in CDCl$_3$.

FIG. 31 shows a $^{13}$C NMR spectrum of a compound (III-1A) (R$^1$=t-butyl and R$^2$=methyl) in CDCl$_3$.

FIG. 32 shows a $^1$H NMR spectrum of a compound (IV-A) (R$^1$=t-butyl and R$^2$=methyl) in CDCl$_3$.

FIG. 33 shows a $^{13}$C NMR spectrum of a compound (IV-A) (R$^1$=t-butyl and R$^2$=methyl) in CDCl$_3$.

FIG. 34 shows a $^1$H NMR spectrum of a compound (VI-A) (R$^1$=t-butyl and R$^2$=methyl) in CDCl$_3$.

FIG. 35 shows a $^{13}$C NMR spectrum of a compound (VI-A) (R$^1$=t-butyl and R$^2$=methyl) in CDCl$_3$.

FIG. 36 shows a $^1$H NMR spectrum of a compound (VII-A) (R$^1$=t-butyl and R$^2$=methyl) in CDCl$_3$.

FIG. 37 shows a $^{13}$C NMR spectrum of a compound (VII-A) (R$^1$=t-butyl and R$^2$=methyl) in CDCl$_3$.

FIG. 38 shows a $^1$H NMR spectrum of a compound (VIII-A) (R$^1$=t-butyl and R$^2$=methyl) in CDCl$_3$.

FIG. 39 shows a $^{13}$C NMR spectrum of a compound (VIII-A) (R$^1$=t-butyl and R$^2$=methyl) in CDCl$_3$.

FIG. 40 shows a $^1$H NMR spectrum of a compound (X-1A) (PG$^1$=Bz and R$^1$=t-butyl and R$^2$=methyl) in CDCl$_3$.

FIG. 41 shows a $^{13}$C NMR spectrum of a compound (X-1A) (PG$^1$=Bz and R$^1$=t-butyl and R$^2$=methyl) in CDCl$_3$.

FIG. 42 shows a $^1$H NMR spectrum of a compound (XI-1A) (PG$^1$=Bz and R$^2$=methyl) in CDCl$_3$.

FIG. 43 shows a $^{13}$C NMR spectrum of a compound (XI-1A) (PG$^1$=Bz and R$^2$=methyl) in CDCl$_3$.

FIG. 44 shows a $^1$H NMR spectrum of a compound (X-2A) (R$^1$=t-butyl and R$^2$=methyl) in CDCl$_3$.

FIG. 45 shows a $^{13}$C NMR spectrum of a compound (X-2A) (R$^1$=t-butyl and R$^2$=methyl) in CDCl$_3$.

FIG. 46 shows a $^1$H NMR spectrum of a compound (XI-2A) (R$^2$=methyl) in DMSO-d$_6$ and CDCl$_3$ mixture.

FIG. 47 shows a $^{13}$C NMR spectrum of a compound (XI-2A) (R$^2$=methyl) in DMSO-d$_6$ and CDCl$_3$ mixture FIG. 48 shows a $^1$H NMR spectrum of a compound (XI-2A) (R$^2$=methyl and C-5-O-TES) in CDCl$_3$.

FIG. 49 shows a $^1$H NMR spectrum of a compound (XII-2A) (R$^2$=methyl) in CDCl$_3$.

FIG. 50 shows a $^{13}$C NMR spectrum of a compound (XII-2A) (R$^2$=methyl) in CDCl$_3$.

FIG. 51 shows a $^1$H NMR spectrum of a compound (III-2A) (R$^1$=t-butyl and R$^2$=methyl) in CDCl$_3$.

FIG. 52 shows a $^1$H NMR spectrum of a compound (Va-A) (R$^1$=t-butyl and R$^2$=methyl) in CDCl$_3$.

FIG. 53 shows a $^{13}$C NMR spectrum of a compound (Va-A) (R$^1$=t-butyl and R$^2$=methyl) in CDCl$_3$.

DETAILED DESCRIPTION

Numerous references are cited herein. The references cited herein, including the U.S. patents cited herein, are each to be considered incorporated by reference in their entirety into the present specification, unless otherwise noted.

Embodiments include, but are not limited to, methods for the preparation of various compounds and intermediates, and the compounds and intermediates themselves. In some embodiments, one or more substituents, one or more compounds, or groups of compounds can be specifically excluded in any one or more of the methods or compounds as described more fully below.

Described herein are methods for synthesizing Salinosporamide A, and analogs thereof. Salinosporamide A and several analogs, as well as methods of making the same are described in U.S. Provisional Patent Applications Nos., 60/480,270, filed Jun. 20, 2003; 60/566,952, filed Apr. 30, 2004; 60/627,461, filed Nov. 12, 2004; 60/633,379, filed Dec. 3, 2004; 60/643,922, filed Jan. 13, 2005; 60/658,884, filed Mar. 4, 2005; 60/676,533, filed Apr. 29, 2005; 60/567,336, filed Apr. 30, 2004; 60/580,838, filed Jun. 18, 2004; 60/591,190, filed Jul. 26, 2004; 60/627,462, filed Nov. 12, 2004; 60/644,132, filed Jan. 13, 2005; 60/659,385, filed Mar. 4, 2005; 60/790,168, filed Apr. 6, 2006; 60/816,968, filed Jun. 27, 2006; 60/836,166, filed Aug. 7, 2006; 60/844,132, filed Sep. 12, 2006; and 60/855,379, filed Jan. 17, 2007; U.S. patent application Ser. Nos., 10/871,368, filed Jun. 18, 2004; 12/136,688, filed Jun. 1, 2008; 11/118,260, now U.S. Pat. No. 7,276,530, filed Apr. 29, 2005; 11/865,704, filed Oct. 1, 2007; 11/412,476, filed Apr. 27, 2006; 11/453,374, filed Jun. 15, 2006; and 11/697,689, filed Apr. 6, 2007; and International Patent Applications Nos., PCT/US2004/019543, filed Jun. 18, 2004; PCT/US2005/044091, filed Dec. 2, 2005, PCT/US2005/01484, filed Apr. 29, 2005, PCT/US2006/016104, filed Apr. 27, 2006; and PCT/US2007/008562, filed Apr. 6, 2007; each of which is hereby incorporated by reference in its entirety.

Provided herein are methods for synthesizing Salinosporamide A and its analogs through an intermediate compound of formula (VII):

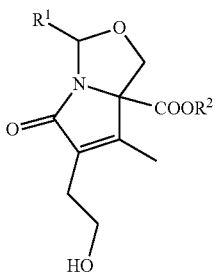

(VII)

Figure 1:
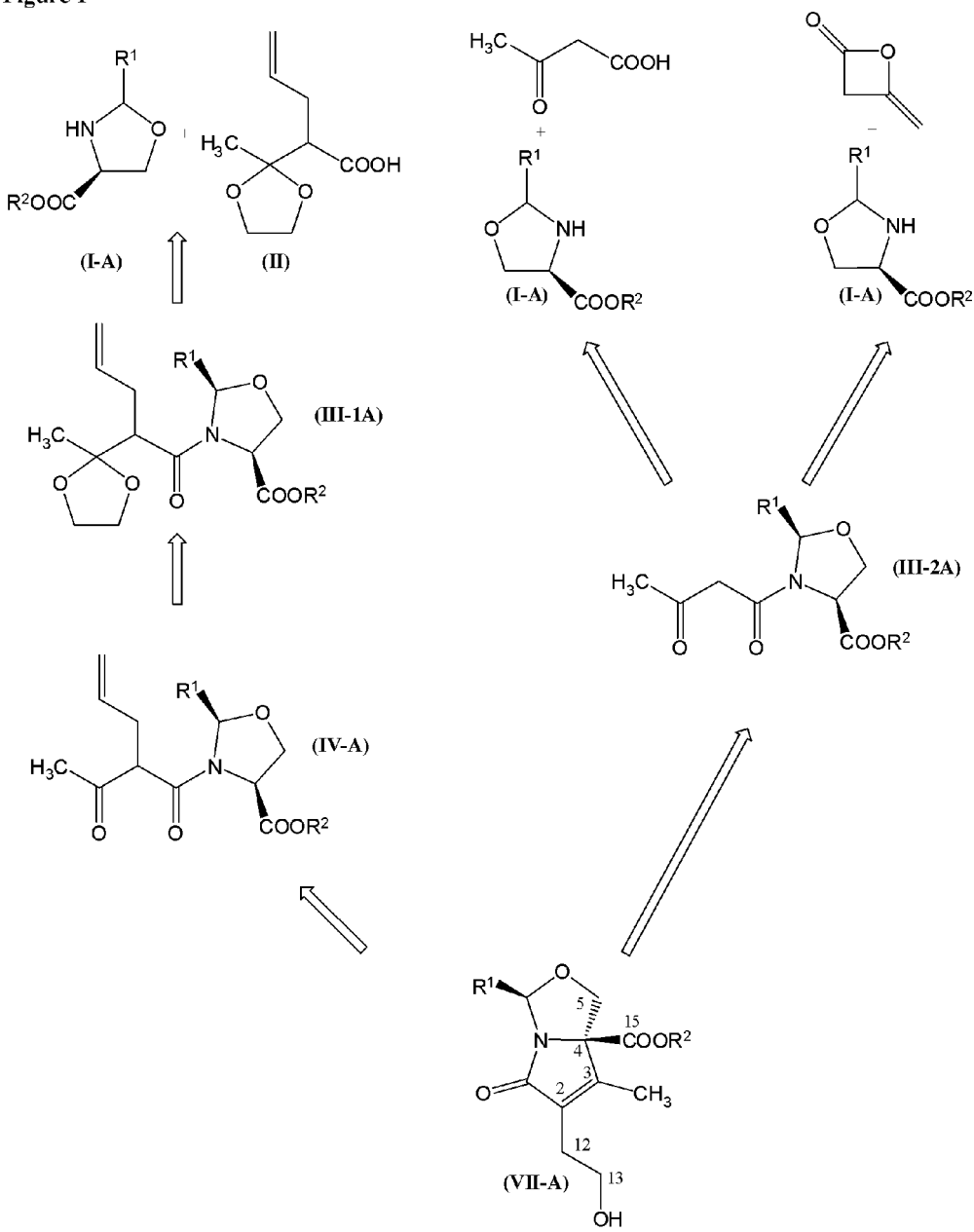
FIG. 1 illustrates retrosynthetic schemes for synthesizing a compound of formula (VII).
Figure 2:
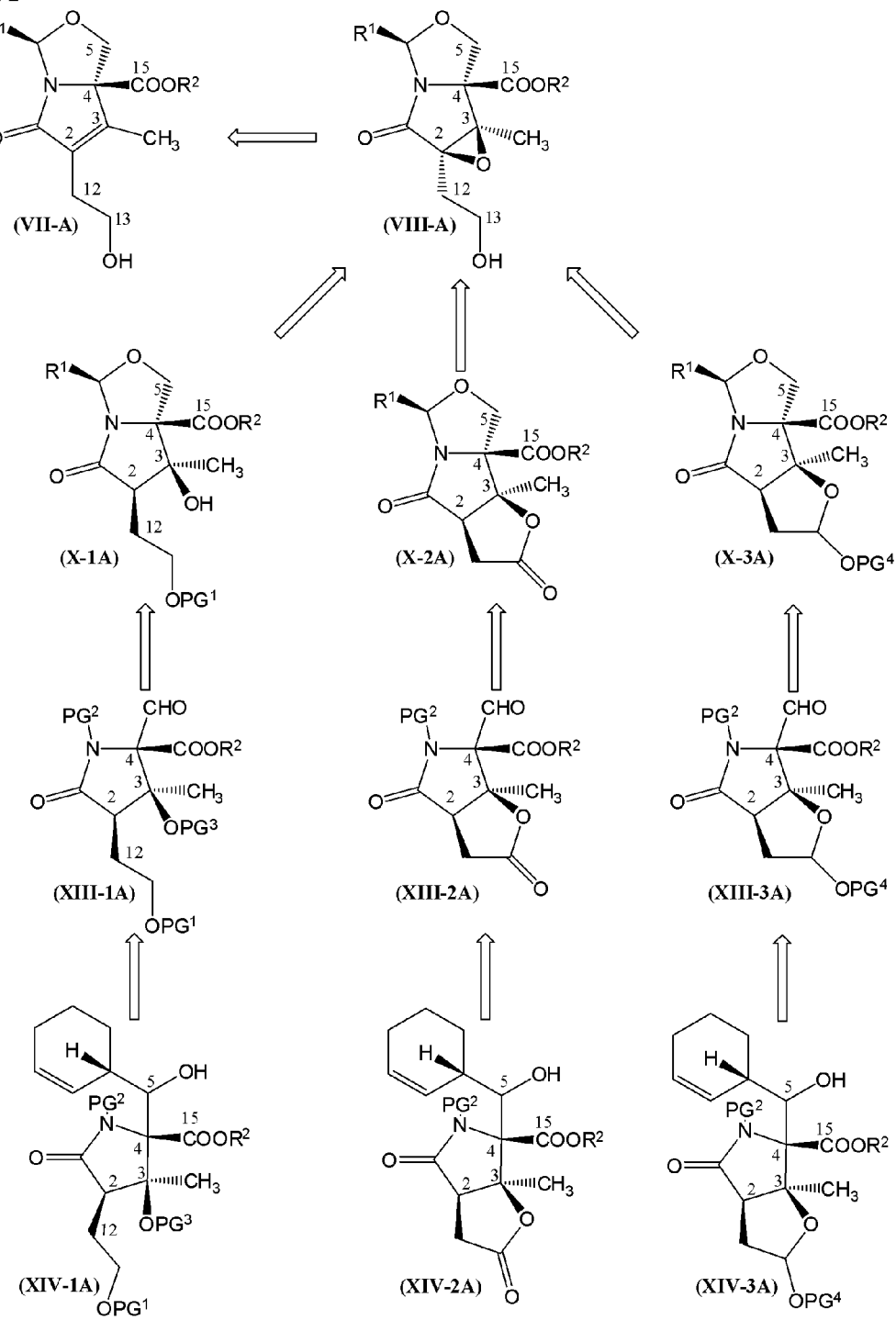
FIG. 2 illustrates retrosynthetic schemes for synthesizing compound of formulae (XIV-1A), (XIV-2A) and (XIV-3A).
Figure 3:
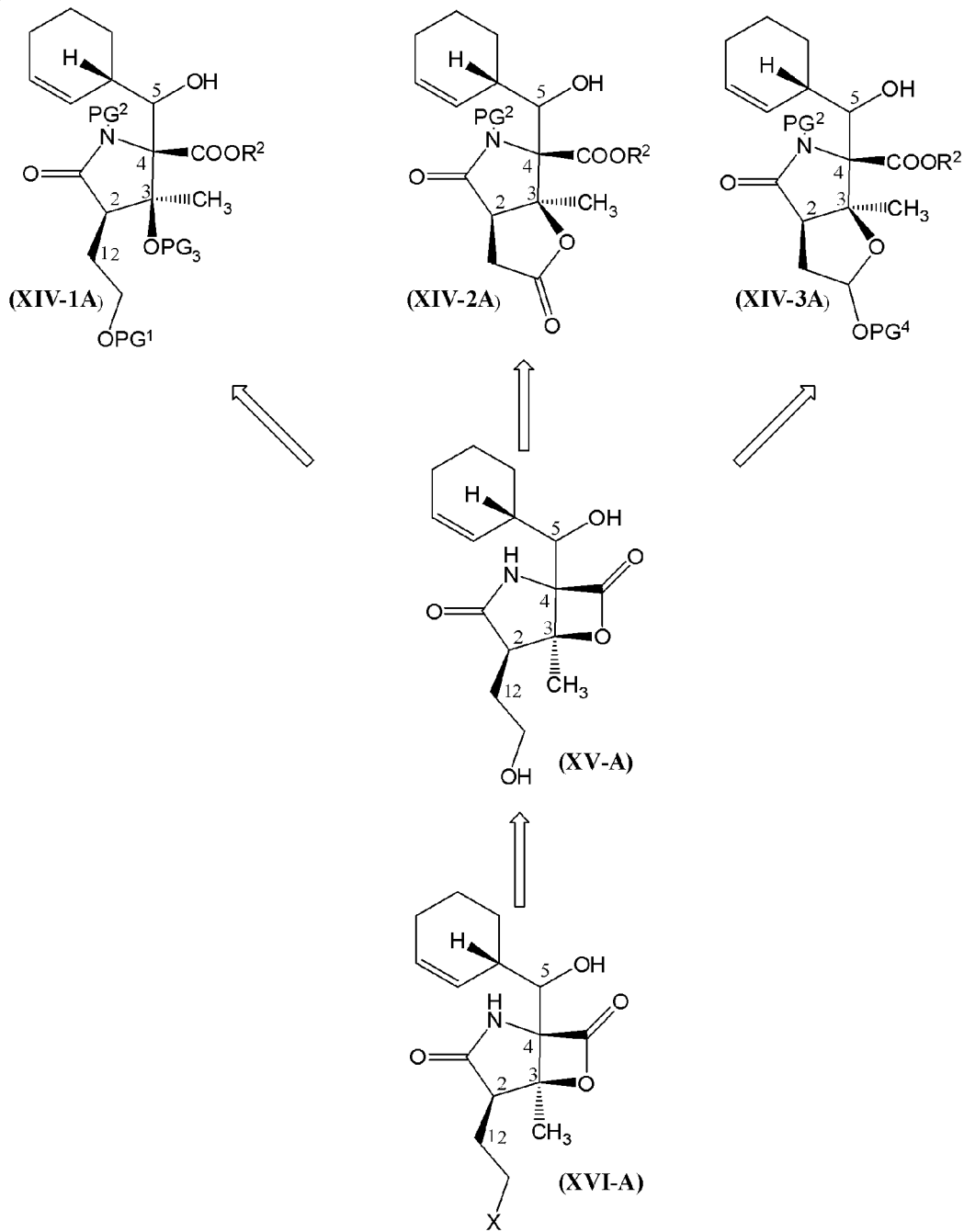
FIG. 3 illustrates retrosynthetic schemes for synthesizing Salinosporamide A and analogs thereof.
Figure 4:
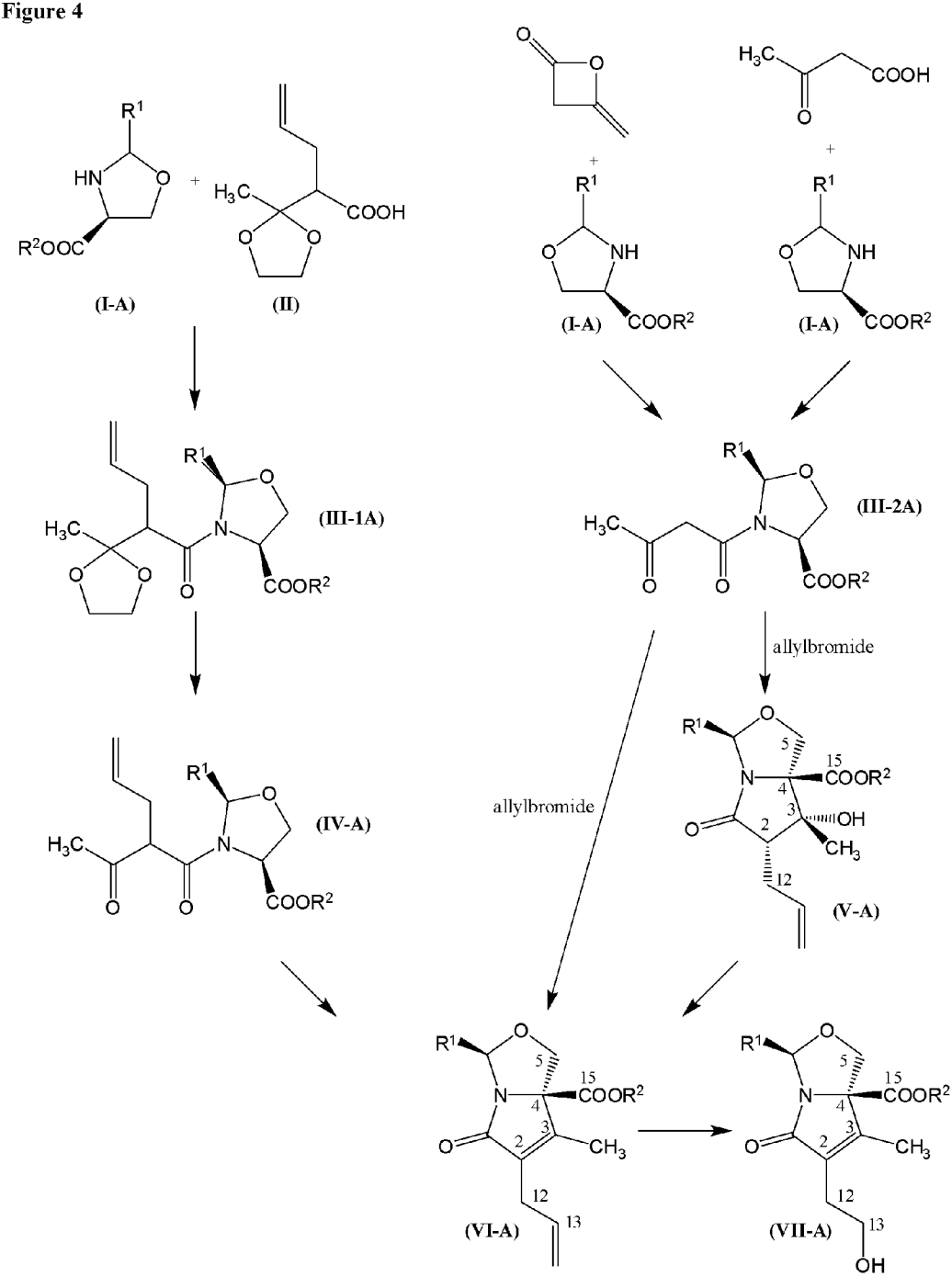

As shown in FIG. 4, the compound of formula (VII) can be synthesized from readily available starting materials, as described herein. The compound of Formula (VII) may be subsequently converted to Salinosporamide A or analogs thereof. For example Salinosporamide A or analogs thereof may be synthesized according to Scheme A. A retrosynthetic scheme providing additional details regarding synthesizing Salinosporamide A is shown in FIGS. 1-3. In an embodiment, Salinosporamide A and its analogs can be obtained through an intermediate compound, a compound of formula (VIII):

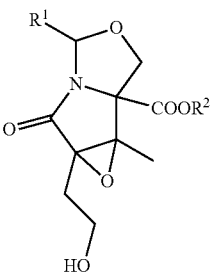

(VIII)

Scheme A

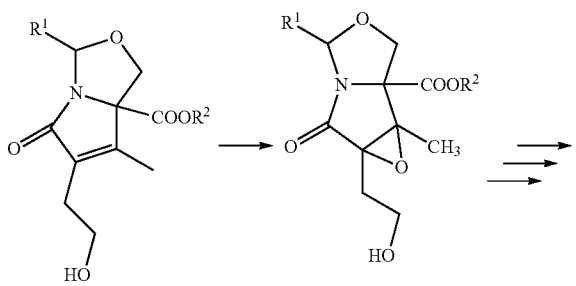

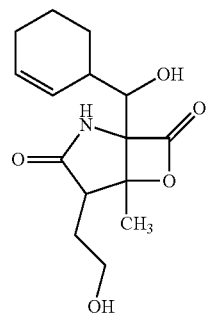

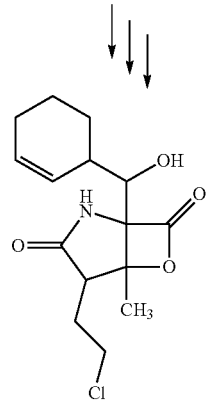

For the compounds described herein, each stereogenic carbon can be of R or S configuration. Although the specific compounds exemplified in this application can be depicted in a particular configuration, compounds having either the opposite stereochemistry at any given chiral center or mixtures thereof are also envisioned unless otherwise specified. When chiral centers are found in the derivatives of the compounds, it is to be understood that the compounds encompasses all possible stereoisomers unless otherwise indicated.

The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Examples of suitable substituents include but are not limited to alkoxy, cycloalkyl, cycloalkenyl, acyl, acylamino, acyloxy, amino, alkyl amino, aminoacyl, aminoacyloxy, oxyacylamino, cyano, halogen, hydroxy, carboxyl, carboxylalkyl, keto, thioketo, thiol, thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$—H, —$SO_2$—OH, —$SO_2$-alkyl, —$SO_2$-substituted alkyl, —$SO_2$-aryl and —$SO_2$-heteroaryl, heteroaryl, boronate alkyl, boronic acid, $(OH)_2$B-alkyl, phosphate and phosphate esters, phosphonooxy, phosphonooxyalkyl, azido, azidoalkyl, ammonium, carboxyalkyl, a salt of a carboxyalkyl, alkylamino, a salt of an alkylamino, dialkylamino, a salt of a dialkylamino, alkylthio, arylthio, carboxy, cyano, alkanesulfonyl, alkanesulfinyl, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl. Each of the substituents can be further substituted. The other above-listed patents also provide standard definitions for the term "substituted" that are well-understood by those of skill in the art.

Whenever a group is described as "optionally substituted" the group may be unsubstituted or substituted with one or more substituents as described herein.

As used herein, any "R" group(s) such as, without limitation, $R^1$, $R^2$, $R^3$, $R^4$, $R^5$ and $R^6$ represent substituents that can be attached to the indicated atom. An R group may be substituted or unsubstituted. If two "R" groups are covalently bonded to the same atom or to adjacent atoms, then they may be "taken together" as defined herein to form a cycloalkyl, aryl, heteroaryl or heterocycle. For example, without limitation, if $R_{1a}$ and $R_{1b}$ of an $NR_{1a}R_{1b}$ group are indicated to be "taken together," it means that they are covalently bonded to one another to form a ring:

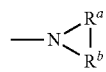

The term "alkyl," as used herein, means any unbranched or branched, substituted or unsubstituted, saturated hydrocarbon, with $C_1$-$C_{24}$ preferred, and $C_1$-$C_6$ hydrocarbons being preferred, with methyl, ethyl, propyl, isopropyl, butyl, isobutyl, and tert-butyl, and pentyl being most preferred.

The term "alkenyl," as used herein, means any unbranched or branched, substituted or unsubstituted, unsaturated hydrocarbon containing one or more double bonds. Some examples of alkenyl groups include allyl, homo-allyl, vinyl, crotyl, butenyl, pentenyl, hexenyl, heptenyl and octenyl.

The term "alkynyl" as used herein, means any unbranched or branched, substituted or unsubstituted, unsaturated hydrocarbon with one or more triple bonds The term "cycloalkyl" refers to any non-aromatic, substituted or unsubstituted, hydrocarbon ring, preferably having five to twelve atoms comprising the ring. Furthermore, in the present context, the term "cycloalkyl" comprises fused ring systems such that the definition covers bicyclic and tricyclic structures.

The term "cycloalkenyl" refers to any non-aromatic, substituted or unsubstituted, hydrocarbon ring that includes a double bond, preferably having five to twelve atoms comprising the ring. Furthermore, in the present context, the term "cycloalkenyl" comprises fused ring systems such that the definition covers bicyclic and tricyclic structures.

The term "cycloalkynyl" refers to any non-aromatic, substituted or unsubstituted, hydrocarbon ring that includes a triple bond, preferably having five to twelve atoms comprising the ring. Furthermore, in the present context, the term "cycloalkynyl" comprises fused ring systems such that the definition covers bicyclic and tricyclic structures.

The term "acyl" refers to hydrogen, lower alkyl, lower alkenyl, or aryl connected, as substituents, via a carbonyl group. Examples include formyl, acetyl, propanoyl, benzoyl, and acryl. An acyl may be substituted or unsubstituted.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. An aryl group may be substituted or unsubstituted.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen. Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one $C_{3-8}$-cycloalkyl ring share at least one chemical bond. A heteroaryl can be substituted or unsubstituted.

The terms "heterocycle" and "heterocyclyl" are intended to mean three-, four-, five-, six-, seven-, and eight-membered rings wherein carbon atoms together with from 1 to 3 heteroatoms constitute said ring. A heterocycle may optionally contain one or more unsaturated bonds situated in such a way, however, that an aromatic π-electron system does not arise. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, cyclic carbamates, and the like. Heterocyclyl rings may optionally also be fused to at least other heterocyclyl ring, at least one $C_{3-8}$-cycloalkyl ring, at least one $C_{3-8}$-cycloalkenyl ring and/or at least one $C_{3-8}$-cycloalkynyl ring such that the definition includes bicyclic and tricyclic structures. Examples of benzo-fused heterocyclyl groups include, but are not limited to, benzimidazolidinone, tetrahydroquinoline, and methylenedioxybenzene ring structures. Some examples of "heterocycles" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyridine, pyridinium, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. A heterocycle group may be substituted or unsubstituted.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred.

The term "cycloalkoxy" refers to any non-aromatic hydrocarbon ring comprising an oxygen heteroatom, preferably having five to twelve atoms comprising the ring. A cycloalkoxy can be substituted or unsubstituted.

The term "alkoxy carbonyl" refers to any linear, branched, cyclic, saturated, unsaturated, aliphatic or aromatic alkoxy attached to a carbonyl group. The examples include methoxycarbonyl group, ethoxycarbonyl group, propyloxycarbonyl group, isopropyloxycarbonyl group, butoxycarbonyl group, sec-butoxycarbonyl group, tert-butoxycarbonyl group, cyclopentyloxycarbonyl group, cyclohexyloxycarbonyl group, benzyloxycarbonyl group, allyloxycarbonyl group, phenyloxycarbonyl group, pyridyloxycarbonyl group, and the like. An alkoxy carbonyl may be substituted or unsubstituted.

The term "(cycloalkyl)alkyl is understood as a cycloalkyl group connected, as a substituent, via a lower alkylene. The (cycloalkyl)alkyl group and lower alkylene of a (cycloalkyl) alkyl group may be substituted or unsubstituted.

The terms "(heterocycle)alkyl" and "(heterocyclyl)alkyl" are understood as a heterocycle group connected, as a substituent, via a lower alkylene. The heterocycle group and the lower alkylene of a (heterocycle)alkyl group may be substituted or unsubstituted.

The term "arylalkyl" is intended to mean an aryl group connected, as a substituent, via a lower alkylene, each as defined herein. The aryl group and lower alkylene of an arylalky may be substituted or unsubstituted. Examples include benzyl, substituted benzyl, 2-phenylethyl, 3-phenylpropyl, and naphthylalkyl.

The term "heteroarylalkyl" is understood as heteroaryl groups connected, as substituents, via a lower alkylene, each as defined herein. The heteroaryl and lower alkylene of a heteroarylalkyl group may be substituted or unsubstituted. Examples include 2-thienylmethyl, 3-thienylmethyl, furylmethyl, thienylethyl, pyrrolylalkyl, pyridylalkyl, isoxazolylalkyl, imidazolylalkyl, and their substituted as well as benzofused analogs.

The term "lower alkylene groups" are straight-chained tethering saturated hydrocarbon groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$(CH_2)_4$—) groups. A lower alkylene group may be substituted or unsubstituted.

The term "halogen atom," as used herein, means any one of the radio-stable atoms of column 7 of the Periodic Table of the Elements, i.e., fluorine, chlorine, bromine, or iodine, with bromine and chlorine being preferred.

As employed herein, the following terms have their accepted meaning in the chemical literature.

9-BBN: 9-borabicyclo[3.3.1]nonane
Bn: benzyl
BnOH: benzyl alcohol
BOC: tert-butoxycarbonyl
BOPCl: bis(2-oxo-3-oxazolidinyl)phosphinic chloride
t-BuOH: tert-butanol/tert-butyl alcohol
t-BuOK: potassium tert-butoxide
Bz: benzoyl
CAN: ceric ammonium nitrate
DBN: 1,5-diazabicyclo[4.3.0]non-5-ene
DBU: 1,8-diazabicyclo[5.4.0]undec-7-ene
DCC: N,N-dicyclohexyl carbodiimide
DDQ: 2,3-dichloro-5,6-dicyanobenzoquinone
DIBALH: diisobutylaluminum hydride
DMDO: dimethyldioxirane
DMF N,N-dimethylformamide
ESI: electrospray ionization
EtOAc: ethyl acetate
ID: internal diameter
LC-MS: liquid chromatography-mass spectrometry
LDA: lithium diisopropylamide
$LiAlH_4$: lithium aluminum hydride.
mCPBA: meta-chloroperoxybenzoic acid
MS: mass spectrum
MsCl: methanesulfonyl chloride
NaOMe: sodium methoxide
NaOEt: sodium ethoxide
NMO: N-methylmorpholine N-oxide
NMR: nuclear magnetic resonance
PCC: pyridinium chlorochromate
Pd—C: palladium on activated carbon
PDC: pyridinium dichromate
PMB: para-methoxybenzyl
PDC: pyridinium dichromate
PPTS: pyridinium p-toluene sulfonate
PTSA: p-toluene sulfonic acid
RT: room temperature
TES: triethylsilyl
TFA: trifluoroacetic acid
TFAA: trifluoroacetic anhydride
TPAP: tetrapropylammonium perruthenate
THF: tetrahydrofuran
TLC: thin layer chromatography The terms "organometallic moiety" and "organometallic moieties" as used herein refer to any chemical compound that contains a metal-element bond(s) of a largely covalent character. The term "metal" as used herein include those elements traditionally classified as metals (e.g., lithium, magnesium, zinc, and tin) and those elements classified as metalloids (e.g., boron).

The terms "protecting group moiety" and "protecting group moieties" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry Plenum Press,* 1973, both of which are hereby incorporated by reference. The protecting group moiety may be chosen in such a way, that they are stable to the reaction conditions applied and readily removed at a convenient stage using methodology known from the art. A non-limiting list of protecting groups include benzyl; substituted benzyl; unsubstituted or substituted alkylcarbonyls (e.g., t-butoxycarbonyl (BOC)); unsubstituted or substituted arylcarbonyls; unsubstituted or substituted arylalkylcarbonyls (e.g., benzyloxycarbonyl, benzoyl); unsubstituted or substituted alkoxycarbonyls; unsubstituted or substituted aryloxycarbonlys; substituted methyl ether (e.g. methoxymethyl ether); substituted ethyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g. benzoate ester); carbonates (e.g. methoxymethylcarbonate); sulfonates (e.g. tosylate, mesylate); acyclic ketal (e.g. dimethyl acetal); cyclic ketals (e.g., 1,3-dioxane or 1,3-dioxolanes); acyclic acetal; cyclic acetal; acyclic hemiacetal; cyclic hemiacetal; and cyclic dithioketals (e.g., 1,3-dithiane or 1,3-dithiolane). As used herein, any "PG" group(s) such as, without limitation, $PG^1$, $PG^2$, $PG^4$, $PG^5$ and $PG^6$ represent a protecting group moiety.

The terms "pure," "purified," "substantially purified," and "isolated" as used herein refer to the compound of the embodiment being free of other, dissimilar compounds with which the compound, if found in its natural state, would be associated in its natural state. In some embodiments described as "pure," "purified," "substantially purified," or "isolated" herein, the compound may comprise at least 50% or 75% of the mass, by weight, of a given sample. In other embodiments, the compound may comprise at least 90% or 95% of the mass, by weight, of a given sample. In still other embodiments, the compound may comprise at least 99% of the mass, by weight, of a given sample.

The terms "derivative," "variant," or other similar term refers to a compound that is an analog of the other compound.

The starting compound of formula (I) may be synthesized from readily available materials. As shown in Scheme 1-1, a compound of formula (I) can be synthesized from a serine ester salt, an aldehyde and a base (e.g., triethylamine) at elevated temperatures. In some embodiments, the $R^1$ group can be hydrogen, unsubstituted or substituted $C_{1-6}$ alkyl or unsubstituted or substituted aryl. In some embodiments, $R_2$ can be selected from hydrogen, an unsubstituted or substituted $C_{1-6}$ alkyl, an unsubstituted or substituted aryl, and an unsubstituted or substituted arylalkyl. In some embodiments, the serine ester salt can be a (L)-serine methylester salt which can form a compound of formula (I) with the stereochemistry shown in Scheme 1-2. In an embodiment, the aldehyde can be t-butyl aldehyde in which $R^1$ is t-butyl. In some embodiments, $R^2$ can be an unsubstituted or substituted $C_{1-6}$ alkyl. In an embodiment, $R^2$ can be methyl.

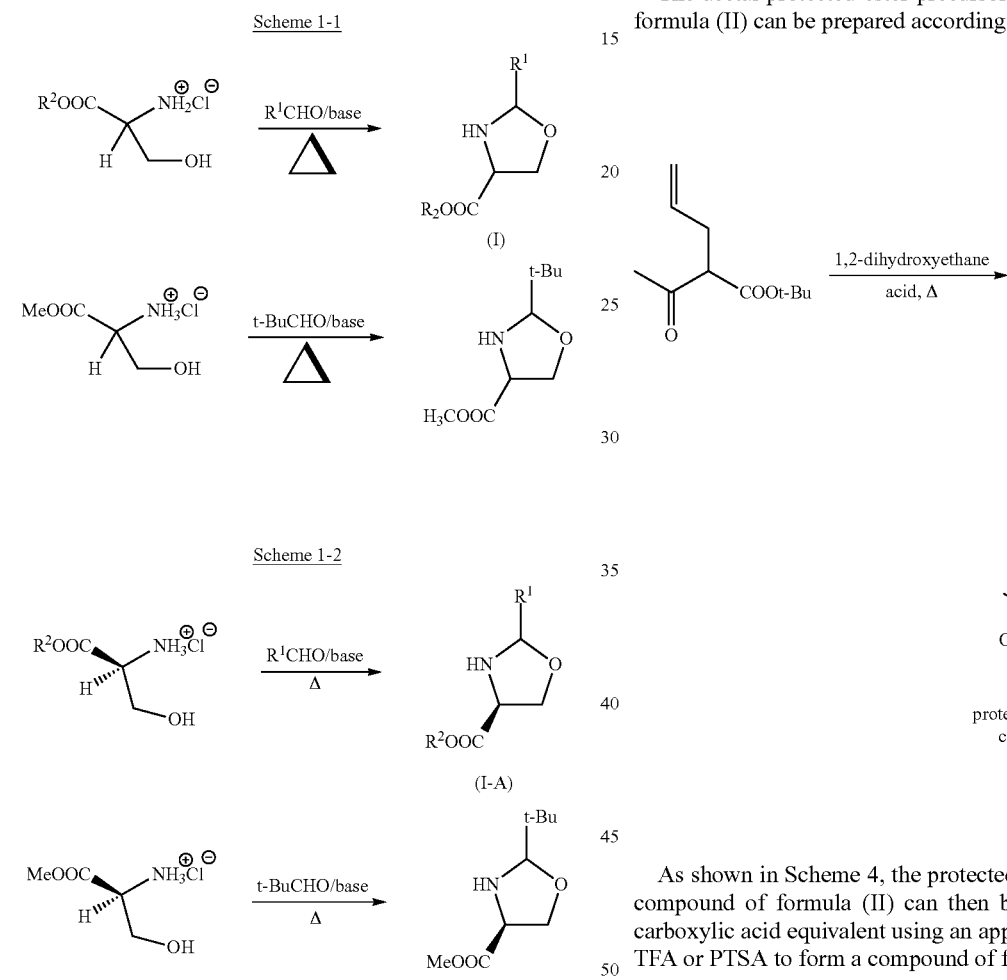

In some embodiments, a compound of formula (II) may be used as a starting material with a compound of formula (I). The compound of formula (II) can be synthesized according to Schemes 2, 3 and 4. The ester precursor of the compound of formula (II) can be prepared according to Scheme 2, starting with tert-butyl 3-oxobutanoate and a base (e.g., t-BuOK or NaH) and then adding an allyl halide.

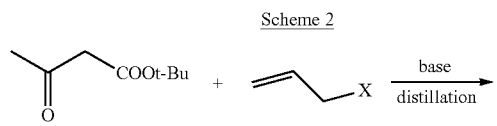

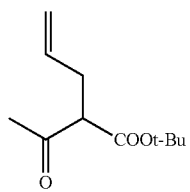

ester precursor of the compound of Formula II

The acetal protected ester precursor of the compound of formula (II) can be prepared according to Scheme 3.

protected ester precursor of the compound of formula II

As shown in Scheme 4, the protected ester precursor of a compound of formula (II) can then be hydrolyzed to the carboxylic acid equivalent using an appropriate acid such as TFA or PTSA to form a compound of formula (II).

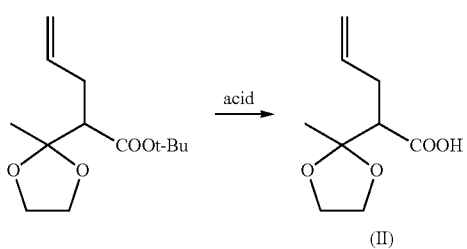

A method of preparing a compound of formula (VII) from the starting compounds of formulae (I) and (II) is shown below in Scheme 5.

Scheme 5

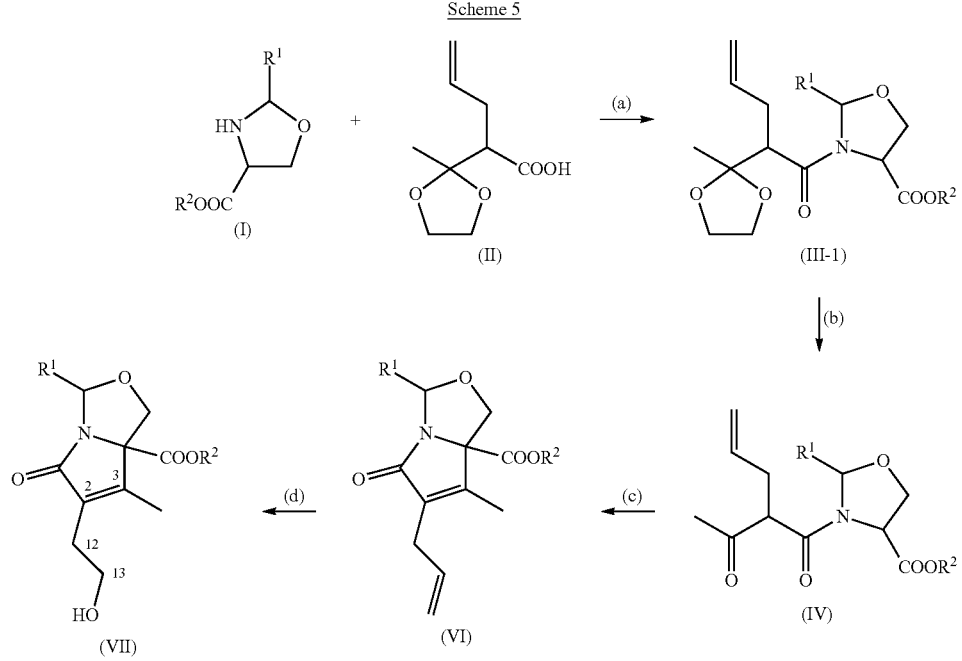

In step (a) of Scheme 5, a compound of formula (III-1) can be formed by reacting a compound of formula (I) with a compound of formula (II) under suitable conditions. In some embodiments, the $R^1$ group can be hydrogen, unsubstituted or substituted $C_{1-6}$ alkyl or unsubstituted or substituted aryl. In an embodiment, the $R^1$ group can be t-butyl. In some embodiments, $R^2$ can be selected from hydrogen, an unsubstituted or substituted $C_{1-6}$ alkyl, an unsubstituted or substituted aryl, and an unsubstituted or substituted arylalkyl. In some embodiments, $R^2$ can be an unsubstituted or substituted $C_{1-6}$ alkyl. In an embodiment, $R^2$ can be methyl. For example, a compound of formula (I) can be added to a mixture containing a compound of formula (II), a mild base (e.g., triethylamine or N-methyl piperidine) and an acylating agent such as methanesulfonyl chloride, trifluoromethanesulfonyl chloride or chloromethylformate.

As examples, the compounds of formulae (I), (II) and (III-1) may have the following structures and stereochemisty:

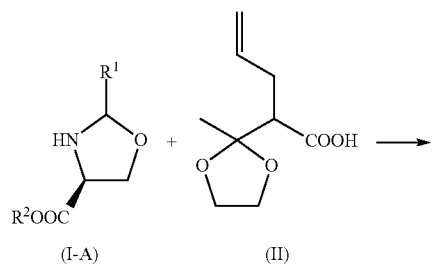

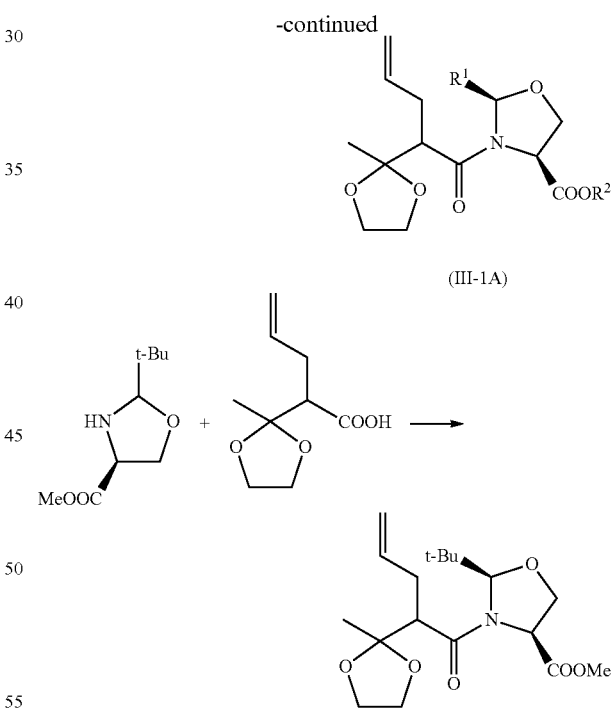

The compound of formula (III-1) can be deprotected to form a compound of formula (IV), as shown in step (b) of Scheme 5. One method for removing the acetyl protecting group includes reacting a compound of formula (III-1) with sodium iodide and a Lewis base such as cerium (III) chloride heptahydrate. A second method includes reacting a compound of formula (III-1) with iodine in acetone at an elevated temperature. Alternatively, a compound of formula (III-1) can be reacted with lithium tetrafluoroboride at an elevated temperature to form a compound of formula (IV).

Exemplary structures and stereochemistry of compounds of formulae (III-1) and (IV) are shown below:

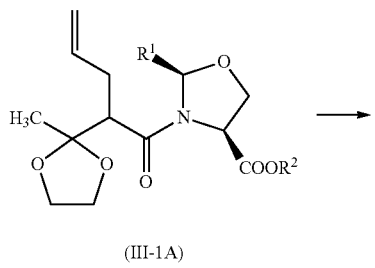

(III-1A)

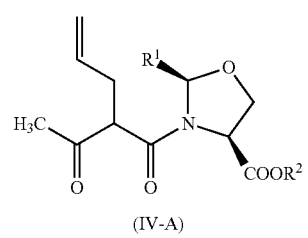

(IV-A)

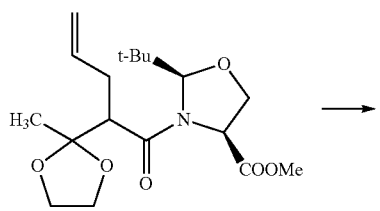

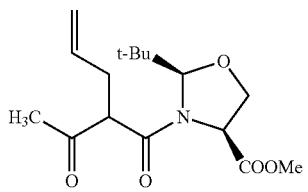

(IV-A)

As shown in step (c) of Scheme 5, treatment of a compound of formula (IV) with an appropriate base (e.g., t-BuOK, NaOMe, NaOEt or LDA) can induce an intramolecular aldol condensation reaction to form a compound of formula (VI).

In an embodiment, the compounds of formulae (IV) and (VI) may have the following structures and stereochemistry.

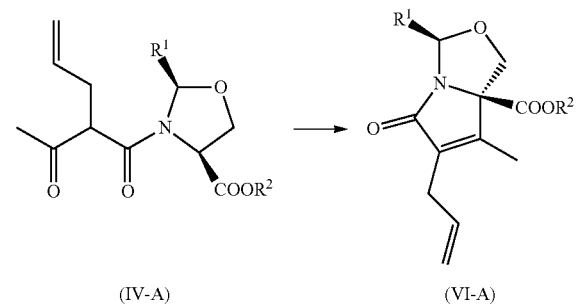

(IV-A)  (VI-A)

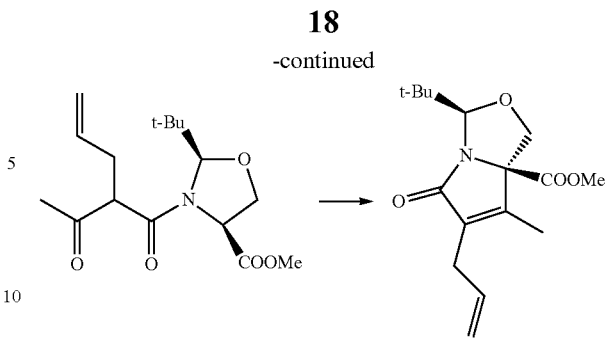

-continued

In step (d) of Scheme 5, the terminal double bond of the allyl substitutent at C-2 of the compound of formula (VI) can be converted to a primary hydroxyl group as shown by a compound of formula (VII). In some embodiments, the $R^1$ group can be hydrogen, unsubstituted or substituted $C_{1-6}$ alkyl or unsubstituted or substituted aryl. In an embodiment, the $R^1$ group can be t-butyl. In some embodiments, $R^2$ can be selected from hydrogen, an unsubstituted or substituted $C_{1-6}$ alkyl, an unsubstituted or substituted aryl, and an unsubstituted or substituted arylalkyl. In some embodiments, $R^2$ can be an unsubstituted or substituted $C_{1-6}$ alkyl. In an embodiment, $R^2$ can be methyl. Using methods known to those skilled in the art, the alkene may be oxidized to an aldehyde using an appropriate oxidizing agent (e.g., ozone, osmium tetraoxide and sodium periodate). The resulting aldehyde can then be reduced to an alcohol to give a compound of formula (VII) using an appropriate reducing agent such as $NaBH_4$, $LiAlH_4$ or diisobutylaluminum hydride (DIBALH).

Examples the structures and stereochemistry of the compounds of formulae (VI) and (VII) are:

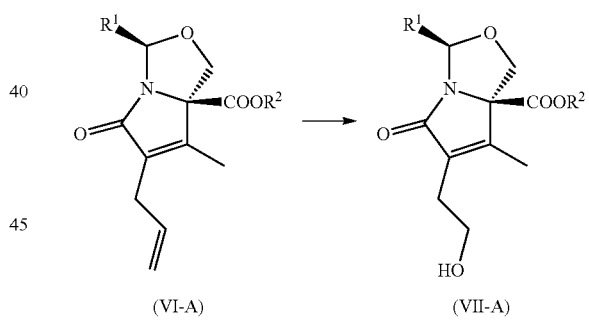

(VI-A)  (VII-A)

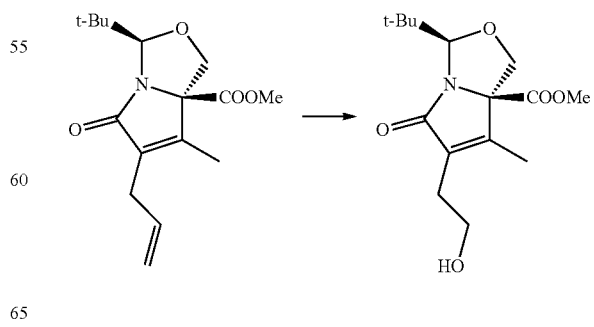

Alternatively, a compound of formula (VII) can be obtained by the methods shown below in Scheme 6.

Scheme 6

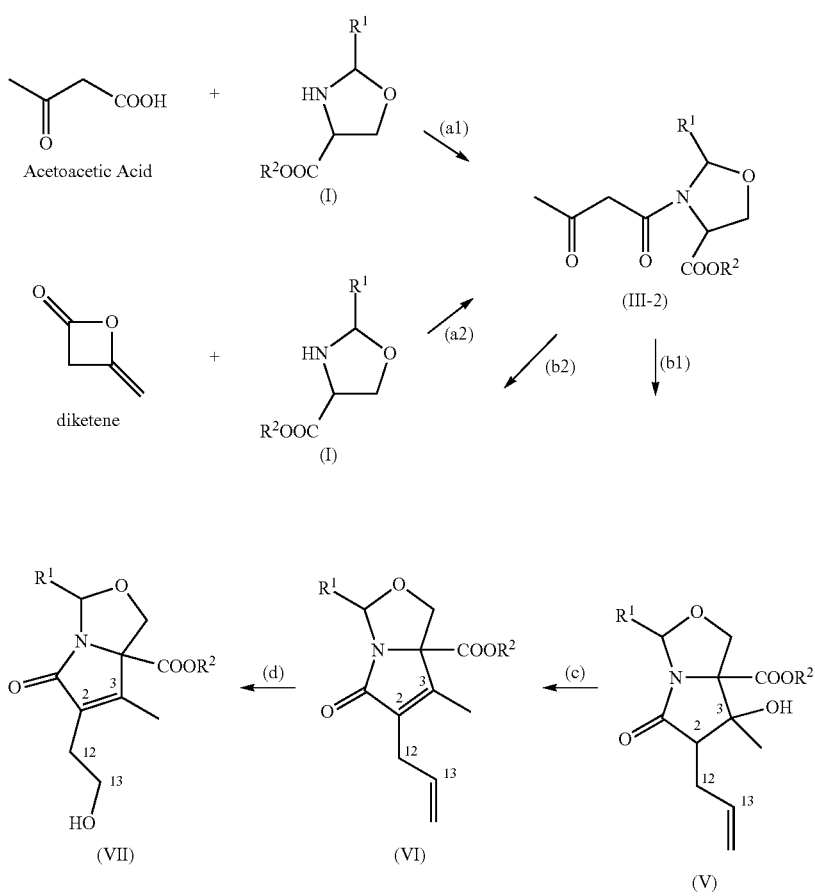

In some embodiments, acetoacetic acid may be used as a starting compound along with a compound of formula (I). Acetoacetic acid may prepared as shown in Scheme 6a by hydrolyzing tert-butyl-3-oxobutanoate with an appropriate acid such as TFA, p-toluenesulphonic acid (PTSA) or HCl.

Scheme 6a

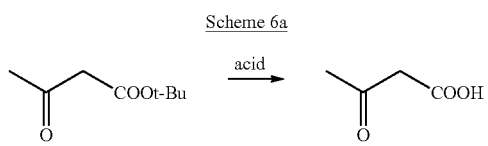

In step (a1) of Scheme 6, acetoacetic acid and a compound of formula (I) can be reacted together to form a compound of formula (III-2). In some embodiments, the $R^1$ group can be hydrogen, unsubstituted or substituted $C_{1-6}$ alkyl or unsubstituted or substituted aryl. In an embodiment, the $R^1$ group can be t-butyl. In some embodiments, $R^2$ can be selected from hydrogen, an unsubstituted or substituted $C_{1-6}$ alkyl, an unsubstituted or substituted aryl, and an unsubstituted or substituted arylalkyl. In some embodiments, $R^2$ can be an unsubstituted or substituted $C_{1-6}$ alkyl. In an embodiment, $R^2$ can be methyl. One method for forming a compound of formula (III-2) includes reacting a compound of formula (I) with acetoacetic acid and an appropriate coupling agent(s) such as dicyclohexylcarbodiimide, N,N'-diisopropylcarbodiimide, and/or 1-ethyl-3-(3-dimethylaminopropyl) carbodiimide.

A compound of formula (III-2) can also be obtained starting with diketene and a compound of formula (I). As shown in step (a2) of Scheme 6, diketene and a compound of formula (I) can be added together to form a compound of formula (III-2). In some embodiments, the $R^1$ group can be hydrogen, unsubstituted or substituted $C_{1-6}$ alkyl or substituted aryl. In an embodiment, the $R^1$ group can be t-butyl. In some embodiments, $R^2$ can be selected from hydrogen, an unsubstituted or substituted $C_{1-6}$ alkyl, an unsubstituted or substituted aryl, and an unsubstituted or substituted arylalkyl. In some embodiments, $R^2$ can be an unsubstituted or substituted $C_1$-6 alkyl. In an embodiment, $R^2$ can be methyl. The additional reaction of a compound of formulae (I) and diketene to form a β-keto amide can be facilitated through the use of a base. Suitable bases include, but are not limited to, amine bases (e.g., triethylamine) and pyridine.

In an embodiment, the compounds of formulae (I) and (III-2) can have the following structure and stereochemistry:

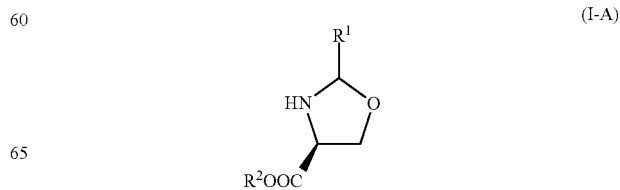

(III-2A)

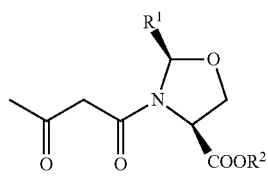

Scheme 7

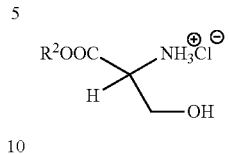 + R¹CHO 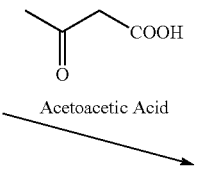 Acetoacetic Acid

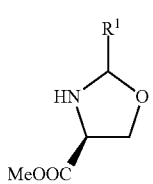

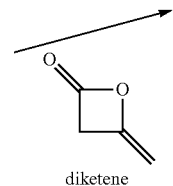 + R¹CHO 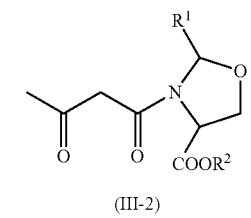
diketene

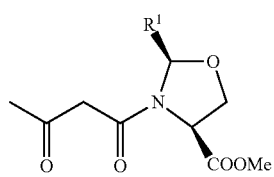

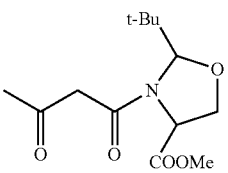
(III-2)

A compound of formula (III-2) can also be formed by combining together an aldehyde (for example, t-butylaldehyde), a compound having the structure

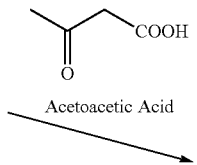 + t-BuCHO 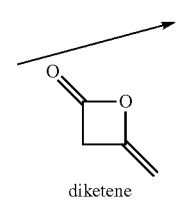 Acetoacetic Acid

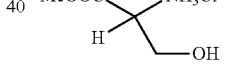

 + t-BuCHO
diketene and acetoacetic acid or diketene, without isolating any of the intermediate compounds formed. In an embodiment,

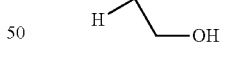

can be a serine ester salt such as a (L)-serine methylester salt. To facilitate the reaction, an appropriate base can be used, for example, an amine base such as triethylamine or pyridine.

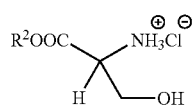

-continued

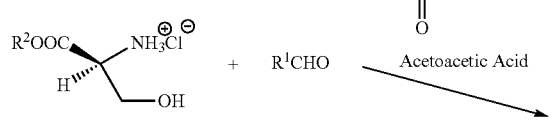

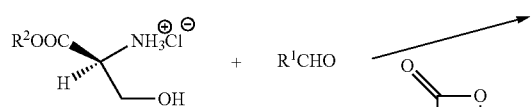

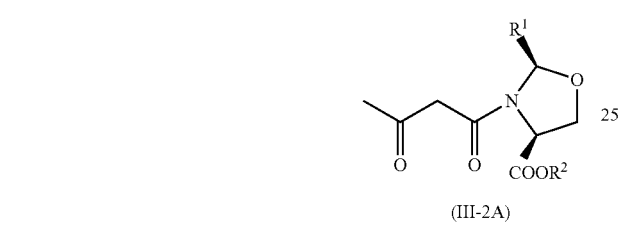

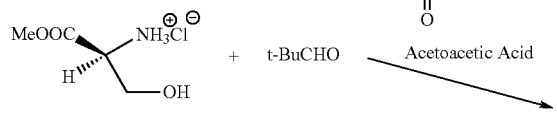

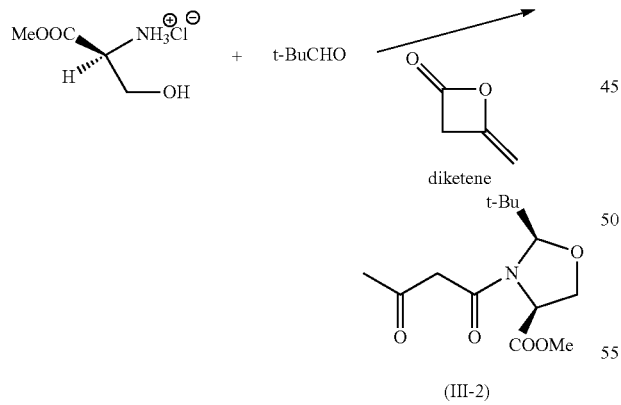

(III-2)

The compound of formula (III-2) can be converted to a compound of formula (V) through an intramolecular aldol reaction and alkylation, as shown in step (b1) of Scheme 6. The compound of formula (III-2) can be alkylated using methods known to those skilled in the art. For example, a compound of formula (III-2) can be reacted with an appropriate alkylating agent such as allyl bromide. The alkylated compound of formula (III-2) can then undergo an intramolecular aldol reaction to form the compound of formula (V).

In some embodiments, the intramolecular aldol reaction can be induced using an appropriate base such as carbonate or bicarbonate base. Examples of suitable carbonate and bicarbonate bases include, but are not limited to, sodium carbonate, potassium carbonate, cerium (IV) carbonate and sodium bicarbonate. In an embodiment, the base can be potassium carbonate. In an embodiment, the reaction can produce one or more diastereomers of a compound of formula (V), including a compound of formula (Va-A), a compound of formula (Vb-A), a compound of formula (Vc-A) and a compound of formula (Vd-A).

Exemplary structures and stereochemistry of compounds of formulae (III-2) and (V) are shown below:

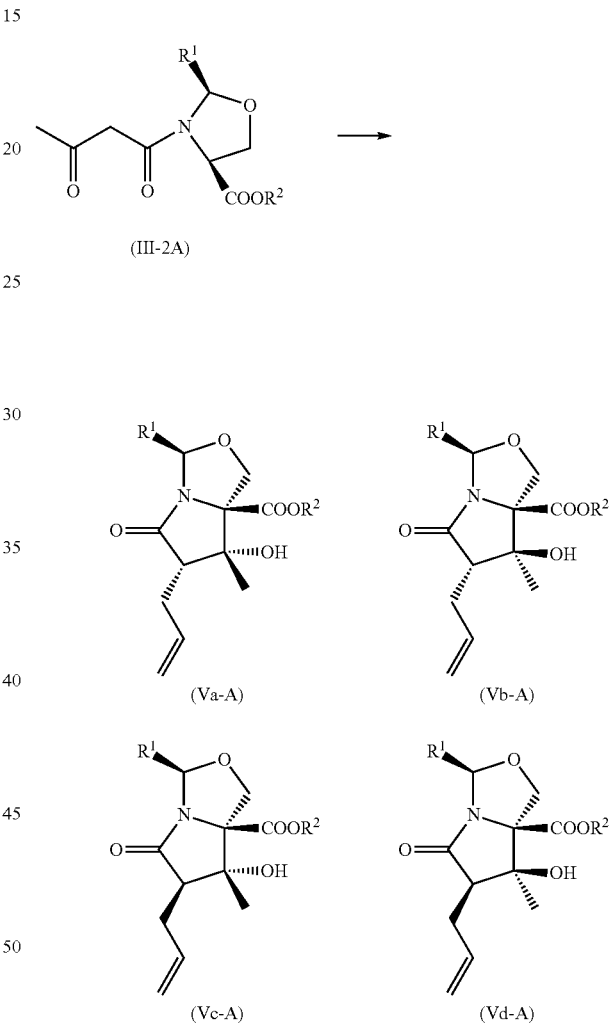

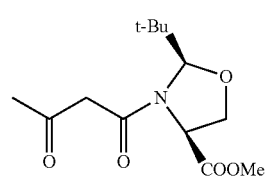

-continued

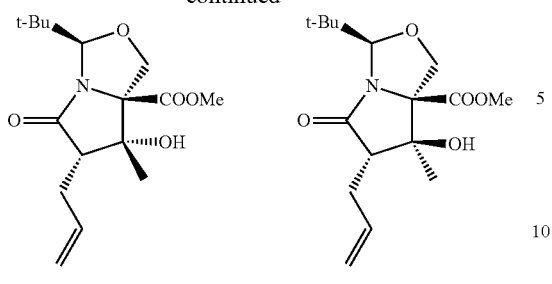

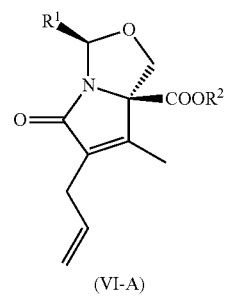

(VI-A)

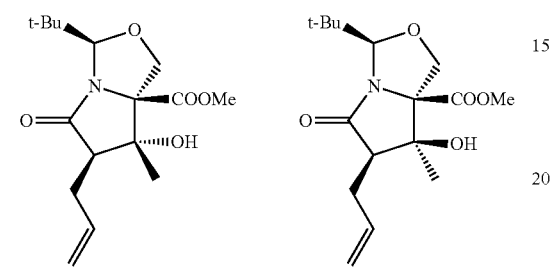

The double bond between C-2 and C-3 can be obtained by dehydrating a compound of formula (V) to form a compound of formula (VI), as shown in step (c) of Scheme 6. A compound of formula (V) can be dehydrated, for example, by reacting the compound of formula (V) with an appropriate base, such as an amidine compound. Two examples of suitable amidine compounds include, but are not limited to, 1,8-diazabicyclo[5.4.0]undec-7-ene (DBU) and 1,5-diazabicyclo[4.3.0]non-5-ene (DBN). One or more of the aforementioned diastereomers of a compound of formula (V), such as a compound of formula (Va-A), a compound of formula (Vb-A), a compound of formula (Vc-A) and a compound of formula (Vd-A), can be used to obtain a compound of formula (VI).

In an embodiment, the compounds of formulae (V) and (VI) can have the following structures and stereochemistry:

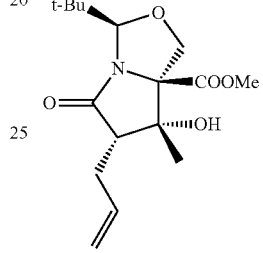

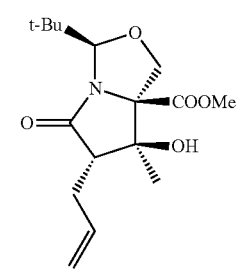

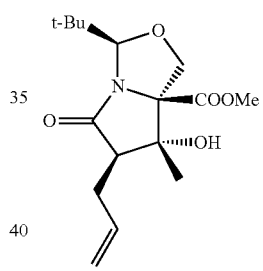

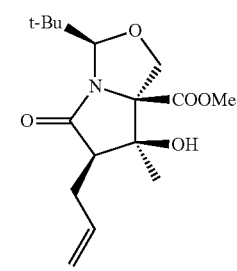

⟶

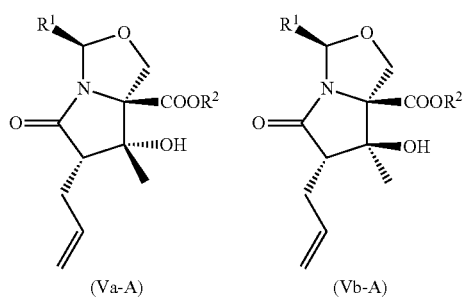

(Va-A)   (Vb-A)

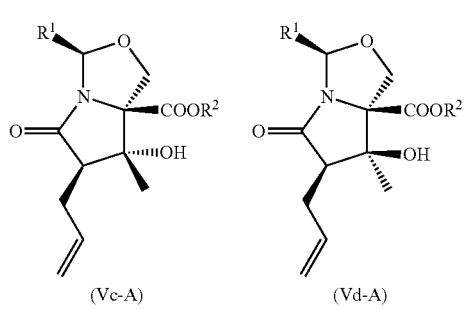

(Vc-A)   (Vd-A)

⟶

In another embodiment, a compound of formula (VI) can be obtained from a compound of formula (III-2), as shown in step (b2) of Scheme 6. In one reaction vessel, a compound of formula (III-2) can be alkylated, undergo an intramolecular aldol condensation reaction in the presence of an appropriate base to obtain a compound of formula (VI). As described previously, allyl bromide (an alkylating reagent), and an amidine compound (base) can be used for obtaining a compound of formula (VI) from a compound of formula (III-2).

As examples, the compounds of formulae (III-2) and (VI) may have the following structures and stereochemistry:

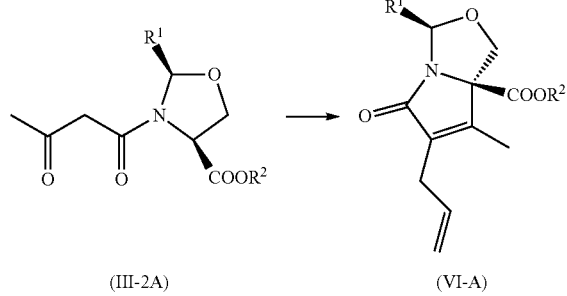

(III-2A) (VI-A)

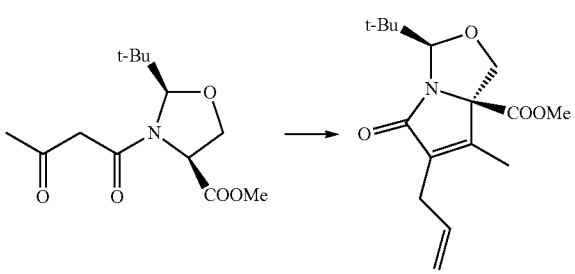

As discussed previously, a compound of formula (VI) can be used to synthesize a compound of formula (VII) as described herein. For example, the alkene may be oxidized to an aldehyde using an appropriate oxidizing agent (e.g., ozone, osmium tetraoxide and sodium periodate). The aldehyde can then be reduced to an alcohol to give a compound of formula (VII) using an appropriate reducing agent such as $NaBH_4$, $LiAlH_4$ or diisobutylaluminum hydride (DIBALH).

Figure 4A:
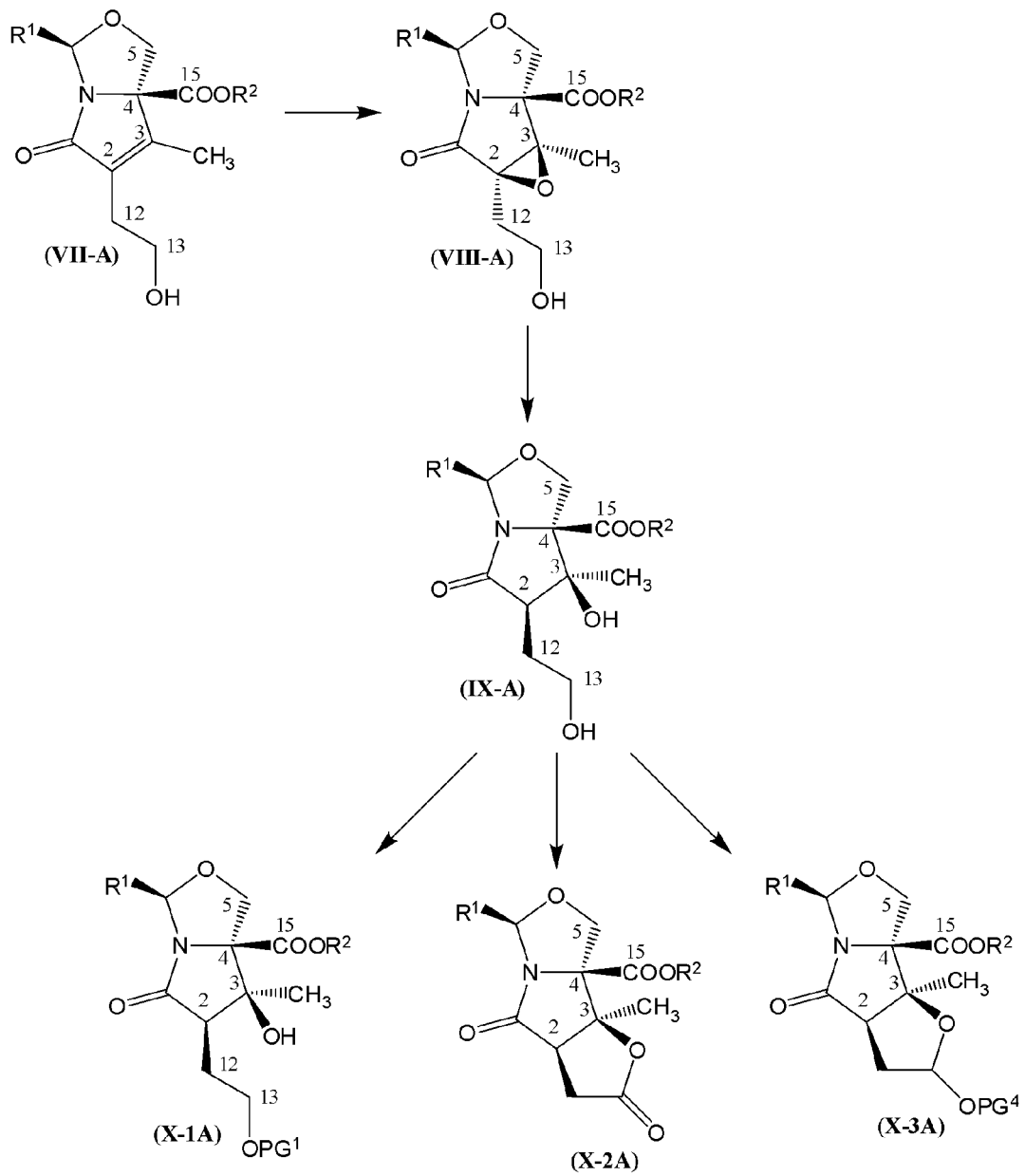

A compound of formula (IX) can be synthesized starting with a compound of formula (VII) is shown in Scheme 8. One example of this synthesis is shown in FIG. 4a.

Scheme 8

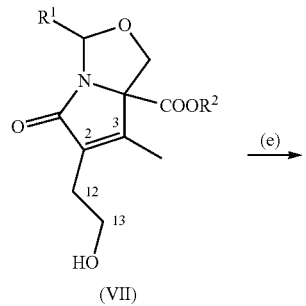

(VII)

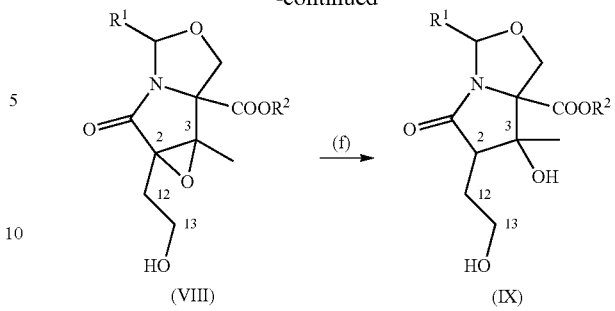

(VIII) (IX)

A compound of formula (VII) can be oxidized to form a compound of formula (VIII) in which an epoxide is formed that includes C-2 and C-3. Various methods are known to those skilled in the art to form the epoxide. In some embodiments, formation of the epoxide can be stereospecific. In an embodiment, formation of the epoxide creates an (R)-stereocenter at C-2 and an (R)-stereocenter at C-3. By forming the epoxide stereospecifically, the desired stereochemistry present in Salinosporamide A and its analogs at C-2 and C-3 can be established upon cleavage of the epoxide. In an embodiment, the epoxide is formed using an appropriate peroxide such as tert-butyl hydroperoxide, meta-chloroperoxybenzoic acid (mCPBA) or dimethyldioxirane (DMDO). If needed, a base (e.g., benzyltrimethyl ammonium hydroxide) can also be employed to facilitate the epoxidation.

In an embodiment, the compounds of formulae (VII) and (VIII) can have the following structures and stereochemistry:

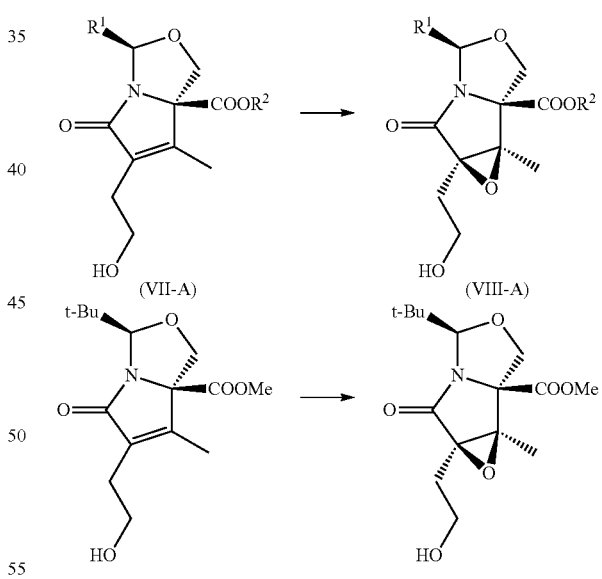

As shown in step (f), the epoxide ring can be opened to form a compound of formula (IX). The epoxide ring may be cleaved using an appropriate reducing agent. For example, the epoxide ring may be opened using samarium iodide. In some embodiments, cleavage of the epoxide can generate an (R)-stereocenter at C-2 and an (S)-stereocenter at C-3. As stated previously, by forming the epoxide stereospecifically and then cleaving the epoxide the desired chirality at C-2 and C-3 can be obtained. Furthermore, additional steps that may be required to attain the stereochemistry at the C-2 and/or C-3 using another method can be avoided.

Examples of the structure and stereochemistry of compounds of formulae (VIII) and (IX) are shown below:

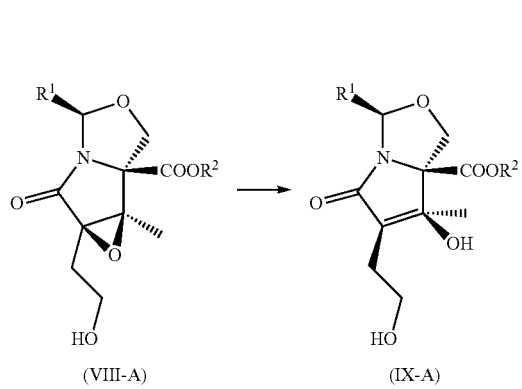

(VIII-A) → (IX-A)

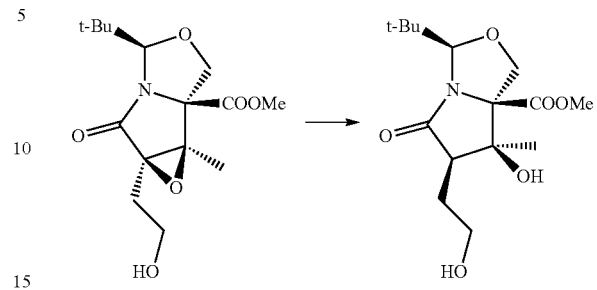

Figure 4B:
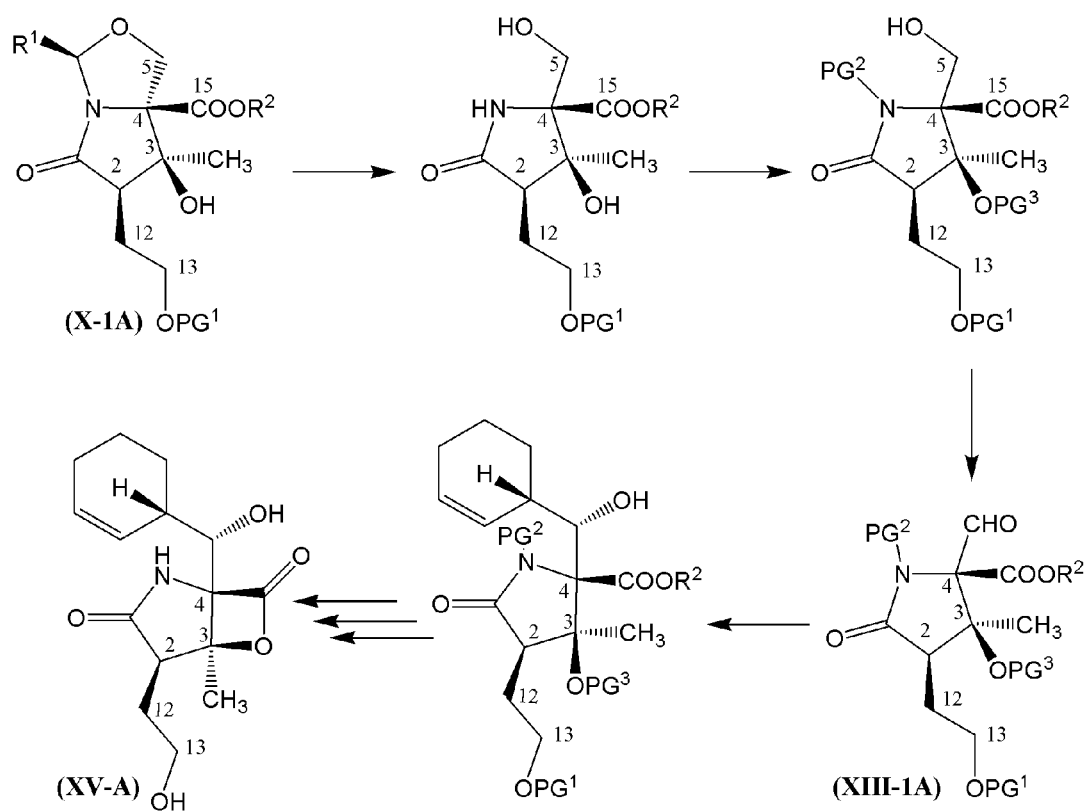

As shown in FIGS. 2-3 and 4a-d, several methods can be used to form a compound of formula (XV). One method for forming a compound of formula (XV) starting from a compound of formula (IX) is shown below in Scheme 9. An example of the synthesis of a compound of formula (XV) from a compound of formula (IX) is shown in FIGS. 4a-b.

Scheme 9

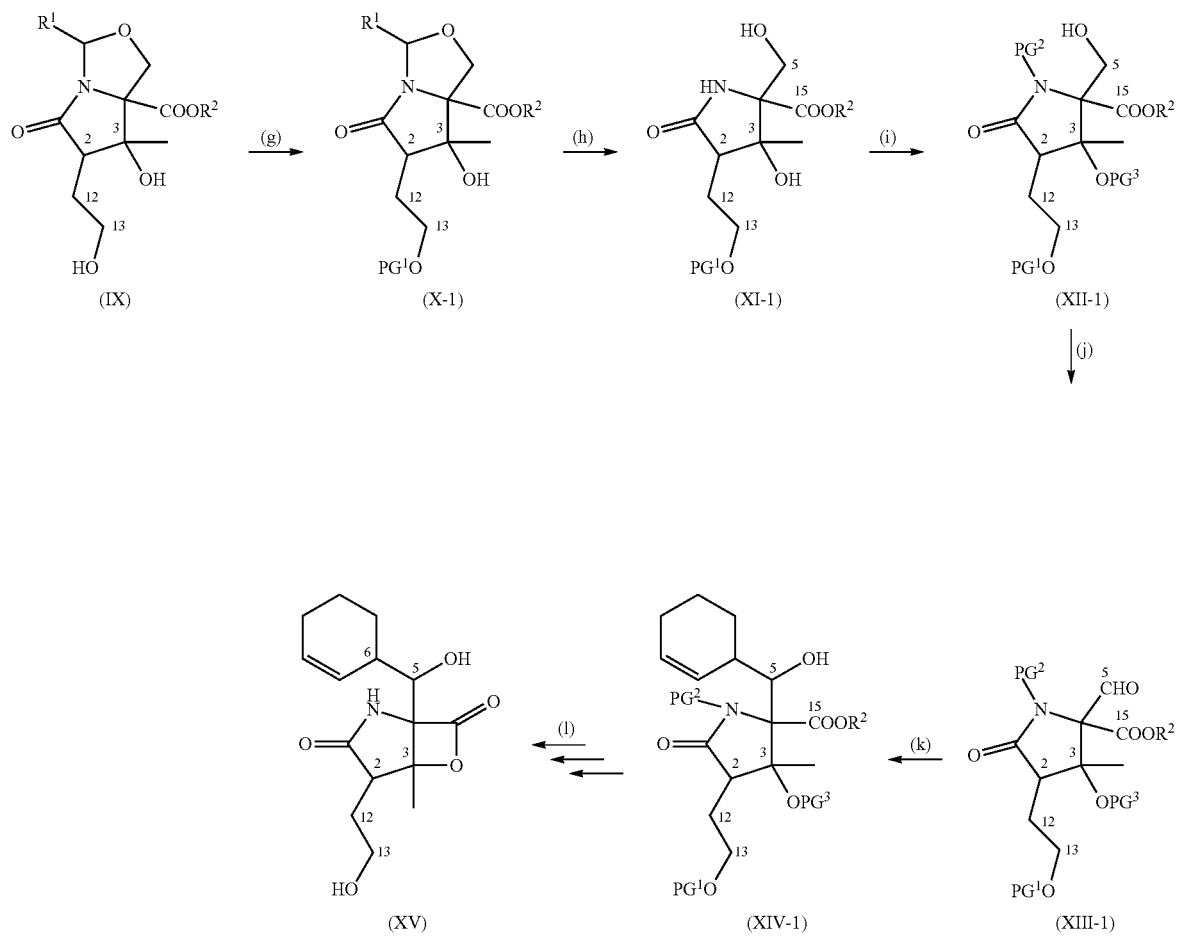

If desired, the C-13 primary hydroxy group of a compound of formula (IX) can be protected using a protecting group moiety to form a compound of formula (X-1), as shown in step (g) of Scheme 9. In some embodiments, $PG^1$ can be selected from substituted or unsubstituted arylcarbonyls (e.g., benzoyl); substituted or unsubstituted alkylcarbonyls (e.g. acetyl); substituted or unsubstituted arylalkylcarbonyls; substituted or unsubstituted alkoxycarbonyls; substituted or unsubstituted aryloxycarbonyls; substituted methyl ether (e.g. methoxymethyl); substituted ethyl ether; substituted or substituted benzyl (e.g. benzyl, 4-methoxybenzyl); tetrahydropyranyl ether; silyl ethers (e.g., trimethylsilyl, triethylsilyl, triisopropylsilyl, t-butyldimethylsilyl, or t-butyldiphenylsilyl); esters, carbonates (e.g. methoxymethylcarbonate); and sulfonates (e.g. mesylate, tosylate). In some embodiments, the $R^1$ group can be hydrogen, unsubstituted or substituted $C_{1-6}$ alkyl or unsubstituted or substituted aryl. In an embodiment, the $R^1$ group can be t-butyl. In some embodiments, $R^2$ can be selected from hydrogen, an unsubstituted or substituted $C_{1-6}$ alkyl, an unsubstituted or substituted aryl, and an unsubstituted or substituted arylalkyl. In some embodiments, $R^2$ can be an unsubstituted or substituted $C_{1-6}$ aln an embodiment, $R^2$ can be methyl.

In an embodiment, compounds of formulae (IX) and (X-1) can have the following structures and stereochemistry:

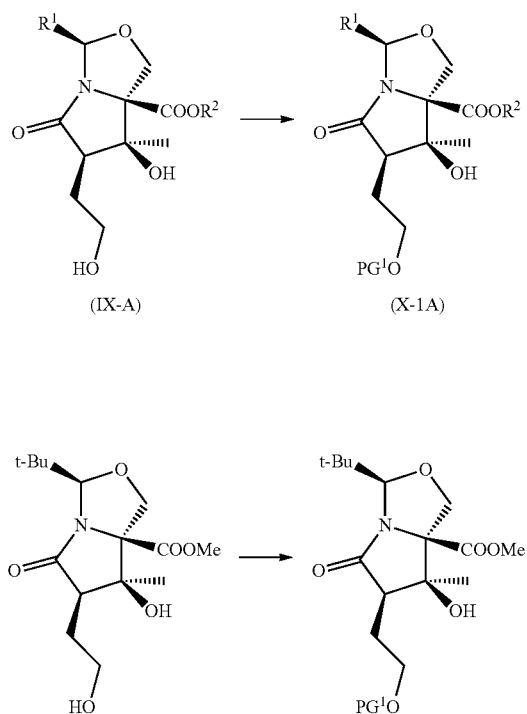

As shown in step (h), the aminal group of a compound of formula (X-1) can be cleaved to form a compound of formula (XI-1). In an embodiment, the aminal can be cleaved using a suitable acid (e.g. triflic acid, HCl, PTSA, PPTS, TFA, camphor sulfonic acid).

Exemplary structures and stereochemistry of the compounds of formulae (X-1) and (XI-1) are shown below:

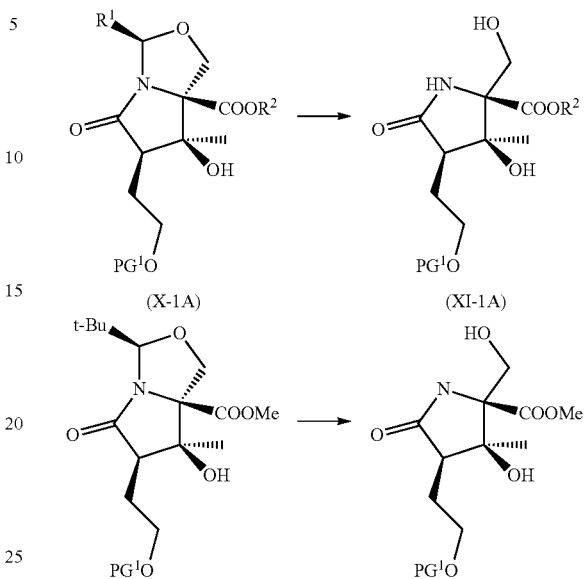

Optionally, the lactam nitrogen and/or the tertiary hydroxy group of a compound of formula (XI-1) may be protected using a protecting group moiety indicated by $PG^2$ and $PG^3$, respectively. Examples of suitable protecting groups include, but are not limited to the following: substituted or unsubstituted arylcarbonyls (e.g., benzoyl); substituted or unsubstituted alkylcarbonyls (e.g. acetyl); substituted or unsubstituted arylalkylcarbonyls; substituted or unsubstituted alkoxycarbonyls; substituted or unsubstituted aryloxycarbonyls; substituted methyl ether (e.g. methoxymethyl); substituted ethyl ether; substituted or substituted benzyl (e.g. benzyl, 4-methoxybenzyl); tetrahydropyranyl ether; silyl ethers (e.g., trimethylsilyl, triethylsilyl, triisopropylsilyl, t-butyldimethylsilyl, or t-butyldiphenylsilyl); esters, carbonates (e.g. methoxymethylcarbonate); and sulfonates (e.g. mesylate, tosylate). In some embodiments, it may be desirable to protect the tertiary hydroxyl group and/or lactam nitrogen group to avoid undesirable side reactions and/or make isolation of the desired compounds easier. In an embodiment, the lactam nitrogen is protected to facilitate the stereospecific addition of the 2-cyclohexenyl moiety. As an example, by protecting the lactam nitrogen with a bulky protecting group such as benzyl groups, the 2-cyclohexenyl ring will add to C-5 to form an (S)-stereocenter. Moreover, having a bulky protecting group on the lactam nitrogen also can facilitate in establishing an (S)-stereocenter at C-6. In some embodiments, $PG^2$ and $PG^3$ are the same. In other embodiments, $PG^2$ and $PG^3$ are different protecting groups. In an embodiment, the protecting groups, $PG^2$ and $PG^3$, can be added almost simultaneously. In another embodiment, the protecting groups, $PG^2$ and $PG^3$, can be added sequentially. For example, in some embodiments, $PG^2$ can be added before $PG^3$. In other embodiments, $PG^3$ can be added before $PG^2$. If protection of the lactam nitrogen and/or tertiary hydroxy group is unnecessary and/or undesired, the remaining steps of Scheme 9 can be carried out wherein $PG^2$ and $PG^3$ are both hydrogen and the steps that show the addition and removal of the protecting group(s), $PG^2$ and/or $PG^3$, can be excluded. Alternatively, the tertiary hydroxy group on C-3 can be protected in compounds previous to a compound of formula (XII-1). For example, the tertiary hydroxy group can be protected on a compound of formula (X-1) and/or a compound of formula (XI-1) using a suitable protecting group such as those described previously.

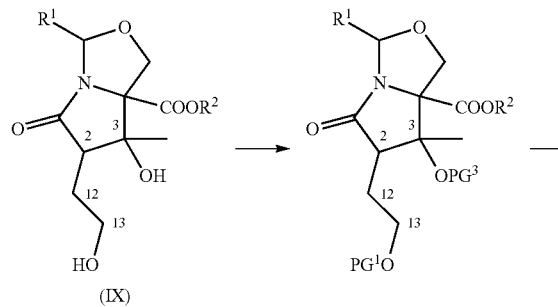

(IX)

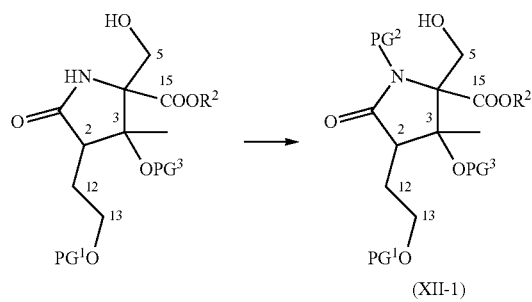

(XII-1)

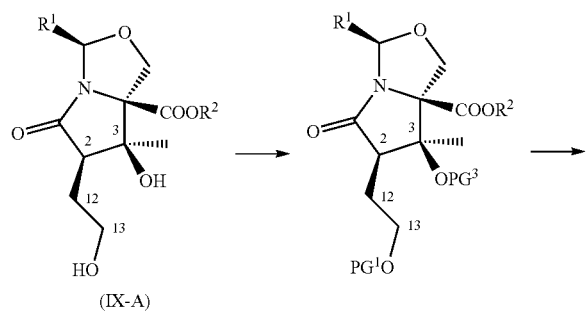

(IX-A)

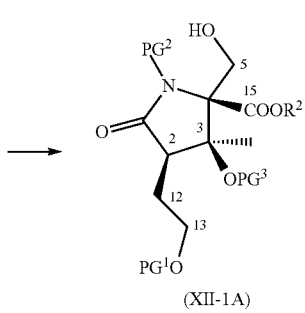

(XII-1A)

As an example, the compounds of formulae (XI-1) and (XII-1) may have the following structures and stereochemistry:

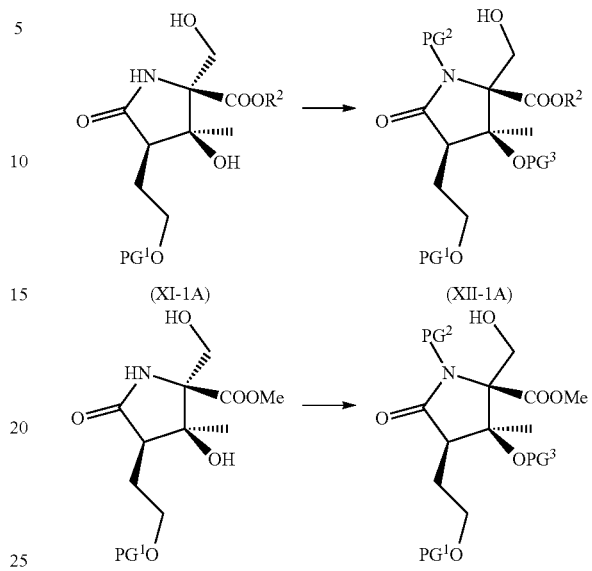

(XI-1A)　　(XII-1A)

The C-5 primary hydroxy group of formula (XII-1) can be oxidized to an aldehyde to form a compound of formula (XIII-1) using an appropriate oxidizing agent. Appropriate oxidizing agents are disclosed herein. In an embodiment, the C-5 primary hydroxy group can be oxidized using Dess-Martin periodinane, TPAP/NMO, Swern oxidation reagent, PCC, and/or PDC.

In an embodiment, the compounds of formulae (XII-1) and (XIII-1) may have the following structures and stereochemistry:

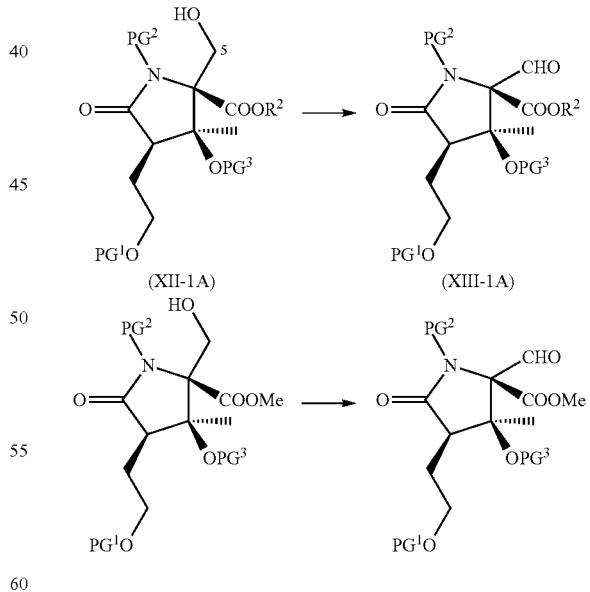

(XII-1A)　　(XIII-1A)

In step (k) of Scheme 9, a cyclohexenyl ring can be added to the C-5 position of a compound of formula (XIII-1) to form a compound of formula (XIV-1). The alkylation methods are known to those skilled in the art. For example, the addition of the cyclohexenyl ring may be accomplished using an organometallic moiety (e.g., zinc chloride) having a cyclohexenyl group.

A non-limiting list of suitable organometallic moieties include organomagnesium compounds, organolithium compounds, organotin compounds, organocuprates compounds, organozinc, and organopalladium compounds, metal carbonyls, metallocenes, carbine complexes, and organometalloids (e.g., organoboranes and organosilanes). In some embodiments, the organometallic moiety can be selected from 2-cyclohexenyl-$MgR^4$, 2-cyclohexenyl-$ZnR^4$, 2-cyclohexenyl-Li, (2-cyclohexenyl)$_p$-$B(R^4)_{3-p}$, and (2-cyclohexenyl)$_q$-Sn$(R^4)_{4-q}$; wherein $R^4$ can selected from halogen, or substituted or unsubstituted variants of the following: alkyl, alkenyl, cycloalkyl, aryl, arylalkyl, isopinocampheyl, hydroxy, alkoxy, and carbonylalkoxy, wherein if more than one $R^4$ is present, the $R^4$ groups can optionally be bond together to form an optionally substituted cycloalkyl (e.g., 9-BBN), optionally substituted cycloalkenyl, optionally substituted heteroalkyl or optionally substituted heteroalkenyl ring; p can be an integer from 1 to 3; and q can be an integer from 1 to 4. In an embodiment, the organometallic moiety can be (2-cyclohexenyl)$_p$-$B(R^4)_{3-p}$. In some embodiments, the organometallic moiety can be (2-cyclohexenyl)$_p$-$B(R^4)_{3-p}$, p is 1, and the two $R^4$ groups are taken together to form an optionally substituted cycloalkyl. In an embodiment, the organometallic moiety can be 2-cyclohexenyl-$MgR^4$. In some embodiments, the organometallic moiety can be 2-cyclohexenyl-$MgR^4$ and $R^4$ is a halogen (e.g., chlorine).

In some embodiments, the organometallic moiety can be 2-cyclohexenyl-$ZnR^4$. In embodiment, 2-cyclohexenyl-$ZnR^4$ can be 2-cyclohexenyl-ZnCl Exemplary structures and stereochemistry for the compounds of formulae (XIII-1) and (XIV-1) include:

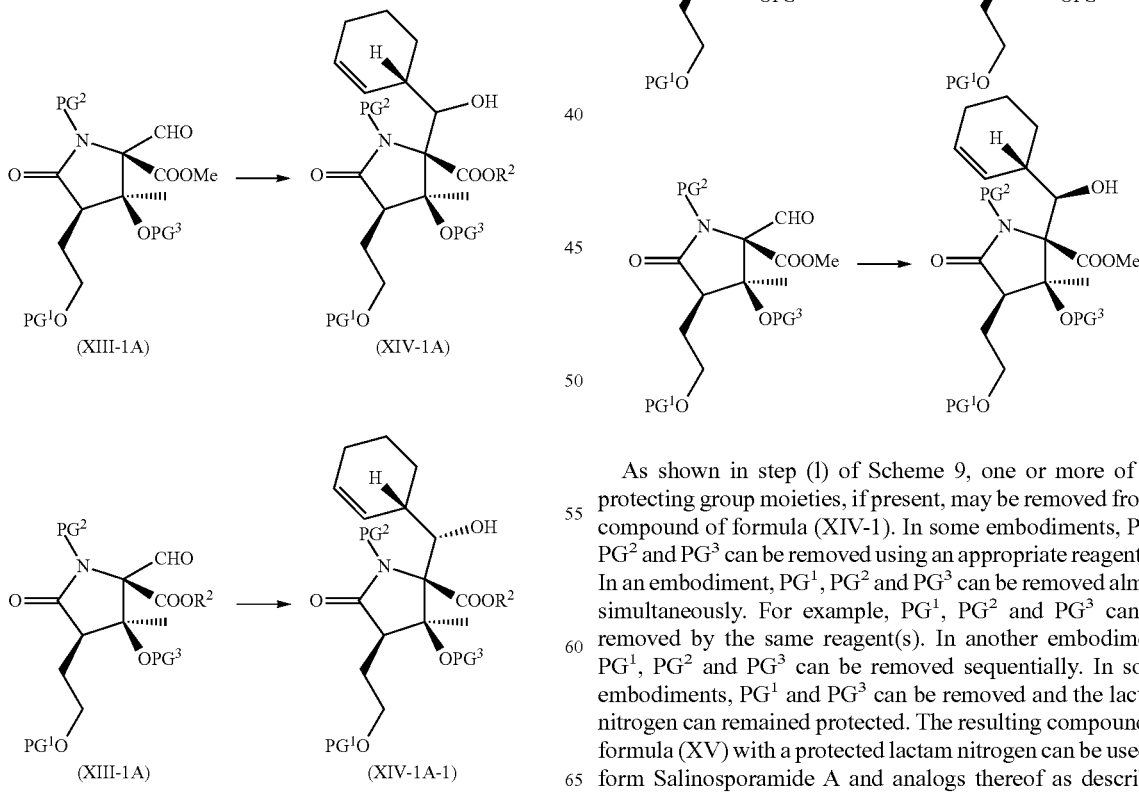

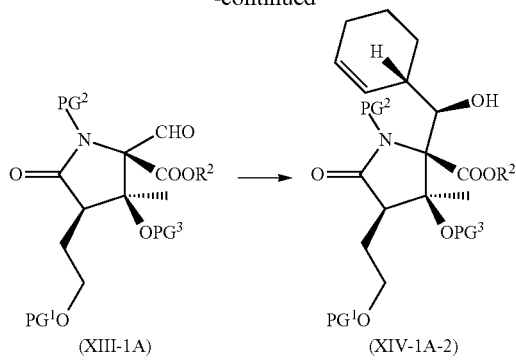

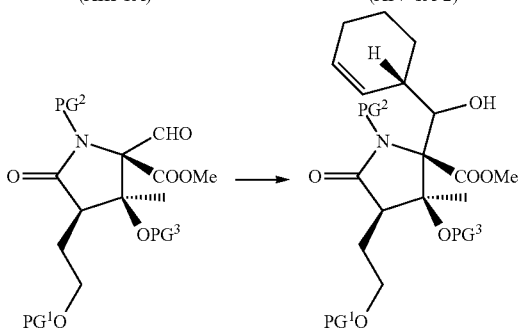

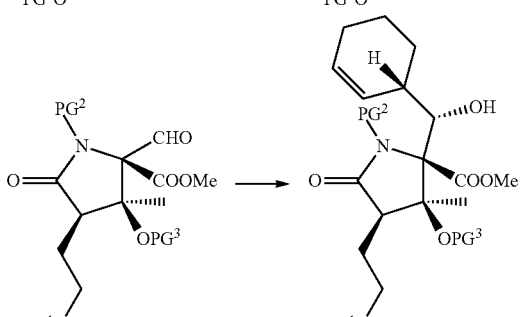

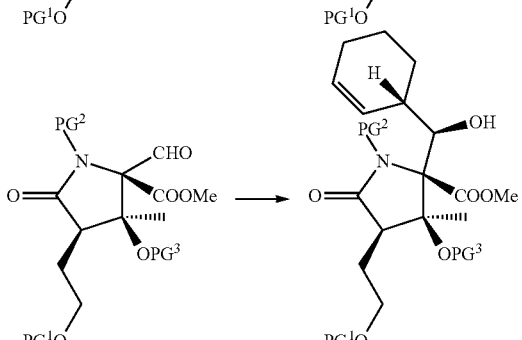

As shown in step (l) of Scheme 9, one or more of the protecting group moieties, if present, may be removed from a compound of formula (XIV-1). In some embodiments, $PG^1$, $PG^2$ and $PG^3$ can be removed using an appropriate reagent(s). In an embodiment, $PG^1$, $PG^2$ and $PG^3$ can be removed almost simultaneously. For example, $PG^1$, $PG^2$ and $PG^3$ can be removed by the same reagent(s). In another embodiment, $PG^1$, $PG^2$ and $PG^3$ can be removed sequentially. In some embodiments, $PG^1$ and $PG^3$ can be removed and the lactam nitrogen can remained protected. The resulting compound of formula (XV) with a protected lactam nitrogen can be used to form Salinosporamide A and analogs thereof as described herein. After formation of Salinosporamide A or an analog thereof, the protecting group on the lactam nitrogen can be removed. The protecting group, PG², can be removed using methods known to those skilled in the art. For example, PG² can be removed using one or more of the following reagents: 2,3-dichloro-5,6-dicyanobenzoquinone DDQ, ceric ammonium nitrate (CAN), TFA (trifluoroacetic acid) and hydrogen/ Pd—C. Similarly, PG¹ and PG³ can be removed at any suitable time during the synthesis. In some embodiments, PG³ can be removed at any time before the formation of the 4-membered heterocyclic ring. Likewise, PG¹ can be removed anytime before the addition of the desired group to C-13.

A 4-membered heterocyclic ring can be formed using methods known to those skilled in the art to give a compound of formula (XV) as shown in step (l) in Scheme 9. For example, a beta-lactone can formed using an appropriate base (e.g., BOPCl/pyridine, triethylamine) to induce lactonization. In an embodiment, the C-15 ester can first be transformed to a carboxylic acid, an activated acid (e.g., acid halide), or an activated ester (e.g., p-nitrophenyl ester, pentafluorophenyl ester, pentafluoroethyl ester, trifluoroethyl ester, trichloroethyl ester, a thioester, etc.) before being treated with an appropriate reagent to induce the lactonization reaction. In an embodiment, the C-15 carboxylic acid can be treated with an appropriate base to affect the lactonization reaction.

In an embodiment, compounds of formulae (XIV-1) and (XV) can have the following structure and stereochemistry:

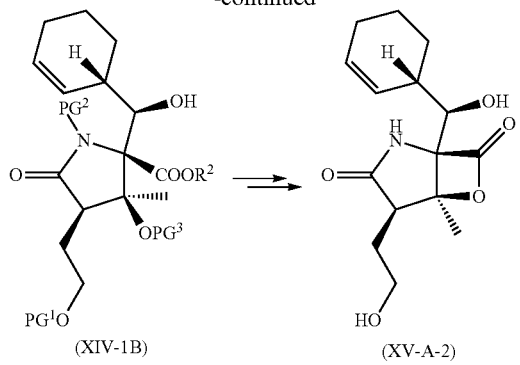

(XIV-1B) → (XV-A-2)

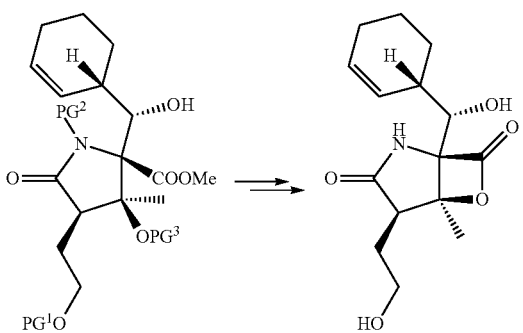

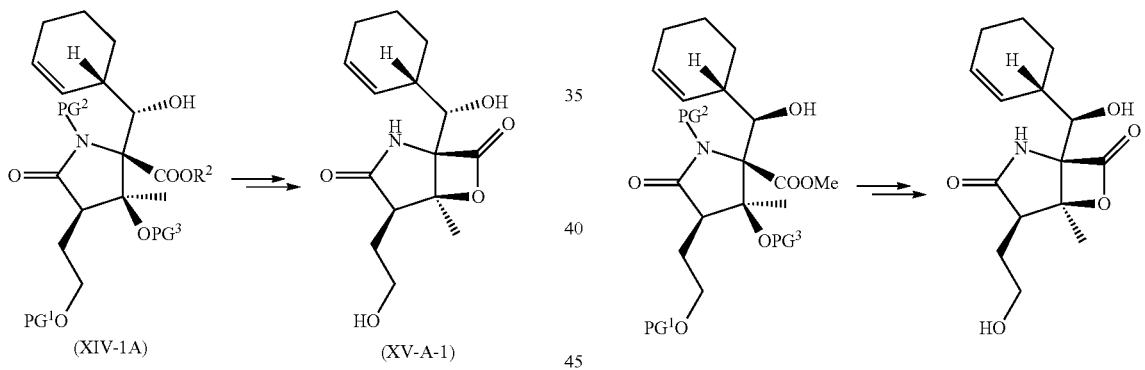

(XIV-1A) → (XV-A-1)

Figure 4C:
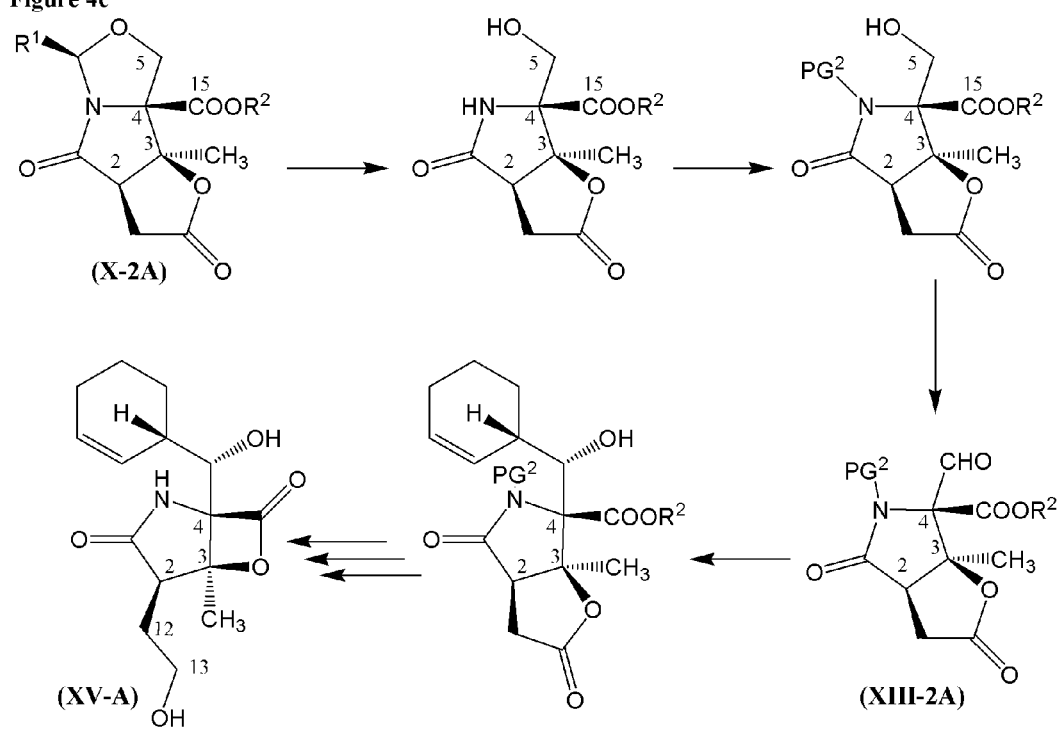

An alternative method for forming a compound of formula (XV) from a compound formula (IX) is shown in Scheme 10. An example of this synthesis is shown in FIGS. 4a and 4c.

Scheme 10

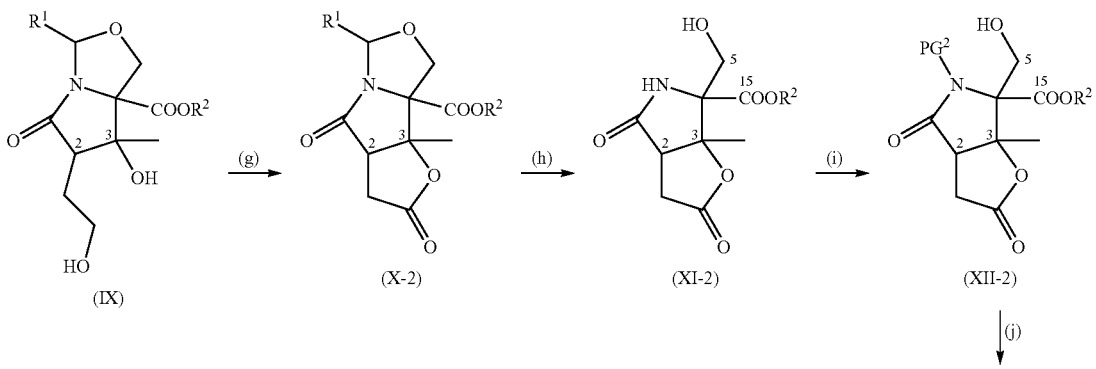

(IX) (g)→ (X-2) (h)→ (XI-2) (i)→ (XII-2)

↓(j)

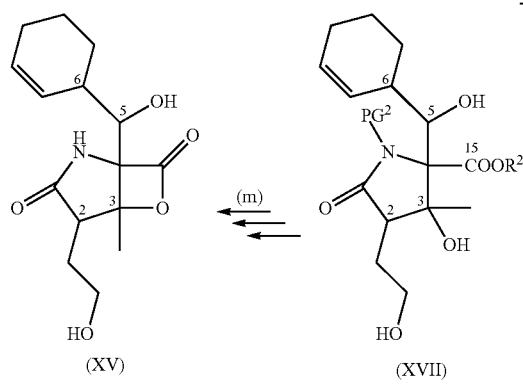

(XV) ← (m) ← (XVII) ← (l) ← (XIV-2) ← (k) ← (XIII-2)

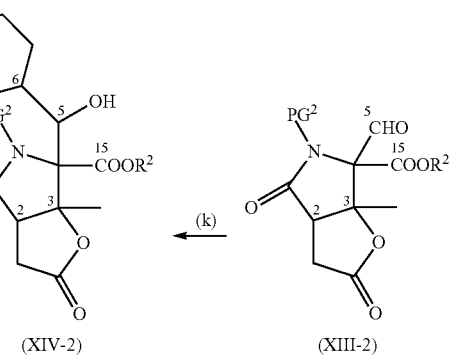

As shown in step (g) in Scheme 10, a 5-membered lactone can be formed by reacting a compound of formula (IX) with an appropriate oxidizing agent. In some embodiments, the $R^1$ group can be hydrogen, unsubstituted or substituted $C_{1-6}$ alkyl or unsubstituted or substituted aryl. In an embodiment, the $R^1$ group can be t-butyl. In some embodiments, $R^2$ can be selected from hydrogen, an unsubstituted or substituted $C_{1-6}$ alkyl, an unsubstituted or substituted aryl, and an unsubstituted or substituted arylalkyl. In some embodiments, $R^2$ can be an unsubstituted or substituted $C_{1-6}$ alkyl. In an embodiment, $R^2$ can be methyl. Appropriate oxidizing agents include, but are not limited to, pyridinium chlorochromate (PCC), $KMnO_4$, $CrO_3$, $Na_2Cr_2O_7$. In an embodiment, the oxidizing agent can be pyridinium chlorochromate (PCC). The resulting oxidized compound can then undergo an intramolecular cyclization reaction to form a compound of formula (X-2). In some embodiment, the C-13 primary alcohol can be oxidized to an aldehyde. The aldehyde and C-3 tertiary alcohol can react together to form a hemi-acetal via an intramolecular cyclization reaction. The hemi-acetal can then be further oxidized to a lactone. In another embodiment, the C-13 primary alcohol can be oxidized to a carboxylic acid. The resulting carboxylic acid and C-3 tertiary alcohol then can cyclize together to form the 5-membered lactone. In an embodiment, forming the 5-membered lactone can be advantageous to prevent the formation of unwanted side-products and/or simplify isolation of the desired compounds. In some embodiment, forming the 5-membered lactone can minimize the number of steps of the overall synthesis by protecting the C-13 and C-3 hydroxy groups with one moiety rather than multiple protecting groups which may need to be added and/or removed separately.

Examples of the structures and stereochemistry of the compounds of formulae (IX) and (X-2) are shown below.

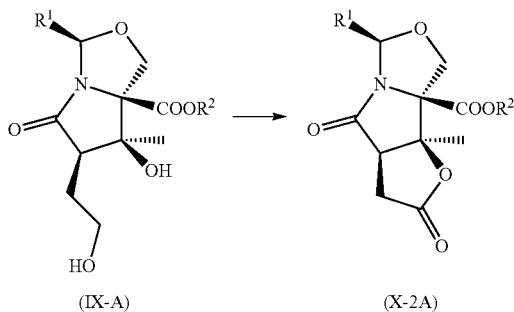

(IX-A) → (X-2A)

-continued

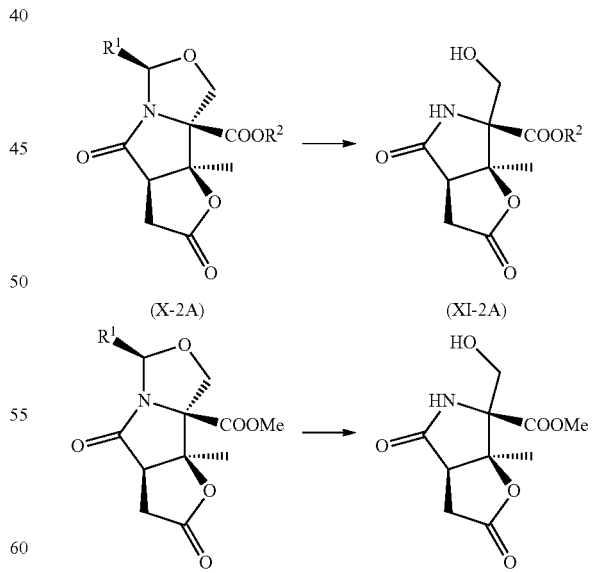

Similar to the reaction shown in Scheme 9, the aminal group of a compound of formula (X-2) can be cleaved to form a compound of formula (XI-2). In some embodiments, the aminal group can be cleaved using a suitable acid (e.g. triflic acid, HCl, PTSA, PPTS, TFA, camphor sulfonic acid).

In an embodiment, the compounds of formulae (X-2) and (XI-2) may have the following structures and stereochemistry:

If desired or necessary, the lactam nitrogen of a compound of formula (XI-2) can be protected with a suitable protecting group moiety denoted by $PG^2$. Examples of suitable protecting groups include, but are not limited to, benzyl, substituted benzyl, silyl, or methoxylmethyl, as shown in step (i) of Scheme 10. If protection of the lactam nitrogen is undesired and/or not necessary, the remaining steps shown in Scheme 10 can be carried out in which $PG^2$ is replaced with a hydrogen, and the steps that show the addition and removal of the protecting group, $PG^2$, can be excluded. As previously noted, the lactam can be protected to facilitate the stereospecific addition of the 2-cyclohexenyl moiety. For example, by protecting the lactam nitrogen with a bulky protecting group such as an optionally substituted benzyl group, the 2-cyclohexenyl ring will add to C-5 to form an (S)-stereocenter and an (S) stereocenter at C-6. In an embodiment, the protecting group on the lactam nitrogen can be a substituted benzyl group, for example, p-methoxybenzyl.

Exemplary structures and stereochemistry of compounds of formulae (XI-2) and (XII-2) are shown below:

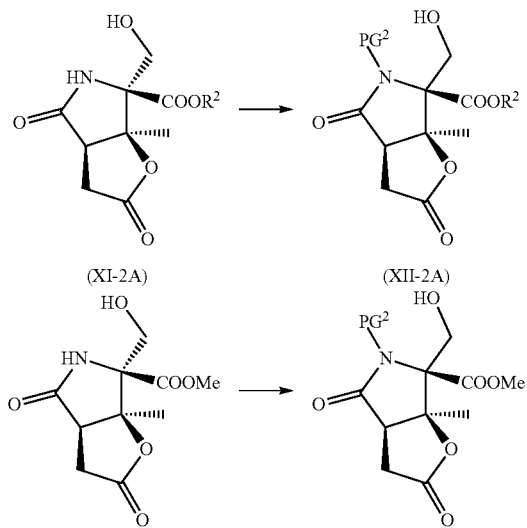

Steps (j) and (k) shown in Scheme 10 can be carried out using reactions and conditions similar to those described above for steps (j) and (k) of Scheme 9.

In an embodiment, the compounds of formulae (XII-2), (XIII-2) and (XIV-2) can have the following structures and stereochemistry.

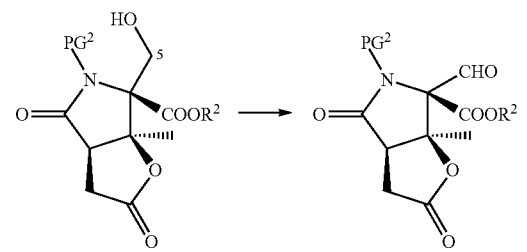

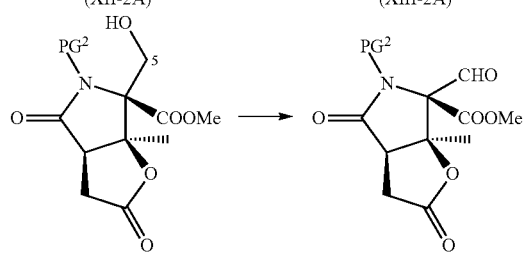

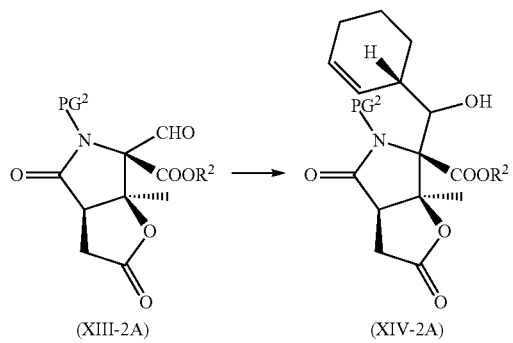

-continued

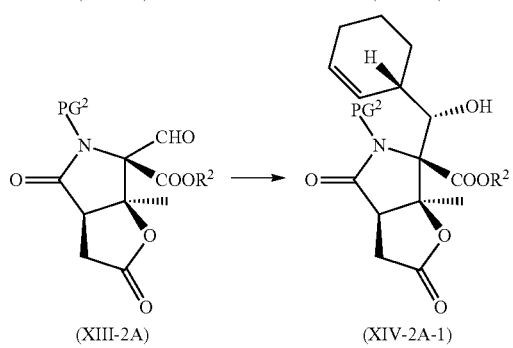

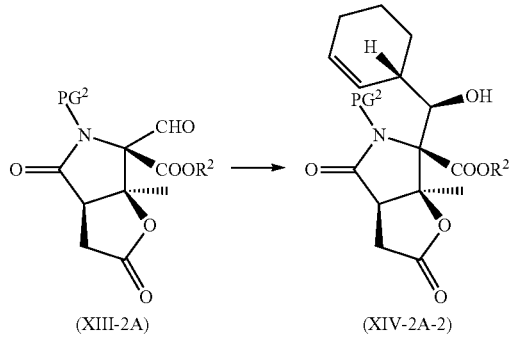

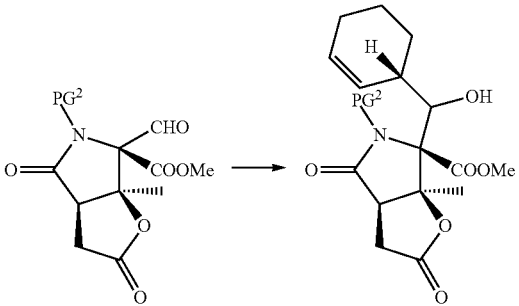

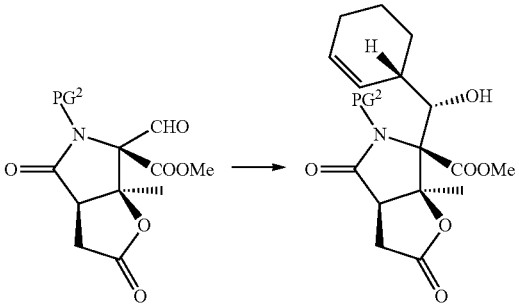

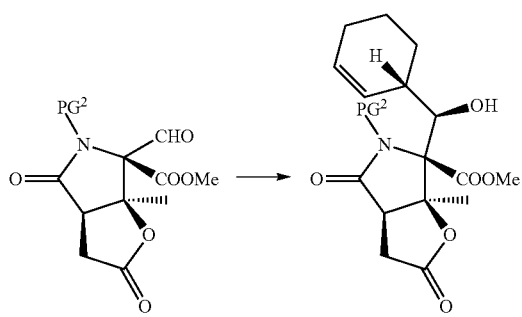
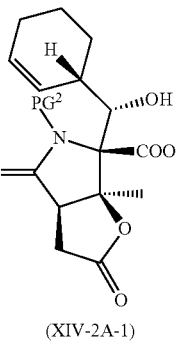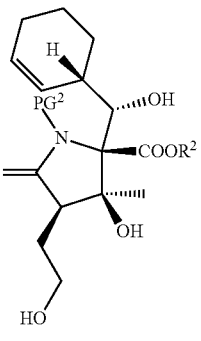

(XIV-2A-1)  (XVII-A-1)

As shown in step (l) in Scheme 10, the 5-membered lactone of a compound of formula (XIV) can be cleaved to form a compound of formula (XVII). Methods and reagents that can be used to cleave the lactone are known to those skilled in the art. In an embodiment, the 5-membered lactone can be cleaved using an appropriate reducing agent. Suitable reducing agents include, but are not limited to, $NaBH_4$ and $LiAlH_4$. In some embodiments, the 5-membered lactone can be opened via a reductive ring opening reaction using an appropriate reducing agent (e.g., $NaBH_4$). Cleavage of the lactone under reducing conditions results in the formation of a primary alcohol at C-13 and a tertiary alcohol at C-3.

In an embodiment, the compounds of formulae (XIV-2) and (XVII) may have the following structures and stereochemistry:

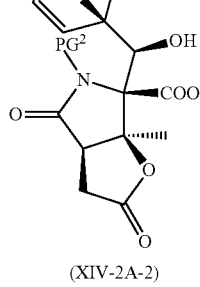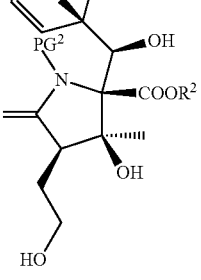

(XIV-2A-2)  (XVII-A-2)

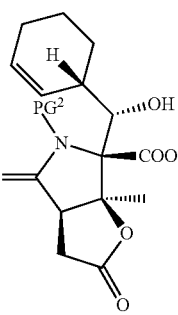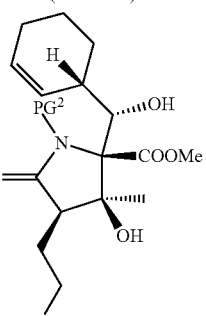

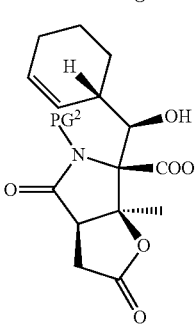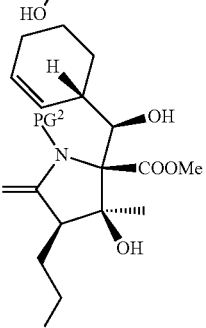

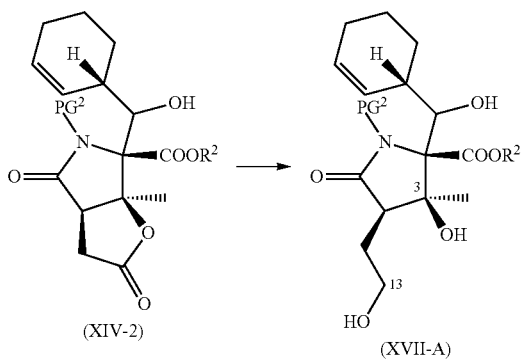

(XIV-2)  (XVII-A)

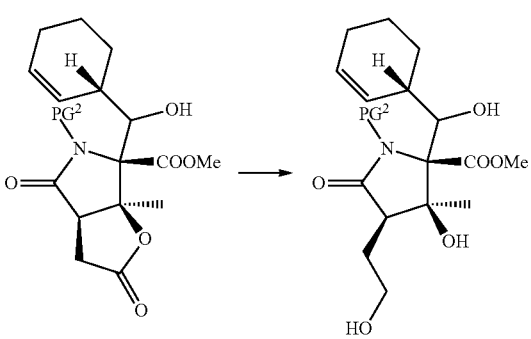

Starting with a compound of formula (XVII), the beta-lactone present in a compound of formula (XV) can be formed as described previously. For example, a lactone can formed using an appropriate base (e.g., BOPCl/pyridine, triethylamine) to induce lactonization. Additionally, if the lactam is protected, the protecting group can be removed using suitable reagents and conditions. Examples of suitable reagent(s) for removing the protecting group $PG^2$, include, but are not limited to, 2,3-dichloro-5,6-dicyanobenzoquinone DDQ, ceric ammonium nitrate (CAN), TFA (trifluoroacetic acid) and hydrogen/Pd—C. Alternatively, if present, the lactam nitrogen protecting group can removed anytime, for example, after the addition of the cyclohexenyl ring. Thus, the protecting group denoted by PG², can be removed using methods known to those skilled in the art, such as those described herein, from compounds of formulae (XIII-2) and (XIV-2). In some embodiments, the lactam nitrogen can remained protected and compounds of the general structure of compounds of formulae (XV) and (XVI) with a protected lactam nitrogen can be formed using the methods and reagents described herein. In the instances where the lactam nitrogen remains protected during the formation of compounds of the general structure of compounds of formulae (XV) and (XVI), the lactam nitrogen protecting group can be removed at anytime using the methods known to those skilled in the art. For example, the lactam nitrogen can be removed before formation of the beta-lactone ring, after formation of the beta-lactone ring but before replacement of the C-13 hydroxy, or after replacement of the C-13 hydroxy.

Examples of the structures and stereochemistry of compounds of formula (XVII) and (XV) include the following:

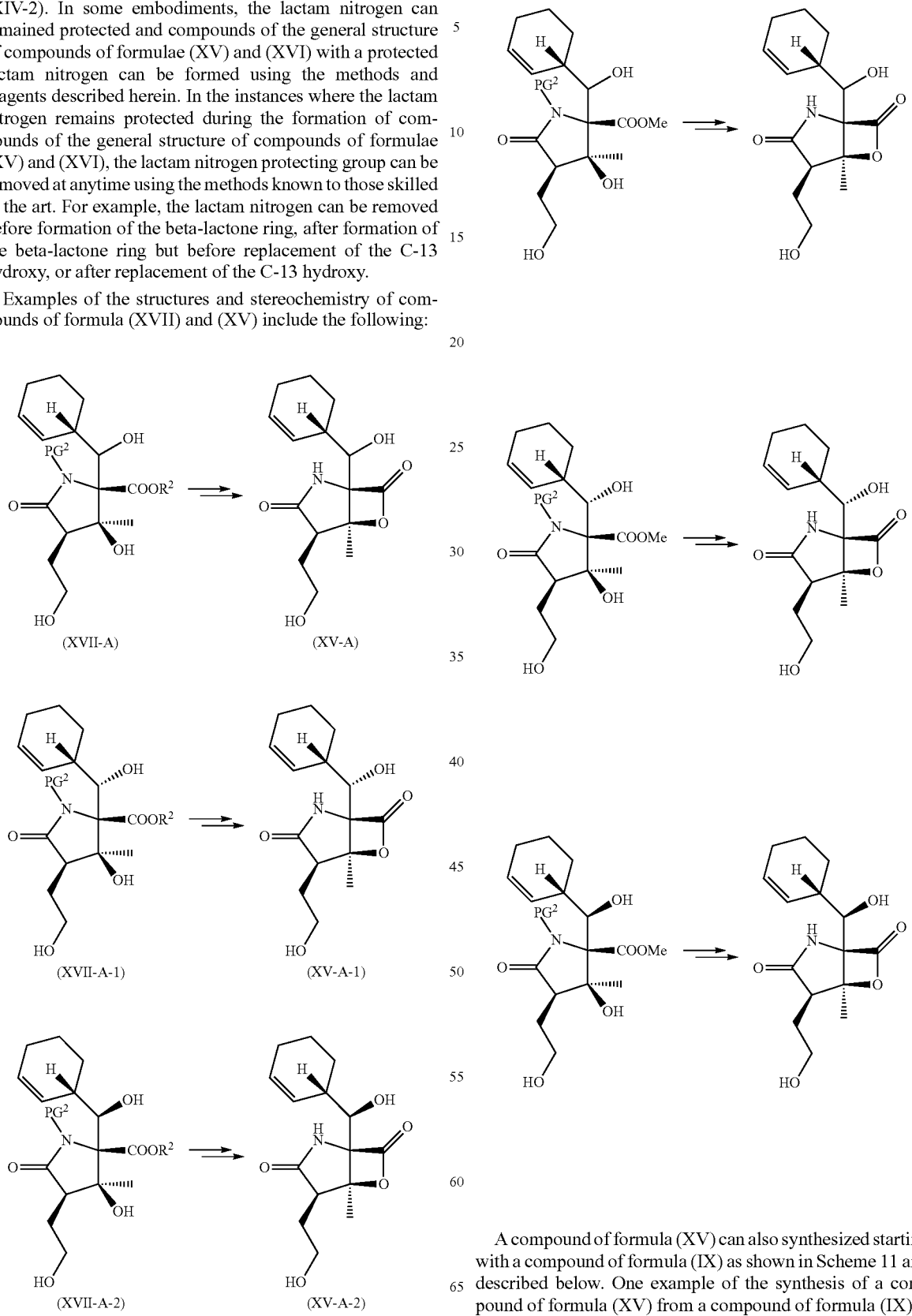

A compound of formula (XV) can also synthesized starting with a compound of formula (IX) as shown in Scheme 11 and described below. One example of the synthesis of a compound of formula (XV) from a compound of formula (IX) is shown in FIGS. 4a and 4d.

Scheme 11

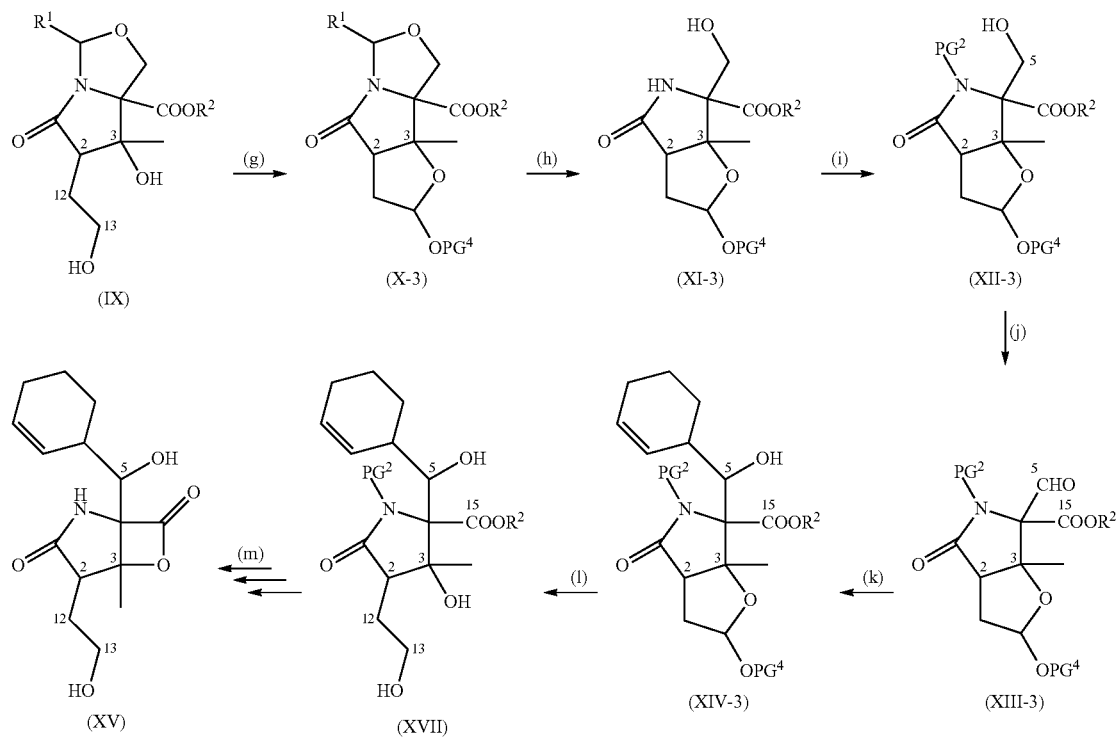

As shown in Scheme 11, C-13 and oxygen of the C-3 tertiary alcohol of a compound of formula (IX) can be cyclized together to form a hemi-acetal. In an embodiment, the C-13 primary alcohol of a compound of formula (IX) can be oxidized to an aldehyde. The aldehyde and C-3 secondary alcohol then can react together and cyclize to form the hemi-acetal. In an embodiment, a method for obtaining a compound of formula (X-3) from a compound of formula (IX) includes reacting a compound of formula (IX) with a suitable oxidant or oxidant combination, such as Dess-Martin periodinane, TPAP/NMO, Swern oxidation reagent, PCC, and PDC. In an embodiment, forming a hemi-acetal can be advantageous to prevent the formation of unwanted side-products and/or simplify isolation of the desired compounds. In some embodiments, the $R^1$ group can be hydrogen, unsubstituted or substituted $C_{1-6}$ alkyl or unsubstituted or substituted aryl. In an embodiment, the $R^1$ group can be t-butyl. In some embodiments, $R^2$ can be selected from hydrogen, an unsubstituted or substituted $C_{1-6}$ alkyl, an unsubstituted or substituted aryl, and an unsubstituted or substituted arylalkyl. In some embodiments, $R^2$ can be an unsubstituted or substituted $C_{1-6}$ alkyl. In an embodiment, $R^2$ can be methyl.

Optionally, the hemi-acetal can be converted to an acetal by protecting the hydroxy group of the hemi-acetal using a suitable protecting group denoted by $PG^4$. Suitable protecting groups include, but are not limited to, substituted or unsubstituted arylcarbonyls (e.g., benzoyl); substituted or unsubstituted alkylcarbonyls (e.g. acetyl); substituted or unsubstituted arylalkylcarbonyls; substituted or unsubstituted alkoxycarbonyls; substituted or unsubstituted aryloxycarbonyls; substituted methyl ether (e.g. methoxymethyl); substituted ethyl ether; substituted or substituted benzyl (e.g. benzyl, 4-methoxybenzyl); tetrahydropyranyl ether; silyl ethers (e.g., trimethylsilyl, triethylsilyl, triisopropylsilyl, t-butyldimethylsilyl, or t-butyldiphenylsilyl); esters, carbonates (e.g. methoxymethylcarbonate); and sulfonates (e.g. mesylate, tosylate). In an embodiment, the protecting group $PG^4$ can be a benzyl group. If the hydroxy group of the hemi-acetal is not protected, a compound of formula (XV) can be obtained from a compound of formula (IX) following the steps shown in Scheme 11 excluding the addition and removal of the protecting group denoted by $PG^4$.

Examples of compounds of formulae (IX) and (X-3) include the following:

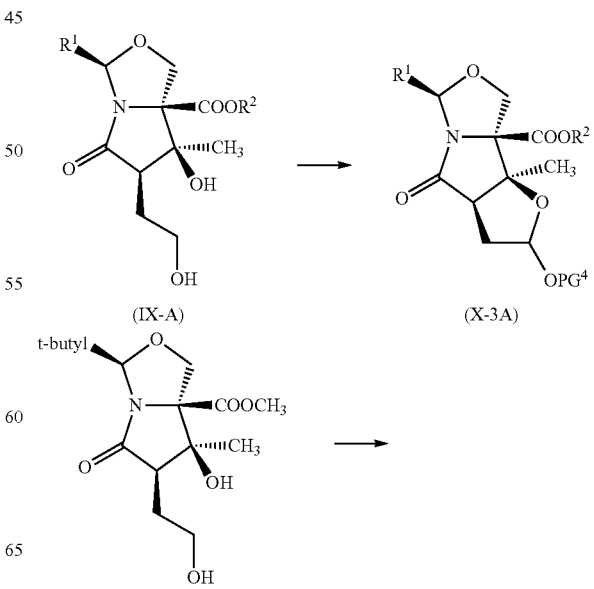

-continued

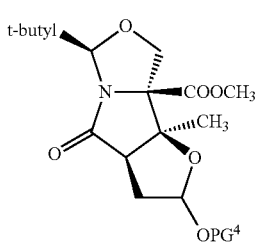

As shown in step (h), the aminal group of a compound of formula (X-3) can be cleaved to form a compound of formula (XI-3). In some embodiments, the aminal group can be cleaved using a suitable acid (e.g. triflic acid, HCl, PTSA, PPTS, TFA, camphor sulfonic acid).

In some embodiments, the compounds of formula (X-3) and (XI-3) can be the structures and stereochemistry shown below.

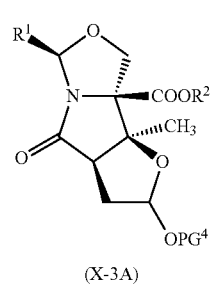 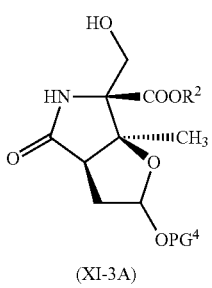

(X-3A)  (XI-3A)

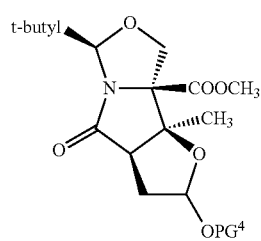 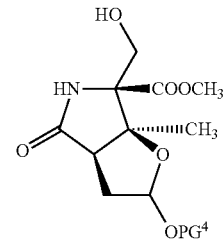

In some embodiments, the lactam nitrogen of a compound of formula (XI-3) can be protected with an appropriate protecting group (denoted by $PG^2$) if desired and/or necessary. Suitable protecting groups include, but are not limited to, benzyl, substituted benzyl, t-butoxycarbonyl (t-Boc), Benzyloxycarbonyl (Cbz), silyl, or methoxylmethyl. If protection of the lactam nitrogen is undesired and/or not necessary, the remaining steps shown in Scheme 11 can be carried out in which $PG^2$ is replaced with a hydrogen, and the steps that show the addition and removal of the protecting group, $PG^2$, can be excluded. As previously noted, the lactam nitrogen can be protected to facilitate the stereospecific addition of the 2-cyclohexenyl moiety such that the 2-cyclohexenyl group adds to form an (S)-stereocenter at C-5. Moreover, protecting the lactam nitrogen can also establish an (S) stereocenter at C-6. In an embodiment, the protecting group on the lactam nitrogen can be an optionally substituted benzyl group, for example, p-methoxybenzyl.

Exemplary structures and stereochemistry of compounds of formulae (XI-3) and (XII-3) are shown below:

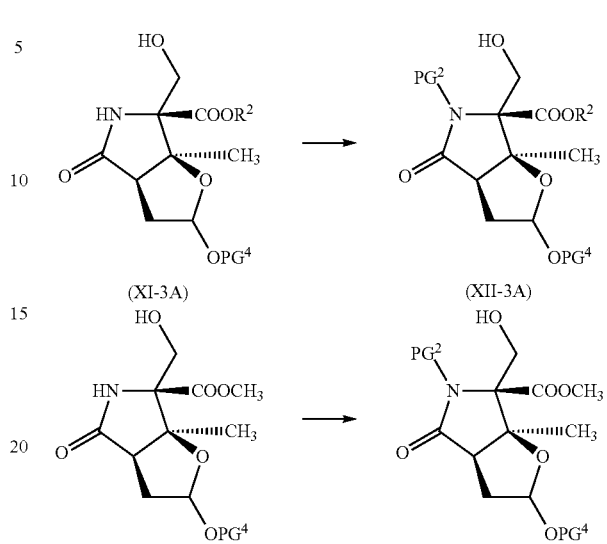

(XI-3A)  (XII-3A)

After formation of the acetal ring, steps (j), and (k) in Scheme 11 can be carried out similarly as described in steps (j), and (k) in Scheme 10. In an embodiment, the compounds of formulae (XIII-3) and (XIV-3) can have the following structures and stereochemistry.

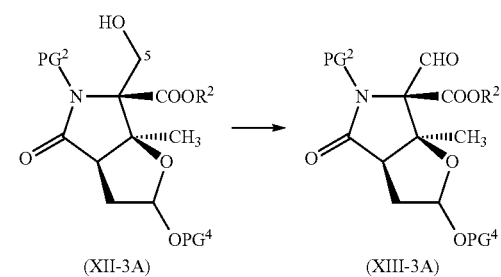

(XII-3A)  (XIII-3A)

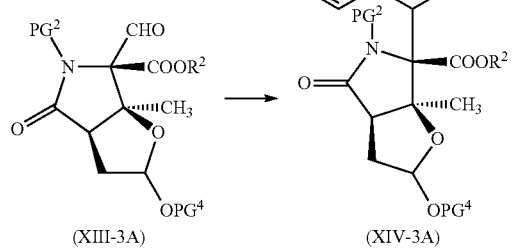

(XIII-3A)  (XIV-3A)

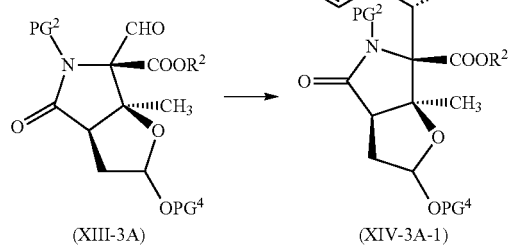

(XIII-3A)  (XIV-3A-1)

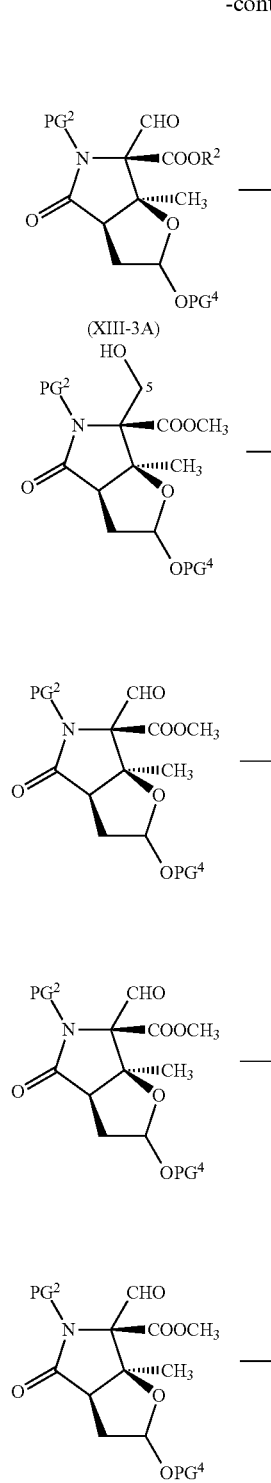

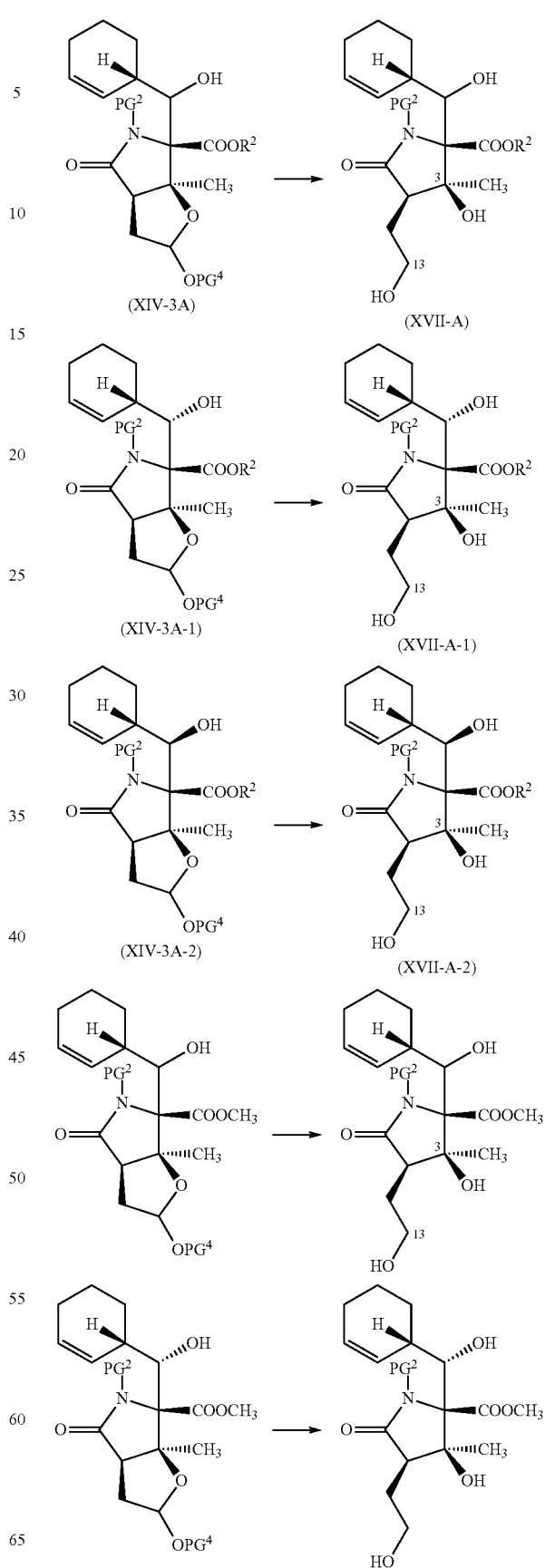

For step (l) shown in Scheme 11, any protecting group, denoted by $PG^4$, present on the acetal ring can be removed and the ring can be opened using reductive methods and reagents known to those skilled in the art to give a hydroxy group attached to C-13 and another hydroxy group attached to C-3. In some embodiments, when $PG^4$ is benzyl, the benzyl group can be removed using sodium metal and liquid ammonium. In an embodiment, the acetal ring can be cleaved using a suitable reducing reagent such as sodium borohydride.

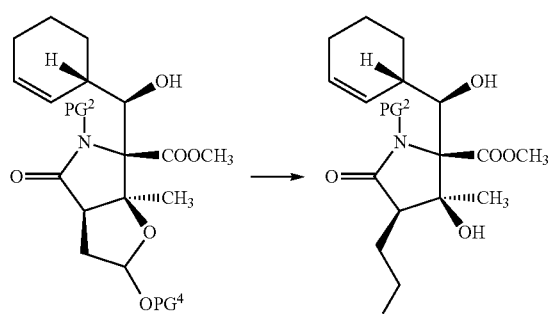

Scheme 12

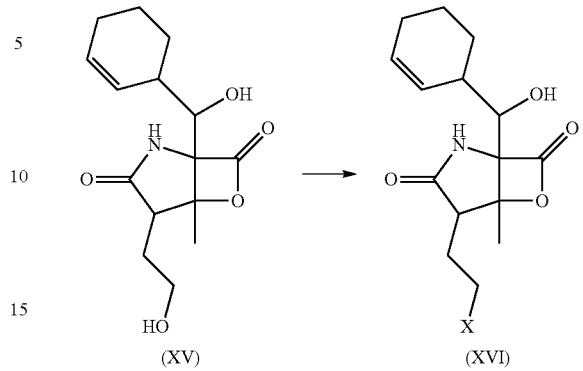

To obtain a compound of formula (XV), the 4-membered heterocyclic ring can be formed starting with a compound of formula (XVII) via a lactonization reaction. Methods for inducing the lactonization reaction have been described previously. In embodiment, a beta-lactone can formed using an appropriate base (e.g., BOPCl/pyridine, triethylamine) to induce lactonization. Additionally, if the lactam nitrogen is protected, the protecting group can be removed using suitable reagents and conditions. In some embodiments, the lactam nitrogen protecting group can removed at anytime, for example, after the addition of the cyclohexenyl ring. Thus, the protecting group denoted by $PG^2$, can be removed using methods known to those skilled in the art, such as those described herein, from compounds of formulae (XIII-3) and (XIV-3). In some embodiments, the lactam nitrogen can remained protected and compounds of the general structure of compounds of formulae (XV) and (XVI) with a protected lactam nitrogen can be formed using the methods and reagents described herein. In the instances where the lactam nitrogen remains protected during the formation of compounds of the general structure of compounds of formulae (XV) and (XVI), the lactam nitrogen protecting group can be removed at anytime using the methods known to those skilled in the art. For example, the lactam nitrogen can be removed before formation of the beta-lactone ring, after formation of the beta-lactone ring but before replacement of the C-13 hydroxy, or after replacement of the C-13 hydroxy.

As shown in Scheme 12, a compound of formula (XV) can be further transformed by replacing the primary hydroxy group of the compound of formula (XV) to form a compound of formula (XVI), wherein X can be a halogen (e.g., F, Cl, Br, and I),

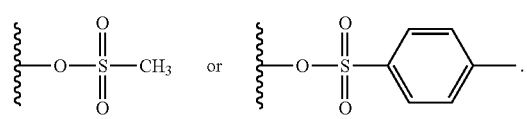

Examples of the structures and stereochemistry of compounds of formulae (XV) and (XVI) are shown below:

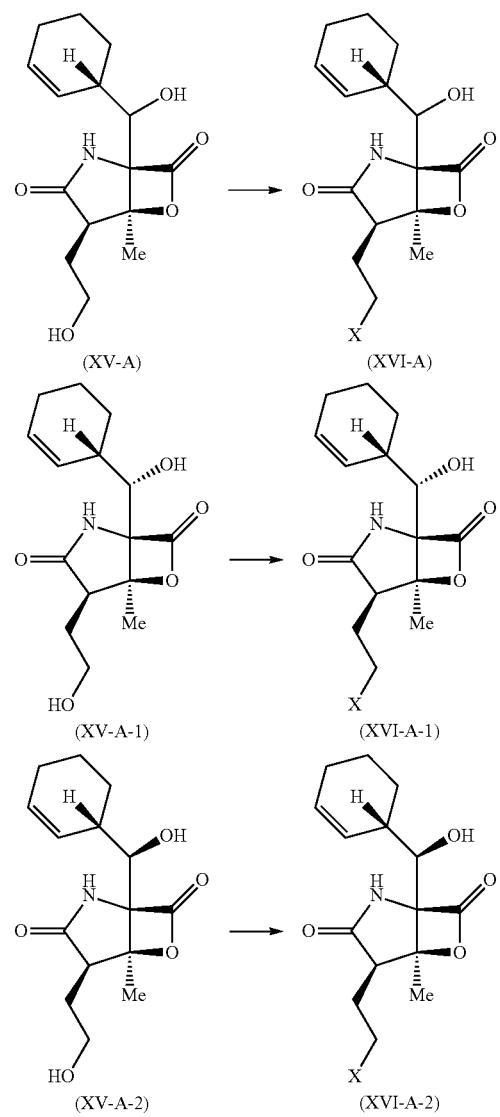

In one embodiment, Salinosporamide A can be synthesized by chlorinating a compound of formula (XV).

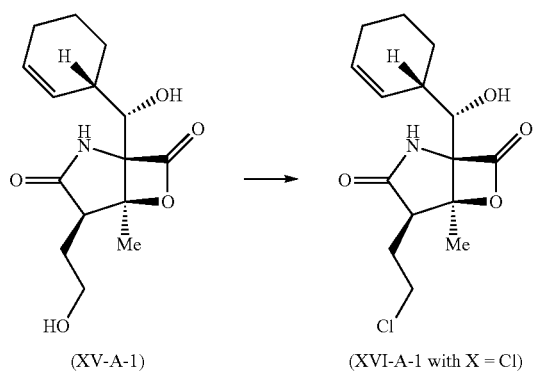

(XV-A-1)　　　(XVI-A-1 with X = Cl)

The stereochemistry of the secondary hydroxy group of the compound of formula (XVI-A-2) can be inverted (e.g., by a Mitsunobu transformation) to form a compound of formula (XVI-A-1).

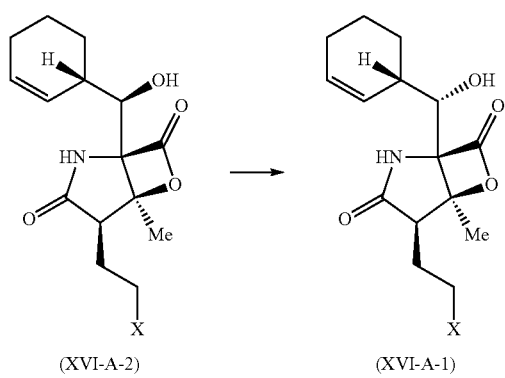

(XVI-A-2)　　　(XVI-A-1)

In one embodiment, Salinosporamide A can be synthesized from a compound with the structure and stereochemistry of formula (XVI-A-2), in which X is Cl, as shown below:

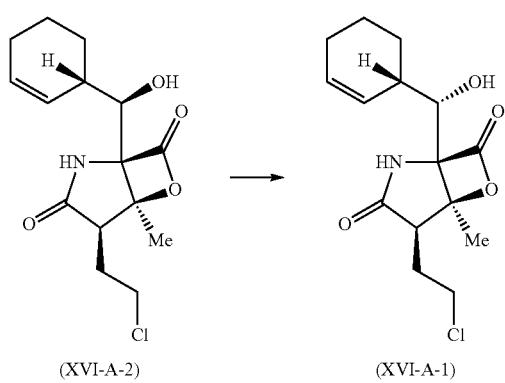

(XVI-A-2)　　　(XVI-A-1)

Alternatively, the stereochemistry of the secondary hydroxy can be inverted via a multistep process, for example, by oxidizing the secondary hydroxy to a ketone and then reducing the ketone to a secondary hydroxy of opposite stereochemistry, as shown in Scheme 13. In one method, the compound of formula (XVI-A-2) can be oxidized with a suitable oxidizing agent (e.g., Dess-Martin periodinane, TPAP/NMO, Swern oxidation reagent, PCC, or PDC) to form the compound of formula (XVIII). The compound of formula (XVIII) can then be reduced to a compound of formula (XVI-A-1) using a suitable chemical reagent such as sodium borohydride. In some embodiments, the reduction can be accomplished via selective enzymatic transformation. In an embodiment, the reducing enzyme is a ketoreductase such as KRED-EXP-C1A and/or KRED-EXP-B1Y.

Scheme 13

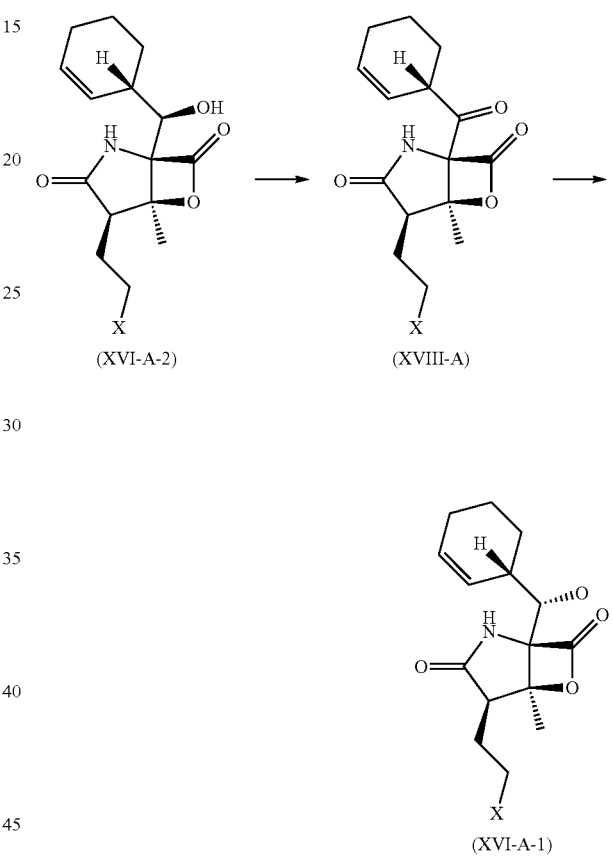

(XVI-A-2)　　　(XVIII-A)

(XVI-A-1)

In another embodiment, Salinosporamide A can be synthesized from a compound with the structure and stereochemistry of formula (XVI-A-2), in which X is Cl, as follows:

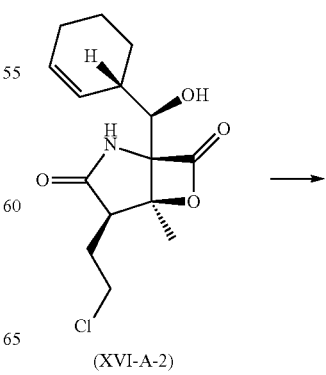

(XVI-A-2)

-continued

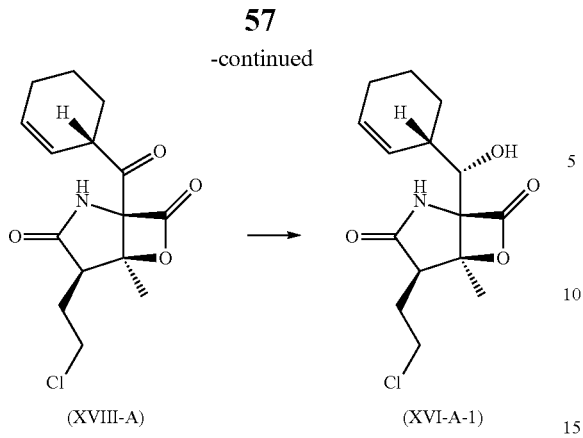

(XVIII-A) → (XVI-A-1)

Moreover, the stereochemistry of the C-5 secondary hydroxy can be inverted at any time after the addition of the cyclohexenyl group to a compound of formula (XIII). For example, the stereochemistry of the secondary hydroxy can be inverted in the compounds of formulae (XIV), (XV) or (XVII). In an embodiment, the stereochemistry of the secondary hydroxy can be inverted in a one step process as described herein (e.g., by a Mitsunobu transformation). The inversion can also take place in multistep process. Methods for inverting the stereochemistry of C-5 are disclosed herein.

Salinosporamide A and additional analogs thereof can be synthesized using one or more of the methods shown in Schemes 14-20. In Schemes 14-20, $R^1$ and $R^2$ can be any of the substituents described previously herein.

Scheme 14

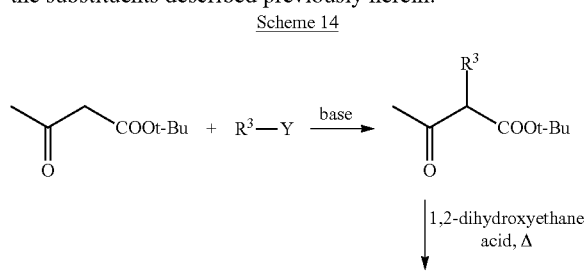

As shown in Scheme 14, analogs of a compound of formula (II) can be obtained in a similar manner as shown in Schemes 2-4 by replacing allylbromide with a compound having the structure $R^3$—Y, wherein Y can be an appropriate leaving group; and $R^3$ can be selected from an unsubstituted or substituted $C_{1-24}$ alkyl, an unsubstituted or substituted $C_{1-24}$ alkenyl, an unsubstituted or substituted $C_{1-24}$ alkynyl, an unsubstituted or substituted aryl, an unsubstituted or substituted heteroaryl, an unsubstituted or substituted $C_{3-24}$ cycloalkyl, an unsubstituted or substituted $C_{3-24}$ cycloalkenyl, an unsubstituted or substituted $C_{3-24}$ cycloalkynyl, an unsubstituted or substituted aryl($C_{1-6}$ alkyl) and an unsubstituted or substituted heteroaryl($C_{1-6}$ alkyl). In some embodiments, $R^3$ can be a substituted $C_{1-24}$ alkyl. In an embodiment, the substituted $C_{1-24}$ alkyl may be substituted with a halogen, triflate, allylsulfonyl, arylsulfonyl, heteroarylsulfonyl, allylsulfonyloxy, arylsulfonyloxy and heteroarylsulfonyloxy. As to the leaving group denoted by Y, in some embodiments, Y can be halogen or triflate.

Scheme 15

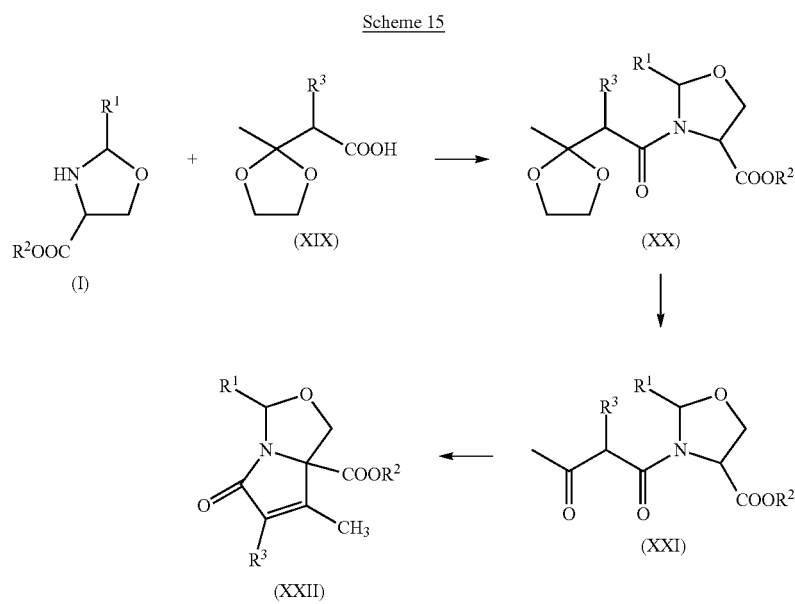

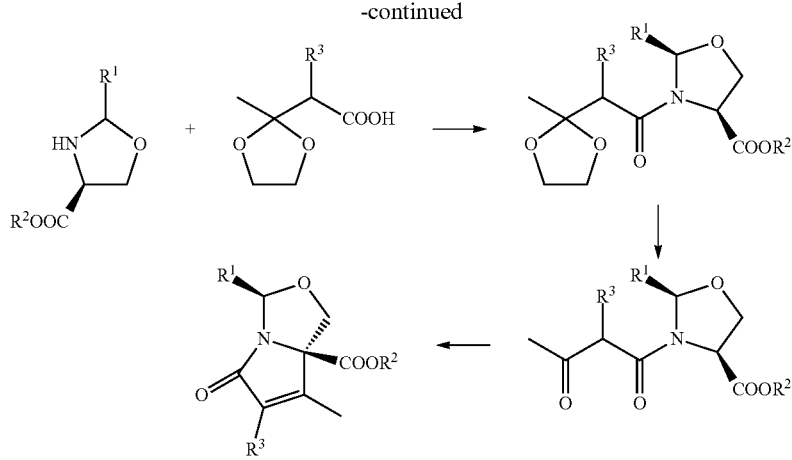

A compound of formula (XIX) can be reacted with a compound of formula (I) to form a compound of formula (XX) using conditions similar for obtaining a compound of formula (III-1). The compound of formula (XX) can be deprotected to form a compound of formula (XXI). Methods for removing the acetyl protecting group are known to those skilled in the art. For example, suitable methods are described herein, such as those described for obtaining a compound of formula (IV) from a compound of formula (III-1).

A compound of formula (XXII) can be synthesized from a compound of formula (XXI) using methods known to those skilled in the art. In some embodiments, a compound of formula (XXI) can be treated with an appropriate base to bring about an intramolecular aldol condensation reaction and give a compound of formula (XXII). Examples of the structure and stereochemistry of compounds of formulae (I), (XIX), (XX), (XXI) and (XXII) are shown in Scheme 15.

Scheme 16

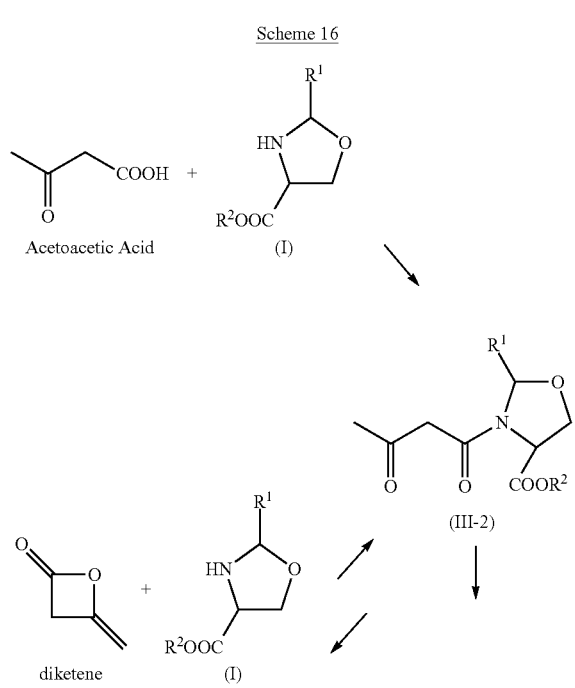

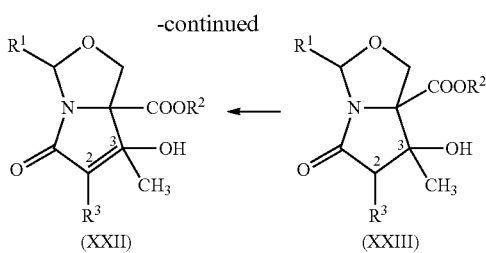

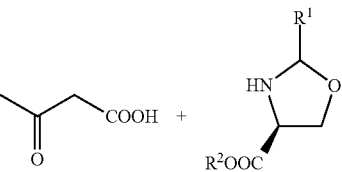

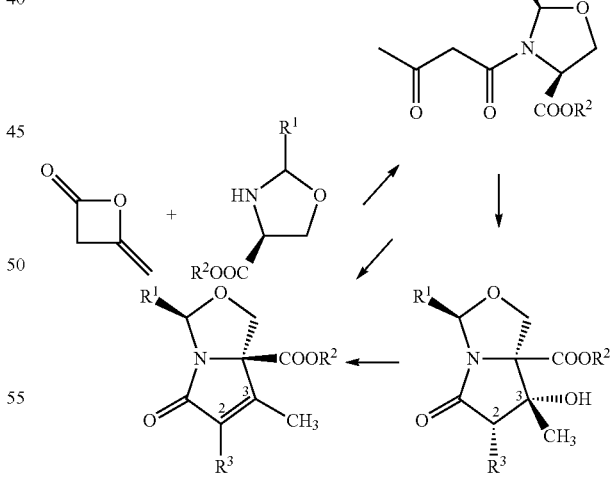

A compound of formula (XXII) can also be obtained following the transformations shown in Scheme 16. Using the aforementioned conditions and starting with acetoacetic acid and a compound of formula (I) or diketene and a compound of formula (I), a compound of formula (III-2) can be obtained. A compound of formula (XXIII) can be obtained from a compound of formula (III-2) and $R^3$—Y via an alkylation reaction and an intramolecular aldol reaction. As previously discussed, the intramolecular aldol reaction can be induced using an appropriate base, such as those described herein with respect to the synthesis of a compound of formula (V). A compound of formula (XXIII) can then be converted to a compound of formula (XXII). A double bond can be formed between C-2 and C-3 by dehydrating a compound of formula (XXIII) using an appropriate base. Appropriate bases are known to those skilled in the art. For example, an amidine base such as DBU and DBN. Alternatively, in some embodiments, a compound of formula (XXII) can be obtained by reacting a compound of formula (III-2), $R^3$—Y and a base. The compound of formula (XXII) can be synthesized from the aforementioned reagents, in the presence of a base, via an intramolecular aldol reaction and alkylation reaction. As described previously, allyl bromide (an alkylating reagent), and an amidine compound (base) can be used for obtaining a compound of formula (XXII) from a compound of formula (III-2). Also shown in Scheme 16 are examples of the structures and stereochemistry of compounds of formulae (I), (XXII) and (XXIII)

Scheme 17

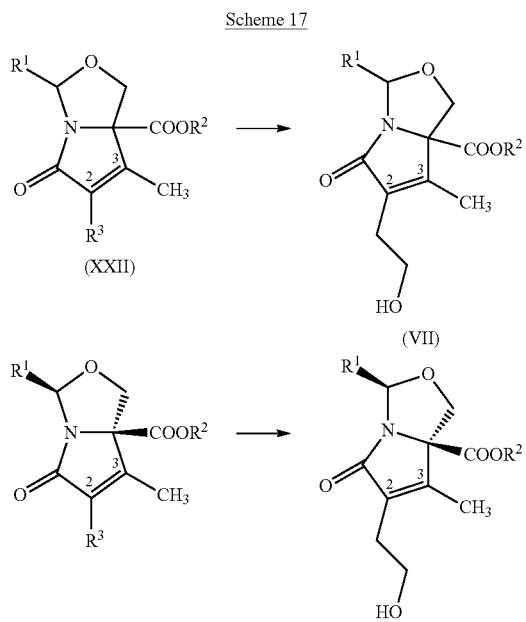

A compound of formula (XXII) can be used to obtain a compound of formula (VII). In some embodiments, a compound of formula (VII) can be synthesized from a compound of formula (XXII) via oxidation/reduction methodology. For example, the double, triple bond or aromatic ring included in a $R^3$ group of a compound of formula (XXII) may be oxidized to an aldehyde using an appropriate oxidizing agent (e.g., ozone, osmium tetraoxide and sodium periodate). The aldehyde can be reduced to an alcohol to give a compound of formula (VII) using an appropriate reducing agent such as $NaBH_4$, $LiAlH_4$ or diisobutylaluminum hydride (DIBALH). In some embodiments, $R^3$ can be selected from one of the followings:

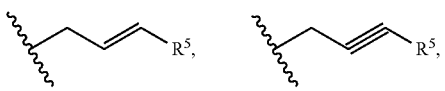

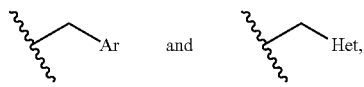

wherein Ar can be an unsubstituted or substituted aryl, Het can be an unsubstituted or substituted heteroaryl; and $R^5$ denotes hydrogen or any one of the substituents listed under the definition of substituted. In some embodiments, $R^5$ can be selected from hydrogen, an unsubstituted or substituted $C_{1-24}$ alkyl, an unsubstituted or substituted $C_{1-24}$ alkenyl, an unsubstituted or substituted $C_{1-24}$ alkynyl, an unsubstituted or substituted aryl, an unsubstituted or substituted heteroaryl, an unsubstituted or substituted $C_{3-24}$ cycloalkyl, an unsubstituted or substituted $C_{3-24}$ cycloalkenyl, an unsubstituted or substituted $C_{3-24}$ cycloalkynyl, an unsubstituted or substituted aryl($C_{1-6}$ alkyl) and an unsubstituted or substituted heteroaryl($C_{1-6}$ alkyl). In an embodiment, $R^5$ can be hydrogen. In some embodiments, $R^3$ can be a substituted $C_{1-24}$ alkyl. In an embodiment, the substituted $C_{1-24}$ alkyl may be substituted with a halogen, triflate, allylsulfonyl, arylsulfonyl, heteroarylsulfonyl, allylsulfonyloxy, arylsulfonyloxy and heteroarylsulfonyloxy. The compound of formula (VII) obtained from a compound of formula (XXII) can be used to synthesize compounds of formulae (VIII), (IX), (X-1), (X-2), (X-3), (XI-1), (XI-2), (XI-3), (XII-1), (XII-2), (XII-3), (XIII-1), (XIII-2), (XIII-3), (XIV-1), (XIV-2), (XIV-3), (XVII), (XVIII), (XV) and (XVI) using the methodologies described herein, such as those described with respect to Schemes 8, 9, 10, 11, 12 and 13.

Scheme 18

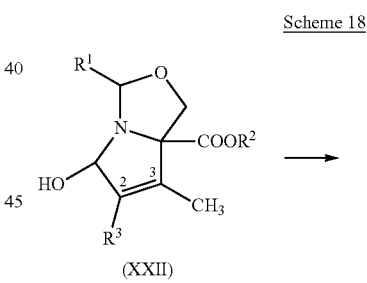

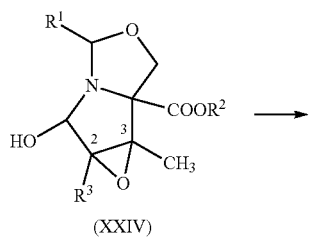

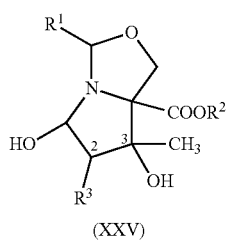

-continued

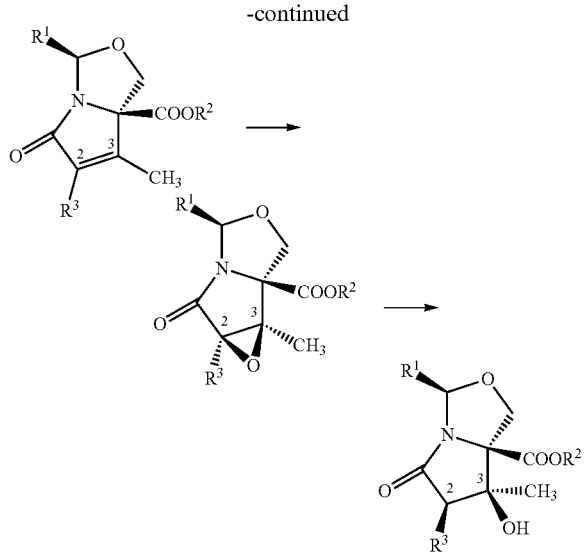

A compound of formula (XXII) can also be used to form a compound of formula (XXIV). The epoxide of the compound of formula (XXIV) can be synthesized in a similar manner as the epoxide of formula (VIII). In some embodiments, a compound of formula (XXII) can be oxidized to form an epoxide that includes C-2 and C-3. In an embodiment, formation of the epoxide establishes an (R)-stereocenter at C-2 and an (R)-stereocenter at C-3. Formation of the epoxide stereospecifically can facilitate in establishing the desired stereochemistry in the final compound. The epoxide ring of a compound of formula (XXIV) can be cleaved using one or more suitable reagents, such as a reducing agent. In an embodiment, cleavage of the epoxides establishes an (R)-stereocenter at C-2 and an (S)-stereocenter at C-3. By establishing the desired chirality at C-2 and C-3, additional steps that may be needed to generate the desired stereochemistry and C-2 and/or C-3 may be averted. Examples of the structures and stereochemistries of compounds of formulae (XXII), (XXIV) and (XXV) are also shown in Scheme 18.

Scheme 19

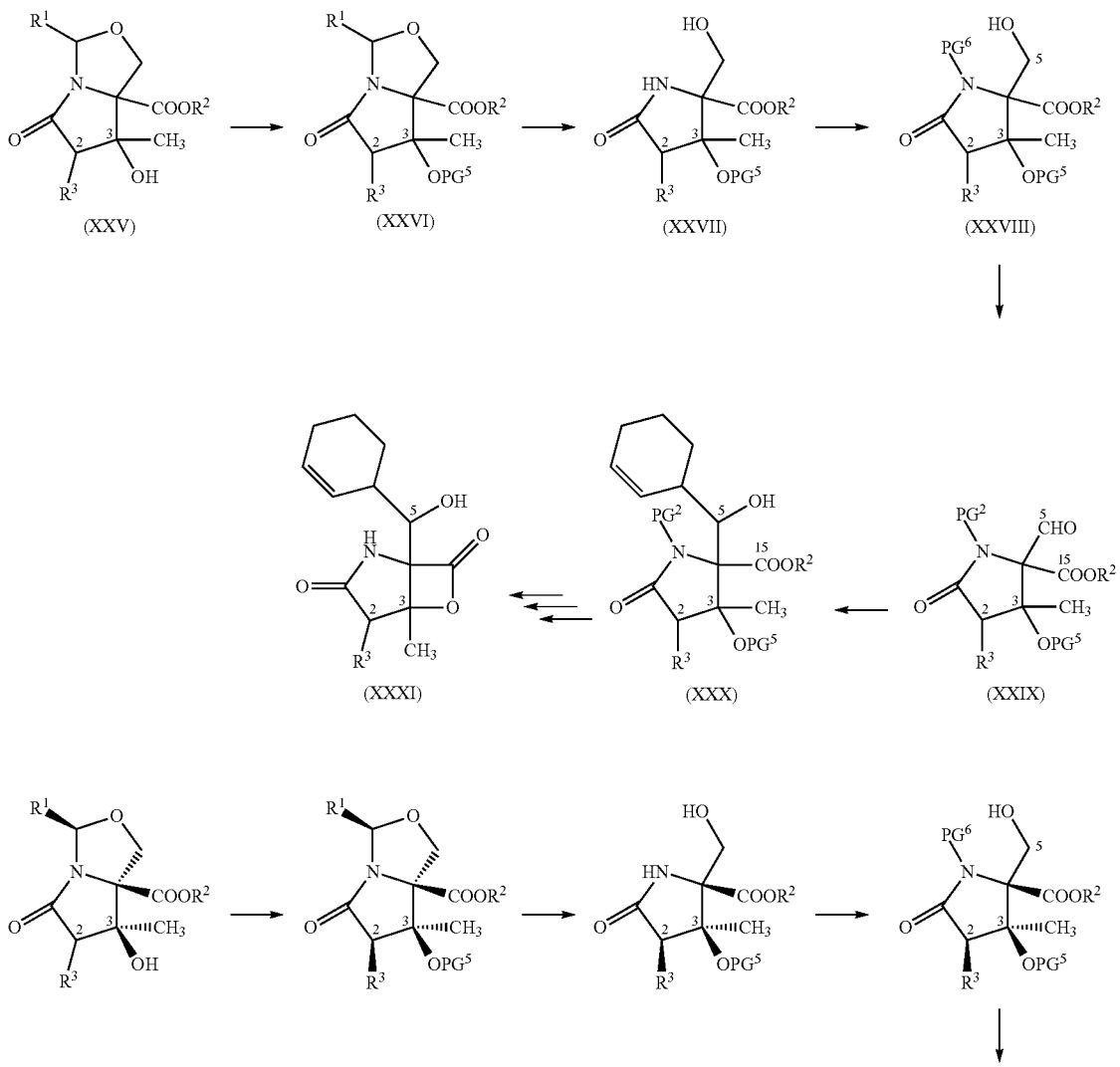

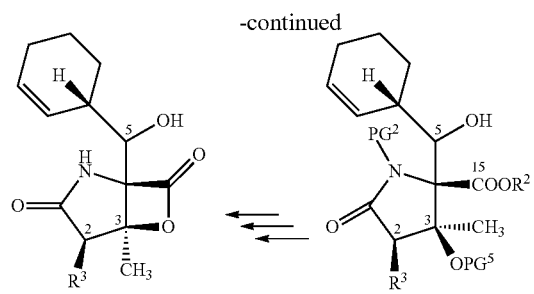
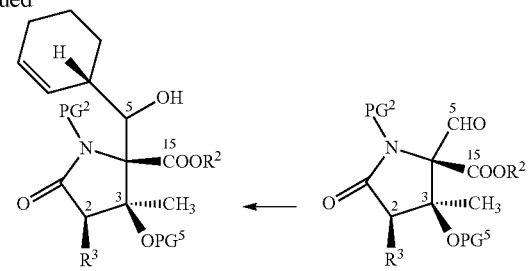

As shown in Scheme 19, the tertiary hydroxy of a compound of formula (XXV) can be protected with a protecting group moiety, $PG^5$ to form a compound of formula (XXVI). Examples of protecting groups that can used include, but are not limited to, the following: substituted or unsubstituted arylcarbonyls (e.g., benzoyl); substituted or unsubstituted alkylcarbonyls (e.g. acetyl); substituted or unsubstituted arylalkylcarbonyls; substituted or unsubstituted alkoxycarbonyls; substituted or unsubstituted aryloxycarbonyls; substituted methyl ether (e.g. methoxymethyl); substituted ethyl ether; substituted or substituted benzyl (e.g. benzyl, 4-methoxybenzyl); tetrahydropyranyl ether; silyl ethers (e.g., trimethylsilyl, triethylsilyl, triisopropylsilyl, t-butyldimethylsilyl, or t-butyldiphenylsilyl); esters, carbonates (e.g. methoxymethylcarbonate); and sulfonates (e.g. mesylate, tosylate).

The aminal of a compound of (XXVI) can be cleaved using an acid to form a compound of formula (XXVII). Examples of suitable acids include, but are not limited to, triflic acid, HCl, PTSA, PPTS, TFA and/or camphor sulfonic acid. As discussed herein, the lactam nitrogen may be protected with a protecting group, $PG^6$, to form a compound of formula (XXVIII). Examples of suitable protecting groups are described herein. In some embodiments, $PG^6$ can be a benzyl, a substitute benzyl, a silyl or methoxymethyl. In an embodiment, the lactam nitrogen is protected so that the 2-cyclohexenyl ring will add to C-5 to form an (S)-stereocenter. As previously discussed, the protection of the lactam nitrogen can also aid in establishing an (S)-stereocenter at C-6. Alternatively, the tertiary hydroxy group on C-3 can be protected after cleavage of the aminal. For example, the tertiary hydroxy group can remain unprotected and the aminal can be cleaved as described herein. After cleavage of the aminal, a suitable protecting group, such as those described herein, can be used to protect the tertiary hydroxy group on C-3 and form a compound of formula (XXVIII).

Scheme 19a

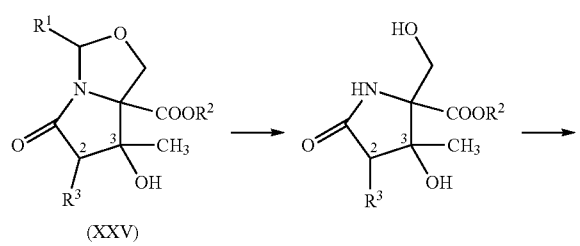

The primary alcohol at C-5 can be oxidized to form a compound of formula (XXIX). A non-limiting list of oxidizing agents include Dess-Martin periodinane, TPAP/NMO, Swern oxidation reagent, PCC, or PDC. A cyclohexenyl ring can be added to C-5 position of a compound of formula (XXIX) to form a compound of formula (XXX). Methods for adding the cyclohexenyl ring are known to those skilled in the art. In some embodiments, the cyclohexenyl ring can be added via an alkylation reaction. In an embodiment, the alkylation reaction utilizes an organometallic moiety. Suitable organometallic moieties are described herein. In an embodiment, the organometallic moiety can be an organomagnesium compound.

The protecting groups, if present, can be removed using methods known to those skilled in the art, and a 4-membered heterocyclic ring can be formed using suitable methodologies to give a compound of formula (XXXI). As an example, the beta-lactone can be formed using an appropriate base (e.g., BOPCl/pyridine, triethylamine) to induce lactonization. In an embodiment, the C-15 ester can first be transformed to a carboxylic acid, an activated acid (e.g., acid halide), or an activated ester (e.g., p-nitrophenyl ester, pentafluorophenyl ester, pentafluoroethyl ester, trifluoroethyl ester, trichloroethyl ester, a thioester, etc.) before being treated with an appropriate reagent to induce the lactonization reaction. In an embodiment, the C-15 carboxylic acid can be treated with an appropriate base to affect the lactonization reaction. Also shown in Scheme 19 are examples of structures and stereochemistries of compounds of formulae (XXV), (XXVI). (XXVII), (XXVIII), (XXIX), (XXX) and (XXXI). Additional examples of structures and stereochemistries of compounds (XXX) and (XXXI) are shown below in Scheme 20.

If the tertiary hydroxy is not protected, a compound of formula (XXXI) can still be obtained using the conditions and reagents described above. Likewise, if the lactam nitrogen is not protected, the conditions and reagents described above can also be used to obtain a compound of formula (XXXI). Removal of $PG^5$ and $PG^6$ can occur at any suitable point in the synthesis of a compound of formula (XXXI). For example, the lactam nitrogen protecting group can removed anytime after the addition of the cyclohexenyl ring. Similarly, the tertiary hydroxy protecting group, $PG^6$, can be removed anytime before the formation of the 4-membered heterocyclic ring.

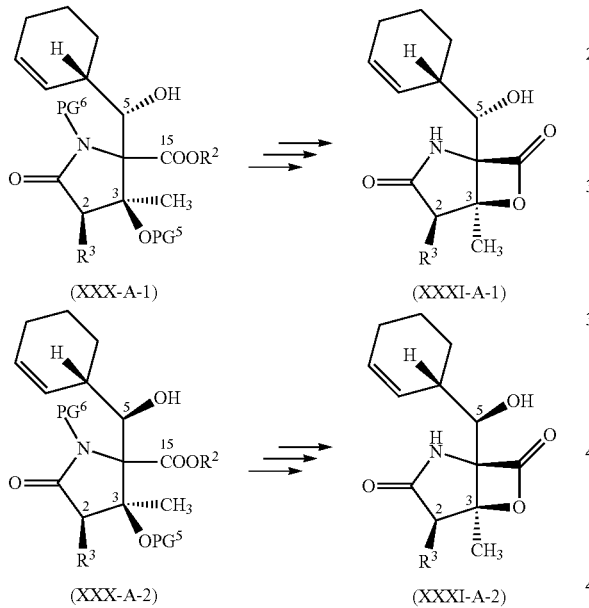

If C-5 is an (R)-stereocenter, the stereocenter can be inverted to an (S)-stereocenter using a method described herein. For example, the chirality of C-5 can be inverted using a one step or multistep process such as those described herein.

Instead of adding 2-cyclohexenyl, various substituents can be utilized to form analogs of Salinosporamide A. As shown in Scheme 21, $R^6$ can be added to a compound of formula (XIII-1), (XIII-2), (XIII-3) or (XXIX-1), wherein $R^6$ can be selected from an unsubstituted or substituted $C_1$-$C_2$ alkyl, an unsubstituted or substituted $C_2$-$C_{24}$ alkenyl, an unsubstituted or substituted $C_2$-$C_{24}$ alkynyl, an unsubstituted or substituted $C_3$-$C_{24}$ cycloalkyl, an unsubstituted or substituted $C_3$-$C_{24}$ cycloalkenyl, an unsubstituted or substituted $C_3$-$C_{24}$ cycloalkynyl, an unsubstituted or substituted heterocyclyl, an unsubstituted or substituted aryl, an unsubstituted or substituted heteroaryl, an unsubstituted or substituted aryl($C_{1-6}$ alkyl), an unsubstituted or substituted heteroaryl($C_{1-6}$ alkyl), an unsubstituted or substituted $C_3$-$C_{24}$ cycloalkyl($C_{1-6}$ alkyl) and an unsubstituted or substituted heterocyclyl($C_{1-6}$ alkyl); and wherein $R^3$, $R^2$, $PG^1$, $PG^2$, $PG^3$, $PG^4$, $PG^5$ and $PG^6$ have been previously defined herein. In some embodiments, $R^6$ can be selected from an unsubstituted or substituted $C_1$-$C_{12}$ alkyl, an unsubstituted or substituted $C_2$-$C_{12}$ alkenyl, an unsubstituted or substituted $C_2$-$C_{12}$ alkynyl, an unsubstituted or substituted $C_3$-$C_{12}$ cycloalkyl, an unsubstituted or substituted $C_3$-$C_{12}$ cycloalkenyl, an unsubstituted or substituted $C_3$-$C_{12}$ cycloalkynyl, an unsubstituted or substituted heterocyclyl, an unsubstituted or substituted aryl, an unsubstituted or substituted heteroaryl, an unsubstituted or substituted aryl($C_{1-6}$ alkyl), an unsubstituted or substituted heteroaryl($C_{1-6}$ alkyl), an unsubstituted or substituted $C_3$-$C_{12}$ cycloalkyl($C_{1-6}$ alkyl) and an unsubstituted or substituted heterocyclyl($C_{1-6}$ alkyl). In an embodiment, $R^6$ can be a $C_{1-24}$ alkyl. In an embodiment, the $C_{1-24}$ alkyl can be isopropyl. Examples of the structures and stereochemistries of compounds of formulae (XIII-1), (XIII-2), (XIII-3) and (XXIX-1), and their respective products after addition of $R^6$, compounds of formulae (XXXII-1), (XXXII-2), (XXXII-3) and (XXXIII), respectively, are also shown in Scheme 21.

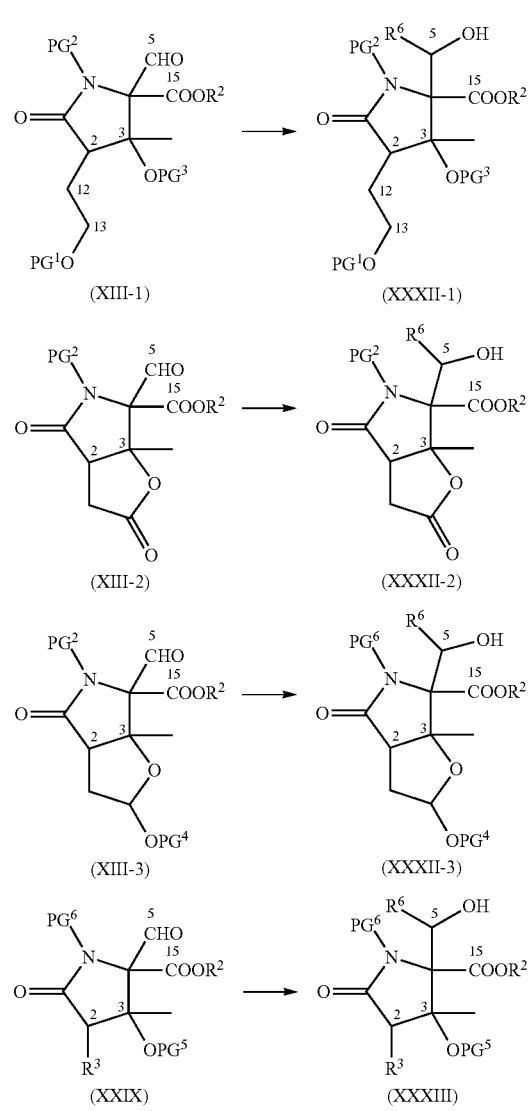

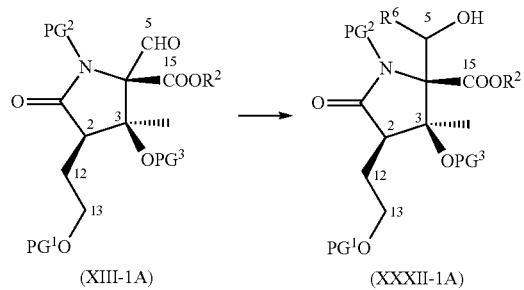

(XIII-1A) → (XXXII-1A)

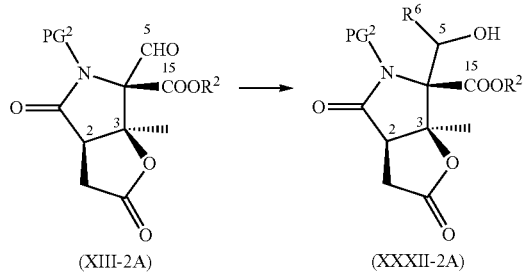

(XIII-2A) → (XXXII-2A)

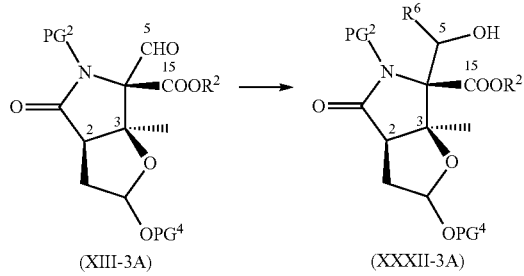

(XIII-3A) → (XXXII-3A)

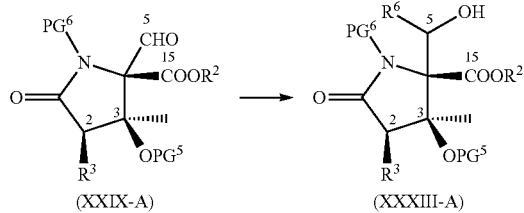

(XXIX-A) → (XXXIII-A)

Additional examples of the structure and stereochemistries of compounds of formulae (XXXII-1), (XXXII-2), (XXXII-3) and (XXXIII) are shown below.

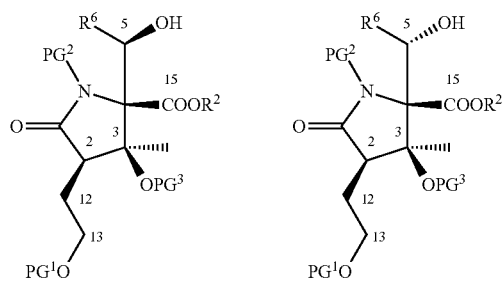

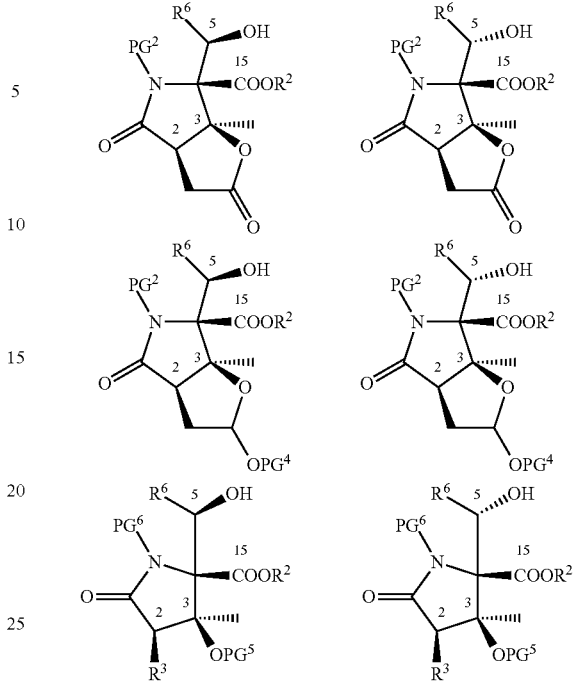

A variety of methods are known to those skilled in the art for adding a $R^6$ moiety to compounds of formulae (XIII-1), (XIII-2), (XIII-3) and (XXIX-1). In some embodiments, $R^6$ can be added using an organometallic moiety such as those described herein. A non-limiting list of suitable organometallic moieties include organomagnesium compounds, organolithium compounds, organotin compounds, organocuprates compounds, organozinc, and organopalladium compounds, metal carbonyls, metallocenes, carbine complexes, and organometalloids (e.g., organoboranes and organosilanes). In some embodiments, the organometallic moiety can be selected from $R^6$—$MgR^7$, $R^6$—ZnR, $R^6$—Li, $(R^6)_s$—B$(R^7)_{3-s}$ and $(R^6)_t$—Sn$(R^7)_{4-t}$; wherein $R^7$ can selected from halogen, or substituted or unsubstituted variants of the following: alkyl, alkenyl, cycloalkyl, aryl, arylalkyl, isopinocampheyl, hydroxy, alkoxy, and carbonylalkoxy, wherein if more than one $R^7$ is present, the $R^7$ groups can optionally be bond together to form an optionally substituted cycloalkyl (e.g., 9-BBN), optionally substituted cycloalkenyl, optionally substituted heteroalkyl or optionally substituted heteroalkenyl ring; s can be an integer from 1 to 3; and t can be an integer from 1 to 4.

After addition of $R^6$, compounds of formulae (XXXII-1), (XXXII-2), (XXXII-3) and (XXXIII) can be used to form analogs of Salinosporamide A via the methodologies discussed with respect to Schemes 9, 10, 11, 12, 13 and 19. For example, any protecting groups on compounds of formulae (XXXII-1), (XXXII-2), (XXXII-3) and (XXXIII) can be removed in any suitable order, and a 4-membered heterocyclic ring can be formed using methods known to those skilled in the art, including those described herein. The resulting compounds such as compounds of formulae (XXXIV) and (XXXV) can have the structures and stereochemistries shown in Scheme 22. If desired or needed, the chirality of C-5 can be inverted using one or methods described herein. As discussed previously, any protecting groups present on compounds of formulae (XIII-1), (XIII-2), (XIII-3) and (XXIX-1) can be removed at anytime. Additionally, the stereochemistry of the C-5 secondary hydroxy can be inverted at any time after the addition of the $R^6$ group to compounds of formulae (XIII-1), (XIII-2), (XIII-3) and (XXIX-1).

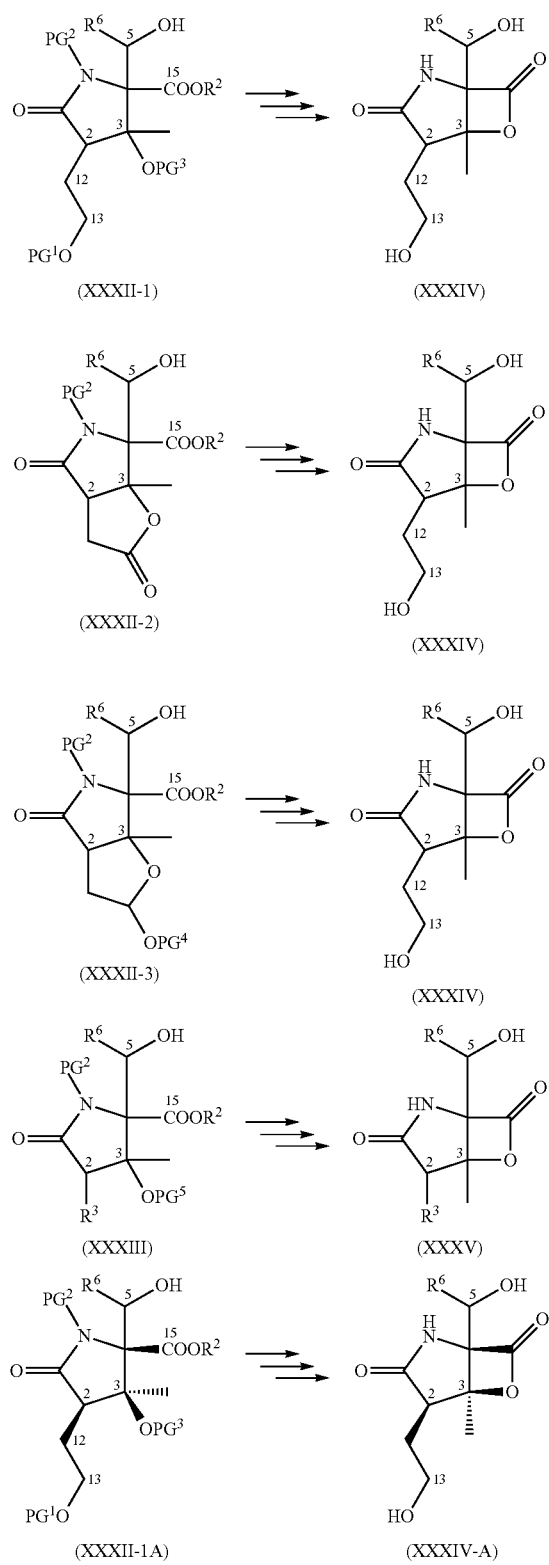

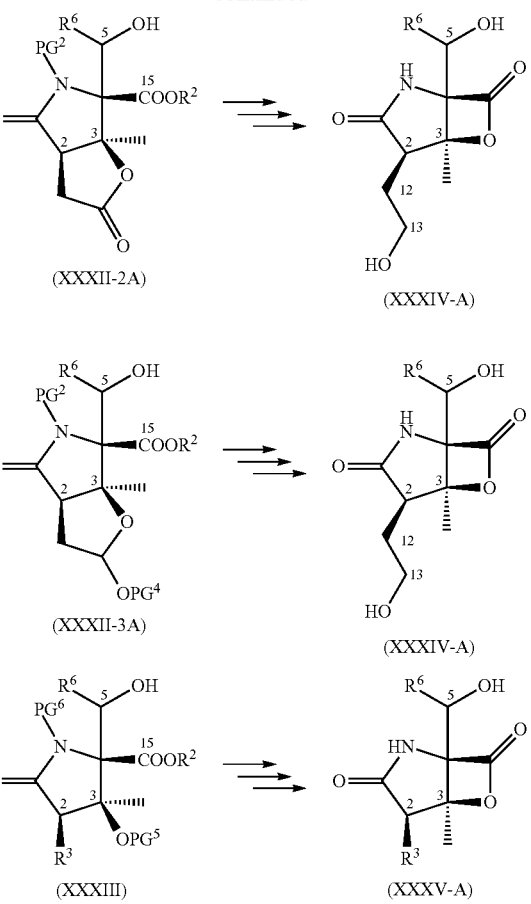

Additional examples of the structure and stereochemistries of compounds of formulae (XXXIV) and (XXXV) are shown below.

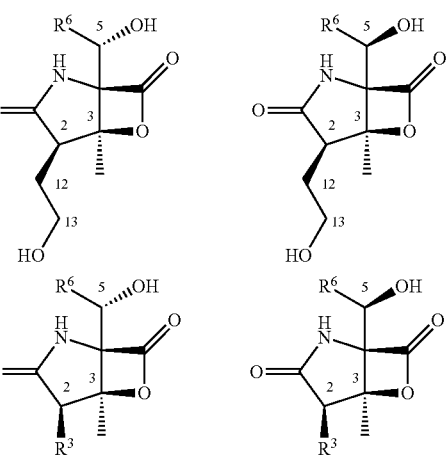

As shown in Scheme 23, additional analogs of Salinsporamide A can be obtained by replacing the hydroxy group attached to C-13 Examples of the structures and stereochemistries of compounds of formulae (XXXIV) and (XXXVI), in which $R^6$ and X have been previously defined herein, are shown below.

Scheme 23

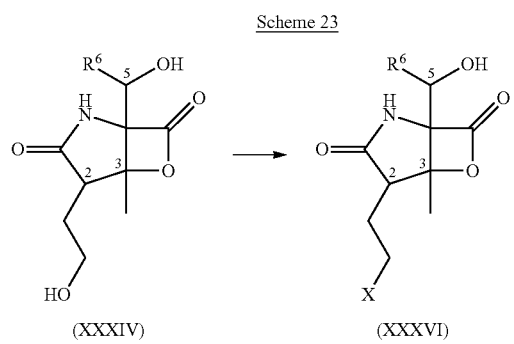

Additional information regarding the conditions and reagents that can be used are disclosed in U.S. Pat. No., 7,183,417, issued Feb. 27, 2007; U.S. application Ser. Nos. 11/697,689, filed Apr. 6, 2007, and 11/434,698, filed May 16, 2006; International Application No. PCT/US2005/012113, filed Apr. 11, 2005 and the following articles: Margalef et al. *Tetrahedron* (2008) 64 (34) 7896-7901 and Takahashi et al., *Angew. Chemie, Int. Ed.* (2008) 47, 1-4.

EXAMPLES

Embodiments are disclosed in further detail in the following examples, which are not in any way intended to limit the scope of the claims.

Example 1

Synthesis of (1-B)

$R^1$=t-Butyl and $R^2$=Methyl

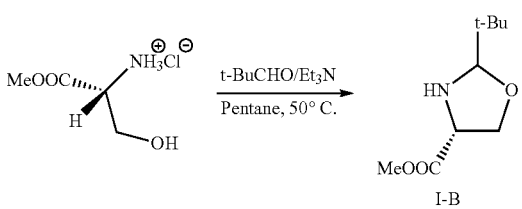

To a suspension of (R)-serine methylester hydrochloride (25 g, 160.67 mmol) in pentane (800 mL) at room temperature were added t-butyl aldehyde (20.73 g, 241 mmol) and Et$_3$N (17.85 g, 176.74 mmol). The reaction mixture was refluxed for 15 hrs at 50° C. using Dean-Stark apparatus. The resulting reaction mixture was cooled to room temperature, filtered through celite, and the celite cake was washed with pentane (2×40 mL). The combined filtrate was concentrated under reduced pressured and dried under high vacuum to afford product, I-B (24.5 g, 131 mmol, 81.5% yield) as clear oil, which can be used without further purification. The compound I-B was characterized by $^1$H-NMR (CDCl$_3$, 500 MHz). See FIG. 7.

Example 2

Synthesis of the Ester Precursor of Compound (II)

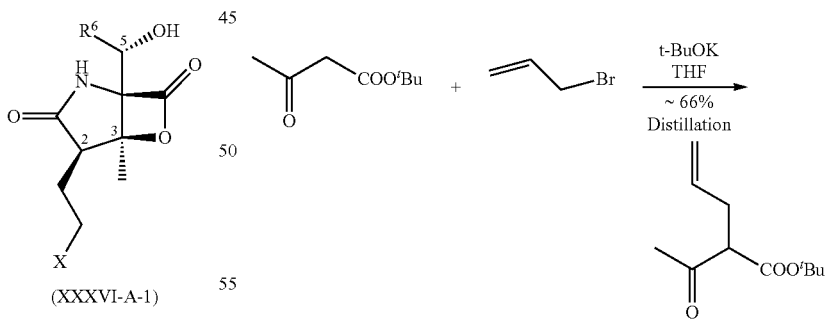

Method A

To a solution of t-butylacetoacetate (30 g, 0.19 mol) in dry THF (800 mL) at 0° C. was added t-BuOK (23.41 g, 95% w/w, 0.21 mol) and the solution was stirred for about 15 minutes. Allylbromide (18.39 g, 0.152 mol) was added and the solution was stirred at 0° C. for additional 15 min. The reaction mixture was then allowed to warm to room temperature and stirred for about 5 hours under an atmosphere of N$_2$. The above reaction mixture was then cooled to 0° C., quenched with H₂O (300 mL), and extracted with EtOAc (3×200 mL). The combined organic phase was dried over Na₂SO₄ and concentrated under reduced pressure. The crude product was purified by silica gel flash chromatography (5 cm ID×45 cm) using a solvent gradient of 100% hexanes (1.5 L) to 1.5% EtOAc/hexanes (3 L) to 2.5% EtOAc/hexanes (1 L) to 4% EtOAc/hexanes (700 mL) to afford pure product (14.5 g, 0.073 mol, 38.5% yield). Alternatively, the crude product was purified by fractional distillation (130° C. oil bath, 90-95° C. bp) under high vacuum (12 mm Hg) to afford product, the ester precursor of the compound II (66% yield).

Method B

To a solution of t-BuOK (50 g, 95% w/w, 0.42 mol) in dry THF (1.5 L) at 0° C. was added t-butylacetoacetate (65 g, 0.41 mol) and the solution was stirred for about 15 minutes under an atmosphere of N₂. Allylbromide (47 g, 0.39 mol) was added slowly and the solution was stirred at 0° C. for about 20 hours. The reaction mixture was allowed to warm to room temperature and stirred for additional 15 hours. The reaction mixture was then quenched with H₂O (1 L) at 0° C. and extracted with EtOAc (3×0.5 mL). The organic phase was dried over MgSO₄ and concentrated under reduced pressure. The crude product was purified by fractional distillation (130° C. oil bath, 90-95° C. bp) under high vacuum (12 mm Hg) to afford the product, the ester precursor of the compound II (54 g, 0.27 mol, 66% yield). ¹H-NMR (CDCl₃, 500 MHz) (8): 5.68 (m, 1H), 5.03 (br dd, J=1, 17 Hz, 1H), 4.97 (br dd, J=1, 10 Hz, 1H), 3.35 (t, J=7.5 1H), 2.48 (br t, J=7.0, 2H), 2.16 (s, 3H), 1.39 (s, 9H). See FIG. 8.

Example 3

Synthesis of the Protected Ester Precursor of Compound (II)

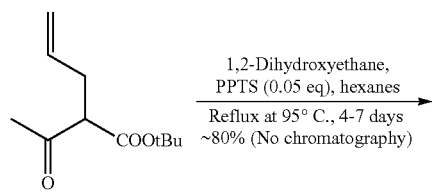

To a solution of the ester precursor (45 g, 0.23 mol) in hexanes (1.6 L) were added ethylene glycol (70.5 g, 1.15 mol) and PPTS (2.85 g, 0.011 mol). The reaction mixture was refluxed at 95° C. using Dean-Stark apparatus for 6 days (Note: 28.5 g, 0.46 mol of ethylene glycol was added to the reaction mixture every two days to maintain its concentration), then cooled to room temperature. The reaction mixture was then neutralized with 800 μL of Et₃N and diluted with H₂O (500 mL). The organic layer was separated, dried over Na₂SO₄ and concentrated under reduced pressure to afford product, the protected ester precursor of the compound II (44 g, 0.18 mmol, 80% yield), which can be used for the next step without purification. ¹H-NMR (CDCl₃, 500 MHz) (δ): 5.72 (m, 1H), 5.06 (dd, J=1, 17 Hz, 1H), 4.97 (d, J=10 Hz, 1H), 3.94 (m, 4H), 2.60 (dd, J=3.6, 11.5 Hz, 1H), 2.43 (m, 1H), 2.29 (m, 1H), 1.42 (s, 9H), 1.38 (s, 3H). See FIG. 9.

Example 4

Synthesis of Compound (II)

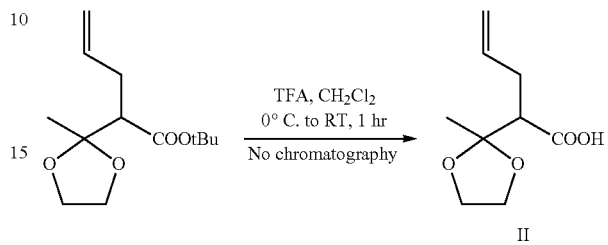

To a solution of the protected ester precursor (28 g, 0.115 mol) in CH₂Cl₂ (28 mL) at 0° C. was added trifluoroacetic acid (TFA neat, 56 mL, 0.727 mol) and the solution was stirred for about 5 min. The reaction mixture was then allowed to warm to room temperature and stirred for one hour. The reaction mixture was diluted with CH₂Cl₂ (400 mL) and extracted with ice cold water (3×300 mL). The organic layer was dried over Na₂SO₄, concentrated under reduced pressure and dried under high-vacuum for about one hour (to remove the residual TFA) to afford the product, compound II (15.5 g, 0.083 mol, 72% yield) as light yellow oil, which can be used for the next step without purification. The compound II was characterized by ¹H-NMR (CDCl₃, 500 MHz): ¹H-NMR (CDCl₃, 500 MHz) (δ): 5.77 (m, 1H), 5.10 (br dd, J=1, 17 Hz, 1H), 5.02 (br d, J=10 Hz, 1H), 4.00 (m, 4H), 2.76 (dd, J=3.8, 11.0 Hz, 1H), 2.43 (m, 2H), 1.41 (s, 3H). See FIG. 10.

Example 5

Synthesis of compound (III-1B)

R¹=t-Butyl and R²=Methyl

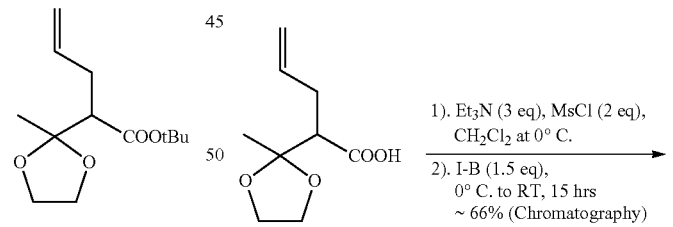

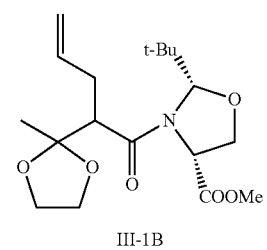

To a solution of compound II (4.8 g, 25.81 mmol) in dry CH₂Cl₂ (200 mL) at 0° C. were added Et₃N (7.82 g, 77.42 mmol) and methanesulfonyl chloride (5.89 g, 51.62 mmol)

and the solution was stirred for about 10 min. Then compound I-B (5.31 g, 28.4 mmol) was added, the reaction mixture was allowed to warm to room temperature slowly and stirred for about 15 hrs. Then the reaction mixture was quenched with H$_2$O (200 mL) and extracted with CH$_2$Cl$_2$ (3×100 mL). The combined organic layer was dried over Na$_2$SO$_4$ and concentrated under reduced pressure to yield III-1B as a mixture of two diastereomers (3:2). See FIG. 11b. The crude product was purified by silica flash chromatography (3 cm ID×30 cm) using a solvent gradient of 19:1 (500 mL) to 9:1 (500 mL) to 17:3 (500 mL) to 4:1 (1.5 L) to 3:1 (1 L) hexane/EtOAc to afford the product, compound III-1B (6 g, 16.9 mmol, 65.5% yield). The compound III-1B was characterized by $^1$H-NMR (CDCl$_3$, 500 MHz) and LC-MS. See FIGS. 11a and 11b. MS (ESI) m/z 356 [M+H]$^+$.

Example 6

Synthesis of Compound (IV-B)

R$^1$=t-Butyl and R$^2$=Methyl

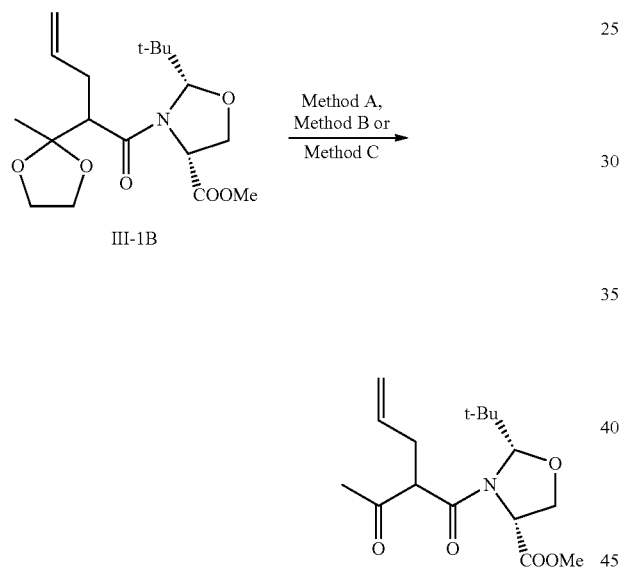

III-1B

IV-B

Figure 12B:
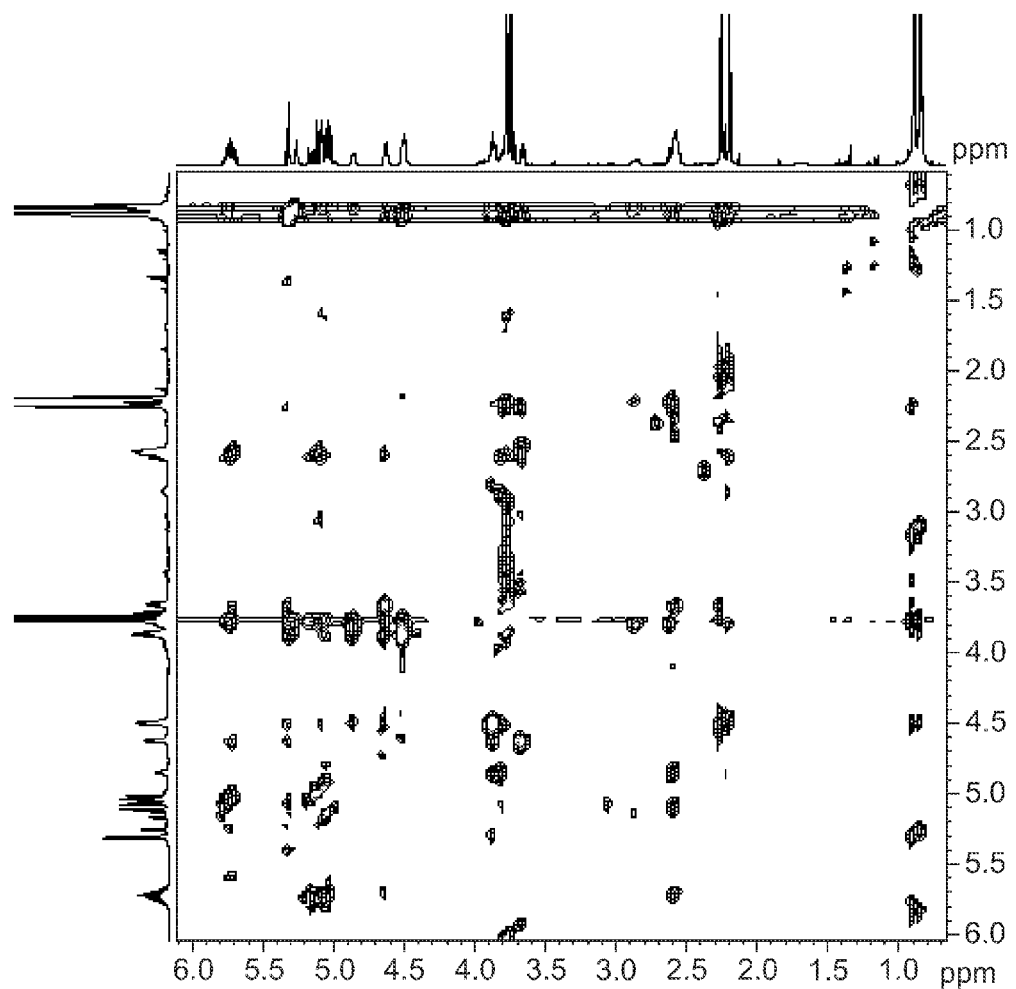
FIG. 12b shows a NOESY spectrum of a compound of formula (IV-B) ($R^1$=t-butyl and $R^2$=methyl) in $CDCl_3$.

Method A: To a solution of compound III-1B (6 g, 16.9 mmol) in CH$_3$CN (350 mL) were added sodium iodide (3.3 g, 21.97 mmol) and cerium (III) chloride heptahydrate (9.45 g, 25.35 mmol) and the reaction mixture was stirred at 60-65° C. for 4 hours (the reaction progress can be monitored by LC-MS). The above reaction mixture was then quenched with water (200 mL) and extracted with EtOAc (3×150 mL). The combined organic layer (cloudy) was concentrated under reduced pressure to remove all of the CH$_3$CN/EtOAc, leaving about 20 mL of H$_2$O (CH$_3$CN soluble part), which was further extracted with EtOAc (100 mL). The organic layer was dried over Na$_2$SO$_4$, and concentrated under reduced pressure to afford the product, IV-B (4.4 g, 14.2 mmol, 83.5% yield) as a mixture of two diastermers (3:2). See FIG. 12e. If desired, the product can be used for the next step without purification. The compound IV-B was characterized by $^1$H-NMR (CDCl$_3$, 500 MHz) and NOESY (CDCl$_3$, 500 MHz). See FIGS. 12a and 12b. MS (ESI) m/z 312 [M+H]$^+$. A portion of the product was further purified by reverse phase HPLC using C-18 column (150 mm×21 mm), and an isocratic solvent system of 40% acetonitrile in H$_2$O at a flowrate of 14.5 mL/min to afford individual diastereomers IV-B1 and IV-B2 as pure samples. The diastereomers IV-B1 and IV-B2 were characterized by $^1$H-NMR (CDCl$_3$, 500 MHz). See FIGS. 12c and 12d.

Compound IV-B1: $^1$H-NMR (CDCl$_3$, 500 MHz) (δ): 5.73 (m, 1H), 5.34 (s, 1H), 5.12 (m, 1H), 5.05 (d, J=10.1 Hz, 1H), 4.64 (d, J=6.3 Hz, 1H), 4.53 (d, J=8.2 Hz, 1H), 3.90 (t, J=7.6 Hz, 1H), 3.80, (s, 3H), 3.67 (t, J=7.6 Hz, 1H), 2.60 (m, 2H), 2.27 (s, 3H), 0.91 (s, 9H); MS (ESI) m/z 312 [M+H]$^+$.

Compound IV-B2: $^1$H-NMR (CDCl$_3$, 500 MHz) (δ): 5.76 (m, 1H), 5.28 (s, 1H), 5.18 (br d, J=17.3 Hz 1H), 5.08 (d, J=10.1 Hz, 1H), 4.88 (m, 1H), 4.52 (d, J=8.2 Hz, 1H), 3.88 (m, 1H), 3.81, (m, 1H), 3.76 (s, 3H), 2.88 (m, 1H), 2.63 (m, 1H), 2.21 (s, 3H), 0.86 (s, 9H); MS (ESI) m/z 312 [M+H]$^+$.

Method B: A mixture of compound III-1B (175 mg, 0.493 mmol) and iodine (12.52 mg, 0.0493 mmol) in acetone (20 mL) was refluxed at 56° C. for one hour. The reaction mixture was then cooled to RT, the acetone was removed under reduced pressure, and the crude reaction product was dissolved in CH$_2$Cl$_2$ (20 mL). The CH$_2$Cl$_2$ solution was washed successively with 5% aqueous sodium thiosulfate (10 mL), H$_2$O (10 mL) and brine (10 mL). The resulting organic phase was dried over Na$_2$SO$_4$, concentrated under reduced pressure and purified by silica gel plug column (2.5 cm ID×6 cm) using a solvent gradient of 19:1 (50 mL) to 9:1 (100 mL) to 4:1 (100 mL) to 3:1 (100 mL) to 7:3 (100 mL) hexanes/EtOAc to afford the product, compound IV-B (97 mg, 0.312 mmol, 63.3% yield).

Method C: A mixture of compound III-1B (500 mg, 1.40 mmol) and LiBF$_4$ (200 mg, 2.1 mmol) in CH$_3$CN (6 mL, wet with 2% H$_2$O) was stirred at 70° C. for 1.5 to 2 hrs (the reaction progress can be monitored by LC-MS). The above reaction mixture was then quickly cooled to 0° C., filtered through a short silica plug and concentrated under reduced pressure. The product was purified by silica gel column chromatography (1.25 cm ID×5 cm) using a solvent gradient of 19:1 (50 mL) to 9:1 (50 mL) to 4:1 (50 mL) hexanes/EtOAc to afford the purified product, compound IV-B (260 mg, 0.84 mmol, 60% yield).

Example 7

Synthesis of Compound (VI-B)

R$^1$=t-Butyl and R$^2$=Methyl

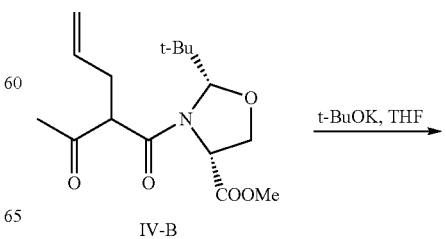

IV-B

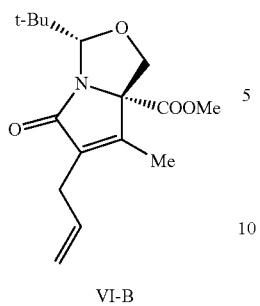

VI-B

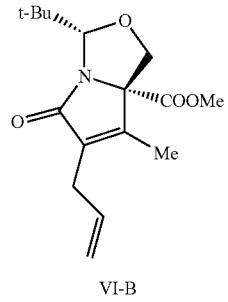

VI-B

To a solution of compound IV-B (26 g, 83.6 mmol) in dry THF (2.7 L) at RT was added t-BuOK (4.68 g, 41.8 mmol). The reaction mixture was stirred at RT for 15 min under an atmosphere of $N_2$ and then quenched with $H_2O$ (900 mL) and extracted with EtOAc (3×400 mL). The combined organic phase was washed with saturated brine solution, dried over $Na_2SO_4$ and concentrated under reduced pressure. The reaction mixture was dissolved in 1:1 ether:hexanes (75 mL each) and transferred to a crystallization dish, where it was allowed to stand and crystallize. After an hour, the crystals (1$^{st}$ crop) were separated by decanting the mother liquor. The crystals were washed with ether (2×10 mL) and hexanes (2×10 mL). The combined mother liquor and washes was concentrated under reduced pressure and redissolved in 1:1 ether:hexanes (50 mL each) and the crystallization process was repeated the crystallization process as described above. The crystals (2$^{nd}$ crop) were separated by decanting the mother liquor. The mother liquor was chromatographed on a silica gel flash column (30×4 cm) using solvent gradient of 19:1 (500 mL) to 9:1 (1 L) to 17:3 (500 mL) EtOAc/hexanes to yield the compound VI-B.

Compound of VI-B: $^1$H-NMR (CDCl$_3$, 500 MHz) (δ): 5.81 (m, 1H), 5.04 (br dd, J=1.5, 7.5 Hz, 1H), 5.02 (s, 1H), 4.78 (d, J=8.5 Hz, 1H), 4.66 (s, 1H), 3.74 (s, 3H), 3.18 (d, J=8.5 Hz, 1H), 2.97 (t, J=6.5 Hz, 1H), 1.83 (s, 3H), 0.91 (s, 9H). See FIG. 13. $^{13}$C-NMR (CDCl$_3$, 125 MHz) (δ): 178.4, 170.0, 151.9, 133.4, 132.8, 116.1, 96.9, 78.0, 70.5, 52.9, 35.2, 27.6, 24.7, 12.1. See FIG. 14. MS (ESI) m/z 294 [M+H]$^+$.

Example 8

Synthesis of Compound (VI-B)

R$^1$=t-Butyl and R$^2$=Methyl

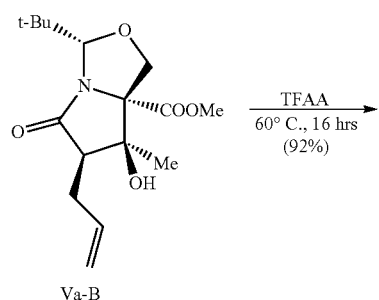

Va-B

A solution of compound V-B (8 mg, 0.026 mmol) in trifluoroacetic anhydride (TFAA, 0.10 mL) was refluxed at 60° C. for 16 hrs. The reaction mixture was then cooled to 25° C. and concentrated under reduced pressure. The crude residue was purified by silica flash chromatography (EtOAc in hexanes, 10% to 20%) to afford compound VI-B (7 mg, 0.024 mmol, 92.3% yield). MS (ESI) m/z 294 [M+H]$^+$.

Example 9

Synthesis of Compound (VII-B)

R$^1$=t-Butyl and R$^2$=Methyl

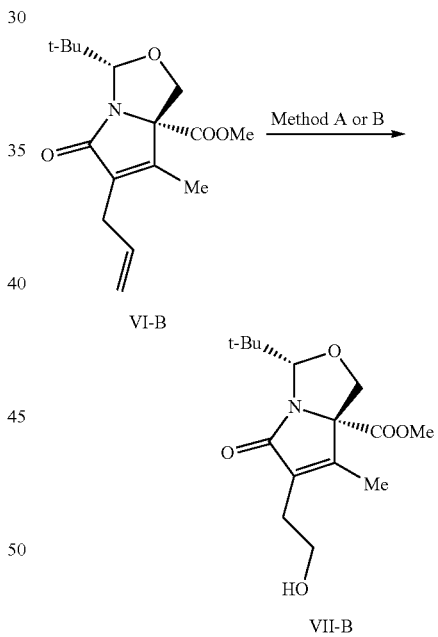

VI-B

VII-B

Method A: i) OsO$_4$, NMO, NIO$_4$; ii) NaBH$_4$; Method B: i) Ozonolysis; ii) NaBH.

Method A: To a solution of compound VI-B (40 mg, 0.14 mmol) in THF/H$_2$O (1:1, 1.0 mL) were added NMO (50% w/w aqueous solution, 0.10 mL, 0.42 mmol) and OsO$_4$ (2.5% wt. % in 2-methyl-2-propanol, 108 µL, 7 µmol). The resulting mixture was stirred at 5° C. for 15 hours. Then NaIO$_4$ (150 mg, 0.70 mmol) was added together with phosphate buffer (pH 7.0, 5 mL), the reaction mixture was stirred for an additional 2 hours at room temperature before diluting with ethyl acetate (5 mL) and washing with water (2×2 mL), saturated aqueous Na$_2$SO$_3$ (2 mL), and brine (2 mL). The organic layer was dried over MgSO$_4$, concentrated under reduced pressure and dried by high vacuum. The crude residue was re-dissolved in THF/H$_2$O ((2:1; 3 mL), then NaBH$_4$ (16 mg, 0.42 mmol) was added and stirred at room temperature for 30 min. The reaction mixture was diluted with H$_2$O (5 mL) and extracted with EtOAc (2×2 mL) followed by CH$_2$Cl$_2$ (3×2 mL). The organic phase was dried over MgSO$_4$ and concentrated under reduced pressure to obtained a crude residue which was purified by silica flash chromatography (EtOAc in hexanes, 10% to 50%) to afford compound VII-B (33 mg, 0.11 mmol, 78% overall yield). Compound VII-B was characterized by $^1$H and $^{13}$C NMR. See FIGS. 15 and 16. MS (ESI) m/z 298 [M+H]$^+$.

Method B: A solution of compound VI-B (1.0 g, 3.40 mmol) in THF (20 mL) was treated with ozone at −80° C. for 0.5 hrs (the O$_3$ was generated by OL80 F ozonation equipment and the ozonolysis reaction progress was monitored by TLC). To this reaction mixture was added NaBH$_4$ (0.64 g, 17.0 mmol) followed by MeOH (5 ml) at −80° C., then the reaction mixture was slowly warmed up to 25° C. and stirred for 30 mins at this temperature. The above reaction mixture was diluted with H$_2$O (30 mL) and extracted with EtOAc (2×20 mL) followed by CH$_2$Cl$_2$ (3×20 mL). The organic phase was dried over MgSO$_4$ and concentrated under reduced pressure. The crude residue was purified by silica flash chromatography (EtOAc in hexanes, 20% to 80%) to afford VII-B (750 mg, 2.53 mmol, 74% yield) with recovery of some starting material VI-B (150 mg, 0.51 mmol). MS (ESI) m/z 298 [M+H]$^+$.

Example 10

Synthesis of Compound (VIII-B)

R$^1$=t-Butyl and R$^2$=Methyl

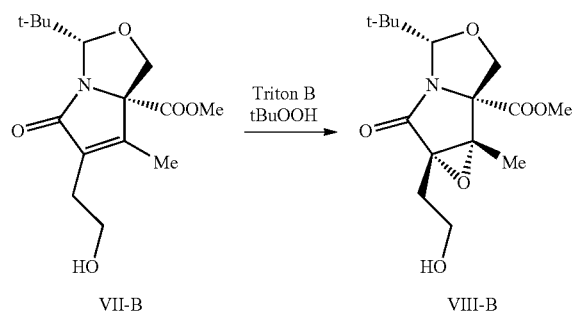

Figure 19:
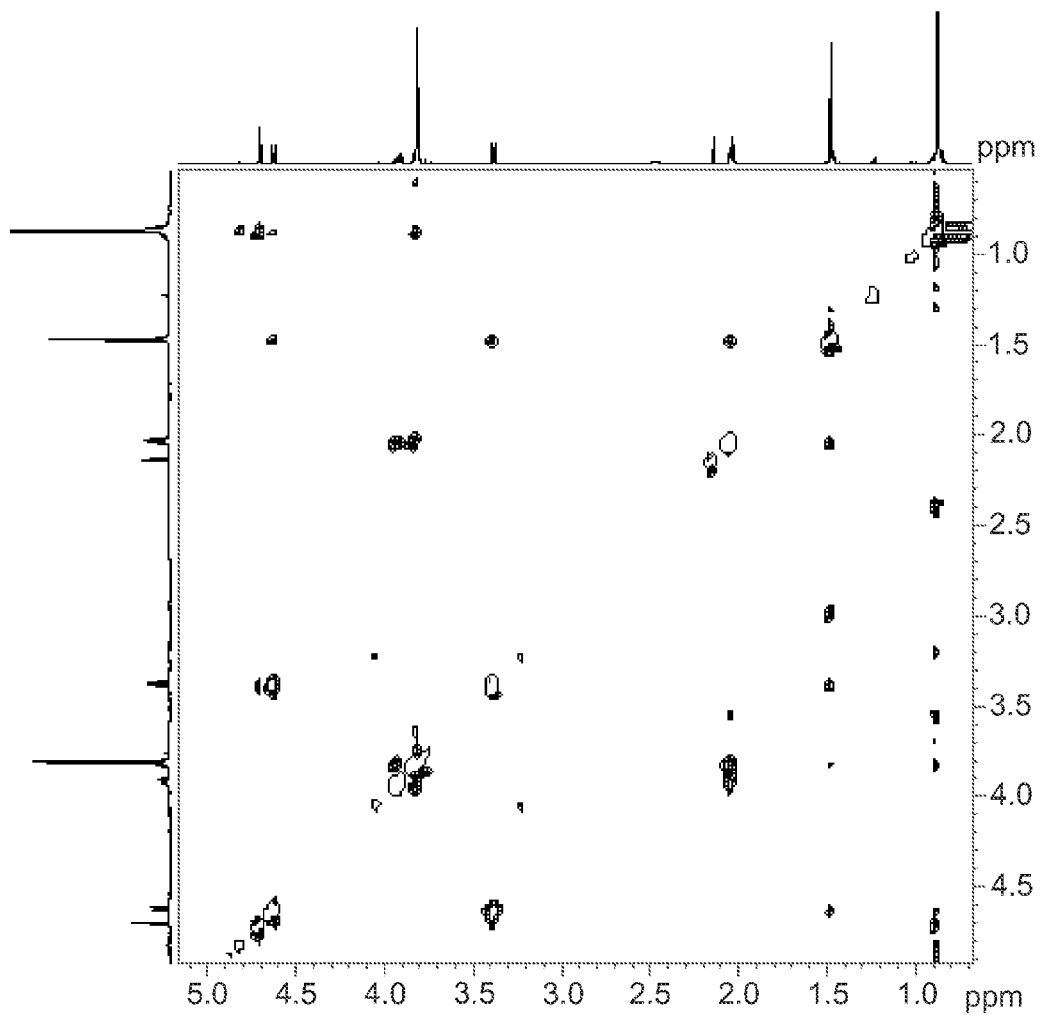
FIG. 19 shows a NOESY spectrum of a compound (VIII-B) (R$^1$=t-butyl and R$^2$=methyl) in CDCl$_3$.

To a concentrated suspension of Triton B (benzyltrimethyl ammonium hydroxide, 80 wt % in methanol, 1.41 g, 8.42 mmol) were added THF (0.5 mL) and t-butyl hydroperoxide solution (5-6 M in decane, 4.21 mL, 21.04 mmol) and the reaction mixture was stirred for 10 minutes at room temperature. A solution of compound VII-B (1.25 g, 4.21 mmol) in THF (0.1 mL) was added to the above reaction mixture and stirred at room temperature for 18 hours. The reaction mixture was concentrated directly under reduced pressure to obtain a crude residue, which was purified by silica flash chromatography (EtOAc in hexanes, 10% to 50%) to afford compound VIII-B (130 mg, 0.42 mmol, 10% Yield) and some starting material VII-B (620 mg, 2.08 mmol). The product was characterized by $^1$H and $^{13}$C NMR. See FIGS. 17 and 18. The stereochemistry was confirmed by NOESY. See FIG. 19. MS (ESI) m/z 314 [M+H]$^+$.

Example 11

Synthesis of Compound (X-1B)

PG$^1$=Bz, R$^1$=t-Butyl and R$^2$=Methyl

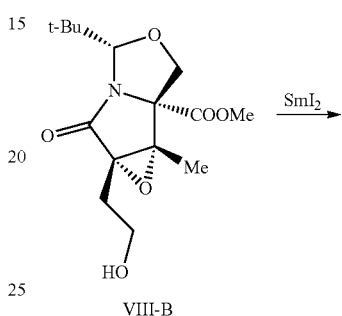

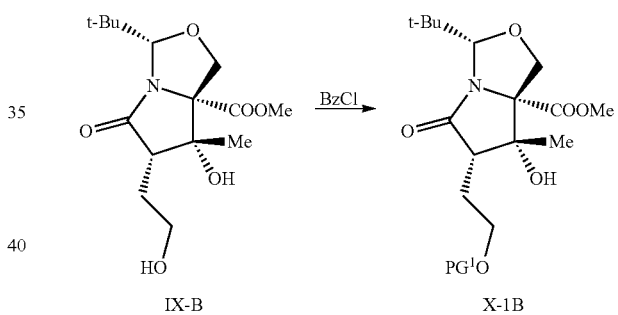

Figure 20:
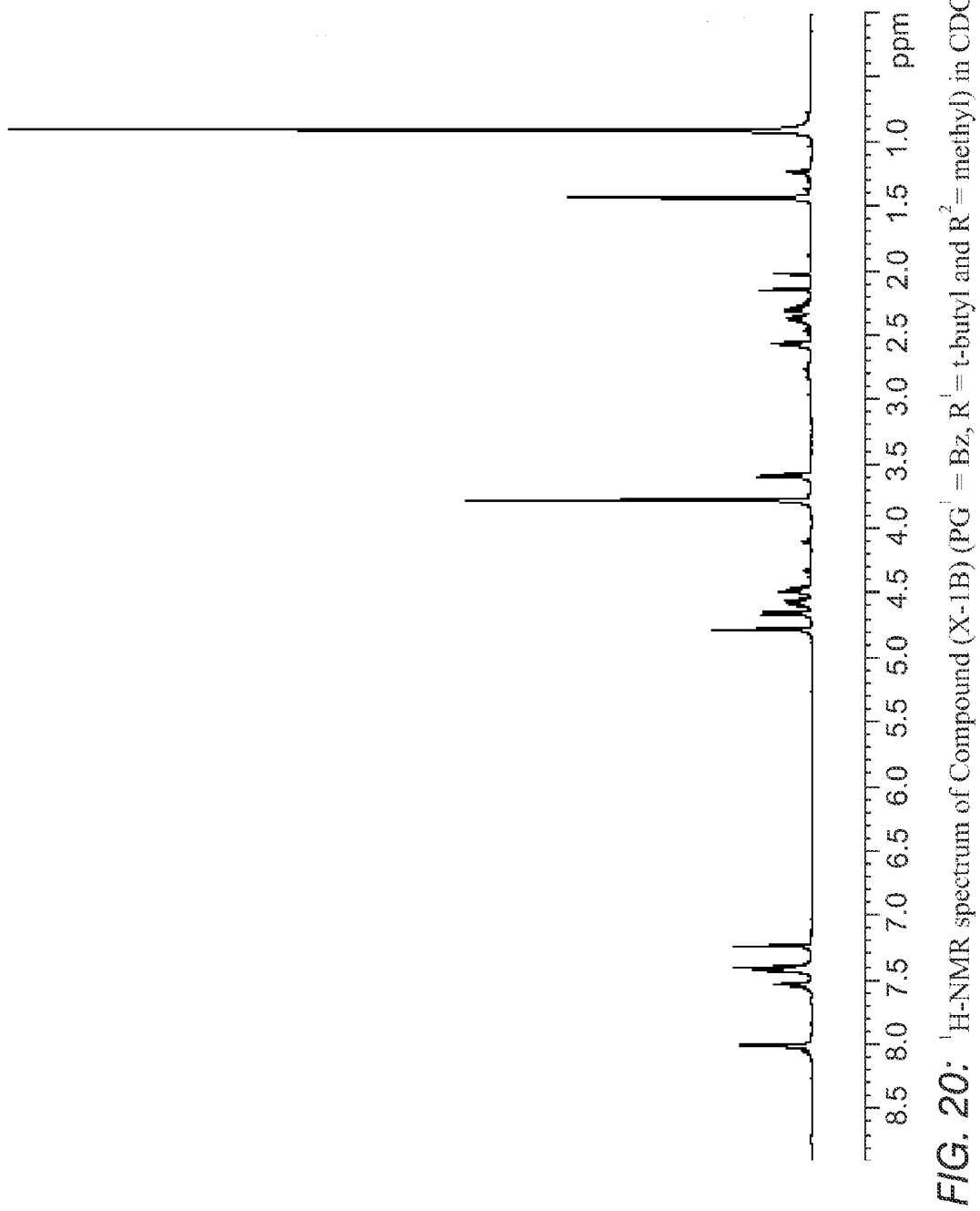
FIG. 20 shows a $^1$H NMR spectrum of a compound (X-1B with PG$^1$=Bz, R$^1$=t-butyl and R$^2$=methyl) in CDCl$_3$.
Figure 21:
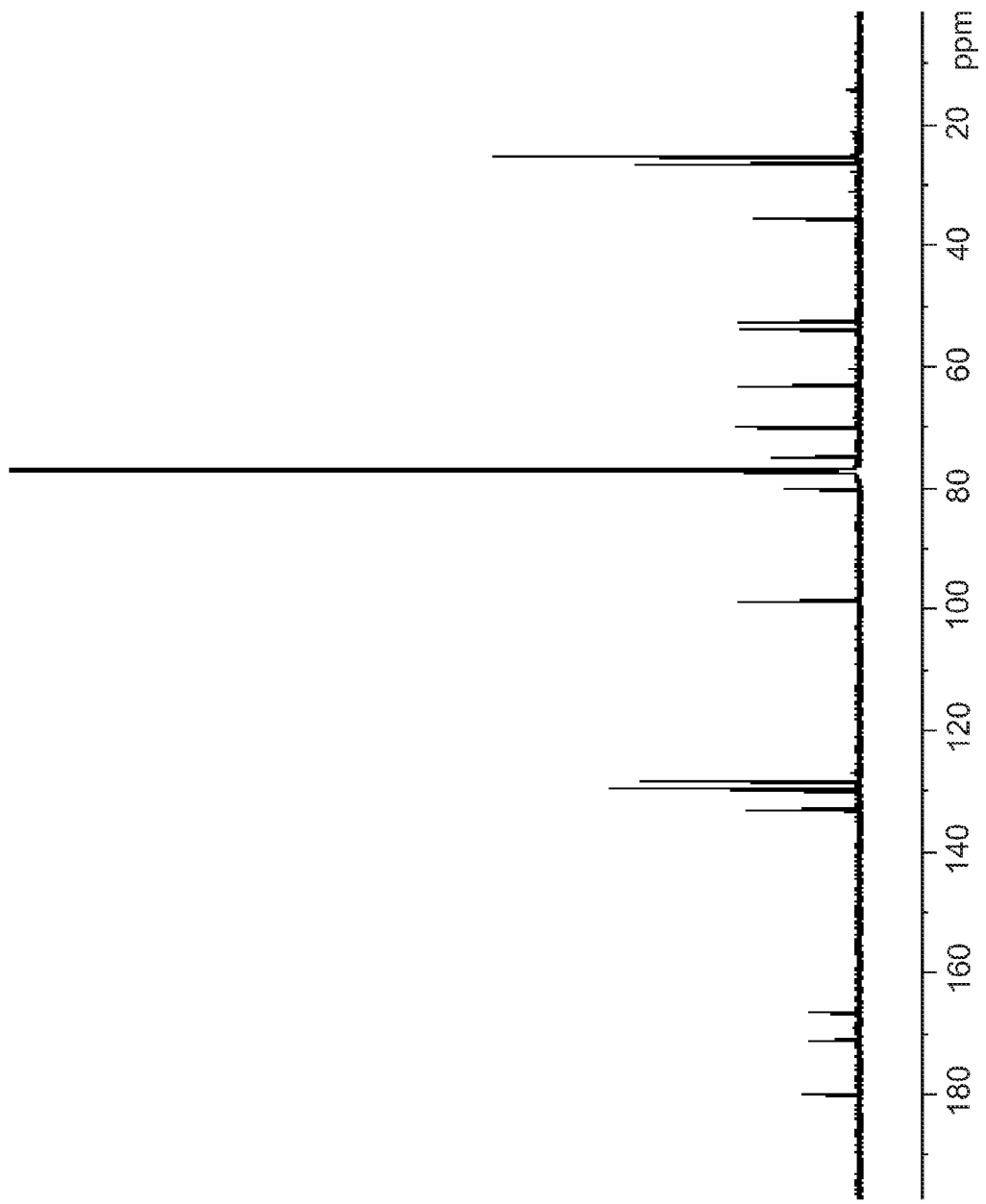
FIG. 21 shows a $^{13}$C NMR spectrum of a compound (X-1B with PG$^1$=Bz, R$^1$=t-butyl and R$^2$=methyl) in CDCl$_3$.
Figure 22:
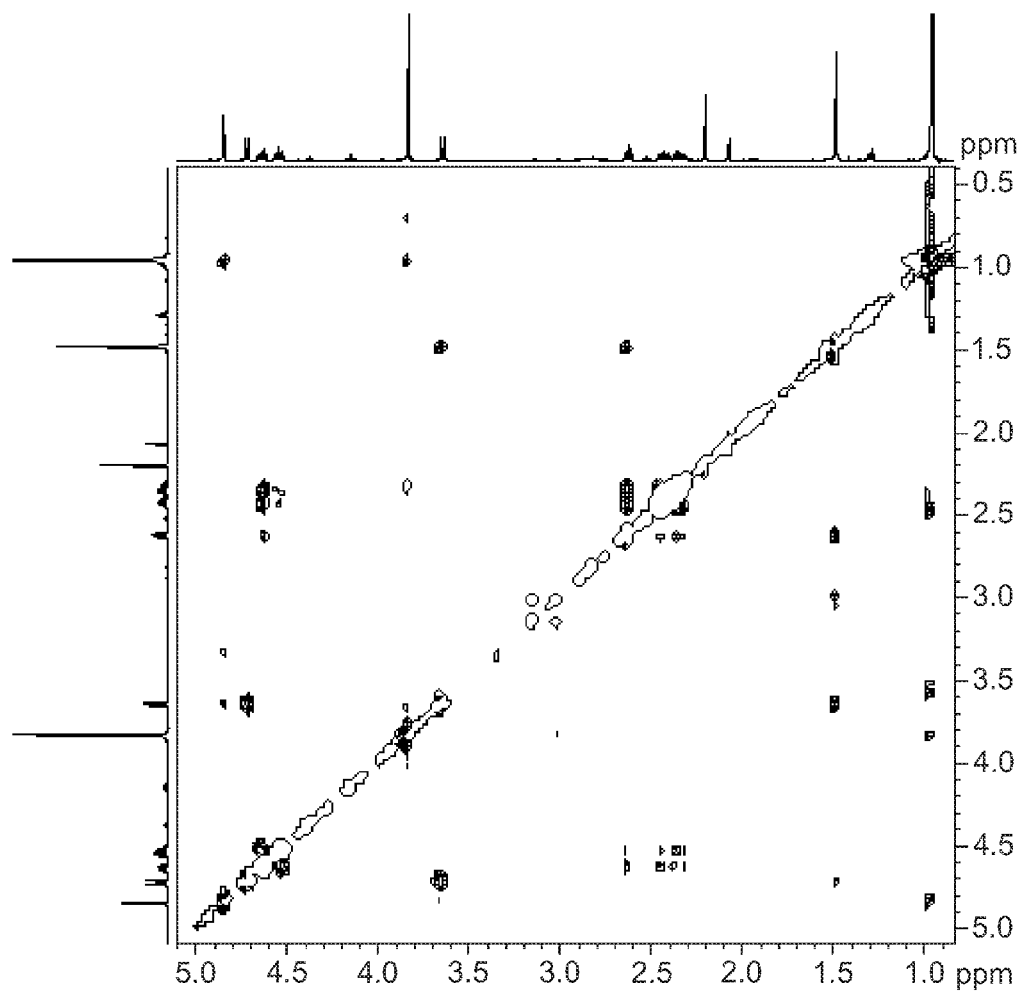
FIG. 22 shows a NOESY spectrum of a compound of formula (X-1B with PG$^1$=Bz, R$^1$=t-butyl and R$^2$=methyl) in CDCl$_3$.

To a solution of compound VIII-B (150 mg, 0.48 mmol) in THF/MeOH (1:1, 2.0 mL) was added Samarium (II) iodide (0.1 M in THF, 14.4 mL, 1.44 mmol) at −80° C. and the reaction mixture was stirred at this temperature for 30 minutes. The reaction was then quenched with aqueous NaHCO$_3$ (10 mL) and Na$_2$S$_2$O$_3$ and extracted with EtOAc (2×20 mL). The organic phase was dried over MgSO$_4$, concentrated under reduced pressure and dried by high vacuum to yield compound IX-B as crude residue. The crude residue was re-dissolved in CH$_2$Cl$_2$ (3 mL), pyridine (116 µL, 1.44 mmol) was added, followed by addition of an appropriate protecting group reactant such as benzoyl chloride (BzCl, 100 µL, 0.86 mmol). The resulting reaction mixture was stirred at room temperature for 15 hours. This reaction mixture was then directly concentrated under reduced pressure and the resulting crude product was purified by silica flash chromatography (EtOAc in hexanes, 10% to 50%) to afford compound X-1B (PG$^1$=Bz) (190 mg, 0.45 mmol, 94% overall yield from VIII-B). Compound X-1B (PG$^1$=Bz) was characterized by both $^1$H and $^{13}$C NMR spectra. See FIGS. 20 and 21. The stereochemistry of compound X-1B (PG$^1$=Bz) was also confirmed by NOESY. See FIG. 22. MS (ESI) m/z 420 [M+H]$^+$.

83

Example 12

Synthesis of Compound (XI-1B)

PG$^1$=Bz, R$^2$=Methyl

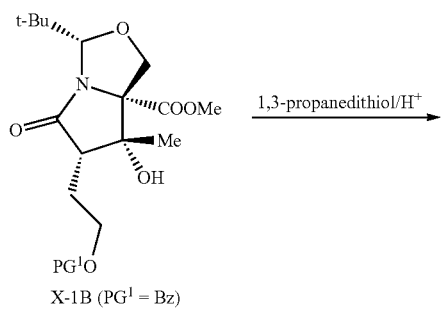

Figure 23:
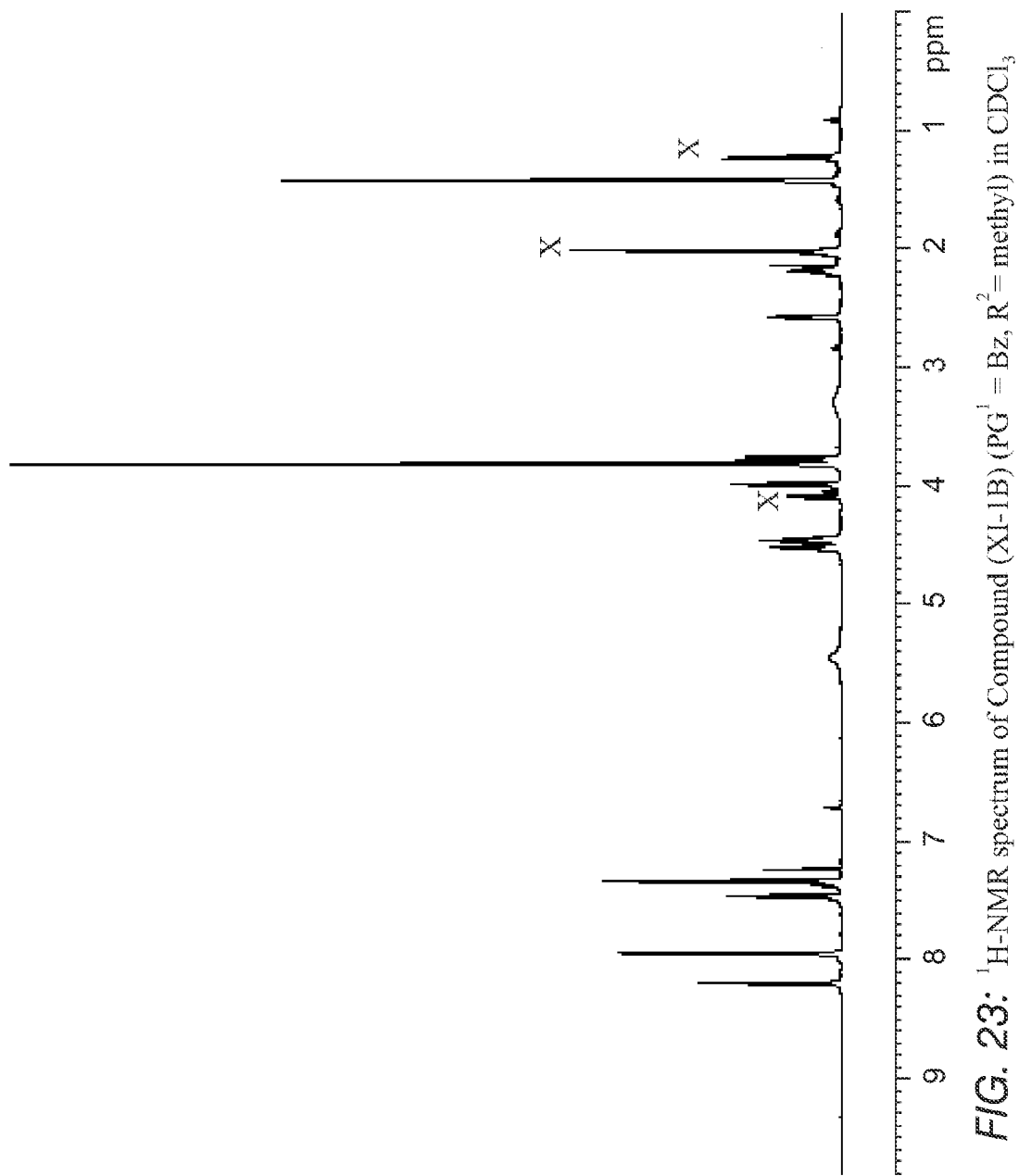
FIG. 23 shows a $^1$H NMR spectrum of a compound (XI-1B) (PG$^1$=Bz and R$^2$=methyl) in CDCl$_3$.
Figure 24:
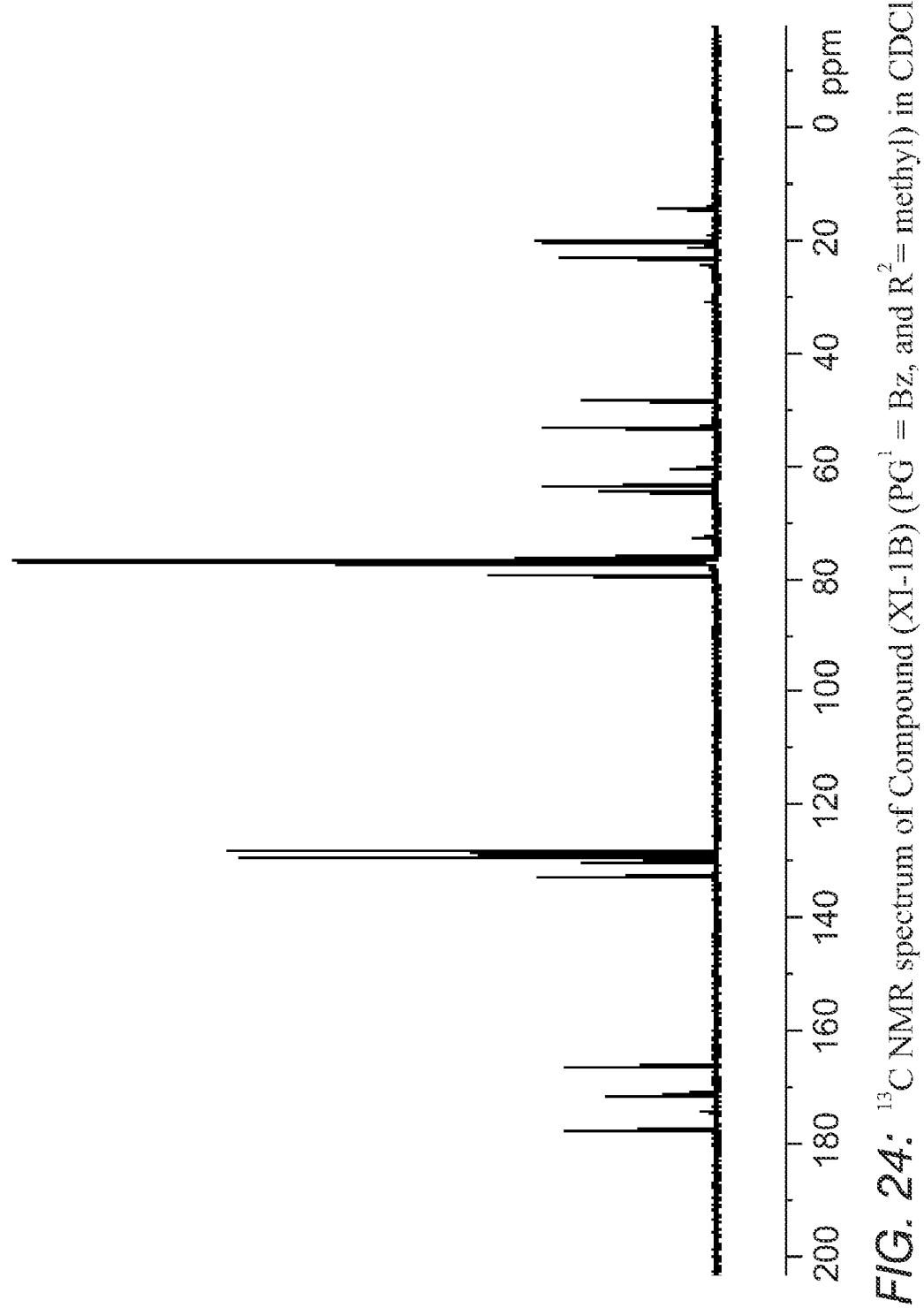
FIG. 24 shows a $^{13}$C NMR spectrum of a compound (XI-1B) (PG$^1$=Bz and R$^2$=methyl) in CDCl$_3$.

To a solution of compound X-1B (PG$^1$=Bz) (15 mg, 36 μmol) in CF$_3$CH$_2$OH (0.5 mL) were added 1,3-propanedithiol (500 μL) and a catalytic amount of aqueous HCl (12 N, 2 μL). The reaction mixture was stirred at 60° C. for 1 hr, concentrated under reduced pressure and the resulting crude product was then purified by silica flash chromatography (EtOAc in hexanes, 20% to 80%) to afford compound XI-1B (PG$^1$=Bz) (11 mg, 31 μmol, 87%). The product was characterized by $^1$H and $^{13}$C NMR. See FIGS. 23 and 24. MS (ESI) m/z 352 [M+H]$^+$.

Example 13

Synthesis of Compound (X-2B)

R$^1$=t-Butyl and R$^2$=Methyl

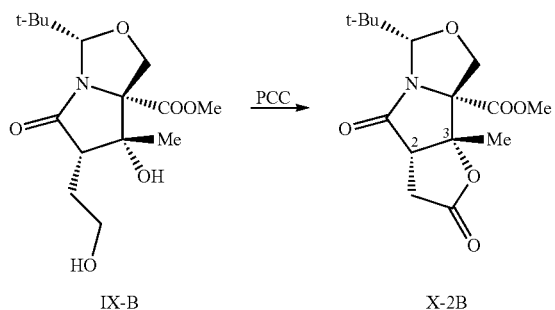

To a solution of compound IX-B (32.0 mg, 0.10 mmol) in CH$_2$Cl$_2$ (0.5 mL) with dried 4 A molecular sieves (0.10 g) was added pyridinium chlorochromate (PCC, 88 mg, 0.40 mmol).

84

Figure 25:
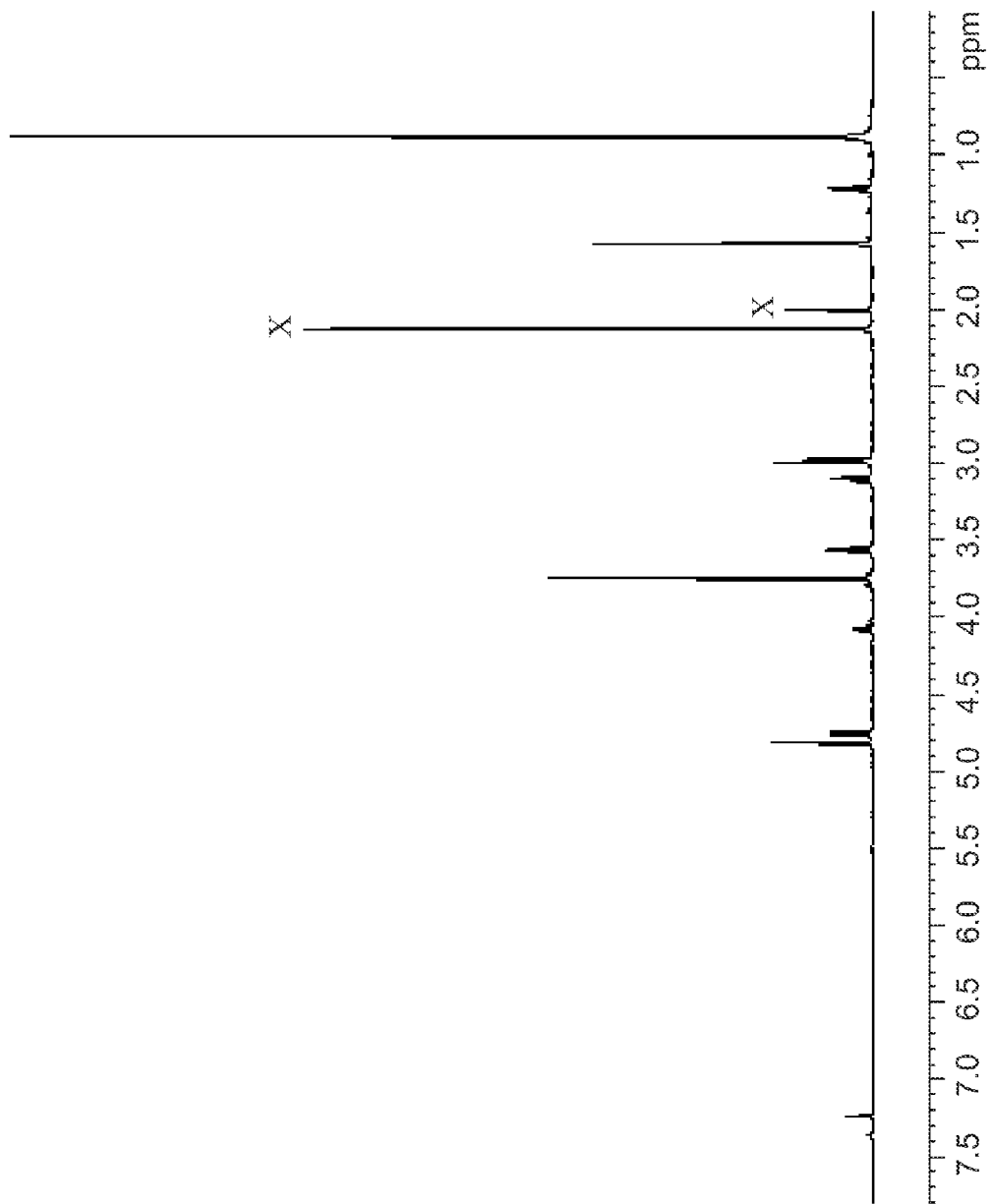
FIG. 25 shows a $^1$H NMR spectrum of a compound (X-2B) (R$^2$=methyl) in CDCl$_3$.
Figure 26:
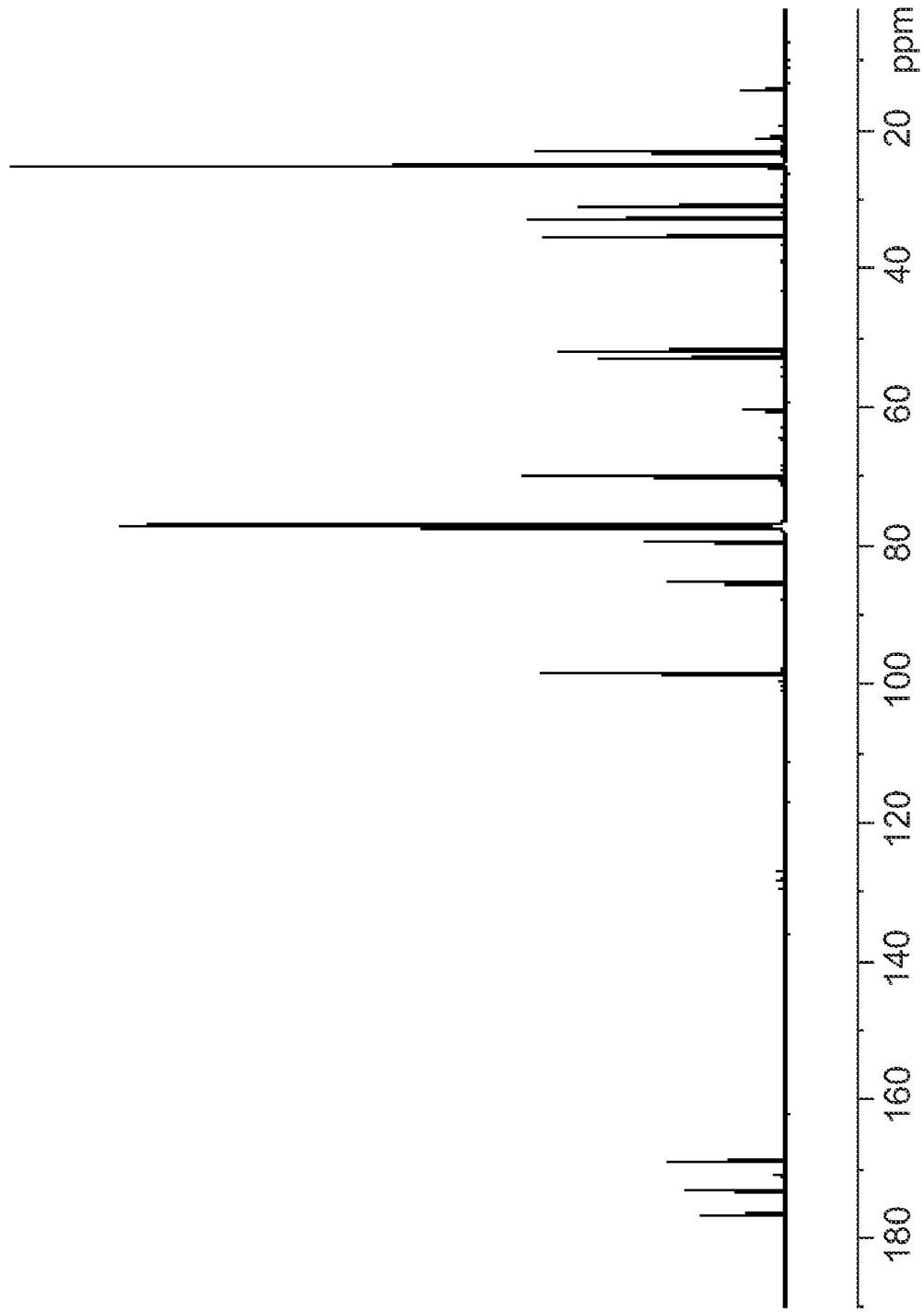
FIG. 26 shows a $^{13}$C NMR spectrum of a compound (X-2B) (R$^2$=methyl) in CDCl$_3$.
Figure 27:
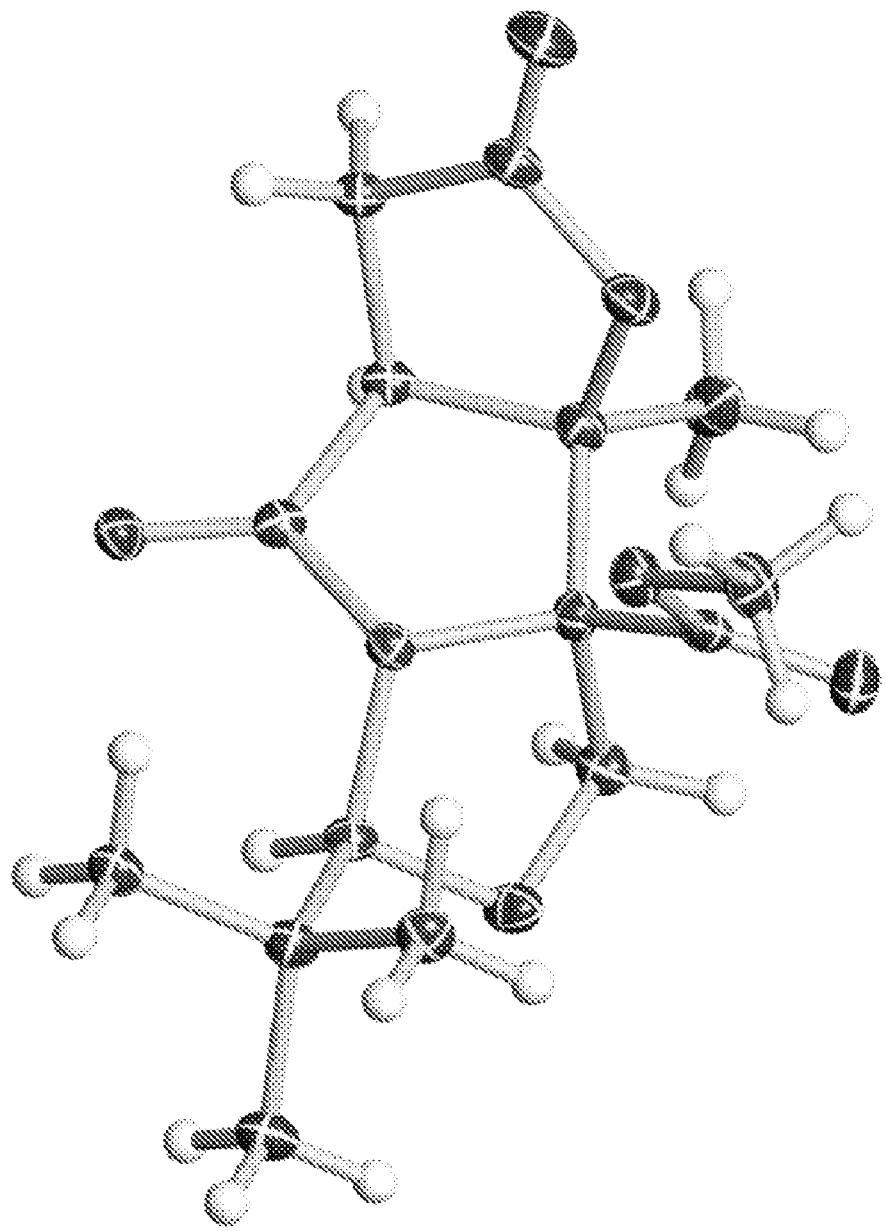
FIG. 27 shows an ORTEP representation of the X-ray crystal structure of compound (X-2B) (R$^2$=methyl) in CDCl$_3$.

The reaction mixture was stirred at 25° C. for 16 hrs, concentrated under reduced pressure and the resulting crude product was then purified by silica flash chromatography (EtOAc in hexanes, 10% to 50%) to afford lactone compound X-2B (25 mg, 0.08 mmol, 80% yield), which was crystallized in ethyl ether/hexane (3:1, 4.0 mL) at 4° C. The product was characterized by $^1$H and $^{13}$C NMR, see FIGS. 25 and 26, and the stereochemistry was confirmed by X-ray crystallography, see FIG. 27; MS (ESI) m/z 312 [M+H]$^+$. Thus, the stereochemistry of the C-2 and C-3 carbon centers can be established using the methods and materials in Examples 1-12.

Example 14

Synthesis of (1-A)

R$^1$=t-Butyl and R$^2$=Methyl

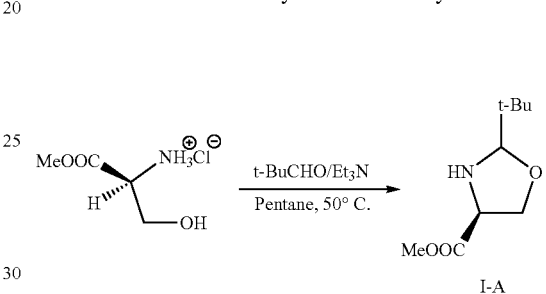

To a suspension of L-serine methylester hydrochloride (1.88 g, 0.012 mmol) in pentane (30 mL) at room temperature were added t-butyl aldehyde (1.57 g, 0.018 mmol) and Et$_3$N (1.47 g, 0.015 mmol). The reaction mixture was refluxed for 15 hrs at 50° C. using Dean-Stark apparatus. The resulting reaction mixture was cooled to room temperature, filtered through celite, and the celite cake was washed with pentane (2×10 mL). The combined filtrate was concentrated under reduced pressured and dried under high vacuum to afford compound I-A (1.95 g, 0.01 mmol, 86.9% yield) as clear oil, which can be used without further purification. The compound I-A was characterized by $^1$H-NMR (CDCl$_3$, 500 MHz) and $^{13}$C-NMR (CDCl$_3$, 125 MHz). See FIGS. 28 and 29.

Example 15

Synthesis of Compound (III-1A)

R$^1$=t-Butyl and R$^2$=Methyl

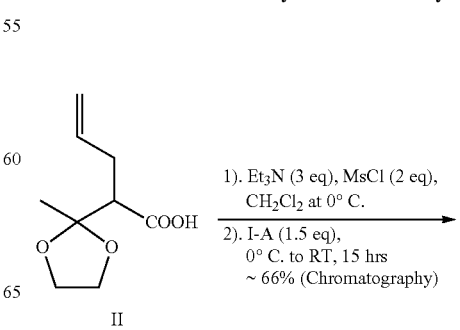

-continued

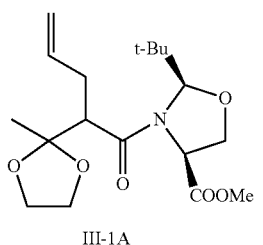

III-1A

To a solution of compound II (1.0 g, 5.32 mmol) in dry CH$_2$Cl$_2$ (15 mL) at 0° C. were added Et$_3$N (2.22 mL, 15.96 mmol) and methanesulfonyl chloride (0.82 mL, 10.6 mmol) and the solution was stirred for about 10 min. Compound I-A (1.09 g, 5.85 mmol) was then added; the reaction mixture was allowed to warm to room temperature slowly and stirred for about 15 hrs. Then the reaction mixture was quenched with H$_2$O (25 mL) and extracted with CH$_2$Cl$_2$ (3×15 mL). The combined organic layer was dried over Na$_2$SO$_4$ and concentrated under reduced pressure to yield III-1A as a mixture of two diastereomers. The crude product was purified by silica flash chromatography (3 cm ID×30 cm) using a solvent gradient of 9:1 (50 mL) to 4:1 (50 mL) to 3:1 (100 mL) hexane/EtOAc to afford the product, compound III-1A as a diastereomeric mixture (1.14 g, 3.19 mmol, 60% yield). The compound III-1A was characterized by $^1$H-NMR (CDCl$_3$, 500 MHz) and $^{13}$C-NMR (CDCl$_3$, 125 MHz). See FIGS. 30 and 31. MS (ESI) m/z 356 [M+H]$^+$.

Example 16

Synthesis of Compound (IV-A)

R$^1$=t-Butyl and R$^2$=Methyl

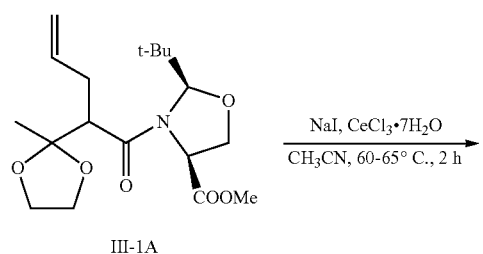

III-1A

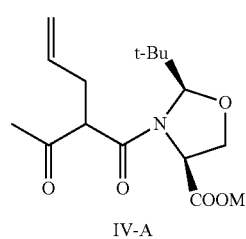

IV-A

To a solution of compound III-1A (1.14 g, 3.19 mmol) in CH$_3$CN (30 mL) were added sodium iodide (0.62 g, 4.15 mmol) and cerium (III) chloride heptahydrate (1.78 g, 4.78 mmol) and the reaction mixture was stirred at 60-65° C. for 4 hours (the reaction progress can be monitored by LC-MS). The above reaction mixture was then quenched with water (100 mL) and extracted with EtOAc (3×50 mL). The combined organic layer (cloudy) was concentrated under reduced pressure to remove all of the CH$_3$CN/EtOAc, leaving about 10 mL of H$_2$O (CH$_3$CN soluble part), which was further extracted with EtOAc (15 mL). The organic layer was dried over Na$_2$SO$_4$, and concentrated under reduced pressure to afford the product, IV-A (0.71 g, 2.26 mmol, 71% yield) as a mixture of two diastereomers. If desired, the product can be used for the next step without purification. The compound IV-A was characterized by $^1$H-NMR (CDCl$_3$, 500 MHz) and $^{13}$C-NMR (CDCl$_3$, 125 MHz) spectra. See FIGS. 32 and 33. MS (ESI) m/z 312 [M+H].

Example 17

Synthesis of Compound (VI-A)

R$^1$=t-Butyl and R$^2$=Methyl

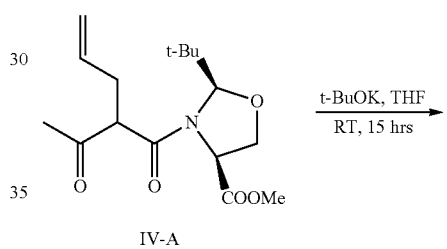

IV-A

VI-A

To a solution of compound IV-A (50 mg, 0.16 mmol) in dry THF (5 mL) at RT was added t-BuOK (9.0 mg, 0.08 mmol). The reaction mixture was stirred at RT for 15 hrs under an atmosphere of N$_2$ and then quenched with H$_2$O (10 mL) and extracted with EtOAc (3×5.0 mL). The combined organic phase was washed with saturated brine solution, dried over Na$_2$SO$_4$ and concentrated under reduced pressure). The crude product was purified by silica flash chromatography (5 mm ID×5 cm) using a solvent gradient of 9:1 (15 mL) to 4:1 (15 mL) hexane/EtOAc to afford the dehydration product VI-A (20.0 mg, 0.067 mmol, 42% yield) as the major compound. The compound VI-A was characterized by $^1$H-NMR (CDCl$_3$, 500 MHz) and $^{13}$C-NMR (CDCl$_3$, 125 MHz) spectra. See FIGS. 34 and 35. MS (ESI) m/z 294 [M+H]$^+$.

Example 18

Synthesis of Compound (VII-A)

$R^1$=t-Butyl and $R^2$=Methyl

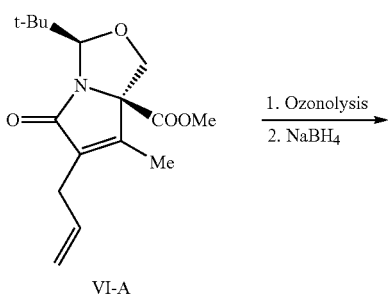

A solution of compound VI-A (1.20 g, 4.10 mmol) in THF (30 mL) was treated with ozone at −80° C. for 0.5 hours. Then NaBH$_4$ (0.77 g, 20.5 mmol) and MeOH (6 mL) were added at −80° C., then slowly warmed up to 25° C. and stirred for 30 min at this temperature. The above reaction mixture was diluted with H$_2$O (40 mL) and extracted with EtOAc (2×30 mL) followed by CH$_2$Cl$_2$ (3×30 mL). The organic phase was dried over MgSO$_4$ and concentrated under reduced pressure, the crude residue was purified by silica flash chromatography (EtOAc in hexanes, 20% to 80%) to afford compound VII-A (1.0 g, 3.36 mmol, 82% overall yield). Compound VII-A was characterized by $^1$H and $^{13}$C NMR. See FIGS. 36 and 37. MS (ESI) m/z 298 [M+H]$^+$.

Example 19

Synthesis of Compound (VIII-A)

$R^1$=t-Butyl and $R^2$=Methyl

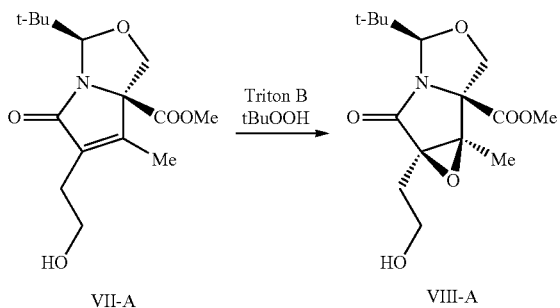

To a concentrated suspension of Triton B (benzyltrimethyl ammonium hydroxide, 80 wt % in methanol, 1.12 g, 6.72 mmol) were added THF (0.6 mL) and t-butyl hydroperoxide solution (5-6 M in decane, 3.36 mL, 16.8 mmol) and the reaction mixture was stirred for 10 minutes at room temperature. A solution of compound VII-A (1.0 g, 3.36 mmol) in THF (0.1 mL) was added to the above reaction mixture and stirred at room temperature for 18 hours. The reaction mixture was concentrated directly under reduced pressure to obtain a crude residue, which was purified by silica flash chromatography (EtOAc in hexanes, 20% to 80%) to afford compound VIII-A (160 mg, 0.51 mmol; 15.2% overall yield) and starting material VII-A (430 mg, 1.45 mmol). The product was characterized by $^1$H and $^{13}$C NMR. See FIGS. 38 and 39. MS (ESI) m/z 314 [M+H]$^+$.

Example 20

Synthesis of Compound (X-1A)

PG$^1$=Bz, $R^1$=t-Butyl and $R^2$=Methyl

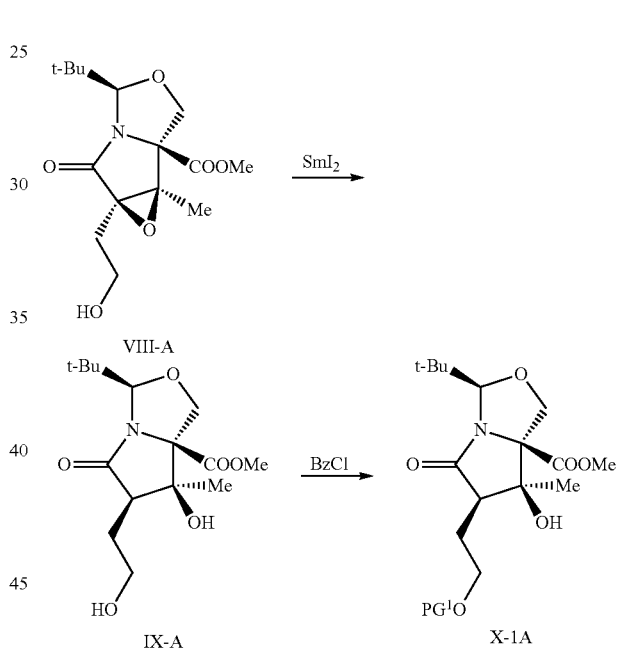

To a solution of compound VIII-A (80 mg, 0.26 mmol) in THF/MeOH (1:1, 2.0 mL) was added samarium (II) iodide (0.1 M in THF, 7.6 mL, 0.76 mmol) at −80° C. and the reaction mixture was stirred at this temperature for 30 minutes. The reaction was then quenched with aqueous NaHCO$_3$ (10 mL), Na$_2$S$_2$O$_3$ (10 mL) at −80° C. and extracted with EtOAc (2×20 mL) and CH$_2$Cl$_2$ (2×20 mL). The organic phase was dried over MgSO$_4$, concentrated under reduced pressure and dried by high vacuum. The crude residue was re-dissolved in CH$_2$Cl$_2$ (2 mL), then pyridine (63 µL, 0.77 mmol) and an appropriate protecting group reactant such as benzoyl chloride (BzCl, 53 µL, 0.46 mmol) were added. The resulting reaction mixture was stirred at room temperature for 15 hours. This reaction mixture was then directly concentrated under reduced pressure and the resulting crude product was purified by silica flash chromatography (EtOAc in hexanes, 10% to 50%) to afford compound X-1A (PG$^1$=Bz) (92 mg, 0.22 mmol, 86% overall yield from VIII-A). Compound X-1A (PG$^1$=Bz) was characterized by both $^1$H and $^{13}$C NMR spectra. See FIGS. 40 and 41. MS (ESI) m/z 420 [M+H]$^+$.

Example 21

Synthesis of Compound (XI-1A)

PG$^1$=Bz and R$^2$=Methyl

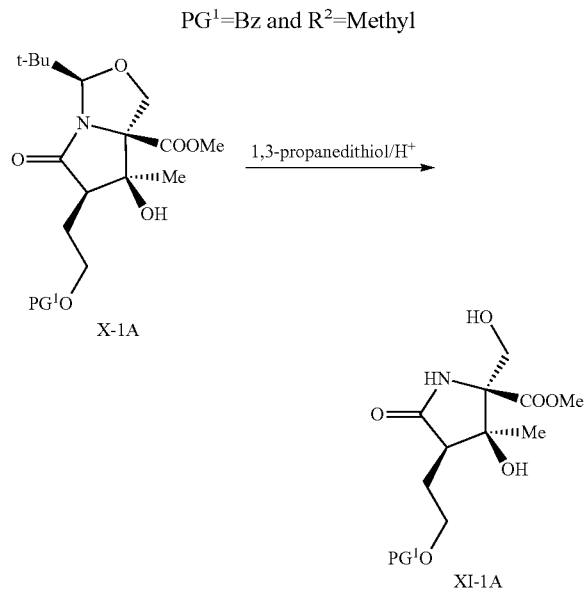

To a solution of compound X-1A (PG$^1$=Bz) (60 mg, 0.14 mmol) in CF$_3$CH$_2$OH (0.2 mL) were added 1,3-propanedithiol (0.2 mL) and a catalytic amount of aqueous HCl (12 N, 2 µL). The reaction mixture was stirred at 60° C. for 1 hr, concentrated under reduced pressure and the resulting crude product was then purified by silica flash chromatography (EtOAc in hexanes, 20% to 80%) to afford compound XI-1A (PG$^1$=Bz) (37 mg, 0.10 mmol, 71.4%). The product was characterized by $^1$H and $^{13}$C NMR. See FIGS. 42 and 43. MS (ESI) m/z 352 [M+H]$^+$.

Example 22

Synthesis of Acetoacetic Acid

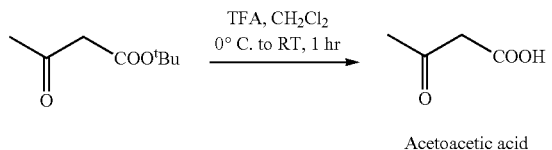

To a solution of tert-butylacetoacetate (1.60 g, 10.1 mmol) in CH$_2$Cl$_2$ (3.0 mL) at 0° C. was added trifluoroacetic acid (TFA neat, 3.0 mL, 40.4 mmol), and the solution was stirred for about 5 min. The reaction mixture was then allowed to warm to room temperature and stirred for one hour. The reaction mixture was directly concentrated under reduced pressure and dried under high-vacuum for about one hour (to remove the residual TFA) to afford the acetoacetic acid (0.9 g, 8.8 mmol, 87% yield) as a light yellow oil. The acetoacetic acid can be used in the next step without purification. The product was characterized by $^1$H NMR (CDCl$_3$, 500 MHz) δ 11.11 (br s, 1H), 3.51 (s, 2H), 2.29 (s, 3H).

Example 23

Synthesis of Compound (III-2A)

R$^1$=t-Butyl and R$^2$=Methyl

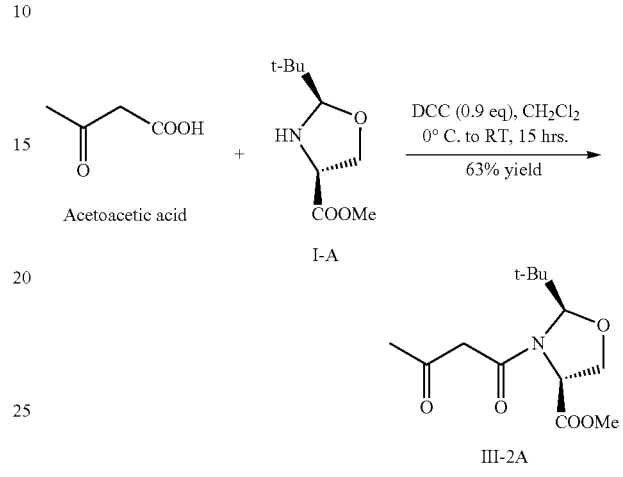

To a solution of acetoacetic acid (0.9 g, 8.8 mmol) in dry CH$_2$Cl$_2$ (15 mL) at 0° C. were added compound I-A (derived from L-serine; 1.65 g, 8.8 mmol) and DCC (1.63 g, 7.92 mmol), and the solution was stirred for about 10 min at this temperature. The reaction mixture was allowed to warm to room temperature slowly and stirred for about 15 hrs. The reaction mixture was then diluted with hexane (150 mL) and filtered via a short celite plug. The filtrate was concentrated under reduced pressure, and the crude product was purified by silica flash chromatography (3 cm ID×30 cm) using a solvent gradient of 9:1 (50 mL) to 4:1 (150 mL) hexane/EtOAc to afford the compound III-2A (1.5 g, 5.53 mmol, 62.8% yield) as a keto-enol tautomers (4:1 ratio). The product was characterized by $^1$H NMR. See FIG. 51. MS (ESI) m/z 272 [M+H]$^+$.

Example 24

Synthesis of Compound (III-2A)

R$^1$=t-Butyl and R$^2$=Methyl

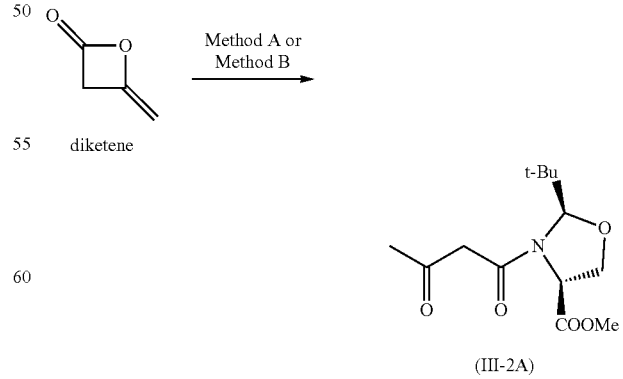

Method A: (I-A) (1.0 eq), diketene (1.5 eq), THF, 50° C., 15 hrs;
Method B: (1.0 eq), pyridine (0.5 eq), diketene (1.5 eq), benzene, 60°C., 18 hrs Method A: To a solution of 1-A (600 mg, 3.19 mmol) in dry THF (3.0 mL) was added diketene (0.37 ml, 4.78 mmol) and Et₃N (89 µl, 0.64 mmol), the reaction mixture was stirred at 50° C. for 15 hrs. The reaction mixture was cooled to room temperature and diluted with ice cold hydrochloric acid (0.5 N, 15 mL), then extracted with dichloromethane (3×15 ml), the combined organic phase was dried over MgSO₄ and concentrated under reduced pressure. The crude product was purified by silica flash chromatography (3 cm ID×30 cm) using a solvent gradient of 9:1 (50 mL) to 4:1 (100 mL) hexane/EtOAc to afford the product III-2A (760 mg, 2.80 mmol, 87.7% yield). ¹H-NMR (CDCl₃, 500 MHz).

Method B: To a solution of 1-A (4.0 g, 0.021 mol) in dry benzene (20.0 mL) was added diketene (2.46 mL, 0.032 mol) and pyridine (0.86 mL, 0.011 mol), the reaction mixture was stirred at 60° C. for 18 hrs. The reaction mixture was cooled to room temperature and directly concentrated under reduced pressure. The crude product was purified by silica flash chromatography (3 cm ID×30 cm) using a solvent gradient of 9:1 (150 mL) to 4:1 (200 mL) hexane/EtOAc to afford the product III-2A (4.30 g, 0.016 mol, 76.2% yield). The ¹H-NMR is the same as in FIG. 51.

Example 25

Synthesis of Compound (Va-A)

R¹=t-Butyl and R²=Methyl

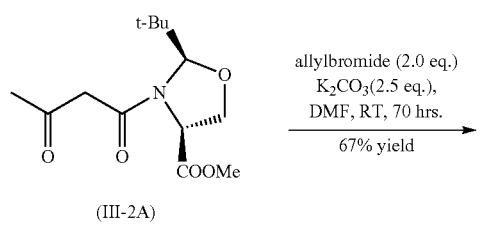

(III-2A)

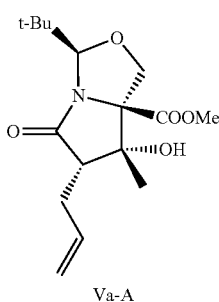

Va-A

To a solution of a compound III-2A (1.10 g, 4.06 mmol) in dry DMF (16.0 mL) at RT was added K₂CO₃ (1.40 g, 10.1 mmol) and allylbromide (0.70 mL, 8.12 mmol). The reaction mixture was stirred at RT for 70 hrs under an atmosphere of N₂ and then filtered via a short celite plug. The filtration was concentrated under reduced pressure to yield a crude product which contained compound Va-A as major and diastereomers Vb-A and Vc-A as minor (5-10%). The crude product was chromatographed on a silica gel flash column (30×4 cm) using a solvent gradient of 19:1 (100 mL) to 9:1 (200 mL) to 4:1 (300 mL) hexanes/EtOAc to yield the compound V-A (840 mg, 2.70 mmol, 66.5% yield) as a white solid. White crystalline solid was obtained from 1:1 diethyl ether:hexanes having a melting point of 114-116° C. [α]²²_D -8.4 (c 0.96, CH₃CN); ¹H-NMR (CDCl₃, 500 MHz) δ 5.92 (m, 1H), 5.11 (br dd, J=1.5, 17.2 Hz, 1H), 5.01 (d, J=10.1 Hz, 1H), 4.88 (s, 1H), 4.47 (d, J=8.8 Hz, 1H), 4.23 (d, J=8.8 Hz, 1H), 3.74 (s, 3H), 3.04 (t, J=6.6 Hz, 1H), 2.52 (m, 1H), 2.28 (m, 1H), 1.27 (s, 3H), 0.83 (s, 9H). ¹³C-NMR (CDCl₃, 125 MHz) δ 177.9, 171.8, 136.7, 116.7, 96.7, 80.4, 79.1, 68.0, 53.2, 52.7, 36.5, 28.0, 25.0 (3×CH₃), 23.0. The product was characterized by ¹H and ¹³C NMR. See FIGS. 52 and 53. MS (ESI) m/z 312 [M+H]⁺.

Example 26

Synthesis of Compound (VI-A)

R¹=t-Butyl and R²=Methyl

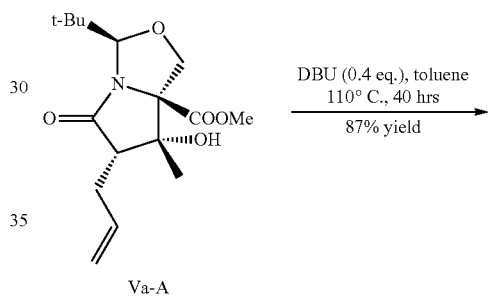

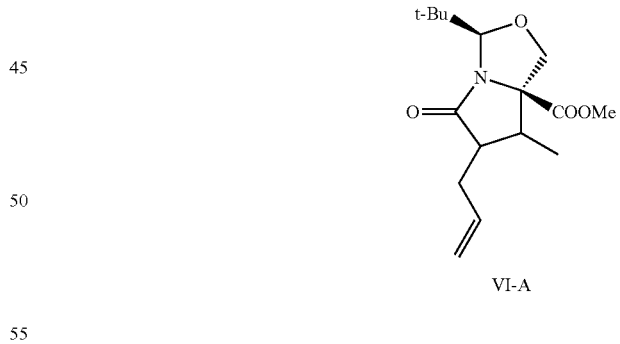

VI-A

To a solution of compound V-A (4.28 g, 13.7 mmol) in dry toluene (50 mL) was added DBU (0.83 g, 5.50 mmol). The reaction mixture was refluxed at 110° C. under an atmosphere of N₂ for 40 hrs and the reaction mixture was then cooled to RT, concentrated under reduced pressure and the crude product was chromatographed on a silica gel flash column (30×4 cm) using a solvent gradient of 19:1 (100 mL) to 9:1 (200 mL) to 4:1 (400 mL) hexanes/EtOAc to afford the product VI-A (3.50 g, 11.9 mmol, 87% yield). The compound VI-A was characterized by ¹H-NMR (CDCl₃, 500 MHz) and ¹³C-NMR (CDCl₃, 125 MHz) spectra. See FIGS. 34 and 35. MS (ESI) m/z 294 [M+H]⁺.

Example 27

Synthesis of Compound (VIII-A)

$R^1$=t-Butyl and $R^2$=Methyl

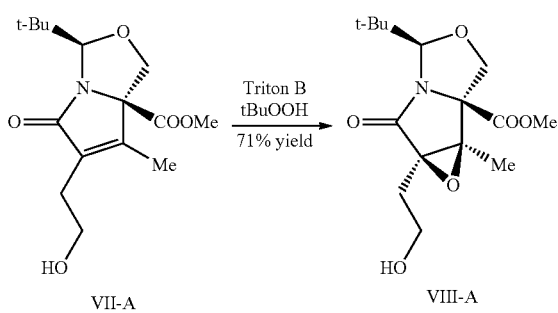

VII-A → VIII-A

Triton B (benzyltrimethyl ammonium hydroxide, 80 wt % in methanol, 15 mg, 0.18 mmol) was added to the concentrated tert-butyl hydroperoxide solution (ten-fold concentrated* from the original 5-6 M solution in decane, 400 μL, excess) with extreme safety precautions and then the reaction mixture was stirred for 5 minutes at room temperature. Compound VII-A (30 mg, 0.10 mmol) in THF (0.1 mL) was added to the above reaction mixture and stirred at 25° C. for 40 hours. The reaction mixture was concentrated directly under reduced pressure to obtain a crude residue, which was purified by silica flash chromatography (EtOAc in hexanes, 10% to 50%) to afford compound VIII-A (22 mg, 0.071 mmol, 71% yield). The product was characterized by $^1$H and $^{13}$C NMR. See FIGS. 38 and 39. MS (ESI) m/z 314 [M+H]$^+$.

*Note: tert-butyl hydroperoxide was concentrated by a stream of nitrogen at room temperature with extreme personal safety precautions.

Example 28

Synthesis of Compound (X-2A)

$R^1$=t-Butyl and $R^2$=Methyl

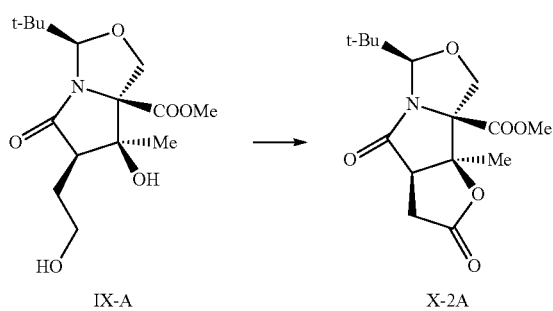

IX-A → X-2A

To a solution of compound IX-A (47 mg, 0.15 mmol) in CH$_2$Cl$_2$ (1.0 mL) with dried 4 Å molecular sieves (0.10 g) was added pyridinium chlorochromate (PCC, 96 mg, 0.45 mmol). The reaction mixture was stirred at 25° C. for 16 hrs, concentrated under reduced pressure and the resulting crude product was then purified by silica flash chromatography (EtOAc in hexanes, 10% to 50%) to afford X-2A (29 mg, 0.125 mmol, 84% yield). The product was characterized by $^1$H and $^{13}$C NMR. See FIGS. 44 and 45. MS (ESI) m/z 312 [M+H]$^+$.

Example 29

Synthesis of Compound (XI-2A)

$R^2$=Methyl

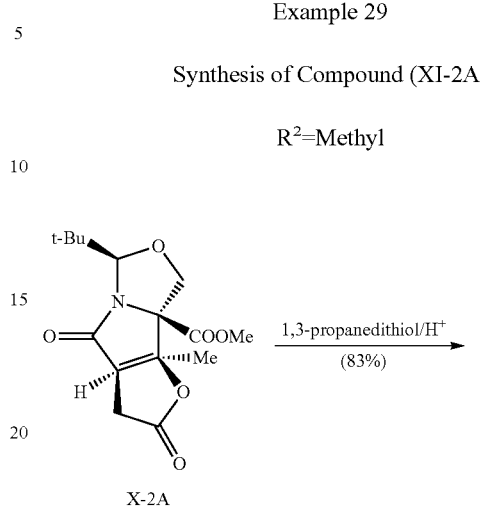

X-2A → XI-2A

To a solution of compound X-2A (39 mg, 0.12 mmol) in CF$_3$CH$_2$OH (1.0 mL) were added 1,3-propanedithiol (1.0 mL) and a catalytic amount of aqueous HCl (12 N, 15 μL). The reaction mixture was stirred at 6° C. for 1.0 hr, concentrated under reduced pressure and the resulting crude product was then purified by silica flash chromatography (EtOAc in hexanes, 20% to 80%) to afford compound XI-2A (25 mg, 0.10 mmol, 83% yield). The product was characterized by $^1$H and $^{13}$C NMR. See FIGS. 46 and 47. MS (ESI) m/z 244 [M+H]$^+$.

Example 30

Synthesis of Compound (XII-2A)

$R^2$=Methyl and C-5 0-TES

Step 1

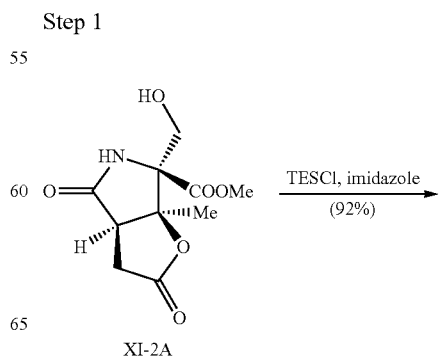

XI-2A

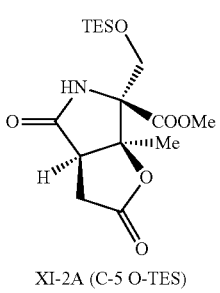

XI-2A (C-5 O-TES)

To a solution of compound XI-2A (12 mg, 0.049 mmol) in dry CH$_2$Cl$_2$ (2.0 mL) was added imidazole (5 mg, 0.073 mmol) followed by TESCl (9 μL, 0.054 mmol) at 25° C., and the reaction mixture was stirred at 25° C. for 15 hours. The reaction mixture was then directly concentrated under reduced pressure and the resulting crude product was purified by silica flash chromatography (EtOAc in hexanes, 10% to 50%) to afford compound XI-2A (C-5 O-TES) (16 mg, 0.045 mmol, 92% yield). The product was characterized by $^1$H NMR. See FIG. 48. MS (ESI) m/z 358 [M+H]$^+$.

Step 2

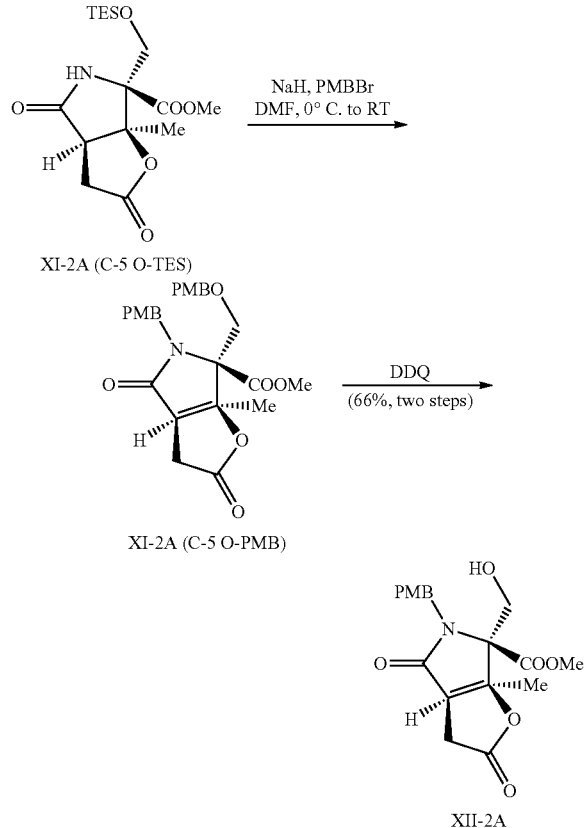

A solution of compound XI-2A (C-5 O-TES) (10 mg, 0.028 mmol) in dry DMF (0.1 mL) was added dropwise to a stirred dispersion of NaH (sodium hydride, 60% in mineral oil, 2 mg, 0.042 mmol) in dry DMF (0.2 mL) at 0° C. under an argon atmosphere. The reaction mixture was stirred at 0° C. for 15 minutes followed by addition of PMBBr (8 μL, 0.056 mmol). The reaction mixture was stirred at 0° C. for 1 hour and then allowed to warm up to RT. After reaching RT, the reaction mixture was stirred for 15 hours. Afterwards, the reaction mixture was quenched with glacial acetic acid (0.2 mL) and ice water (0.5 mL) then extracted with CH$_2$Cl$_2$ (3×1 mL). The combined organic phase was dried over MgSO$_4$ and concentrated under reduced pressure to yield the crude product, compound XI-2A (C-5 O-PMB). The crude compound XI-2A (C-5 O-PMB) was directly subjected to the next step without further purification. The compound XI-2A (C-5 O-PMB) was redissolved in CH$_2$Cl$_2$/H$_2$O (20:1, v/v; 0.2 mL), then DDQ (2,3-dichloro-5,6-dicyano-1,4-benzoquinone, 13 mg, 0.056 mmol) was added at RT, and the reaction mixture was stirred at this temperature for 6 hours. The reaction mixture was quenched with aqueous NaHCO$_3$ (1 ml) and extracted with CH$_2$Cl$_2$ (3×1 mL). The combined organic phase was dried over MgSO$_4$ and concentrated under reduced pressure, and the resulting crude product was subjected to silica flash chromatography (EtOAc in hexanes, 10% to 50%) to afford compound XII-2A (6.2 mg, 0.017 mmol, 60% overall yield for two steps). The product was characterized by $^1$H and $^{13}$C NMR. See FIGS. 49 and 50. MS (ESI) m/z 364 [M+H]$^+$.

Example 31

Synthesis of Compound (VI-A)

R$^1$=t-Butyl and R$^2$=Methyl

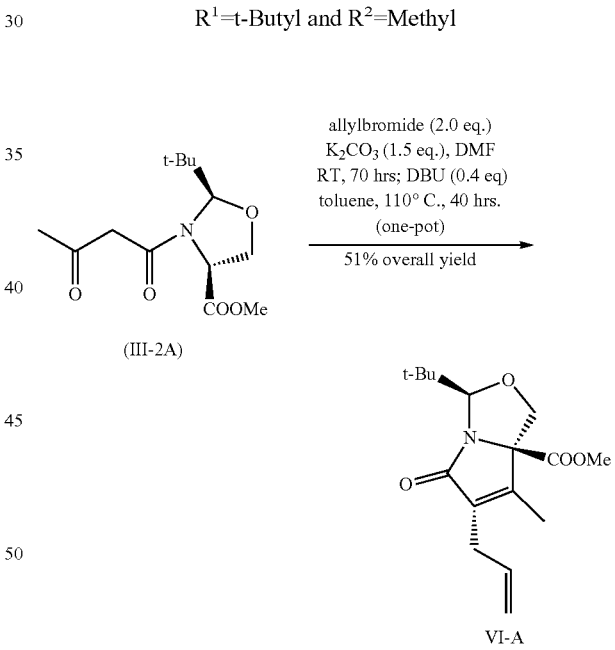

To a solution of III-2A (560 mg, 2.06 mmol) in dry DMF (0.50 mL) at RT was added K$_2$CO$_3$ (430 mg, 3.10 mmol) and allylbromide (0.36 mL, 4.13 mmol), and the reaction mixture was stirred at RT for 70 hrs under an atmosphere of N$_2$. The above reaction mixture was directly diluted with dry toluene (25 mL) and was added 1,8-diazabicyclo[5.4.0]undec-7-ene (DBU, 0.12 mL, 0.83 mmol), refluxed at 110° C. for 40 hrs under an atmosphere of N$_2$ and then cooled to RT. The reaction mixture was filtered via a short celite plug, the filtration was concentrated under reduced pressure, the crude product was chromatographed on a silica gel flash column (30×4 cm) using a solvent gradient of 19:1 (100 mL) to 9:1 (200 mL) to

Example 32

Synthesis of Compound (III-2A)

R¹=t-Butyl and R²=Methyl

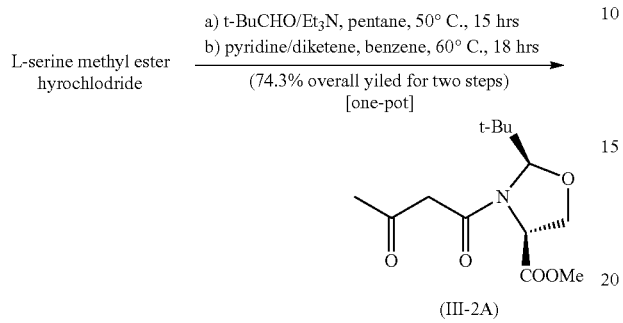

(III-2A)

To a suspension of (L)-serine methylester hydrochloride (5.50 g, 0.035 mol) in pentane (40 mL) at room temperature were added t-butyl aldehyde (3.62 g, 0.042 mol) and $Et_3N$ (3.93 g, 0.039 mol). The reaction mixture was refluxed for 15 hrs at 50° C. using Dean-Stark apparatus. The resulting reaction mixture was cooled to room temperature, filtered through celite, and the celite cake was washed with pentane (2×20 mL). The combined filtrate was concentrated under reduced pressured and dried under high vacuum to afford crude product as clear oil, which can be used directly for the next step without further purification. To a solution of the above crude product in dry benzene (20.0 mL) was added diketene (4.0 mL, 0.052 mol) and pyridine (1.41 mL, 0.017 mol), the reaction mixture was stirred at 60° C. for 18 hrs. The reaction mixture was cooled to room temperature and directly concentrated under reduced pressure. The crude product was purified by silica flash chromatography (5 cm ID×400 cm) using a solvent gradient of 9:1 (400 mL) to 4:1 (500 mL) hexane/EtOAc to afford the compound III-2A (7.05 g, 0.026 mol, 74.3% yield). $^1$H-NMR ($CDCl_3$, 500 MHz) was confirmed to be the same as FIG. 51.

It will be understood by those of skill in the art that numerous and various modifications can be made without departing from the spirit of the present application. Therefore, it should be clearly understood that the forms of the present application are illustrative only and not intended to limit the scope of the present application.

What is claimed is:

1. A compound of formula (VII):

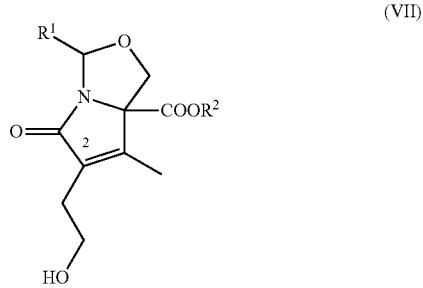

(VII)

wherein: $R^1$ is selected from the group consisting of hydrogen, an unsubstituted or substituted $C_{1-6}$ alkyl, and an unsubstituted or substituted aryl; and $R^2$ is selected from the group consisting of hydrogen, an unsubstituted or substituted $C_{1-6}$ alkyl, an unsubstituted or substituted aryl, and an unsubstituted or substituted arylalkyl.

2. The compound of claim 1, wherein $R^1$ is an unsubstituted or substituted $C_{1-6}$ alkyl; and $R^2$ is an unsubstituted or substituted $C_{1-6}$ alkyl.

3. The compound of claim 1, wherein $R^1$ is t-butyl; and $R^2$ is methyl.

4. The compound of claim 1, having a structure selected from the group consisting of:

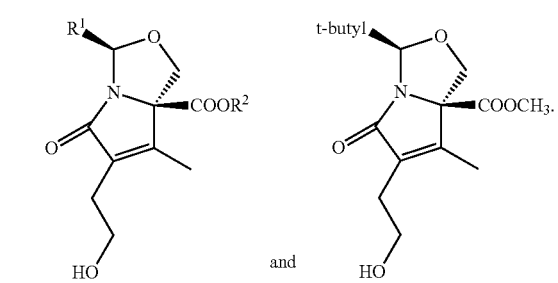

and

5. A method of preparing the compound of claim 1 comprising oxidizing the terminal double bond of the allyl substitutent at C-2 of a compound of formula (VI) to an aldehyde and reducing the aldehyde to a hydroxy group to form a compound of formula (VII):

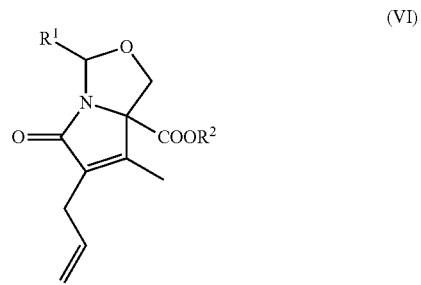

(VI)

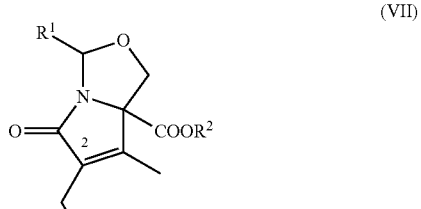

(VII)

wherein: $R^1$ is selected from the group consisting of hydrogen, an unsubstituted or substituted $C_{1-6}$ alkyl, and an unsubstituted or substituted aryl; and $R^2$ is selected from the group consisting of hydrogen, an unsubstituted or substituted $C_{1-6}$ alkyl, an unsubstituted or substituted aryl, and an unsubstituted or substituted arylalkyl.

* * * * *